(12) United States Patent
Dryer et al.

(10) Patent No.: US 12,429,940 B2
(45) Date of Patent: Sep. 30, 2025

(54) SYSTEMS, METHODS, AND GRAPHICAL USER INTERFACES FOR AUTOMATIC MEASUREMENT IN AUGMENTED REALITY ENVIRONMENTS

(71) Applicant: Apple Inc., Cupertino, CA (US)

(72) Inventors: Allison W. Dryer, Tiburon, CA (US); Giancarlo Yerkes, San Carlos, CA (US); Lisa K. Forssell, Palo Alto, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/576,735

(22) Filed: Jan. 14, 2022

(65) Prior Publication Data

US 2022/0261066 A1    Aug. 18, 2022

Related U.S. Application Data

(60) Provisional application No. 63/149,553, filed on Feb. 15, 2021.

(51) Int. Cl.
*G06F 3/01* (2006.01)
*G06F 3/04842* (2022.01)
(Continued)

(52) U.S. Cl.
CPC .......... *G06F 3/011* (2013.01); *G06F 3/04845* (2013.01); *G06Q 30/0643* (2013.01);
(Continued)

(58) Field of Classification Search
CPC .... G06F 3/011; G06F 3/04845; G06F 3/0484; G06F 3/04842; G06F 9/453; G06T 7/50;
(Continued)

(56) References Cited

U.S. PATENT DOCUMENTS 9,245,180 B1     1/2016  Hansen
10,456,102 B2 *  10/2019 Don .................... G01N 23/046
(Continued)

FOREIGN PATENT DOCUMENTS

CA     2812021 A1 * 10/2013  ............ G03B 13/18
JP     2004364100 A  * 12/2004

OTHER PUBLICATIONS

International Search Report and Written Opinion, dated May 13, 2022, received in International Payent Application No. PCT/US2022/012856, which corresponds with U.S. Appl. No. 17/576,735, 19 pages.

*Primary Examiner* — Hwei-Min Lu
(74) *Attorney, Agent, or Firm* — Morgan, Lewis & Bockius LLP

(57) ABSTRACT

A computer system displays, in a user interface, a first representation of a body part that is in a field of view of the one or more cameras. The computer system detects, using the one or more cameras, movement of the body part. The displayed first representation of the body part is updated in accordance with the movement of the body part. The computer system, while displaying the first representation of the body part, displays an indicator at a fixed location relative to the first representation of the body part. The indicator is displayed at a first position in the user interface that overlays at least a portion of the representation of the body part, the indicator is updated in accordance with the movement of the body part, and the indicator includes an indication of a suggested direction of movement of the body part.

51 Claims, 74 Drawing Sheets

(51) Int. Cl.
   *G06F 3/04845* (2022.01)
   *G06Q 30/0601* (2023.01)
   *G06T 3/40* (2024.01)
   *G06T 7/20* (2017.01)
   *G06T 7/50* (2017.01)
   *G06T 7/60* (2017.01)
   *G06T 11/00* (2006.01)

(52) U.S. Cl.
   CPC ............ *G06T 3/40* (2013.01); *G06T 7/20* (2013.01); *G06T 7/50* (2017.01); *G06T 7/60* (2013.01); *G06T 11/001* (2013.01); *G06F 3/04842* (2013.01); *G06T 2200/24* (2013.01); *G06T 2207/30196* (2013.01)

(58) Field of Classification Search
   CPC .... G06T 7/20; G06T 7/60; G06T 3/40; G06T 11/001; G06T 2200/24; G06T 2207/30196; G06Q 30/0643; G06Q 30/0641
   USPC .............................. 715/709, 708, 5, 700, 705
   See application file for complete search history.

(56) References Cited

U.S. PATENT DOCUMENTS

| | | | | |
|---|---|---|---|---|
| 2001/0012016 A1* | 8/2001 | Ide | | G01S 17/89 345/582 |
| 2005/0265620 A1* | 12/2005 | Hung | | G09G 5/395 382/254 |
| 2006/0036125 A1* | 2/2006 | Viswanathan | | A61B 34/20 600/11 |
| 2007/0083384 A1* | 4/2007 | Geslak | | G09B 19/00 705/2 |
| 2010/0303289 A1* | 12/2010 | Polzin | | G06V 40/103 348/135 |
| 2012/0320080 A1* | 12/2012 | Giese | | G06F 3/011 345/619 |
| 2013/0159141 A1 | 6/2013 | Gadiyar et al. | | |
| 2013/0295539 A1* | 11/2013 | Wilson | | H04N 9/3185 434/247 |
| 2014/0201690 A1* | 7/2014 | Holz | | G06F 3/04817 715/863 |
| 2014/0282137 A1* | 9/2014 | Lin | | G06Q 30/0643 715/765 |
| 2016/0051345 A1* | 2/2016 | Levin | | A61B 1/00045 433/29 |
| 2016/0058337 A1* | 3/2016 | Blahnik | | A61B 5/1123 |
| 2016/0063235 A1* | 3/2016 | Tussy | | G06V 40/70 726/6 |
| 2016/0196052 A1* | 7/2016 | Franklin | | G06F 3/04817 715/765 |
| 2016/0227128 A1* | 8/2016 | Um | | G08B 13/19641 |
| 2018/0085203 A1* | 3/2018 | Ramirez | | A61C 5/77 |
| 2019/0080189 A1* | 3/2019 | Van Os | | H04N 23/62 |
| 2019/0347817 A1* | 11/2019 | Ferrantelli | | G06F 18/217 |
| 2020/0078103 A1* | 3/2020 | Duindam | | A61B 1/009 |
| 2020/0106955 A1* | 4/2020 | Fleizach | | H04N 23/64 |
| 2021/0049817 A1* | 2/2021 | Lee | | G06F 3/011 |
| 2022/0078339 A1* | 3/2022 | Yang | | G06T 7/62 |
| 2022/0301041 A1* | 9/2022 | Lee | | G06F 9/453 |

* cited by examiner

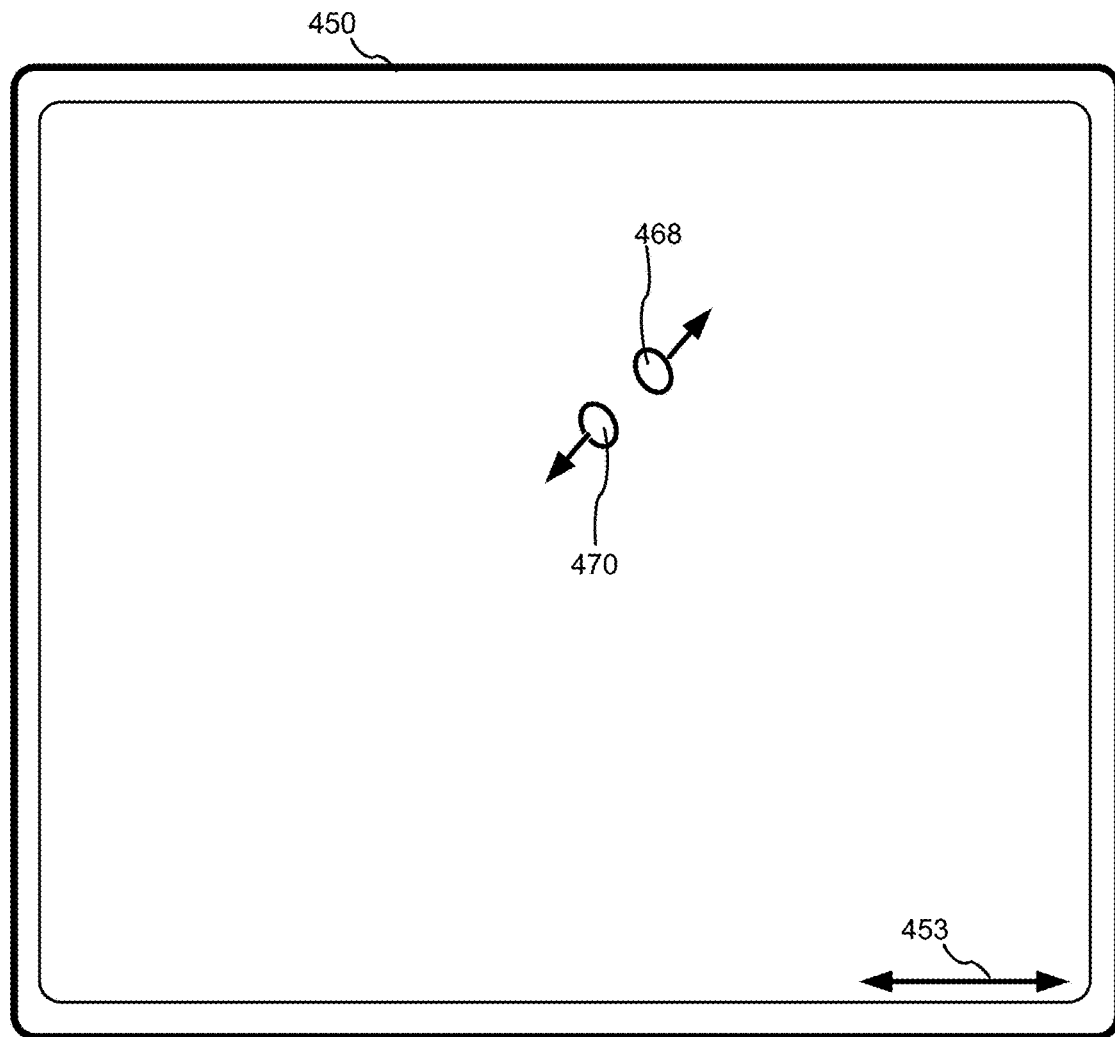
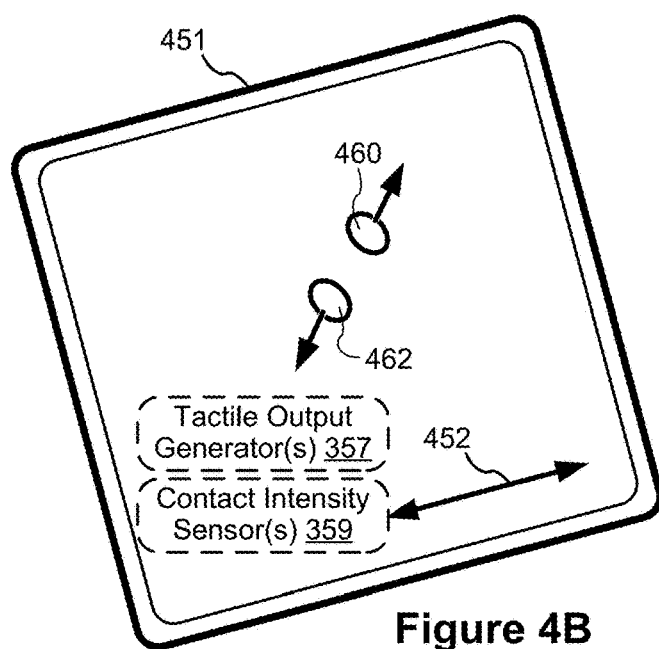
Figure 4B

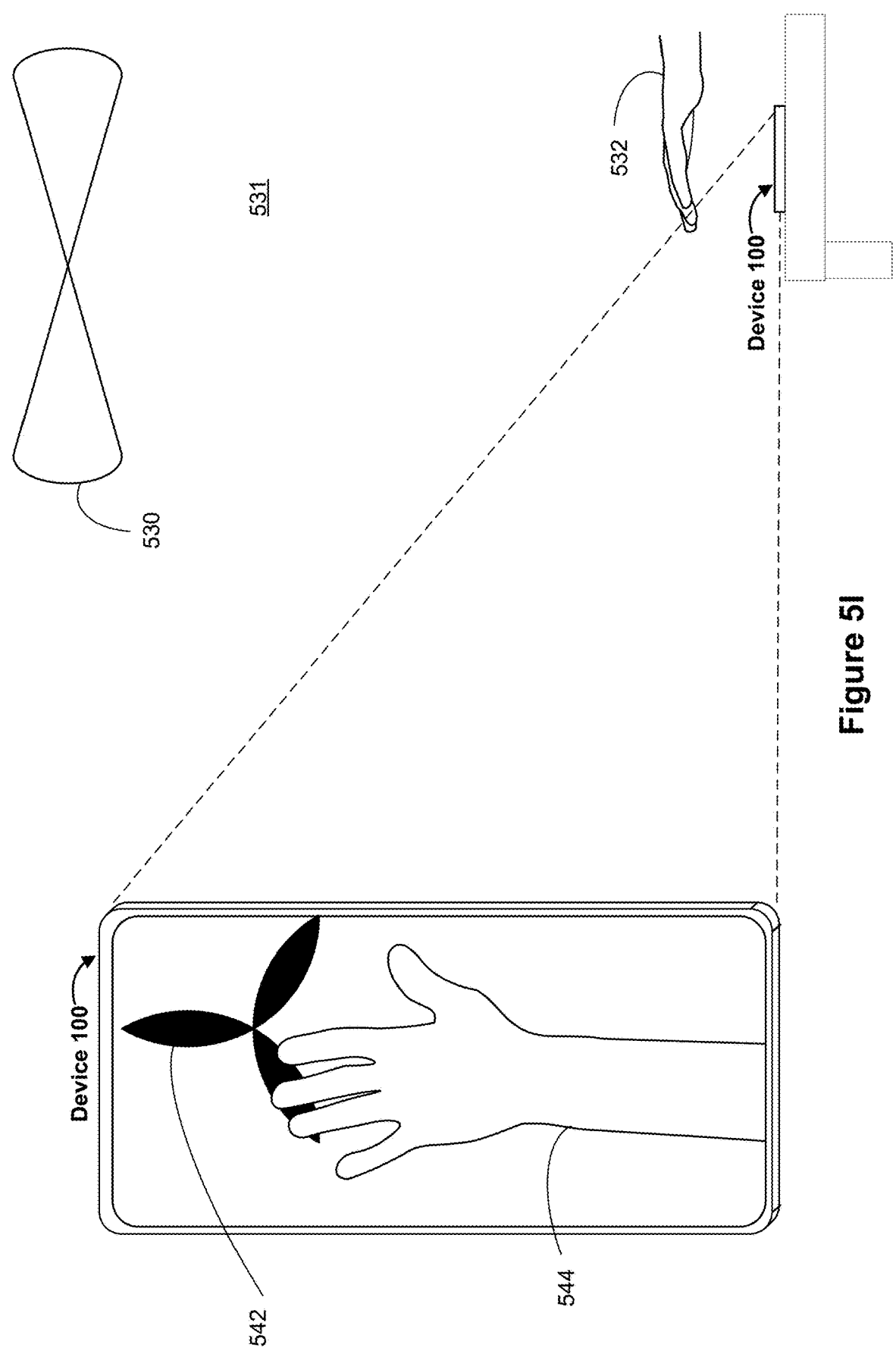

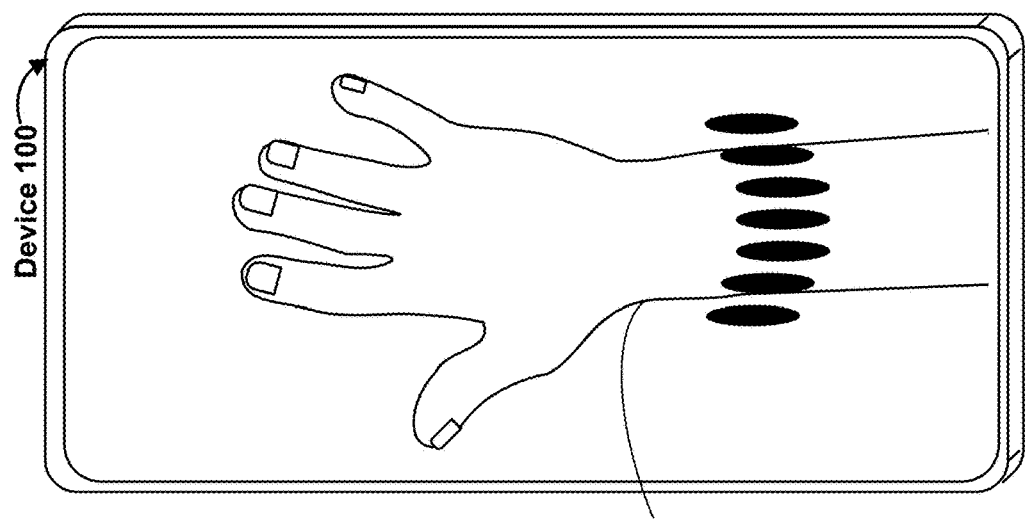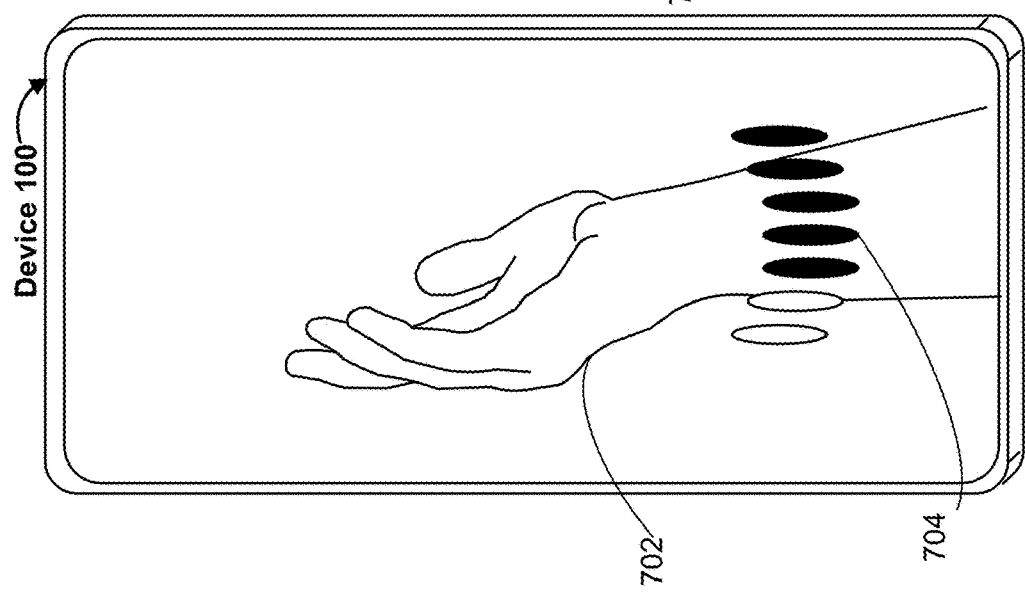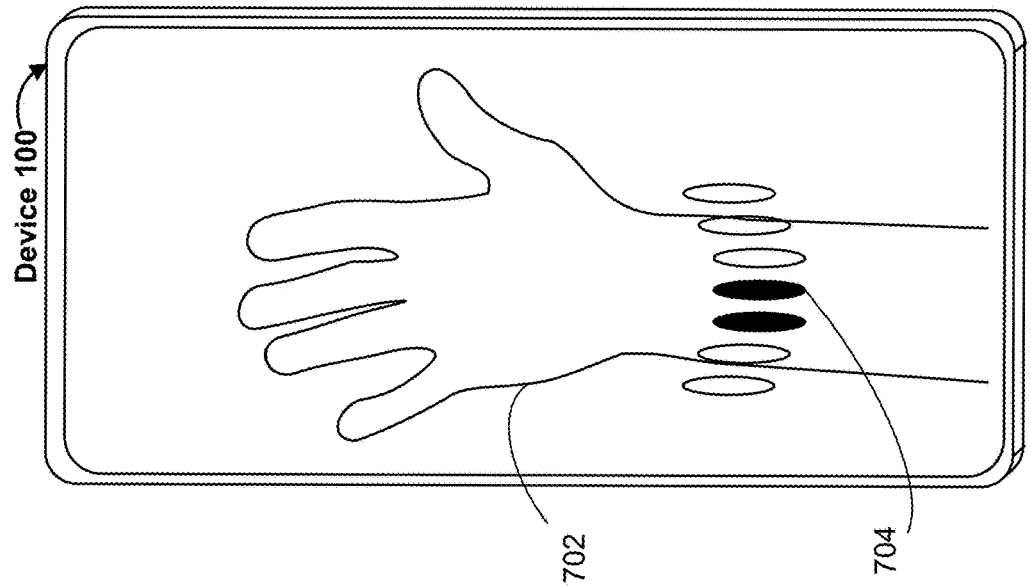
Figure 7A

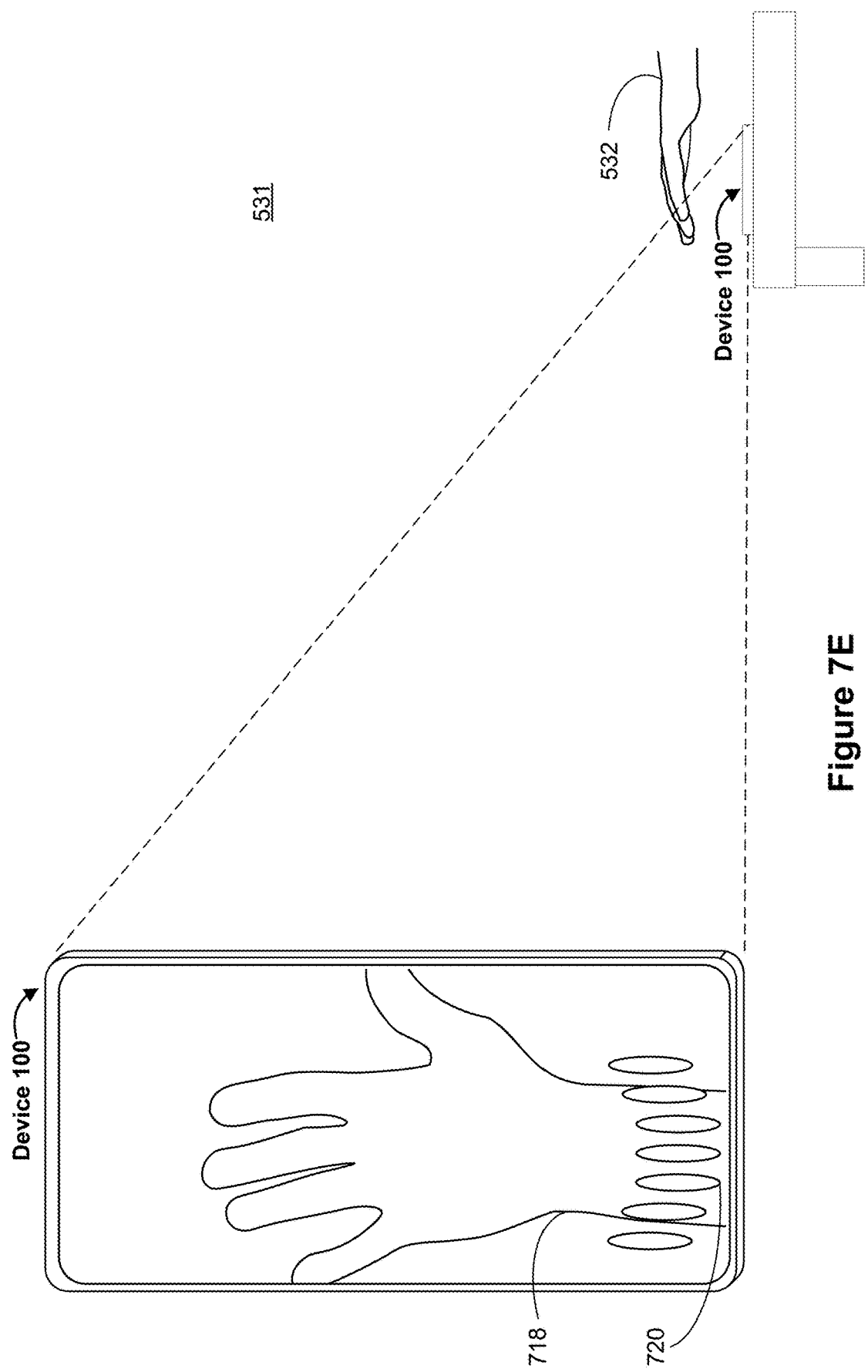

914 While displaying the visual prompt to move the body part into the field of view of the one or more cameras, display an animated transition in which at least a portion of the visual prompt is moved to a location that is near the representation of the portion of the user's body.

916 The at least a portion of the visual prompt comprises an outline that snaps to the representation of the portion of the user's body.

918 The at least a portion of the visual prompt is displayed in a shape that matches a shape of the representation of the portion of the user's body in the field of view of the one or more cameras 920 The visual prompt comprises a representation of a hand.

922 The portion of the user's body comprises a hand.

924 In accordance with the determination that the portion of the user's body that is in the field of view of the one or more cameras fails to meet the first criteria, display text that indicates that the first criteria have not been met 926 Displaying the representation of the portion of the user's body to have a second degree of transparency that indicates that the first criteria have not been met comprises visually deemphasizing the representation of the portion of the user's body.

928 The portion of the user's body is in a physical environment.

Prior to detecting the portion of the user's body, display a background.

In response to detecting the portion of the user's body is in the field of view of the one or more cameras, display the representation of the portion of the user's body that is in the field of view of the one or more cameras over the background 930 The portion of the user's body is in a physical environment.

Display a representation of the field of view of the one or more cameras that includes a representation of the physical environment.

In response to detecting the portion of the user's body is in the field of view of the one or more cameras, visually deemphasize the representation of the physical environment

Figure 9B

932 In response to detecting the portion of the user's body, in accordance with the determination that the portion of the user's body meets the first criteria, display an indicator that at least partially overlays the representation of the portion of the user's body.

934 Display a second user interface, the second user interface including:
    an option to select a product having a plurality of size options, selectable in accordance with a measurement of the portion of the user's body that is in a field of view of the one or more cameras; and
an affordance that, when selected, initiates display of the first user interface 936 Display, in a third user interface, an instruction to identify the first body part as a right-side body part or a left-side body part.

938 Display, in the first user interface, a first color in a second region of the first user interface; and replace display of the first color with display of a second color, distinct from the first color

1002 Display, in a user interface, a first representation of a body part that is in a field of view of the one or more cameras.

1004 Detect, using the one or more cameras, movement of the body part, wherein the displayed first representation of the body part is updated in accordance with the movement of the body part.

1006 While displaying the first representation of the body part, display an indicator at a fixed location relative to the first representation of the body part.

1008 The indicator is displayed at a first position in the user interface that overlays at least a portion of the representation of the body part, the indicator is updated in accordance with the movement of the body part; and the indicator includes an indication of a suggested direction of movement of the body part.

1010 The indication of the suggested direction of movement comprises an animation of the indicator indicating the direction of movement.

1012 The body part is a wrist and/or a hand.

1014 The body part is in a physical environment; and the computer system displays, in the first user interface, a background, detects, using the one or more cameras, a portion of the physical environment and the body part that are within the field of view of the one or more cameras, and displays the representation of the body part over the background without displaying a representation of the portion of the physical environment that is within the field of view of the one or more cameras.

1016 Display a background having a first color; and replace display of the background having the first color with display of a background having a second color.

1018 The first color and the second color correspond to color options for a physical object to be worn on the body part.

1020 Detect movement of the body part in a first direction. In response to detecting the movement of the body part in the first direction:
display the representation of the body part at a second position in the user interface in accordance with the movement of the body part; and
display the indicator at the fixed location relative to the first representation of the body part displayed at the second position.

1022 The first representation of the body part and the indicator are displayed at respective first sizes in the user interface. Detect movement of the body part that changes a distance between the one or more cameras and the body part. In response to detecting the change in distance between the one or more cameras and the body part:
display the first representation of the body part at a second size in accordance with the changed distance; and
display the indicator at a respective second size in accordance with the changed distance.

1024 Detecting movement of the body part comprises detecting rotation of the body part. While detecting rotation of the body part, scan, using the one or more cameras, one or more images to determine a measurement of the body part; and update the indicator to indicate a progress of scanning the one or more images.

1026 The indication of the suggested direction of movement of the body part comprises an indication to rotate the body part.

1028 While displaying the first representation of the body part, capture, using the one or more cameras, one or more images of the body part. The one or more images are used to determine a measurement of the body part. Display, in a second user interface, a size corresponding to the measurement of the body part.

1030 The fixed location relative to the first representation of the body part is a first fixed location relative to the first representation of the body part. Receive a first user input in a first direction, and in response to the first user input, update the first fixed location of the indicator relative to the body part to a second fixed location, distinct from the first fixed location, relative to the body part.

1032 Replace display of the indicator at the first position in the user interface with a user interface element at the first position in the user interface, wherein the user interface element is displayed at the fixed location relative to the first representation of the body part, and the user interface element indicates a first size of a portion of the body part corresponding to the portion of the representation of the body part at the fixed location.

1034 The fixed location relative to the first representation of the body part is a first fixed location. Receive a second user input to move the user interface element. In response to receiving the second input, move the user interface element from the first position in the user interface that overlays at least a portion of the representation of the body part to a third fixed location relative to the first representation of the body part.

1036 In accordance with a determination that the user interface element is at the third fixed location relative to the first representation of the body part, update the user interface element to indicate a second size of a portion of the body part corresponding to the third fixed location.

1038 Capture an image that includes the first representation of the body part and the user interface element at the first fixed location relative to the first representation of the body part, wherein the user interface element indicates a size of the portion of the body part corresponding to the first fixed location of user interface element.

1040 While displaying the image, receive a third user input to move the user interface element to a different fixed location relative to the first representation of the body part in the image.

┌─────────────────────────────────────────────────────────────────┐
│ 1042 The user interface is a first user interface. Display a second user interface, the
│ second user interface including:
│ an option to select a product having a plurality of size options, selectable in
│ accordance with a measurement of the body part that is in the field of view of the
│ one or more cameras; and
│ an affordance that, when selected, initiates display of the first user interface.
└─────────────────────────────────────────────────────────────────┘

┌─────────────────────────────────────────────────────────────────┐
│ 1044 The user interface is a user interface within a respective application executed
│ by the computer system.
└─────────────────────────────────────────────────────────────────┘

┌─────────────────────────────────────────────────────────────────┐
│ 1046 The indicator gradually changes in appearance as the body part moves to
│ indicate a progress of rotation of the body part.
└─────────────────────────────────────────────────────────────────┘

┌─────────────────────────────────────────────────────────────────┐
│ 1048 In response to detecting movement of the body part:
│ in accordance with a determination that the movement of the body part moves at a
│ speed that is below a threshold speed, gradually change an appearance of indicator
│ in appearance as the body part moves to indicate a progress of movement of the
│ body part toward a target pose; and
│ in accordance with a determination that the movement of the body part moves at a
│ speed that is above the threshold speed, forgo at least a portion of a change in
│ appearance of indicator in appearance as the body part moves to indicate that
│ movement of the body part toward the target pose was too fast.
└─────────────────────────────────────────────────────────────────┘

1112 At a second computer system, scan the machine-readable code. In response to scanning the machine-readable code, initiate a process for displaying information about the wearable object on the second computer system or a third computer system communicatively coupled to the second computer system.

1114 At the second computer system or the third computer system, in accordance with a determination that the machine-readable code has been scanned, display a first application on a first portion, less than all, of user interface displayed using a display generation component of the second computer system or third computer system. The first application includes the information that identifies the one or more sizing parameters of the wearable object or that describes the measurement of the portion of the user's body within a first application.

1116 At the second computer system or the third computer system, in response to scanning the machine-readable code, display, using a display generation component of the second computer system or third computer system, a card that includes information about the wearable object, including the information stored in the machine-readable code that identifies one or more sizing parameters of the wearable object.

1118 Display an option for adding a virtual card that includes the information about the wearable object to a virtual wallet. In response to detecting a user input selecting the option, store the virtual card in the virtual wallet.

1120 At a respective computer system on which the virtual card is stored or accessed, in accordance with a determination that the respective computer system is within a predefined proximity to a predefined location, display, using a display generation component of the respective computer system, a visual prompt for displaying the virtual card that is stored in the virtual wallet.

1122 At the respective computer system: detect a user input selecting the visual prompt for displaying the virtual card. In response to detecting the user input selecting the visual prompt, display, using the display generation component of the respective computer system, the virtual card.

1124 Displaying the virtual card includes the displaying the machine-readable code.

1126 Displaying the virtual card includes displaying a description of the wearable object.

1218 In accordance with a determination that the body part moves in a first direction, move the second visual prompt on the display in a second direction that corresponds to the first direction of movement of the body part. In accordance with a determination that the body part moves in a third direction different from the first direction, move the second visual prompt on the display in a fourth direction that corresponds to the third direction of movement of the body part and is different from the second direction.

1220 The first visual prompt is displayed at a fixed size and at a fixed position in the first user interface as the body part of the user moves.

1222 A displayed size of the second visual prompt is updated in accordance with a change in position of the body part relative to the one or more cameras.

1224 In accordance with a determination that the portion of the user's body changes position relative to the one or more cameras, update a position of the second visual prompt within the first user interface while maintaining the position of the second visual prompt at the fixed predefined position relative to the representation of the portion of the user's body.

1226 The second visual prompt is displayed at a first angle. In accordance with a determination that the body part changes position relative to the one or more cameras, update the second visual prompt to be displayed at a second angle, wherein the second angle is determined based on the changed position of the body part.

1228 Display text that includes instructions to move the body part in order to satisfy the body part positioning precondition.

1230 In response to the body part satisfying the body part positioning precondition, display a first timer indicating an amount of time that the user must maintain the body part in a position satisfying the body part positioning precondition.

1232 In response to the body part satisfying the body part positioning precondition, display an indication that a first scan of the body part is complete.

1234 Displaying the indication that the first scan of the body part is complete comprises:
    increasing brightness of the displayed first user interface from a first level to a second level for a predetermined time period; and
    after increasing the brightness to the second level, decreasing the brightness of the displayed first user interface.

1236 Displaying the indication that the first scan of the body part is complete comprises displaying a check mark.

1238 In accordance with a determination that the body part satisfies the body part positioning precondition:
    display text that includes instructions to move the body part in order to satisfy a second body part positioning precondition;
    maintain display of the first visual prompt at the first fixed location within the first user interface; and
    replace the second visual prompt with a third visual prompt that is fixed at a second predefined position relative to the representation of the portion of the user's body, wherein a position of the third visual prompt relative to a position of the first visual prompt indicates a movement of the body part that is required to satisfy the second body part positioning precondition.

1240 In response to the body part satisfying the second body part positioning precondition, display a second timer indicating an amount of time that the user must maintain the body part in a position satisfying the second body part positioning precondition.

1242 In accordance with a determination that the body part satisfies the second body part positioning precondition, display an indication that a second scan of the body part is complete.

1244 Before scanning, using the one or more cameras, the portion of the user's body, display one or more instructions on the display device.

1246 The one or more instructions include instructions for placing the computing device into a proper position for scanning.

1248 The one or more instructions include instructions for selecting which body part will be scanned using the one or more cameras.

1250 The one or more instructions include instructions for moving the body part such that the body part is in the field of view of the one or more cameras.

1252 The one or more instructions include displaying a representation of a body part in a position that satisfies the body part positioning precondition.

1254 Before displaying the second visual prompt, update display of the representation of the portion of the user's body.

Figure 12D

SYSTEMS, METHODS, AND GRAPHICAL USER INTERFACES FOR AUTOMATIC MEASUREMENT IN AUGMENTED REALITY ENVIRONMENTS

RELATED APPLICATIONS

This application claims priority to U.S. Provisional Patent Application No. 63/149,553, filed Feb. 15, 2021, which is hereby incorporated by reference in its entirety.

TECHNICAL FIELD

This relates generally to computer systems for augmented reality, including but not limited to electronic devices for measuring using virtual objects displayed in an augmented reality environment.

BACKGROUND

The development of computer systems for augmented reality has increased significantly in recent years. But methods and interfaces for interacting with environments that include at least some virtual elements (e.g., augmented reality environments, mixed reality environments, and virtual reality environments) are cumbersome and inefficient.

Conventional methods of measuring using augmented reality do not provide guides to help a user move into a correct position for measurement of a body part, and do not provide dynamic positioning guides as a position of the user progresses. In some cases, conventional methods of storing measurements obtained using augmented reality do not easily allow a device to share measurement information with another device. In addition, these methods take longer than necessary, thereby wasting energy. This latter consideration is particularly important in battery-operated devices.

SUMMARY

Accordingly, there is a need for computer systems with faster, more efficient methods and interfaces for measuring using augmented reality environments. Such methods and interfaces optionally complement or replace conventional methods for measuring using augmented reality environments. Such methods and interfaces reduce the number, extent, and/or nature of the inputs from a user and produce a more efficient human-machine interface. For battery-operated devices, such methods and interfaces conserve power and increase the time between battery charges.

The above deficiencies and other problems associated with user interfaces for virtual/augmented reality are reduced or eliminated by the disclosed computer systems. In some embodiments, the computer system includes a desktop computer. In some embodiments, the computer system is portable (e.g., a notebook computer, tablet computer, or handheld device). In some embodiments, the computer system includes a personal electronic device (e.g., a wearable electronic device, such as a watch). In some embodiments, the computer system has (and/or is in communication with) a touchpad. In some embodiments, the computer system has (and/or is in communication with) a touch-sensitive display (also known as a "touch screen" or "touchscreen display"). In some embodiments, the computer system has a graphical user interface (GUI), one or more processors, memory and one or more modules, programs or sets of instructions stored in the memory for performing multiple functions. In some embodiments, the user interacts with the GUI in part through stylus and/or finger contacts and gestures on the touch-sensitive surface. In some embodiments, the functions optionally include game playing, image editing, drawing, presenting, word processing, spreadsheet making, telephoning, video conferencing, e-mailing, instant messaging, workout support, digital photographing, digital videoing, web browsing, digital music playing, note taking, and/or digital video playing. Executable instructions for performing these functions are, optionally, included in a non-transitory computer readable storage medium or other computer program product configured for execution by one or more processors.

In accordance with some embodiments, a method is performed at a computer system in communication with a display device and one or more cameras. The method includes displaying, in a first region of a first user interface, a visual prompt to move a body part into a field of view of the one or more cameras. The method includes, while displaying the visual prompt to move the body part into the field of view of the one or more cameras, detecting, using the one or more cameras, a portion of a user's body that is in the field of view of the one or more cameras and corresponds to the body part and in response to detecting the portion of the user's body, displaying a representation of the portion of the user's body. The method further includes, in accordance with a determination that the portion of the user's body that is in the field of view of the one or more cameras meets first position criteria displaying, via the display device, the representation of the portion of the user's body that is in the field of view of the one or more cameras with a first degree of transparency, and in accordance with a determination that the portion of the user's body that is in the field of view of the one or more cameras fails to meet first criteria, displaying the representation of the portion of the user's body to have a second degree of transparency that indicates that the first criteria have not been met.

In accordance with some embodiments, a method is performed at a computer system in communication with a display device and one or more cameras. The method includes displaying, in a user interface, a first representation of a body part that is in a field of view of the one or more cameras. The method includes detecting, using the one or more cameras, movement of the body part, wherein the displayed first representation of the body part is updated in accordance with the movement of the body part. The method includes, while displaying the first representation of the body part, displaying an indicator at a fixed location relative to the first representation of the body part. The indicator is displayed at a first position in the user interface that overlays at least a portion of the representation of the body part. The indicator is updated in accordance with the movement of the body part. The indicator includes an indication of a suggested direction of movement of the body part.

In accordance with some embodiments, a method is performed at a computer system in communication with a display device and one or more cameras. The method includes detecting, using the one or more cameras, a portion of a user's body that is in the field of view of the one or more cameras. The method includes scanning the portion of the user's body that is in the field of view of the one or more cameras to determine a measurement of the portion of the user's body that is in the field of view of the one or more cameras. The method further includes, after scanning the portion of the user's body, generating a machine-readable code that includes information that identifies one or more sizing parameters of a wearable object based on the measurement of the portion of the user's body or that describes the measurement of the portion of the user's body.

In accordance with some embodiments, a method is performed at a computer system in communication with a display device and one or more cameras. The method includes displaying, at a first fixed location within a first user interface, a first visual prompt indicating a position for moving a body part into a field of view of the one or more cameras. The method includes, while displaying the first visual prompt indicating the position for moving the body part into the field of view of the one or more cameras, detecting, using the one or more cameras, a portion of a user's body that is in the field of view of the one or more cameras and corresponds to the body part. The method includes, in response to detecting the portion of the user's body in the field of view of the one or more cameras, displaying a representation of the portion of the user's body and displaying a second visual prompt that is fixed at a predefined position relative to the representation of the portion of the user's body, wherein a position of the second visual prompt relative to a position of the first visual prompt indicates a movement of the body part that is required to satisfy a body part positioning precondition.

In accordance with some embodiments, a computer system includes (and/or is in communication with) a display generation component (e.g., a display, a projector, a head-mounted display, a heads-up display, or the like), one or more cameras (e.g., video cameras that continuously, or repeatedly at regular intervals, provide a live preview of at least a portion of the contents that are within the field of view of the cameras and optionally generate video outputs including one or more streams of image frames capturing the contents within the field of view of the cameras), and one or more input devices (e.g., a touch-sensitive surface, such as a touch-sensitive remote control, or a touch-screen display that also serves as the display generation component, a mouse, a joystick, a wand controller, and/or cameras tracking the position of one or more features of the user such as the user's hands), optionally one or more pose sensors, optionally one or more sensors to detect intensities of contacts with the touch-sensitive surface, optionally one or more tactile output generators, one or more processors, and memory storing one or more programs; the one or more programs are configured to be executed by the one or more processors and the one or more programs include instructions for performing or causing performance of the operations of any of the methods described herein. In accordance with some embodiments, a computer readable storage medium has stored therein instructions that, when executed by a computer system that includes (and/or is in communication with) a display generation component, one or more cameras, one or more input devices, optionally one or more pose sensors, optionally one or more sensors to detect intensities of contacts with the touch-sensitive surface, and optionally one or more tactile output generators, cause the computer system to perform or cause performance of the operations of any of the methods described herein. In accordance with some embodiments, a graphical user interface on a computer system that includes (and/or is in communication with) a display generation component, one or more cameras, one or more input devices, optionally one or more pose sensors, optionally one or more sensors to detect intensities of contacts with the touch-sensitive surface, optionally one or more tactile output generators, a memory, and one or more processors to execute one or more programs stored in the memory includes one or more of the elements displayed in any of the methods described herein, which are updated in response to inputs, as described in any of the methods described herein. In accordance with some embodiments, a computer system includes (and/or is in communication with) a display generation component, one or more cameras, one or more input devices, optionally one or more pose sensors, optionally one or more sensors to detect intensities of contacts with the touch-sensitive surface, optionally one or more tactile output generators, and means for performing or causing performance of the operations of any of the methods described herein. In accordance with some embodiments, an information processing apparatus, for use in a computer system that includes (and/or is in communication with) a display generation component, one or more cameras, one or more input devices, optionally one or more pose sensors, optionally one or more sensors to detect intensities of contacts with the touch-sensitive surface, and optionally one or more tactile output generators, includes means for performing or causing performance of the operations of any of the methods described herein.

Thus, computer systems that have (and/or are in communication with) a display generation component, one or more cameras, one or more input devices, optionally one or more pose sensors, optionally one or more sensors to detect intensities of contacts with the touch-sensitive surface, and optionally one or more tactile output generators, are provided with improved methods and interfaces for measuring using augmented reality environments, thereby increasing the effectiveness, efficiency, and user satisfaction with such computer systems. Such methods and interfaces may complement or replace conventional methods for measuring using augmented reality environments.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 4B illustrates an example user interface for a multifunction device with a touch-sensitive surface that is separate from the display in accordance with some embodiments.

FIGS. 9A-9C are flow diagrams of a process for providing visual feedback to a user to indicate a correct position for measurement in accordance with some embodiments.

FIGS. 10A-10D are flow diagrams of a process for providing virtualized progress indicators for measuring a portion of a user's body in accordance with some embodiments.

FIGS. 11A-11C are flow diagrams of a process for generating a machine-readable code that stores information about a measurement in accordance with some embodiments.

FIGS. 12A-12D are flow diagrams of a process for prompting a user to adjust a position of a body part of the user into a correct position for measurement in accordance with some embodiments.

DESCRIPTION OF EMBODIMENTS

As noted above, augmented reality environments are useful for measuring objects in physical environment, including a portion of a user's body, by enabling visual indicators to be superimposed on the physical environment, where the visual indicators facilitate placing the portion of the user's body that is to be measured into a proper position and visually indicate progress toward completing a measurement of the portion of the user's body. Conventional methods of measuring using augmented reality do not provide guides to help a user move into a correct position for measurement, or provide dynamic guides as a position of the user progresses. In some cases, conventional methods of storing measurements obtained using augmented reality do not easily allow a device to share measurement information to another device.

The systems, methods, and GUIs described herein improve user interface interactions with virtual/augmented reality environments in multiple ways. For example, they make it easier to measure a portion of the user's body, by providing automatic detection of features of the portion of the user's body, providing visual indications of a proper position (e.g., relative the device or system making the measurement) for the portion of the user's body to be measured, and improved guides for showing a user how the measuring process is progressing as the user moves.

Figure 11A:
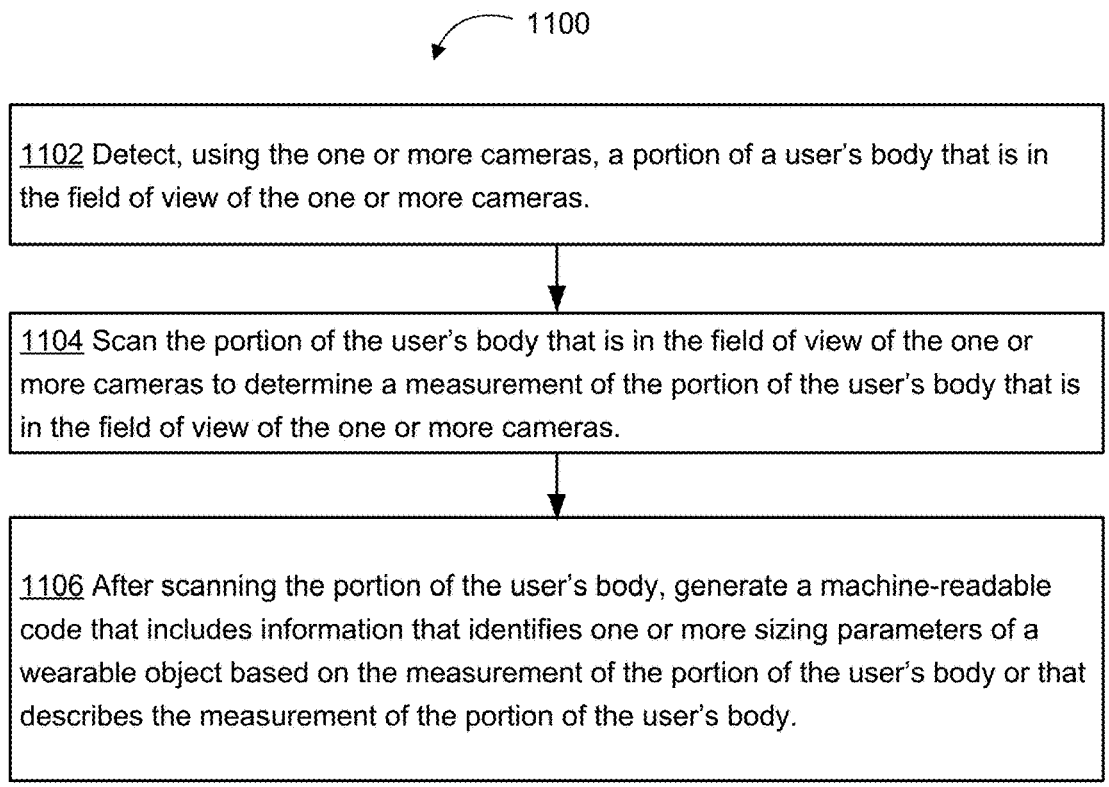
Figure 12A:
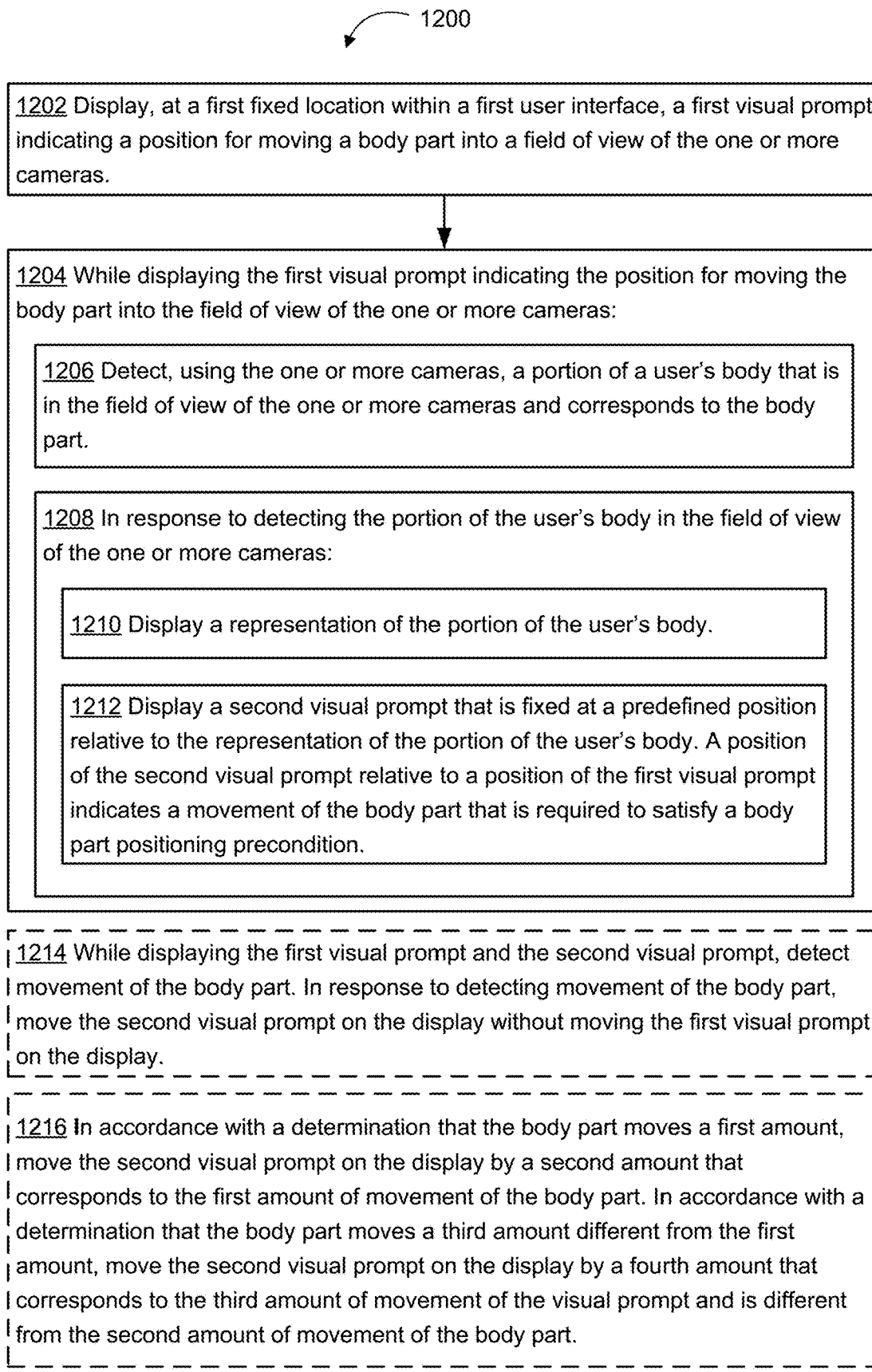

Below, FIGS. 1A-1B, 2, and 3A-3C illustrate example devices. FIGS. 4A-4B, 5A-5P, 6A-6N, 7A-7T, and 8A-8F illustrate example user interfaces for measuring a portion of a user's body in augmented reality environments. FIGS. 9A-9C illustrate a flow diagram of a method of providing visual feedback to a user to indicate a correct position for measurement. FIGS. 10A-10D illustrate a flow diagram of a method of providing virtualized progress indicators for measuring a portion of a user's body. FIGS. 11A-11C illustrate a flow diagram of a method of generating a machine-readable code that stores information about a measurement. FIGS. 12A-12D illustrate a flow diagram of a method of prompting a user to adjust a position of the user's body part into a correct position for measurement. The user interfaces in FIGS. 5A-5P, 6A-6N, 7A-7T, and 8A-8F are used to illustrate the processes in FIGS. 9A-9C, 10A-10D, 11A-11C, and 12A-12D.

Example Devices

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact, unless the context clearly indicates otherwise.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Computer systems for virtual/augmented reality include electronic devices that produce virtual/augmented reality environments. Embodiments of electronic devices, user interfaces for such devices, and associated processes for using such devices are described. In some embodiments, the device is a portable communications device, such as a mobile telephone, that also contains other functions, such as PDA and/or music player functions. Example embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch-screen displays and/or touch-pads), are, optionally, used. It should also be understood that, in some embodiments, the device is not a portable communications device, but is a desktop computer with a touch-sensitive surface (e.g., a touch-screen display and/or a touchpad) that also includes, or is in communication with, one or more cameras.

In the discussion that follows, a computer system that includes an electronic device that has (and/or is in communication with) a display and a touch-sensitive surface is described. It should be understood, however, that the computer system optionally includes one or more other physical user-interface devices, such as a physical keyboard, a mouse, a joystick, a wand controller, and/or cameras tracking the position of one or more features of the user such as the user's hands.

The device typically supports a variety of applications, such as one or more of the following: a gaming application, a note taking application, a drawing application, a presentation application, a word processing application, a spreadsheet application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed by the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
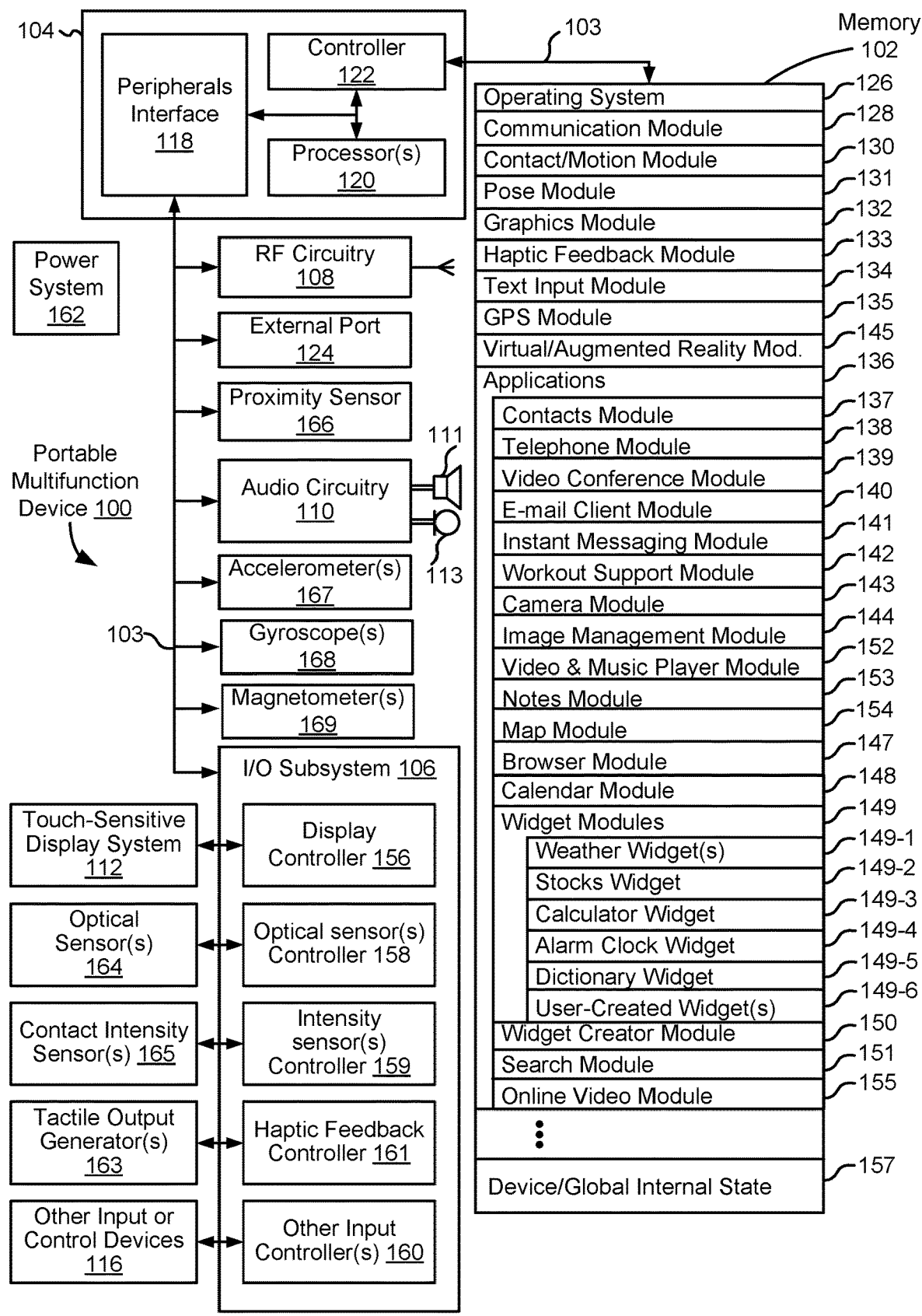
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display system 112 is sometimes called a "touch screen" for convenience and is sometimes simply called a touch-sensitive display. Device 100 includes memory 102 (which optionally includes one or more computer readable storage mediums), memory controller 122, one or more processing units (CPUs) 120, peripherals interface 118, RF circuitry 108, audio circuitry 110, speaker 111, microphone 113, input/output (I/O) subsystem 106, other input or control devices 116, and external port 124. Device 100 optionally includes one or more optical sensors 164 (e.g., as part of one or more cameras). Device 100 optionally includes one or more intensity sensors 165 for detecting intensities of contacts on device 100 (e.g., a touch-sensitive surface such as touch-sensitive display system 112 of device 100). Device 100 optionally includes one or more tactile output generators 163 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user. Using tactile outputs to provide haptic feedback to a user enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, firmware, or a combination thereof, including one or more signal processing and/or application specific integrated circuits.

Memory 102 optionally includes high-speed random-access memory and optionally also includes non-volatile memory, such as one or more magnetic disk storage devices, flash memory devices, or other non-volatile solid-state memory devices. Access to memory 102 by other components of device 100, such as CPU(s) 120 and the peripherals interface 118, is, optionally, controlled by memory controller 122.

Peripherals interface 118 can be used to couple input and output peripherals of the device to CPU(s) 120 and memory 102. The one or more processors 120 run or execute various software programs and/or sets of instructions stored in memory 102 to perform various functions for device 100 and to process data.

In some embodiments, peripherals interface 118, CPU(s) 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPA), long term evolution (LTE), near field communication (NFC), wideband code division multiple access (W-CDMA), code division multiple access (CDMA), time division multiple access (TDMA), Bluetooth™, Wireless Fidelity (Wi-Fi™) (e.g., IEEE 802.11a, IEEE 802.11ac, IEEE 802.11ax, IEEE 802.11b, IEEE 802.11g and/or IEEE 802.11n), voice over Internet Protocol (VOIP), Wi-MAX™, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2A). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch-sensitive display system 112 and other input or control devices 116, with peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input or control devices 116. The other input or control devices 116 optionally include physical buttons (e.g., push buttons, rocker buttons, etc.), dials, slider switches, joysticks, click wheels, and so forth. In some alternate embodiments, input controller(s) 160 are, optionally, coupled with any (or none) of the following: a keyboard, infrared port, USB port, stylus, and/or a pointer device such as a mouse. The one or more buttons (e.g., 208, FIG. 2A) optionally include an up/down button for volume control of speaker 111 and/or microphone 113. The one or more buttons optionally include a push button (e.g., 206, FIG. 2A).

Touch-sensitive display system 112 provides an input interface and an output interface between the device and a user. Display controller 156 receives and/or sends electrical signals from/to touch-sensitive display system 112. Touch-sensitive display system 112 displays visual output to the user. The visual output optionally includes graphics, text, icons, video, and any combination thereof (collectively termed "graphics"). In some embodiments, some or all of the visual output corresponds to user interface objects. As used herein, the term "affordance" refers to a user-interactive graphical user interface object (e.g., a graphical user interface object that is configured to respond to inputs directed toward the graphical user interface object). Examples of user-interactive graphical user interface objects include, without limitation, a button, slider, icon, selectable menu item, switch, hyperlink, or other user interface control.

Touch-sensitive display system 112 has a touch-sensitive surface, sensor or set of sensors that accepts input from the user based on haptic and/or tactile contact. Touch-sensitive display system 112 and display controller 156 (along with any associated modules and/or sets of instructions in memory 102) detect contact (and any movement or breaking of the contact) on touch-sensitive display system 112 and converts the detected contact into interaction with user-interface objects (e.g., one or more soft keys, icons, web pages or images) that are displayed on touch-sensitive display system 112. In some embodiments, a point of contact between touch-sensitive display system 112 and the user corresponds to a finger of the user or a stylus.

Touch-sensitive display system 112 optionally uses LCD (liquid crystal display) technology, LPD (light emitting polymer display) technology, or LED (light emitting diode) technology, although other display technologies are used in other embodiments. Touch-sensitive display system 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch-sensitive display system 112. In some embodiments, projected mutual capacitance sensing technology is used, such as that found in the iPhone®, iPod Touch®, and iPad® from Apple Inc. of Cupertino, California.

Touch-sensitive display system 112 optionally has a video resolution in excess of 100 dpi. In some embodiments, the touch screen video resolution is in excess of 400 dpi (e.g., 500 dpi, 800 dpi, or greater). The user optionally makes contact with touch-sensitive display system 112 using any suitable object or appendage, such as a stylus, a finger, and so forth. In some embodiments, the user interface is designed to work with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch-sensitive display system 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164 (e.g., as part of one or more cameras). FIG. 1A shows an optical sensor coupled with optical sensor controller 158 in I/O subsystem 106. Optical sensor(s) 164 optionally include charge-coupled device (CCD) or complementary metal-oxide semiconductor (CMOS) phototransistors. Optical sensor(s) 164 receive light from the environment, projected through one or more lens, and converts the light to data representing an image. In conjunction with imaging module 143 (also called a camera module), optical sensor(s) 164 optionally capture still images and/or video. In some embodiments, an optical sensor is located on the back of device 100, opposite touch-sensitive display system 112 on the front of the device, so that the touch screen is enabled for use as a viewfinder for still and/or video image acquisition. In some embodiments, another optical sensor is located on the front of the device so that the user's image is obtained (e.g., for selfies, for videoconferencing while the user views the other video conference participants on the touch screen, etc.). All references to images captured by the one or more cameras of device 100 shall be understood to optionally include depth information from one or more depth sensors (e.g., one or more time-of-flight sensors, structured-light sensors (also known as structured-light scanners), etc.) of device 100 to facilitate measurement of objects in view of the one or more cameras.

Device 100 optionally also includes one or more contact intensity sensors 165. FIG. 1A shows a contact intensity sensor coupled with intensity sensor controller 159 in I/O subsystem 106. Contact intensity sensor(s) 165 optionally include one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor(s) 165 receive contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch-screen display system 112 which is located on the front of device 100.

Device 100 optionally also includes one or more proximity sensors 166. FIG. 1A shows proximity sensor 166 coupled with peripherals interface 118. Alternately, proximity sensor 166 is coupled with input controller 160 in I/O subsystem 106. In some embodiments, the proximity sensor turns off and disables touch-sensitive display system 112 when the multifunction device is placed near the user's ear (e.g., when the user is making a phone call).

Device 100 optionally also includes one or more tactile output generators 163. FIG. 1A shows a tactile output generator coupled with haptic feedback controller 161 in I/O subsystem 106. In some embodiments, tactile output generator(s) 163 include one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Tactile output generator(s) 163 receive tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch-sensitive display system 112, which is located on the front of device 100.

Device 100 optionally also includes one or more accelerometers 167, gyroscopes 168, and/or magnetometers 169 (e.g., as part of an inertial measurement unit (IMU)) for obtaining information concerning the pose (e.g., position and orientation or attitude) of the device. FIG. 1A shows sensors 167, 168, and 169 coupled with peripherals interface 118. Alternately, sensors 167, 168, and 169 are, optionally, coupled with an input controller 160 in I/O subsystem 106. In some embodiments, information is displayed on the touch-screen display in a portrait view or a landscape view based on an analysis of data received from the one or more accelerometers. Device 100 optionally includes a GPS (or GLONASS or other global navigation system) receiver for obtaining information concerning the location of device 100.

In some embodiments, the software components stored in memory 102 include operating system 126, communication module (or set of instructions) 128, contact/motion module (or set of instructions) 130, graphics module (or set of instructions) 132, haptic feedback module (or set of instructions) 133, text input module (or set of instructions) 134, Global Positioning System (GPS) module (or set of instructions) 135, and applications (or sets of instructions) 136. Furthermore, in some embodiments, memory 102 stores device/global internal state 157, as shown in FIGS. 1A and 3. Device/global internal state 157 includes one or more of: active application state, indicating which applications, if any, are currently active; display state, indicating what applications, views or other information occupy various regions of touch-sensitive display system 112; sensor state, including information obtained from the device's various sensors and other input or control devices 116; and location and/or positional information concerning the device's pose (e.g., location and/or attitude).

Operating system 126 (e.g., iOS, Android, Darwin, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used in some iPhone®, iPod Touch®, and iPad® devices from Apple Inc. of Cupertino, California. In some embodiments, the external port is a Lightning connector that is the same as, or similar to and/or compatible with the Lightning connector used in some iPhone®, iPod Touch®, and iPad® devices from Apple Inc. of Cupertino, California. In some embodiments, the external port is a USB Type-C connector that is the same as, or similar to and/or compatible with the USB Type-C connector used in some electronic devices from Apple Inc. of Cupertino, California.

Contact/motion module 130 optionally detects contact with touch-sensitive display system 112 (in conjunction with display controller 156) and other touch-sensitive devices (e.g., a touchpad or physical click wheel). Contact/motion module 130 includes various software components for performing various operations related to detection of contact (e.g., by a finger or by a stylus), such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts or stylus contacts) or to multiple simultaneous contacts (e.g., "multitouch"/multiple finger contacts). In some embodiments, contact/motion module 130 and display controller 156 detect contact on a touchpad.

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (lift off) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (lift off) event. Similarly, tap, swipe, drag, and other gestures are optionally detected for a stylus by detecting a particular contact pattern for the stylus.

In some embodiments, detecting a finger tap gesture depends on the length of time between detecting the finger-down event and the finger-up event, but is independent of the intensity of the finger contact between detecting the finger-down event and the finger-up event. In some embodiments, a tap gesture is detected in accordance with a determination that the length of time between the finger-down event and the finger-up event is less than a predetermined value (e.g., less than 0.1, 0.2, 0.3, 0.4 or 0.5 seconds), independent of whether the intensity of the finger contact during the tap meets a given intensity threshold (greater than a nominal contact-detection intensity threshold), such as a light press or deep press intensity threshold. Thus, a finger tap gesture can satisfy particular input criteria that do not require that the characteristic intensity of a contact satisfy a given intensity threshold in order for the particular input criteria to be met. For clarity, the finger contact in a tap gesture typically needs to satisfy a nominal contact-detection intensity threshold, below which the contact is not detected, in order for the finger-down event to be detected. A similar analysis applies to detecting a tap gesture by a stylus or other contact. In cases where the device is capable of detecting a finger or stylus contact hovering over a touch sensitive surface, the nominal contact-detection intensity threshold optionally does not correspond to physical contact between the finger or stylus and the touch sensitive surface.

The same concepts apply in an analogous manner to other types of gestures. For example, a swipe gesture, a pinch gesture, a depinch gesture, and/or a long press gesture are optionally detected based on the satisfaction of criteria that are either independent of intensities of contacts included in the gesture, or do not require that contact(s) that perform the gesture reach intensity thresholds in order to be recognized. For example, a swipe gesture is detected based on an amount of movement of one or more contacts; a pinch gesture is detected based on movement of two or more contacts towards each other; a depinch gesture is detected based on movement of two or more contacts away from each other; and a long press gesture is detected based on a duration of the contact on the touch-sensitive surface with less than a threshold amount of movement. As such, the statement that particular gesture recognition criteria do not require that the intensity of the contact(s) meet a respective intensity threshold in order for the particular gesture recognition criteria to be met means that the particular gesture recognition criteria are capable of being satisfied if the contact(s) in the gesture do not reach the respective intensity threshold, and are also capable of being satisfied in circumstances where one or more of the contacts in the gesture do reach or exceed the respective intensity threshold. In some embodiments, a tap gesture is detected based on a determination that the finger-down and finger-up event are detected within a predefined time period, without regard to whether the contact is above or below the respective intensity threshold during the predefined time period, and a swipe gesture is detected based on a determination that the contact movement is greater than a predefined magnitude, even if the contact is above the respective intensity threshold at the end of the contact movement. Even in implementations where detection of a gesture is influenced by the intensity of contacts performing the gesture (e.g., the device detects a long press more quickly when the intensity of the contact is above an intensity threshold or delays detection of a tap input when the intensity of the contact is higher), the detection of those gestures does not require that the contacts reach a particular intensity threshold so long as the criteria for recognizing the gesture can be met in circumstances where the contact does not reach the particular intensity threshold (e.g., even if the amount of time that it takes to recognize the gesture changes).

Contact intensity thresholds, duration thresholds, and movement thresholds are, in some circumstances, combined in a variety of different combinations in order to create heuristics for distinguishing two or more different gestures directed to the same input element or region so that multiple different interactions with the same input element are enabled to provide a richer set of user interactions and responses. The statement that a particular set of gesture recognition criteria do not require that the intensity of the contact(s) meet a respective intensity threshold in order for the particular gesture recognition criteria to be met does not preclude the concurrent evaluation of other intensity-dependent gesture recognition criteria to identify other gestures that do have criteria that are met when a gesture includes a contact with an intensity above the respective intensity threshold. For example, in some circumstances, first gesture recognition criteria for a first gesture—which do not require that the intensity of the contact(s) meet a respective intensity threshold in order for the first gesture recognition criteria to be met—are in competition with second gesture recognition criteria for a second gesture—which are dependent on the contact(s) reaching the respective intensity threshold. In such competitions, the gesture is, optionally, not recognized as meeting the first gesture recognition criteria for the first gesture if the second gesture recognition criteria for the second gesture are met first. For example, if a contact reaches the respective intensity threshold before the contact moves by a predefined amount of movement, a deep press gesture is detected rather than a swipe gesture. Conversely, if the contact moves by the predefined amount of movement before the contact reaches the respective intensity threshold, a swipe gesture is detected rather than a deep press gesture. Even in such circumstances, the first gesture recognition criteria for the first gesture still do not require that the intensity of the contact(s) meet a respective intensity threshold in order for the first gesture recognition criteria to be met because if the contact stayed below the respective intensity threshold until an end of the gesture (e.g., a swipe gesture with a contact that does not increase to an intensity above the respective intensity threshold), the gesture would have been recognized by the first gesture recognition criteria as a swipe gesture. As such, particular gesture recognition criteria that do not require that the intensity of the contact(s) meet a respective intensity threshold in order for the particular gesture recognition criteria to be met will (A) in some circumstances ignore the intensity of the contact with respect to the intensity threshold (e.g. for a tap gesture) and/or (B) in some circumstances still be dependent on the intensity of the contact with respect to the intensity threshold in the sense that the particular gesture recognition criteria (e.g., for a long press gesture) will fail if a competing set of intensity-dependent gesture recognition criteria (e.g., for a deep press gesture) recognize an input as corresponding to an intensity-dependent gesture before the particular gesture recognition criteria recognize a gesture corresponding to the input (e.g., for a long press gesture that is competing with a deep press gesture for recognition).

Pose module 131, in conjunction with accelerometers 167, gyroscopes 168, and/or magnetometers 169, optionally detects pose information concerning the device, such as the device's pose (e.g., roll, pitch, yaw and/or position) in a particular frame of reference. Pose module 131 includes software components for performing various operations related to detecting the position of the device and detecting changes to the pose of the device.

Graphics module 132 includes various known software components for rendering and displaying graphics on touch-sensitive display system 112 or other display, including components for changing the visual impact (e.g., brightness, transparency, saturation, contrast or other visual property) of graphics that are displayed. As used herein, the term "graphics" includes any object that can be displayed to a user, including without limitation text, web pages, icons (such as user-interface objects including soft keys), digital images, videos, animations and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions (e.g., instructions used by haptic feedback controller 161) to produce tactile outputs using tactile output generator(s) 163 at one or more locations on device 100 in response to user interactions with device 100.

Text input module 134, which is, optionally, a component of graphics module 132, provides soft keyboards for entering text in various applications (e.g., contacts module 137, e-mail client module 140, IM module 141, browser module 147, and any other application that needs text input).

GPS module 135 determines the location of the device and provides this information for use in various applications (e.g., to telephone module 138 for use in location-based dialing, to camera module 143 as picture/video metadata, and to applications that provide location-based services such as weather widgets, local yellow page widgets, and map/navigation widgets).

Virtual/augmented reality module 145 provides virtual and/or augmented reality logic to applications 136 that implement augmented reality, and in some embodiments virtual reality, features. Virtual/augmented reality module 145 facilitates superposition of virtual content, such as a virtual user interface object, on a representation of at least a portion of a field of view of the one or more cameras. For example, with assistance from the virtual/augmented reality module 145, the representation of at least a portion of a field of view of the one or more cameras may include a respective physical object and the virtual user interface object may be displayed at a location, in a displayed augmented reality environment, that is determined based on the respective physical object in the field of view of the one or more cameras or a virtual reality environment that is determined based on the pose of at least a portion of a computer system (e.g., a pose of a display device that is used to display the user interface to a user of the computer system).

Applications 136 optionally include the following modules (or sets of instructions), or a subset or superset thereof:
  contacts module 137 (sometimes called an address book or contact list);
  telephone module 138;
  video conferencing module 139;
  e-mail client module 140;
  instant messaging (IM) module 141;
  workout support module 142;
  camera module 143 for still and/or video images;
  image management module 144;

browser module 147;
calendar module 148;
widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
widget creator module 150 for making user-created widgets 149-6;
search module 151;
video and music player module 152, which is, optionally, made up of a video player module and a music player module;
notes module 153;
map module 154; and/or
online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch-sensitive display system 112, display controller 156, contact module 130, graphics module 132, and text input module 134, contacts module 137 includes executable instructions to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers and/or e-mail addresses to initiate and/or facilitate communications by telephone module 138, video conference module 139, e-mail module 140, or IM module 141; and so forth.

In conjunction with RF circuitry 108, audio circuitry 110, speaker 111, microphone 113, touch-sensitive display system 112, display controller 156, contact module 130, graphics module 132, and text input module 134, telephone module 138 includes executable instructions to enter a sequence of characters corresponding to a telephone number, access one or more telephone numbers in address book 137, modify a telephone number that has been entered, dial a respective telephone number, conduct a conversation and disconnect or hang up when the conversation is completed. As noted above, the wireless communication optionally uses any of a plurality of communications standards, protocols and technologies.

In conjunction with RF circuitry 108, audio circuitry 110, speaker 111, microphone 113, touch-sensitive display system 112, display controller 156, optical sensor(s) 164, optical sensor controller 158, contact module 130, graphics module 132, text input module 134, contact list 137, and telephone module 138, videoconferencing module 139 includes executable instructions to initiate, conduct, and terminate a video conference between a user and one or more other participants in accordance with user instructions.

In conjunction with RF circuitry 108, touch-sensitive display system 112, display controller 156, contact module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch-sensitive display system 112, display controller 156, contact module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, Apple Push Notification Service (APNs) or IMPS for Internet-based instant messages), to receive instant messages, and to view received instant messages. In some embodiments, transmitted and/or received instant messages optionally include graphics, photos, audio files, video files and/or other attachments as are supported in a MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, APNs, or IMPS).

In conjunction with RF circuitry 108, touch-sensitive display system 112, display controller 156, contact module 130, graphics module 132, text input module 134, GPS module 135, map module 154, and video and music player module 152, workout support module 142 includes executable instructions to create workouts (e.g., with time, distance, and/or calorie burning goals); communicate with workout sensors (in sports devices and smart watches); receive workout sensor data; calibrate sensors used to monitor a workout; select and play music for a workout; and display, store and transmit workout data.

In conjunction with touch-sensitive display system 112, display controller 156, optical sensor(s) 164, optical sensor controller 158, contact module 130, graphics module 132, and image management module 144, camera module 143 includes executable instructions to capture still images or video (including a video stream) and store them into memory 102, modify characteristics of a still image or video, and/or delete a still image or video from memory 102.

In conjunction with touch-sensitive display system 112, display controller 156, contact module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch-sensitive display system 112, display controller 156, contact module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch-sensitive display system 112, display controller 156, contact module 130, graphics module 132, text input module 134, e-mail client module 140, and browser module 147, calendar module 148 includes executable instructions to create, display, modify, and store calendars and data associated with calendars (e.g., calendar entries, to do lists, etc.) in accordance with user instructions.

In conjunction with RF circuitry 108, touch-sensitive display system 112, display controller 156, contact module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch-sensitive display system 112, display controller 156, contact module 130, graphics module 132, text input module 134, and browser module 147, the widget creator module 150 includes executable instructions to create widgets (e.g., turning a user-specified portion of a web page into a widget).

In conjunction with touch-sensitive display system 112, display controller 156, contact module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch-sensitive display system 112, display controller 156, contact module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present or otherwise play back videos (e.g., on touch-sensitive display system 112, or on an external display connected wirelessly or via external port 124). In some embodiments, device 100 optionally includes the functionality of an MP3 player, such as an iPod (trademark of Apple Inc.).

In conjunction with touch-sensitive display system 112, display controller 156, contact module 130, graphics module 132, and text input module 134, notes module 153 includes executable instructions to create and manage notes, to do lists, and the like in accordance with user instructions.

In conjunction with RF circuitry 108, touch-sensitive display system 112, display controller 156, contact module 130, graphics module 132, text input module 134, GPS module 135, and browser module 147, map module 154 includes executable instructions to receive, display, modify, and store maps and data associated with maps (e.g., driving directions; data on stores and other points of interest at or near a particular location; and other location-based data) in accordance with user instructions.

In conjunction with touch-sensitive display system 112, display controller 156, contact module 130, graphics module 132, audio circuitry 110, speaker 111, RF circuitry 108, text input module 134, e-mail client module 140, and browser module 147, online video module 155 includes executable instructions that allow the user to access, browse, receive (e.g., by streaming and/or download), play back (e.g., on the touch screen 112, or on an external display connected wirelessly or via external port 124), send an e-mail with a link to a particular online video, and otherwise manage online videos in one or more file formats, such as H.264. In some embodiments, instant messaging module 141, rather than e-mail client module 140, is used to send a link to a particular online video.

Each of the above identified modules and applications correspond to a set of executable instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various embodiments. In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touch-sensitive surface. In some other embodiments, the menu button is a physical push button or other physical input control device instead of a touch-sensitive surface.

Figure 1B:
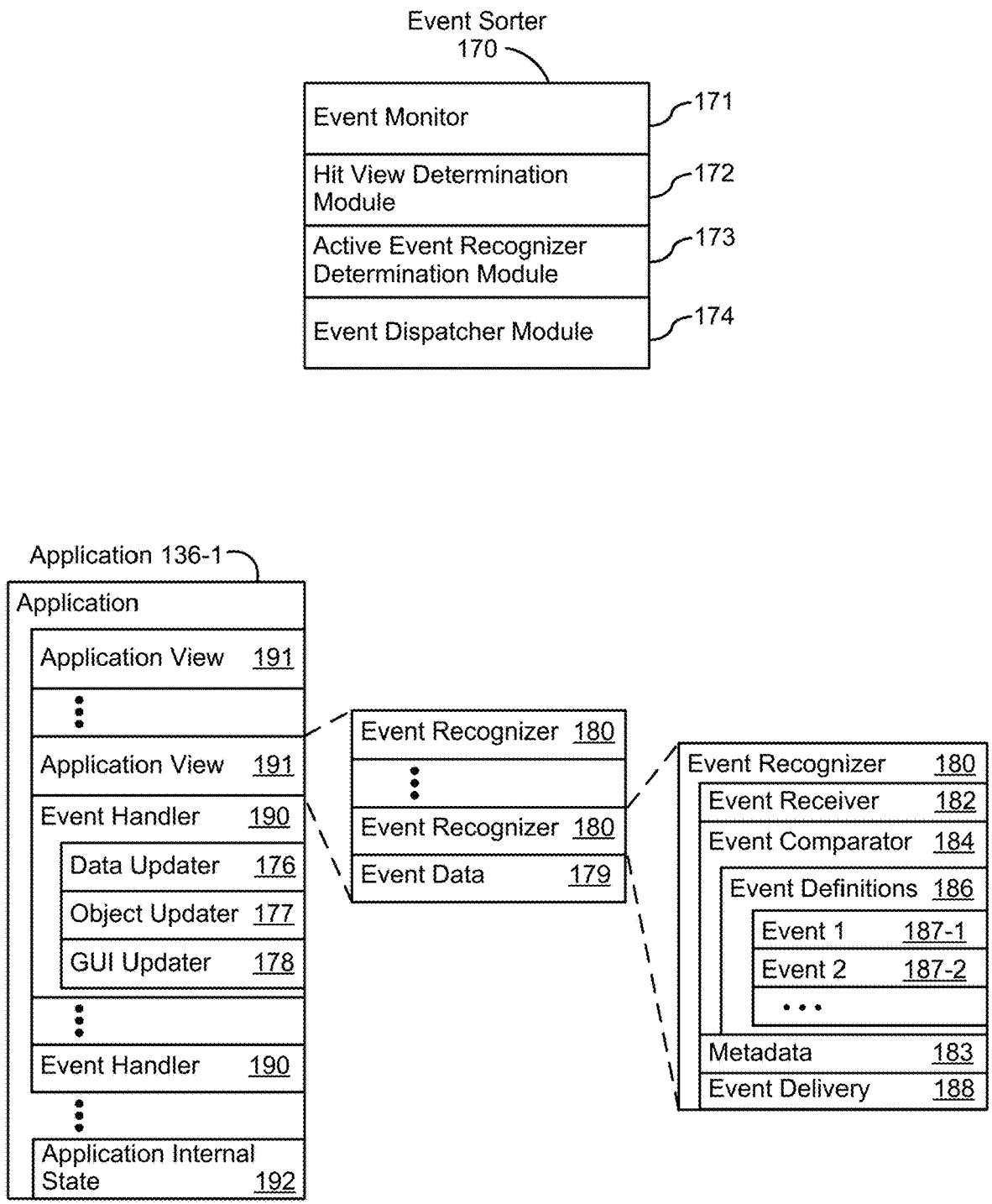
FIG. 1B is a block diagram illustrating example components for event handling in accordance with some embodiments.

FIG. 1B is a block diagram illustrating example components for event handling in accordance with some embodiments. In some embodiments, memory 102 (in FIG. 1A) or 370 (FIG. 3A) includes event sorter 170 (e.g., in operating system 126) and a respective application 136-1 (e.g., any of the aforementioned applications 136, 137-155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display system 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display system 112, as part of a multi-touch gesture). Peripherals interface 118 transmits information it receives from I/O subsystem 106 or a sensor, such as proximity sensor 166, accelerometer(s) 167, and/or microphone 113 (through audio circuitry 110). Information that peripherals interface 118 receives from I/O subsystem 106 includes information from touch-sensitive display system 112 or a touch-sensitive surface.

In some embodiments, event monitor 171 sends requests to the peripherals interface 118 at predetermined intervals. In response, peripherals interface 118 transmits event information. In other embodiments, peripheral interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views, when touch-sensitive display system 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (i.e., the first sub-event in the sequence of sub-events that form an event or potential event). Once the hit view is identified by the hit view determination module, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver module 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher-level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177 or GUI updater 178 to update the application internal state 192. Alternatively, one or more of the application views 191 includes one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170, and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current pose (e.g., position and orientation) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event 187 include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first lift-off (touch end) for a predetermined phase, a second touch (touch begin) on the displayed object for a predetermined phase, and a second lift-off (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display system 112, and lift-off of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display system 112, when a touch is detected on touch-sensitive display system 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event 187 also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video and music player module 152. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input-devices, not all of which are initiated on touch screens. For example, mouse movement and mouse button presses, optionally coordinated with single or multiple keyboard presses or holds; contact movements such as taps, drags, scrolls, etc., on touch-pads; pen stylus inputs; inputs based on real-time analysis of video images obtained by one or more cameras; movement of the device; oral instructions; detected eye movements; biometric inputs; and/or any combination thereof are optionally utilized as inputs corresponding to sub-events which define an event to be recognized.

Figure 2A:
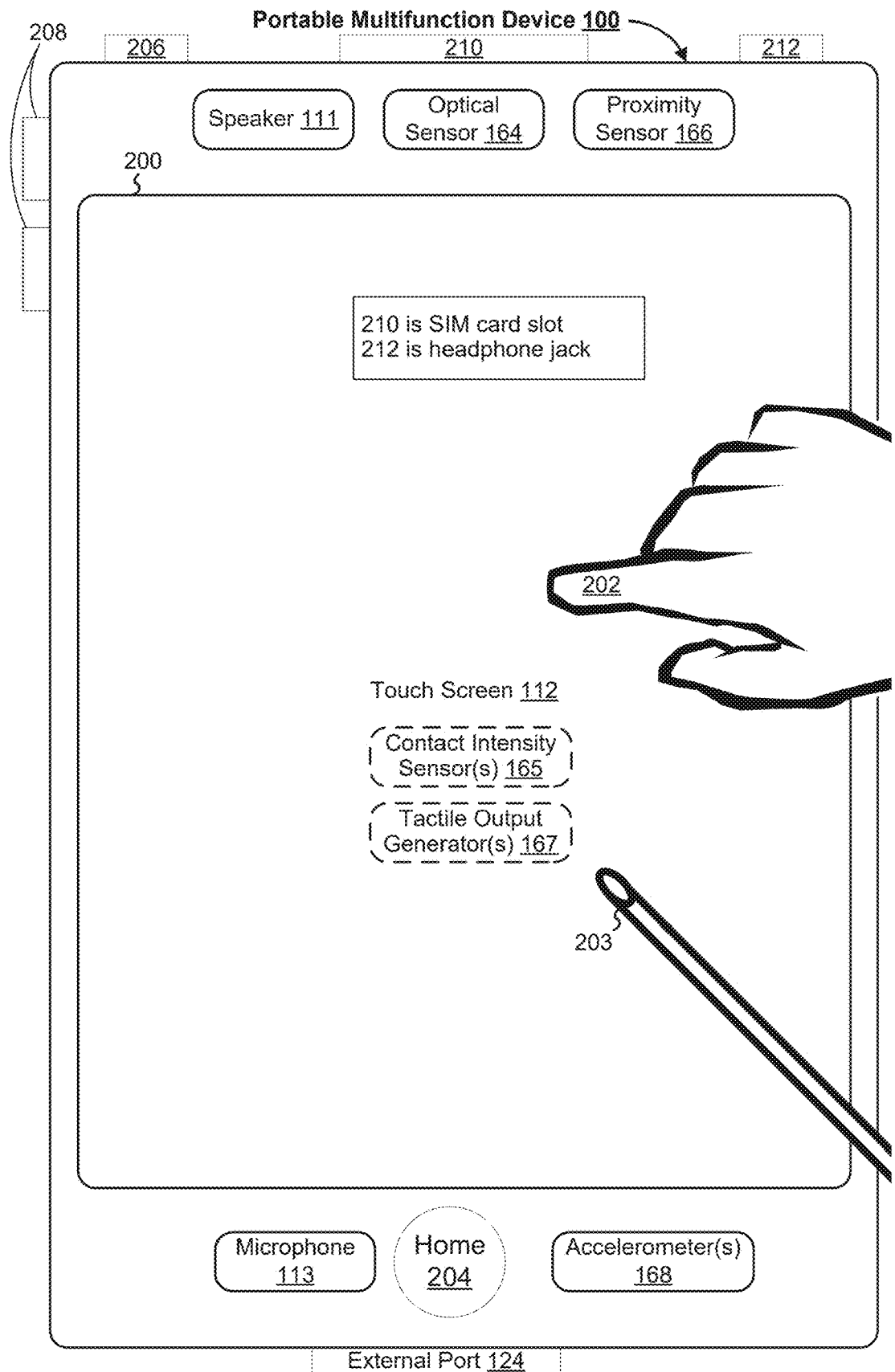
FIG. 2A illustrates a portable multifunction device having a touch screen in accordance with some embodiments.

FIG. 2A illustrates a portable multifunction device 100 having a touch screen (e.g., touch-sensitive display system 112, FIG. 1A) in accordance with some embodiments. The touch screen optionally displays one or more graphics within user interface (UI) 200. In these embodiments, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward) and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also includes one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on the touch-screen display.

In some embodiments, device 100 includes the touch-screen display, menu button 204 (sometimes called home button 204), push button 206 for powering the device on/off and locking the device, volume adjustment button(s) 208, Subscriber Identity Module (SIM) card slot 210, head set jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In some embodiments, device 100 also accepts verbal input for activation or deactivation of some functions through microphone 113. Device 100 also, optionally, includes one or more contact intensity sensors 165 for detecting intensities of contacts on touch-sensitive display system 112 and/or one or more tactile output generators 163 for generating tactile outputs for a user of device 100.

Figure 2B:
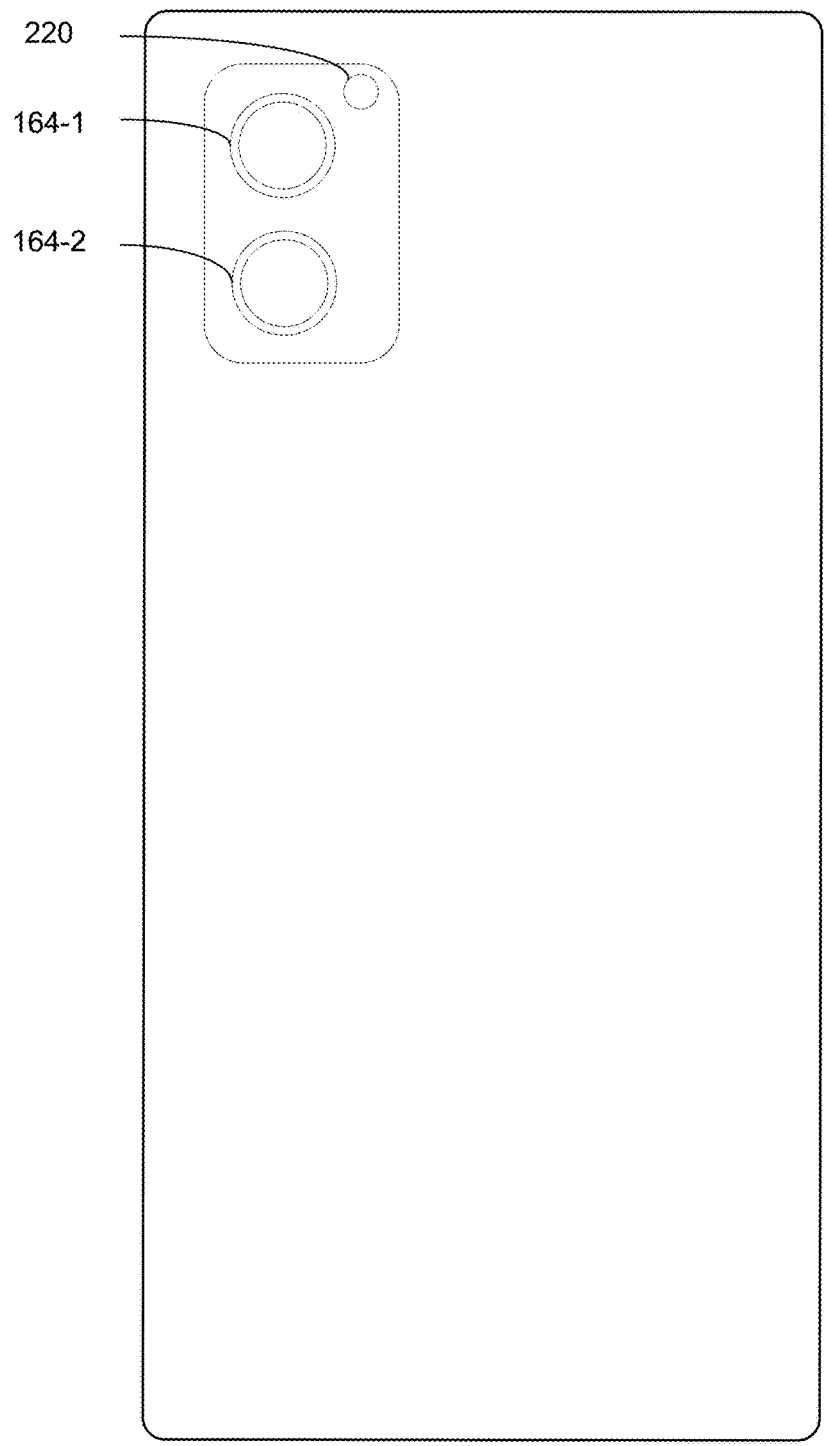
FIG. 2B illustrates a portable multifunction device having optical sensors and a depth sensor (e.g., time-of-flight sensor) in accordance with some embodiments.

FIG. 2B illustrates a portable multifunction device 100 (e.g., a view of the back of device 100) that optionally includes optical sensors 164-1 and 164-2, and a depth sensor 220 (e.g., one or more time-of-flight ("ToF") sensors, structured-light sensors (also known as structured-light scanners), etc.). When optical sensors (e.g., cameras) 164-1 and 164-2 concurrently capture a representation of a physical environment (e.g., an image or a video), the portable multifunction device can determine depth information from the disparity between the information concurrently captured by the optical sensors (e.g., disparities between the captured images). Depth information provided by (e.g., image) disparities determined using optical sensors 164-1 and 164-2 may lack accuracy, but typically provides high resolution. To improve the accuracy of depth information provided by the disparity between images, depth sensor 220 is optionally used in conjunction with optical sensors 164-1 and 164-2. In some embodiments, depth sensor 220 emits a waveform (e.g., light from a light emitting diode (LED) or a laser), and measures the time it takes for the reflection(s) of the waveform (e.g., light) to return back to ToF sensor 220. Depth information is determined from the measured time it takes for the light to return back to depth sensor 220. A depth sensor typically provides high accuracy (e.g., accuracy of 1 cm or better with respect to measured distances or depths), but may lack high resolution (e.g., depth sensor 220 optionally has a resolution that is one quarter of the resolution of optical sensors 164, or less than one quarter of the resolution of optical sensors 164, or one sixteenth of the resolution of optical sensors 164, or less than one sixteenth of the resolution of optical sensors 164). Therefore, combining depth information from depth sensor (e.g., depth sensor 220, such as a ToF sensor) with depth information provided by (e.g., image) disparities determined using optical sensors (e.g., cameras) provides a depth map that is both accurate and has high resolution.

Figure 3A:
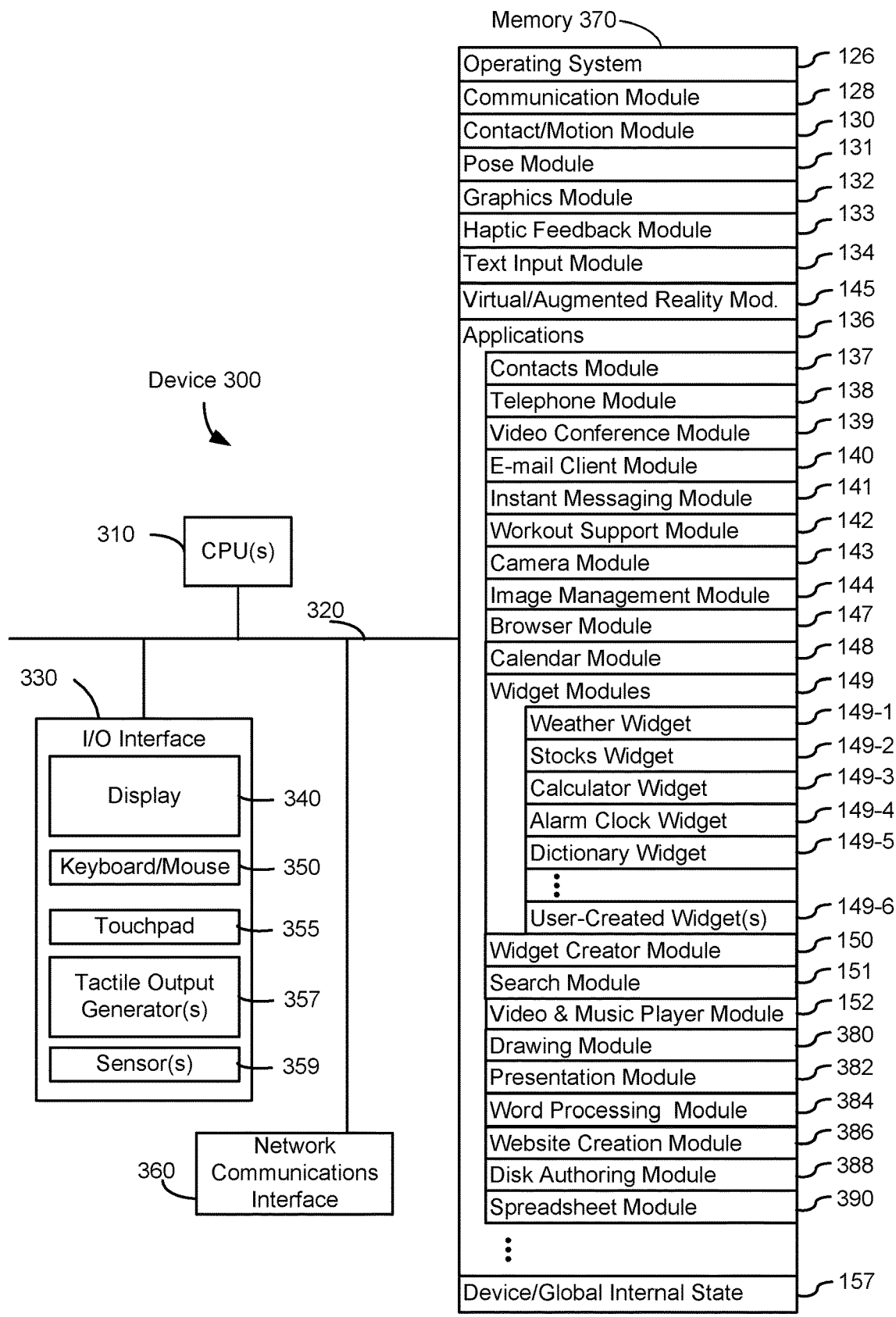
FIG. 3A is a block diagram of an example multifunction device with a display and a touch-sensitive surface in accordance with some embodiments.

FIG. 3A is a block diagram of an example multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPU's) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is optionally a touch-screen display. I/O interface 330 also optionally includes a keyboard and/or mouse (or other pointing device) 350 and touchpad 355, tactile output generator 357 for generating tactile outputs on device 300 (e.g., similar to tactile output generator(s) 163 described above with reference to FIG. 1A), sensors 359 (e.g., optical, depth, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above identified elements in FIG. 3A are, optionally, stored in one or more of the previously mentioned memory devices. Each of the above identified modules corresponds to a set of instructions for performing a function described above. The above identified modules or programs (e.g., sets of instructions) need not be implemented as separate software programs, procedures or modules, and thus various subsets of these modules are, optionally, combined or otherwise re-arranged in various embodiments. In some embodiments, memory 370 optionally stores a subset of the modules and data structures identified above. Furthermore, memory 370 optionally stores additional modules and data structures not described above.

Figure 3B:
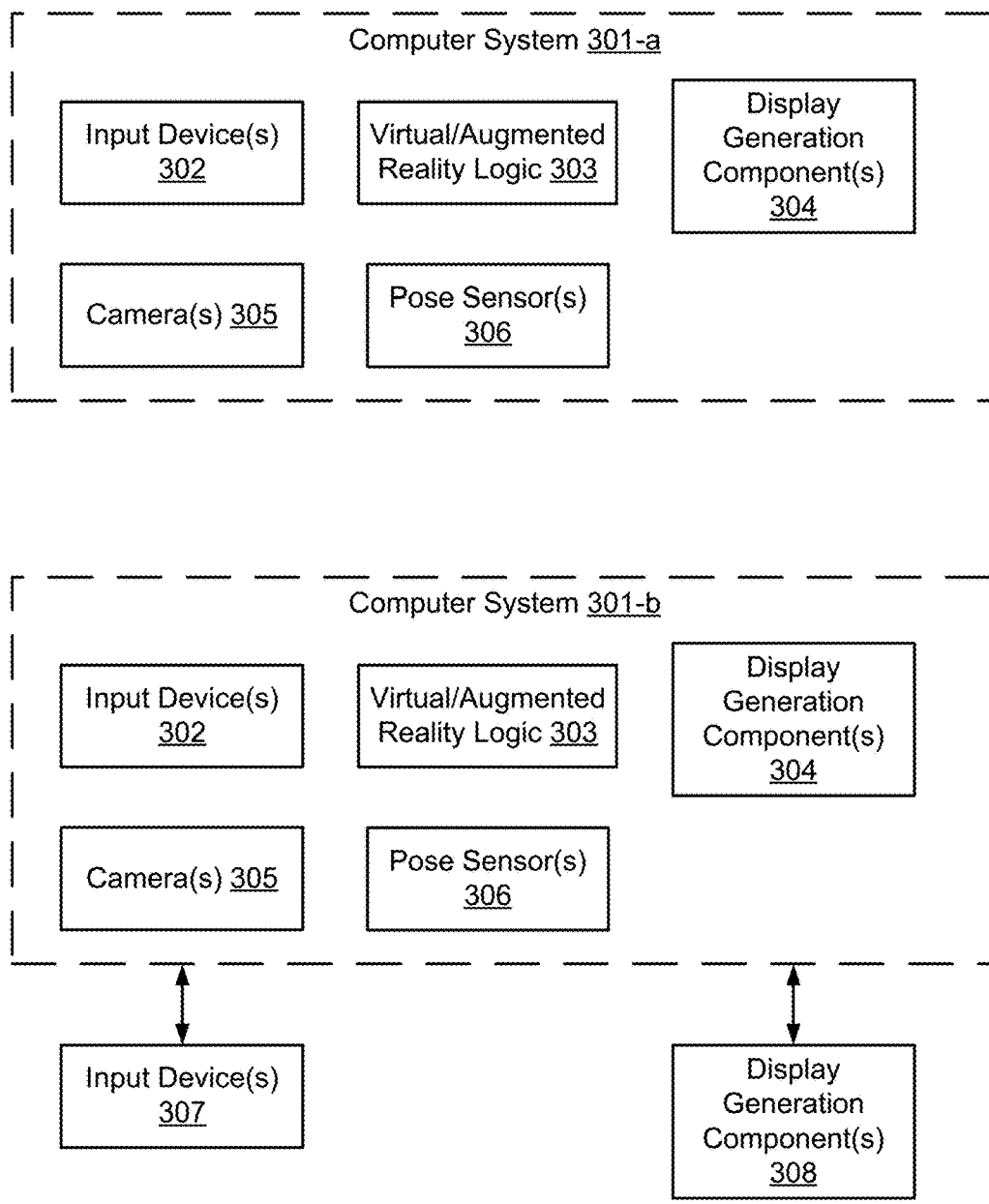
FIGS. 3B-3C are block diagrams of example computer systems in accordance with some embodiments.
Figure 3C:
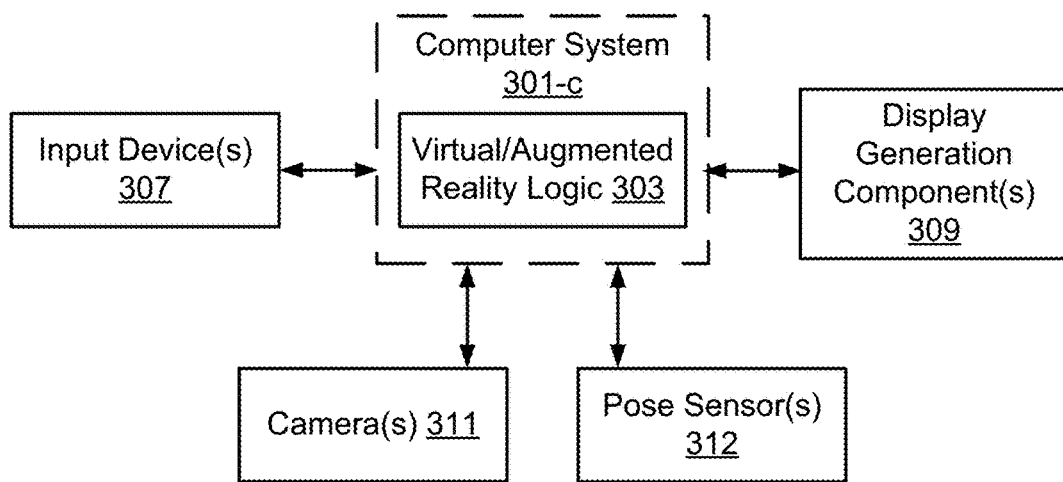

FIGS. 3B-3C are block diagrams of example computer systems 301 in accordance with some embodiments.

In some embodiments, computer system 301 includes and/or is in communication with:

- input device(s) (302 and/or 307, e.g., a touch-sensitive surface, such as a touch-sensitive remote control, or a touch-screen display that also serves as the display generation component, a mouse, a joystick, a wand controller, and/or cameras tracking the position of one or more features of the user such as the user's hands);
- virtual/augmented reality logic 303 (e.g., virtual/augmented reality module 145);
- display generation component(s) (304 and/or 308, e.g., a display, a projector, a head-mounted display, a heads-up display, or the like) for displaying virtual user interface elements to the user;
- camera(s) (e.g., 305 and/or 311) for capturing images of a field of view of the device, e.g., images that are used to determine placement of virtual user interface elements, determine a pose of the device, and/or display a portion of the physical environment in which the camera(s) are located; all references to images captured by the one or more cameras of the computer system (e.g., 301-a, 301-b or 301-c) shall be understood to optionally include depth information from one or more depth sensors (e.g., one or more time-of-flight sensors, structured-light sensors (also known as structured-light scanners), etc.) of the computer system, to facilitate measurement of objects in view of the one or more cameras; and pose sensor(s) (e.g., 306 and/or 312) for determining a pose of the device relative to the physical environment and/or changes in pose of the device.

In some computer systems (e.g., 301-*a* in FIG. 3B), input device(s) 302, virtual/augmented reality logic 303, display generation component(s) 304, camera(s) 305; and pose sensor(s) 306 are all integrated into the computer system (e.g., portable multifunction device 100 in FIGS. 1A-1B or device 300 in FIG. 3 such as a smartphone or tablet).

In some computer systems (e.g., 301-*b*), in addition to integrated input device(s) 302, virtual/augmented reality logic 303, display generation component(s) 304, camera(s) 305; and pose sensor(s) 306, the computer system is also in communication with additional devices that are separate from the computer system, such as separate input device(s) 307 such as a touch-sensitive surface, a wand, a remote control, or the like and/or separate display generation component(s) 308 such as virtual reality headset or augmented reality glasses that overlay virtual objects on a physical environment.

In some computer systems (e.g., 301-*c* in FIG. 3C), the input device(s) 307, display generation component(s) 309, camera(s) 311; and/or pose sensor(s) 312 are separate from the computer system and are in communication with the computer system. In some embodiments, other combinations of components in computer system 301 and in communication with the computer system are used. For example, in some embodiments, display generation component(s) 309, camera(s) 311, and pose sensor(s) 312 are incorporated in a headset that is either integrated with or in communication with the computer system.

In some embodiments, all of the operations described below with reference to FIGS. 5A-5P, 6A-6N, 7A-7T and 8A-8F are performed on a single computing device with virtual/augmented reality logic 303 (e.g., computer system 301-*a* described below with reference to FIG. 3B). However, it should be understood that frequently multiple different computing devices are linked together to perform the operations described below with reference to FIGS. 5A-5P, 6A-6N, 7A-7T and 8A-8F (e.g., a computing device with virtual/augmented reality logic 303 communicates with a separate computing device with a display 450 and/or a separate computing device with a touch-sensitive surface 451). In any of these embodiments, the computing device that is described below with reference to FIGS. 5A-5P, 6A-6N, 7A-7T and 8A-8F is the computing device (or devices) that contain(s) the virtual/augmented reality logic 303. Additionally, it should be understood that the virtual/augmented reality logic 303 could be divided between a plurality of distinct modules or computing devices in various embodiments; however, for the purposes of the description herein, the virtual/augmented reality logic 303 will be primarily referred to as residing in a single computing device so as not to unnecessarily obscure other aspects of the embodiments.

In some embodiments, the virtual/augmented reality logic 303 includes one or more modules (e.g., one or more event handlers 190, including one or more object updaters 177 and one or more GUI updaters 178 as described in greater detail above with reference to FIG. 1B) that receive interpreted inputs and, in response to these interpreted inputs, generate instructions for updating a graphical user interface in accordance with the interpreted inputs which are subsequently used to update the graphical user interface on a display. In some embodiments, an interpreted input for an input that has been detected (e.g., by a contact motion module 130 in FIGS. 1A and 3), recognized (e.g., by an event recognizer 180 in FIG. 1B) and/or distributed (e.g., by event sorter 170 in FIG. 1B) is used to update the graphical user interface on a display. In some embodiments, the interpreted inputs are generated by modules at the computing device (e.g., the computing device receives raw contact input data so as to identify gestures from the raw contact input data). In some embodiments, some or all of the interpreted inputs are received by the computing device as interpreted inputs (e.g., a computing device that includes the touch-sensitive surface 451 processes raw contact input data so as to identify gestures from the raw contact input data and sends information indicative of the gestures to the computing device that includes the virtual/augmented reality logic 303).

In some embodiments, both a display and a touch-sensitive surface are integrated with the computer system (e.g., 301-*a* in FIG. 3B) that contains the virtual/augmented reality logic 303. For example, the computer system may be a desktop computer or laptop computer with an integrated display (e.g., 340 in FIG. 3) and touchpad (e.g., 355 in FIG. 3). As another example, the computing device may be a portable multifunction device 100 (e.g., a smartphone, PDA, tablet computer, etc.) with a touch screen (e.g., 112 in FIG. 2A).

In some embodiments, a touch-sensitive surface is integrated with the computer system while a display is not integrated with the computer system that contains the virtual/augmented reality logic 303. For example, the computer system may be a device 300 (e.g., a desktop computer or laptop computer) with an integrated touchpad (e.g., 355 in FIG. 3) connected (via wired or wireless connection) to a separate display (e.g., a computer monitor, television, etc.). As another example, the computer system may be a portable multifunction device 100 (e.g., a smartphone, PDA, tablet computer, etc.) with a touch screen (e.g., 112 in FIG. 2A) connected (via wired or wireless connection) to a separate display (e.g., a computer monitor, television, etc.).

In some embodiments, a display is integrated with the computer system while a touch-sensitive surface is not integrated with the computer system that contains the virtual/augmented reality logic 303. For example, the computer system may be a device 300 (e.g., a desktop computer, laptop computer, television with integrated set-top box) with an integrated display (e.g., 340 in FIG. 3) connected (via wired or wireless connection) to a separate touch-sensitive surface (e.g., a remote touchpad, a portable multifunction device, etc.). As another example, the computer system may be a portable multifunction device 100 (e.g., a smartphone, PDA, tablet computer, etc.) with a touch screen (e.g., 112 in FIG. 2A) connected (via wired or wireless connection) to a separate touch-sensitive surface (e.g., a remote touchpad, another portable multifunction device with a touch screen serving as a remote touchpad, etc.).

In some embodiments, neither a display nor a touch-sensitive surface is integrated with the computer system (e.g., 301-*c* in FIG. 3C) that contains the virtual/augmented reality logic 303. For example, the computer system may be a stand-alone computing device 300 (e.g., a set-top box, gaming console, etc.) connected (via wired or wireless connection) to a separate touch-sensitive surface (e.g., a remote touchpad, a portable multifunction device, etc.) and a separate display (e.g., a computer monitor, television, etc.).

In some embodiments, the computer system has an integrated audio system (e.g., audio circuitry 110 and speaker 111 in portable multifunction device 100). In some embodiments, the computing device is in communication with an audio system that is separate from the computing device. In some embodiments, the audio system (e.g., an audio system integrated in a television unit) is integrated with a separate display. In some embodiments, the audio system (e.g., a stereo system) is a stand-alone system that is separate from the computer system and the display.

Attention is now directed towards embodiments of user interfaces ("UI") that are, optionally, implemented on portable multifunction device 100.

Figure 4A:
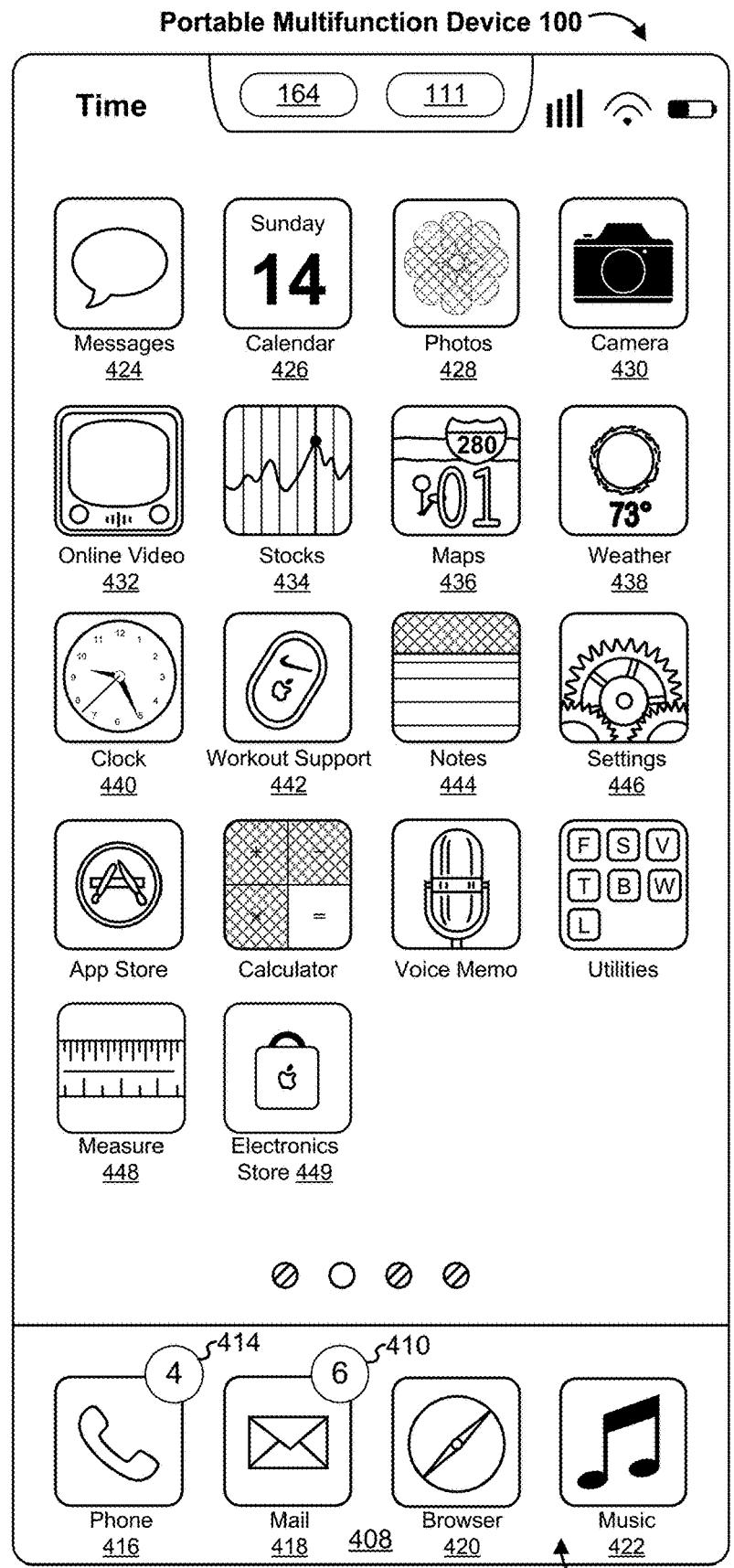
FIG. 4A illustrates an example user interface for a menu of applications on a portable multifunction device in accordance with some embodiments.

FIG. 4A illustrates an example user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) for wireless communication(s), such as cellular and Wi-Fi™ signals;

Time;

a Bluetooth™ indicator;

a Battery status indicator;

Tray 408 with icons for frequently used applications, such as:

Icon 416 for telephone module 138, labeled "Phone," which optionally includes an indicator 414 of the number of missed calls or voicemail messages;

Icon 418 for e-mail client module 140, labeled "Mail," which optionally includes an indicator 410 of the number of unread e-mails;

Icon 420 for browser module 147, labeled "Browser"; and

Icon 422 for video and music player module 152, labeled "Music"; and

Icons for other applications, such as:

Icon 424 for IM module 141, labeled "Messages";

Icon 426 for calendar module 148, labeled "Calendar";

Icon 428 for image management module 144, labeled "Photos";

Icon 430 for camera module 143, labeled "Camera";

Icon 432 for online video module 155, labeled "Online Video";

Icon 434 for stocks widget 149-2, labeled "Stocks";

Icon 436 for map module 154, labeled "Maps";

Icon 438 for weather widget 149-1, labeled "Weather";

Icon 440 for alarm clock widget 149-4, labeled "Clock";

Icon 442 for workout support module 142, labeled "Workout Support";

Icon 444 for notes module 153, labeled "Notes";

Icon 446 for a settings application or module, labeled "Settings," which provides access to settings for device 100 and its various applications 136;

Icon 448 for measure widget, labeled "Measure"; and

Icon 449 for a store module, labeled "Electronics Store".

It should be noted that the icon labels illustrated in FIG. 4A are merely examples. For example, other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an example user interface on a device (e.g., device 300, FIG. 3A) with a touch-sensitive surface 451 (e.g., a tablet or touchpad 355, FIG. 3A) that is separate from the display 450. Although many of the examples that follow will be given with reference to inputs on touch screen display 112 (where the touch sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, contact 460 corresponds to 468 and contact 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures, etc.), it should be understood that, in some embodiments, one or more of the finger inputs are replaced with input from another input device (e.g., a mouse based input or a stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

User Interfaces and Associated Processes

Attention is now directed towards embodiments of user interfaces ("UI") and associated processes that may be implemented on a computer system (e.g., portable multifunction device 100, device 300, or device 800) that includes (and/or is in communication with) a display generation component (e.g., a display, a projector, a head-mounted display, a heads-up display, or the like), one or more cameras (e.g., video cameras that continuously provide a live preview of at least a portion of the contents that are within the field of view of the cameras and optionally generate video outputs including one or more streams of image frames capturing the contents within the field of view of the cameras), and one or more input devices (e.g., a touch-sensitive surface, such as a touch-sensitive remote control, or a touch-screen display that also serves as the display generation component, a mouse, a joystick, a wand controller, and/or cameras tracking the position of one or more features of the user such as the user's hands), optionally one or more pose sensors, optionally one or more sensors to detect intensities of contacts with the touch-sensitive surface, and optionally one or more tactile output generators.

Figure 5A:
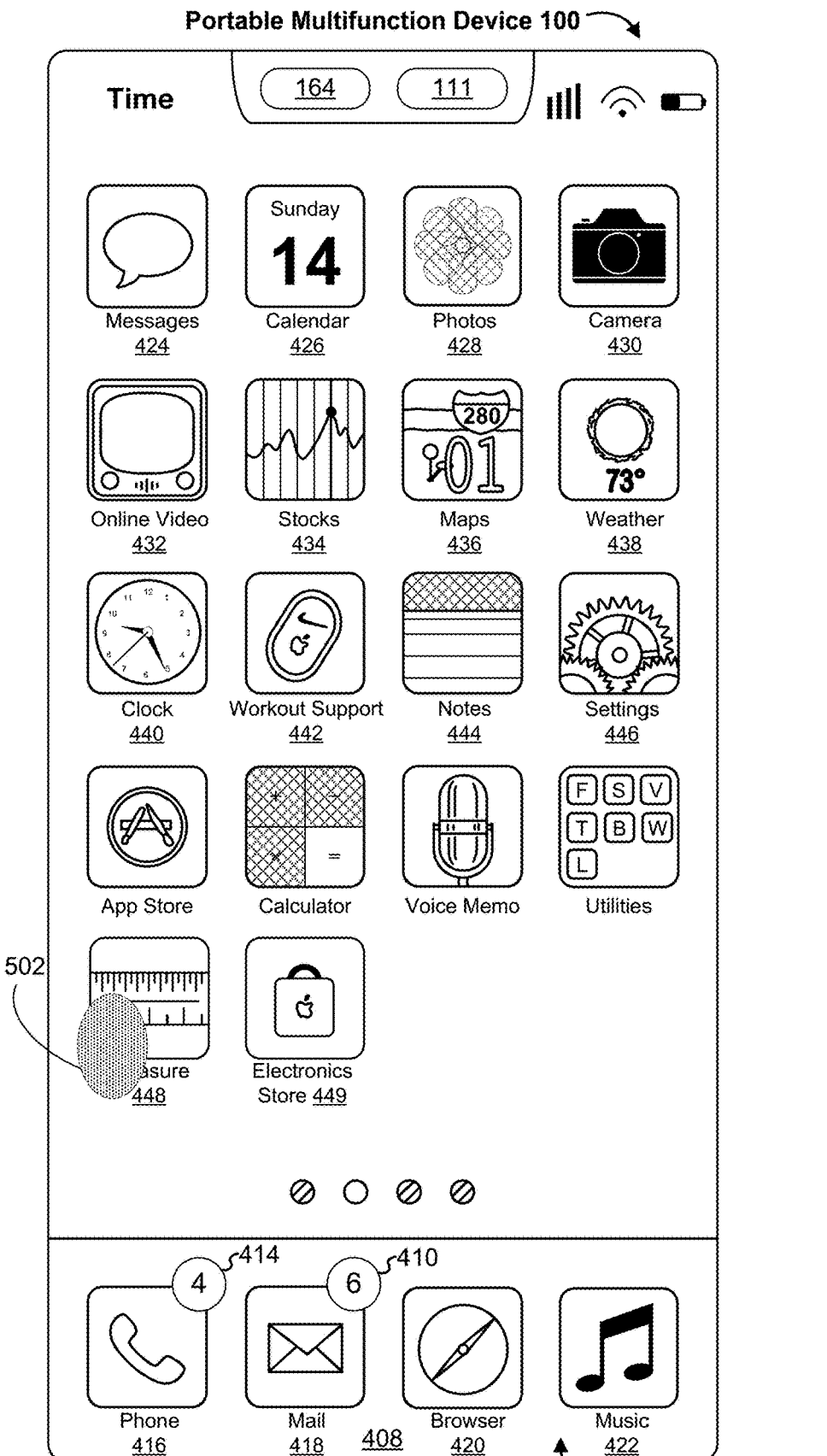
FIGS. 5A-5P illustrate example user interfaces for initiating a process for measuring a body part, e.g. a hand or wrist, of a user and prompting the user to position the body part in the field of view of one or more cameras of a computer system, in accordance with some embodiments.
Figure 5B:
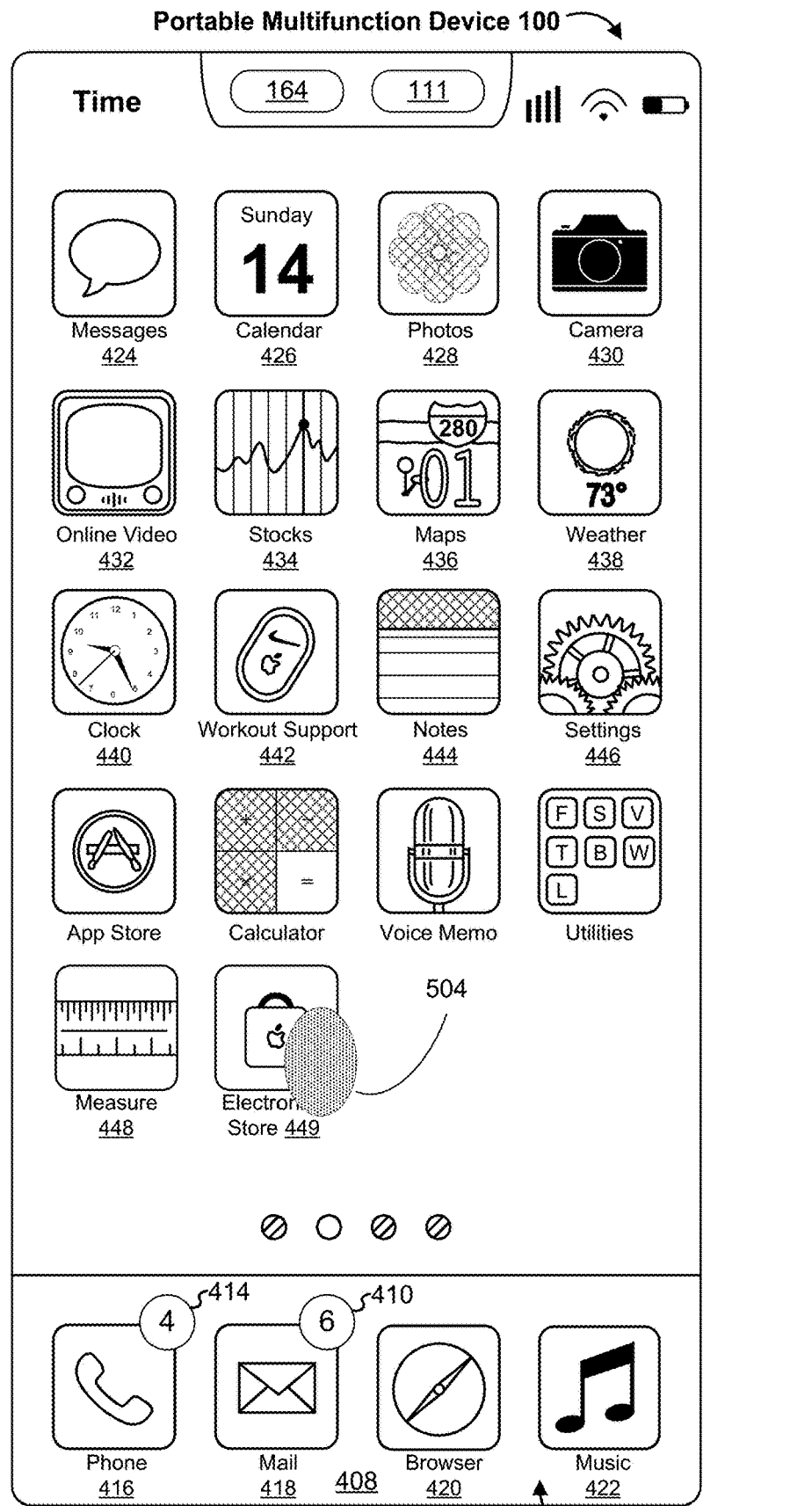
Figure 5C:
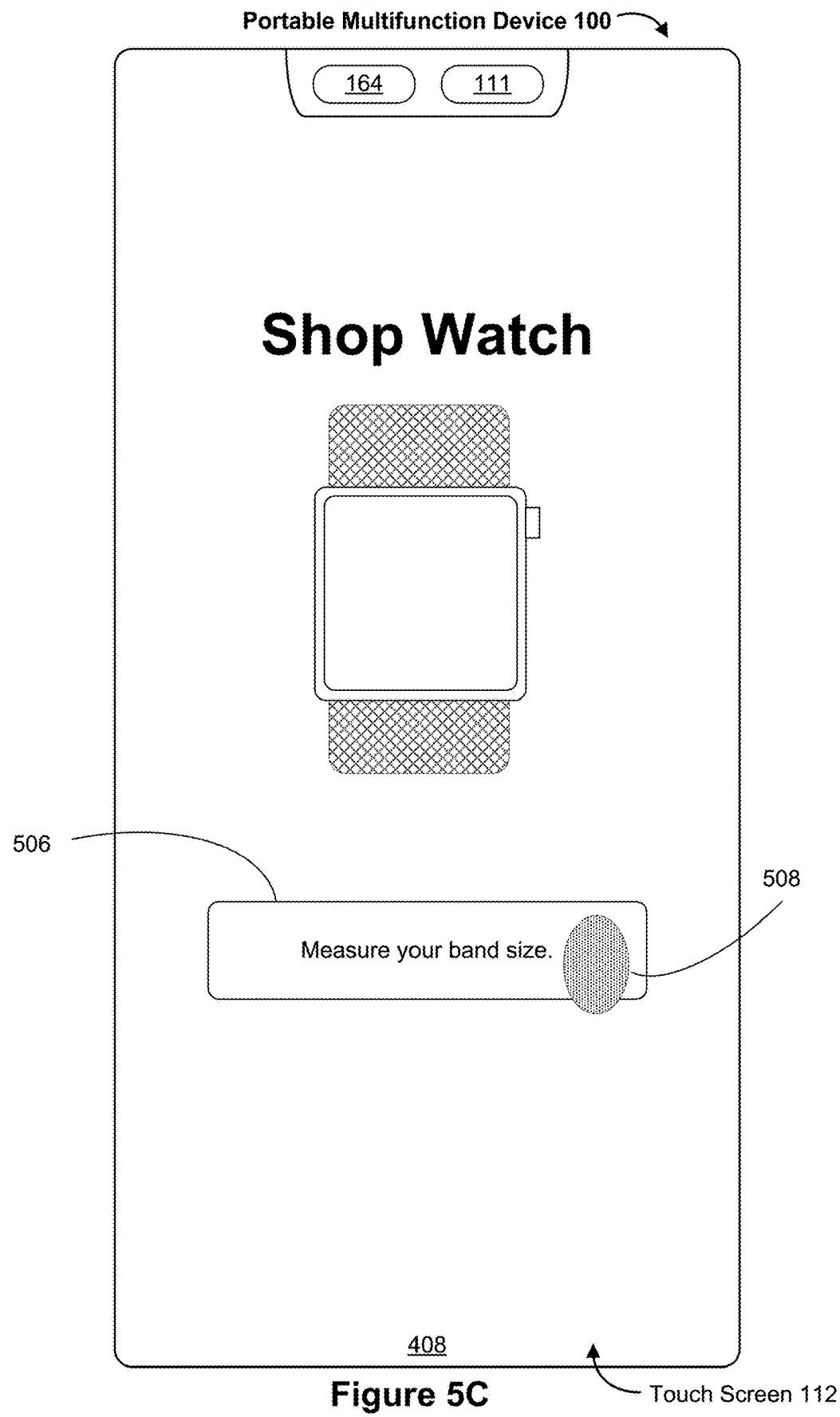
Figure 5D:
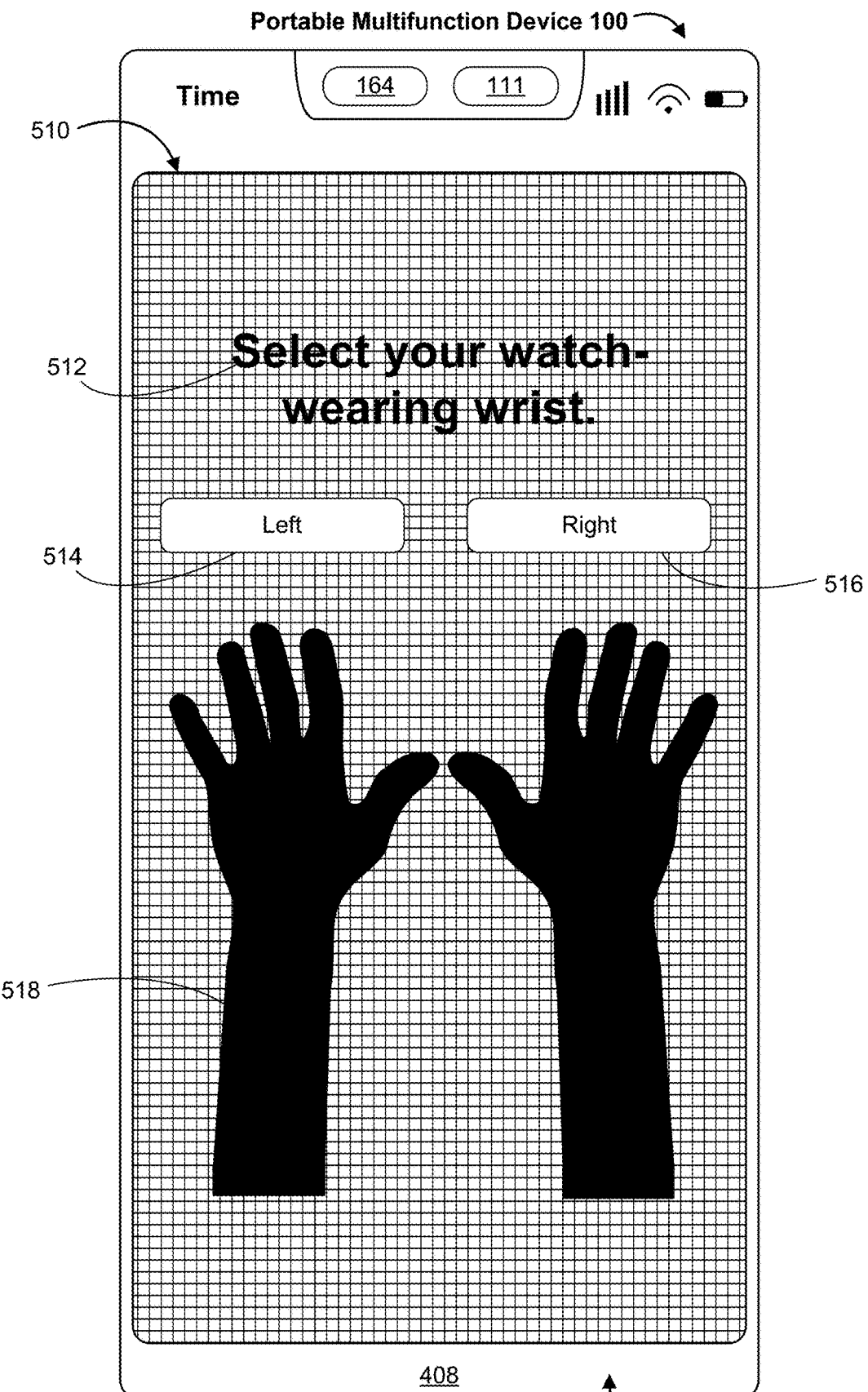
Figure 5E:
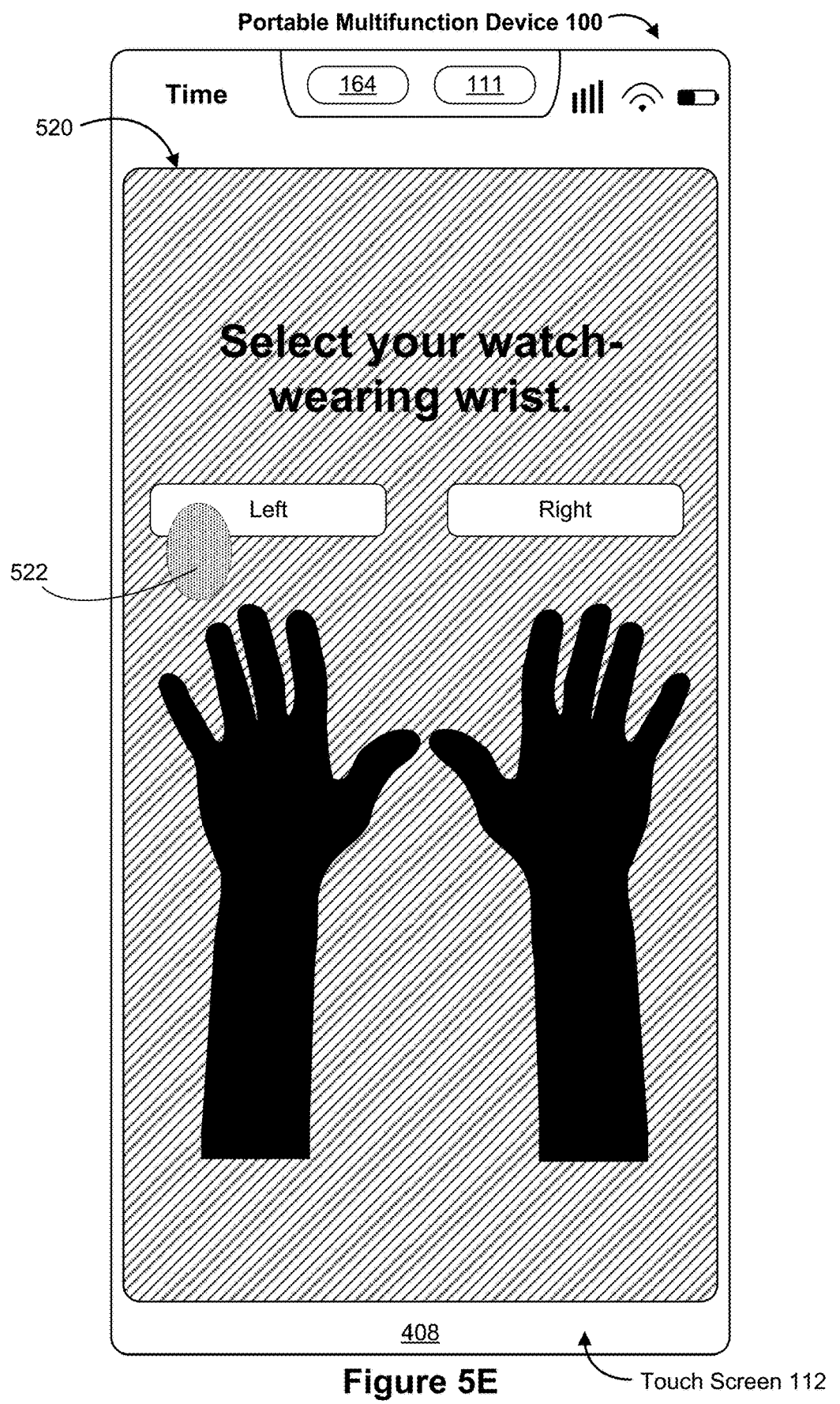
Figure 5F:
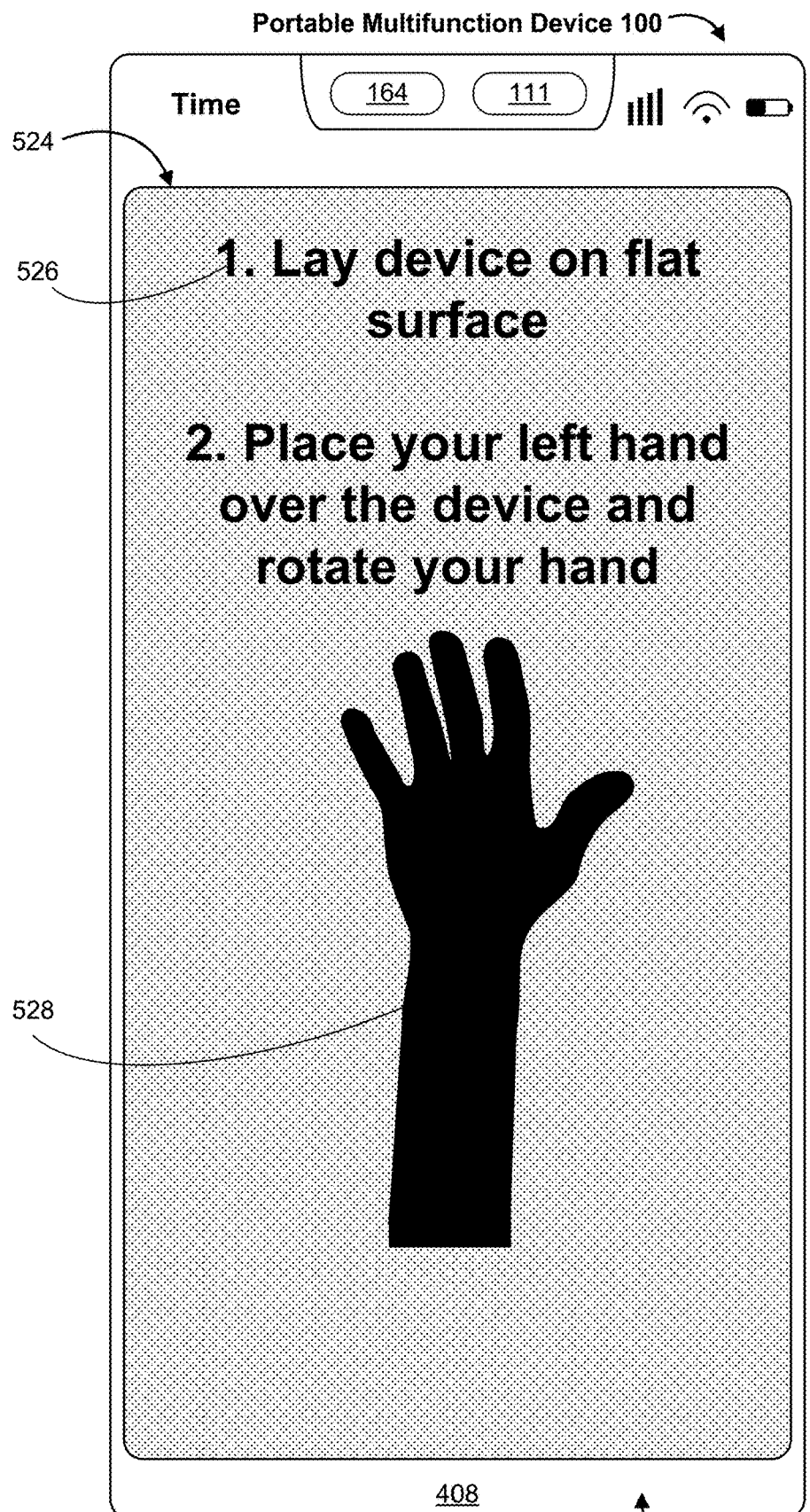
Figure 5G:
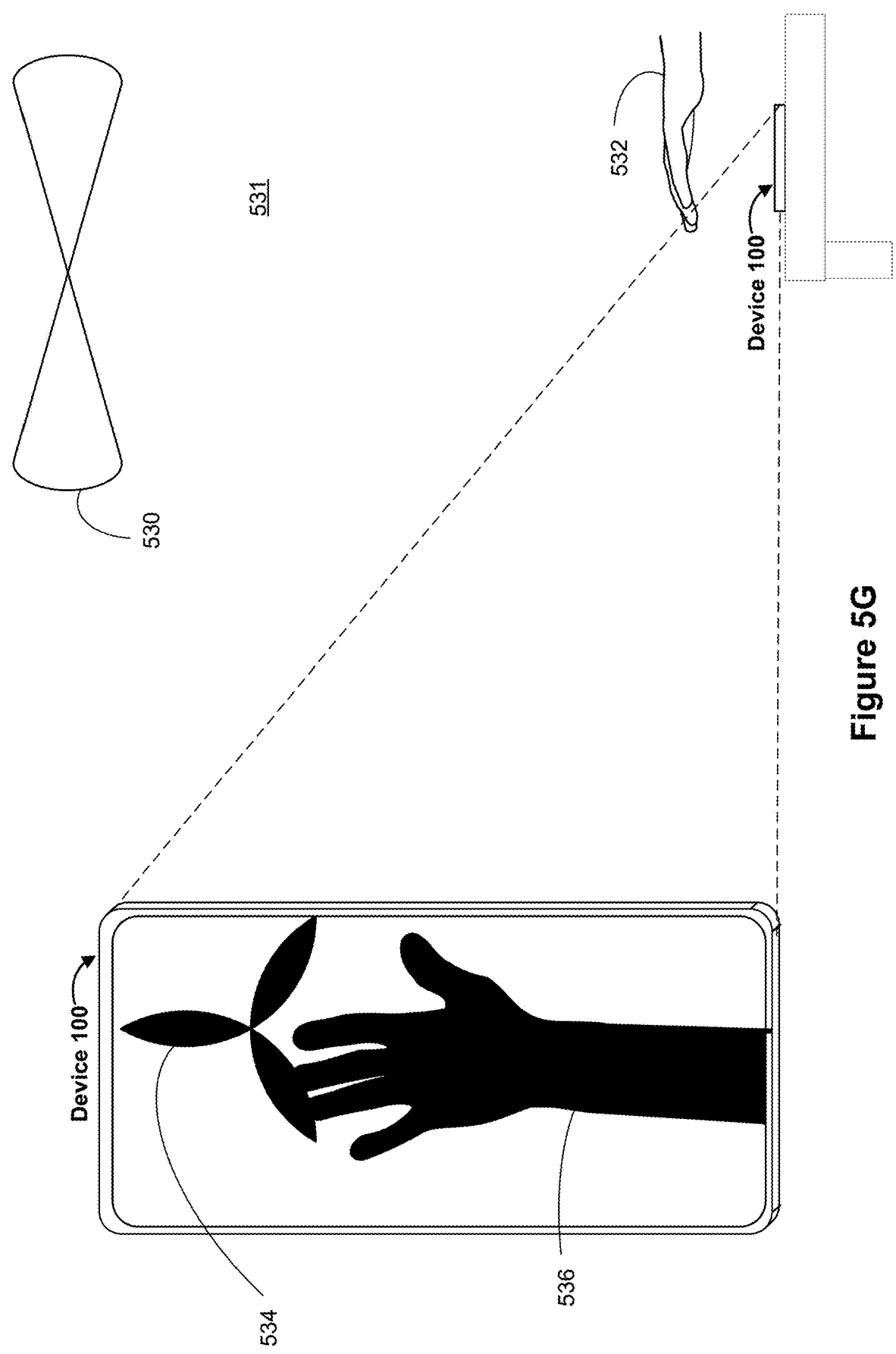
Figure 5H:
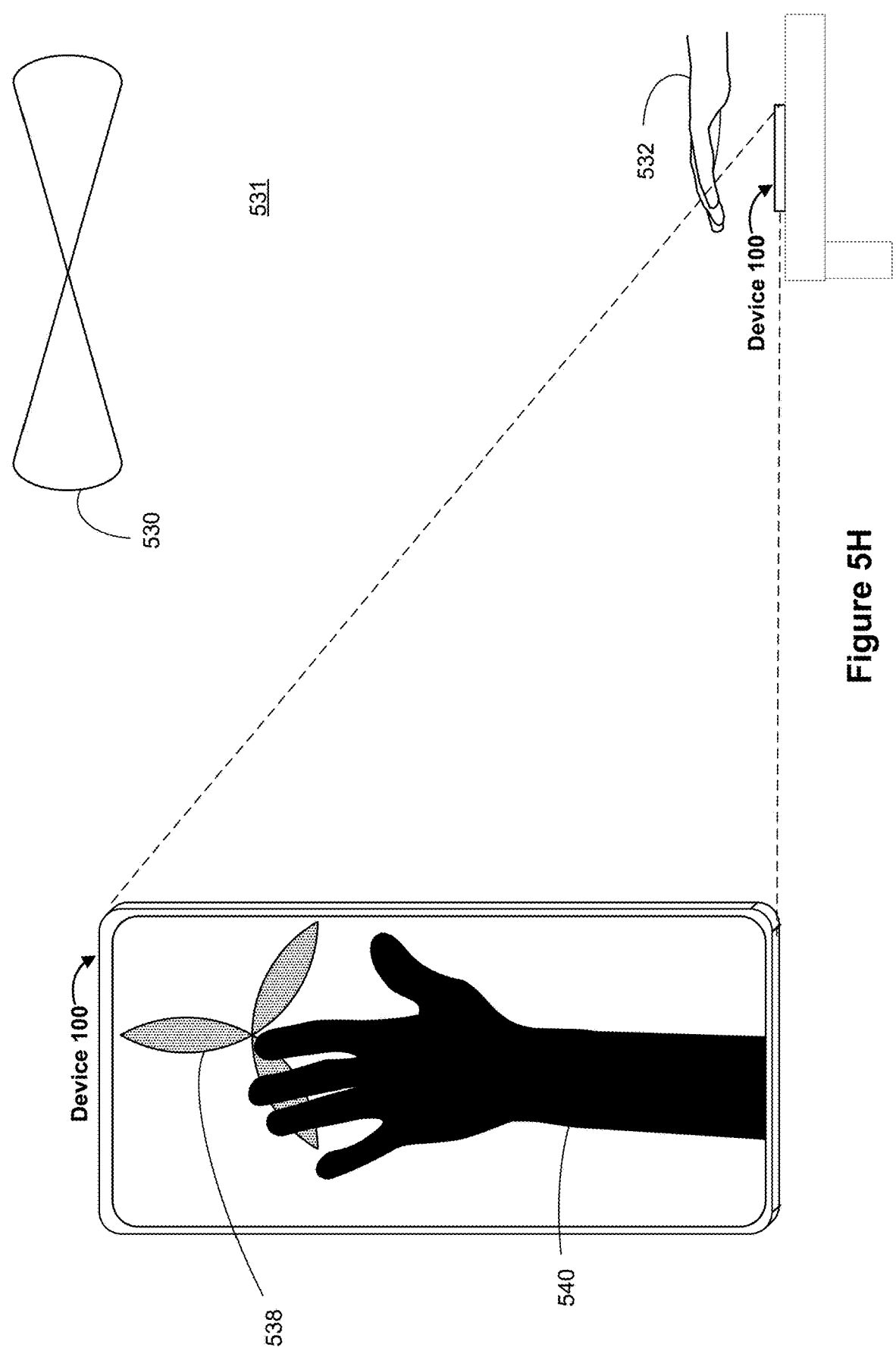
Figure 5J:
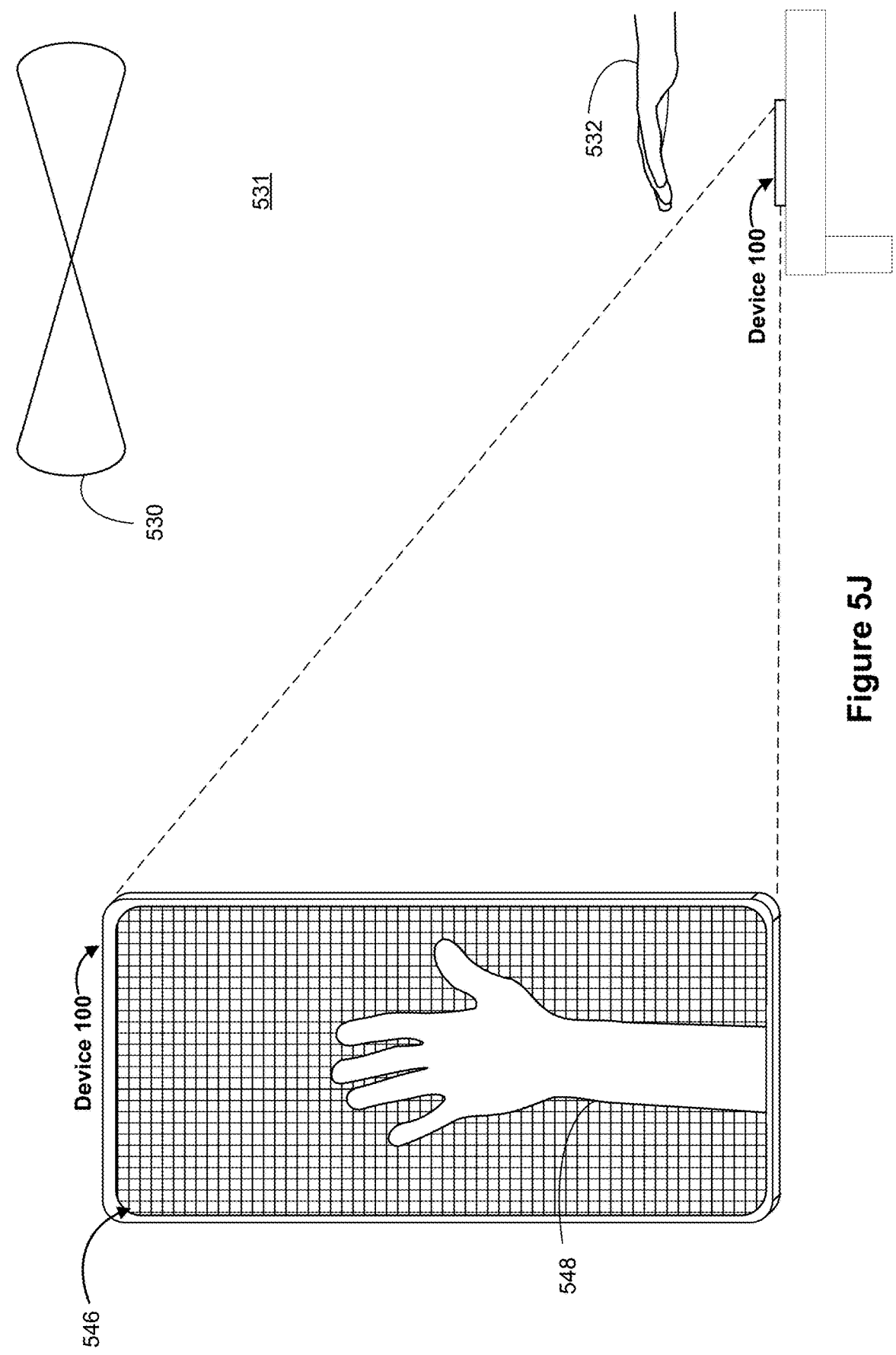
Figure 5K:
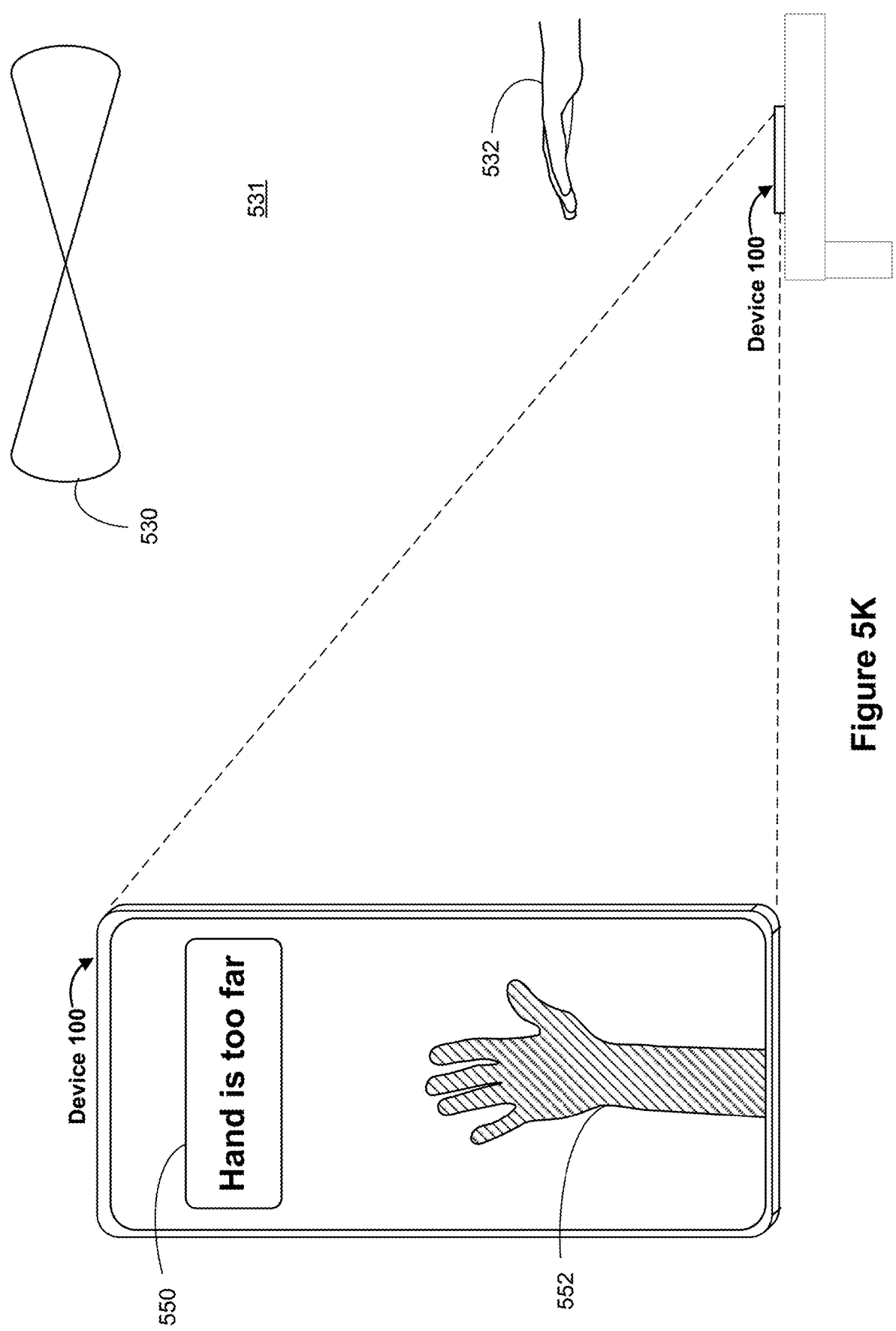
Figure 5L:
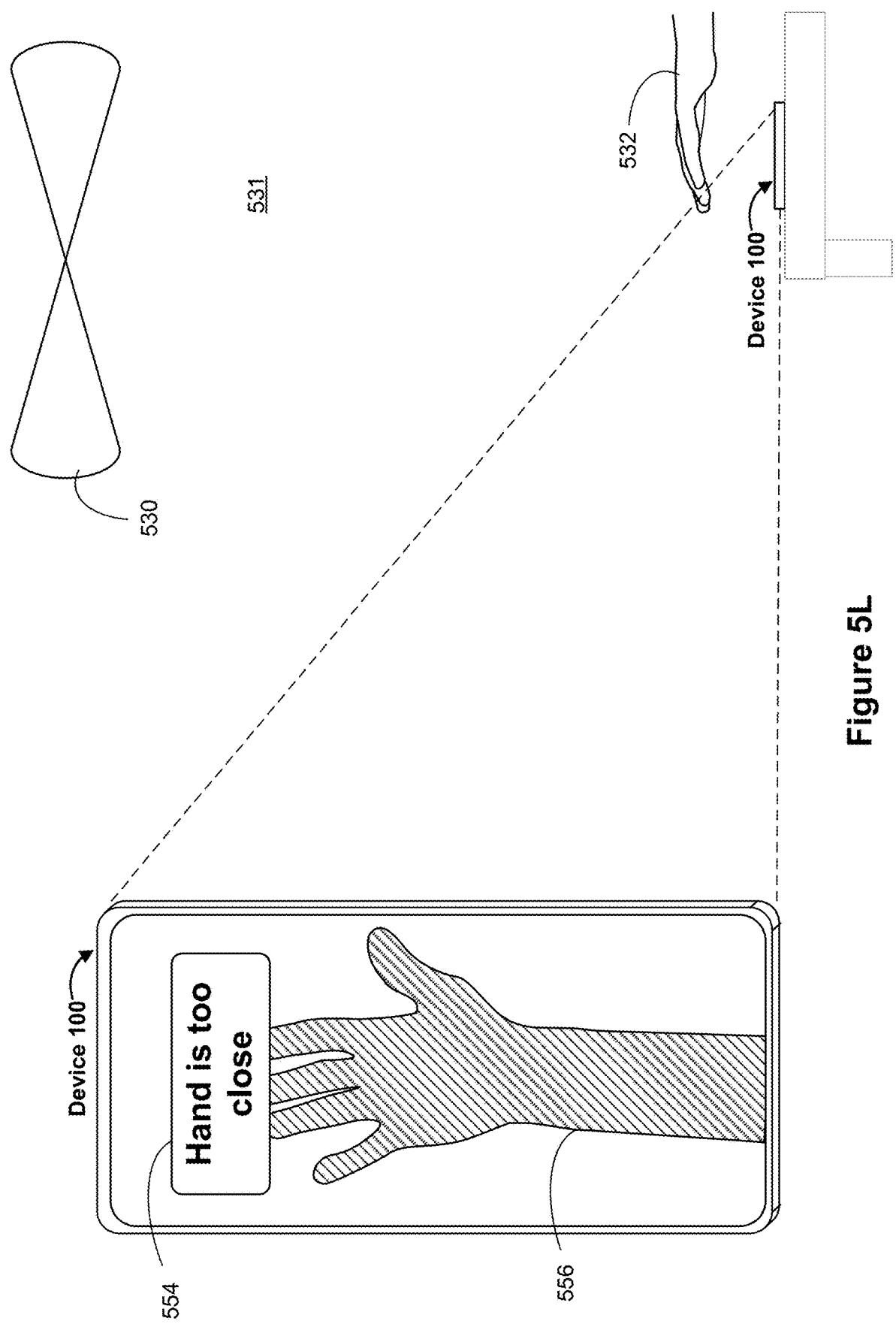
Figure 5M:
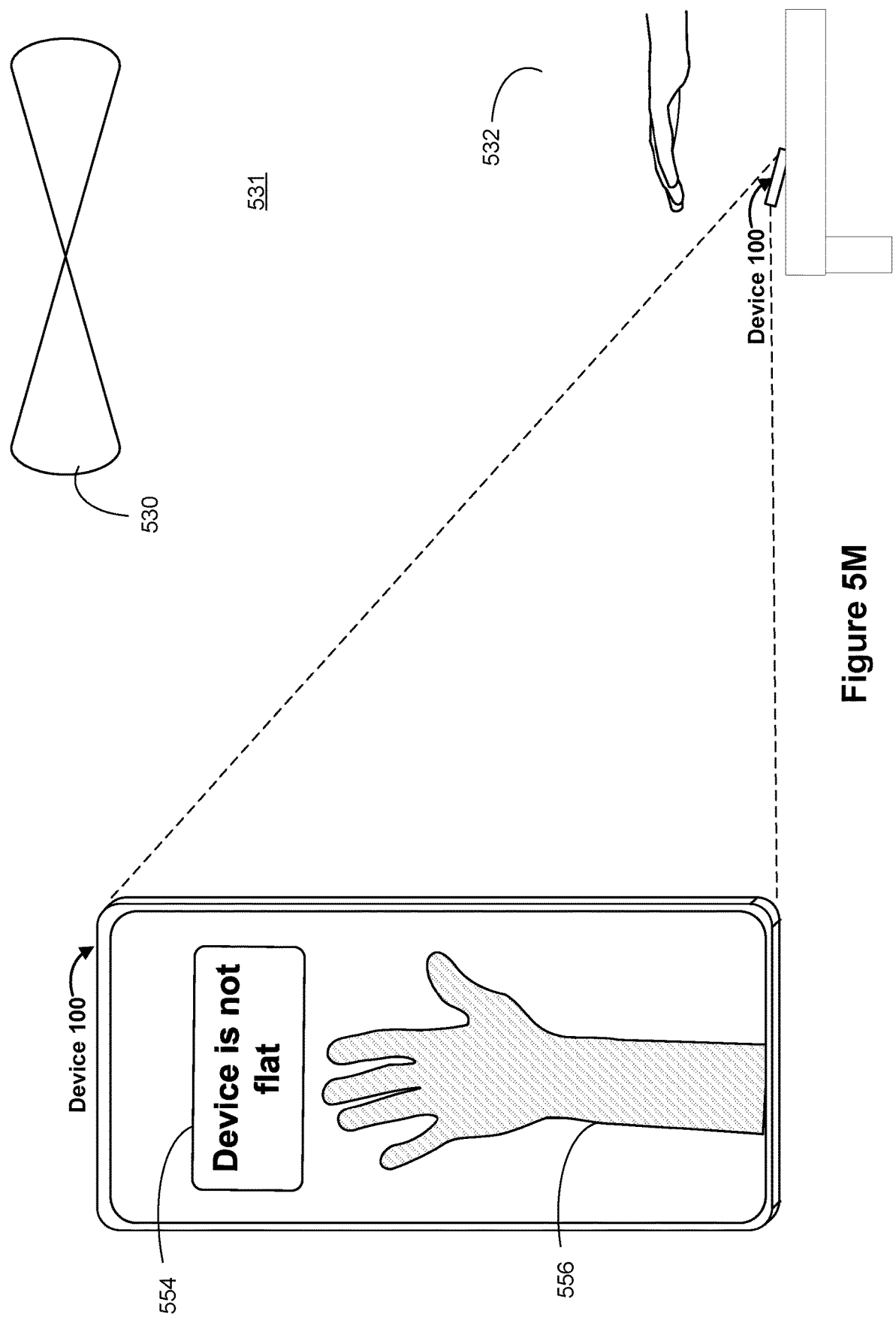
Figure 5N:
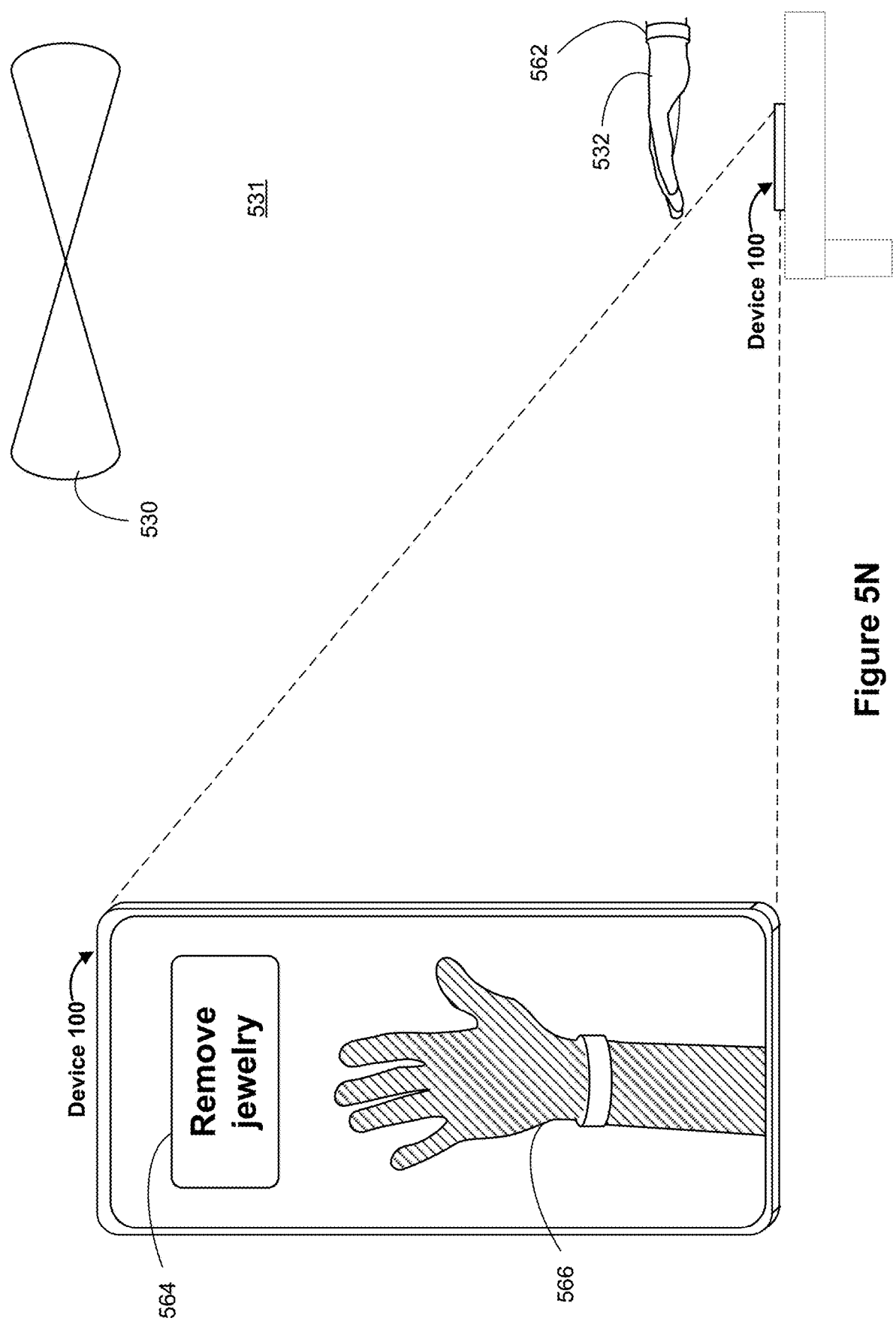
Figure 5P:
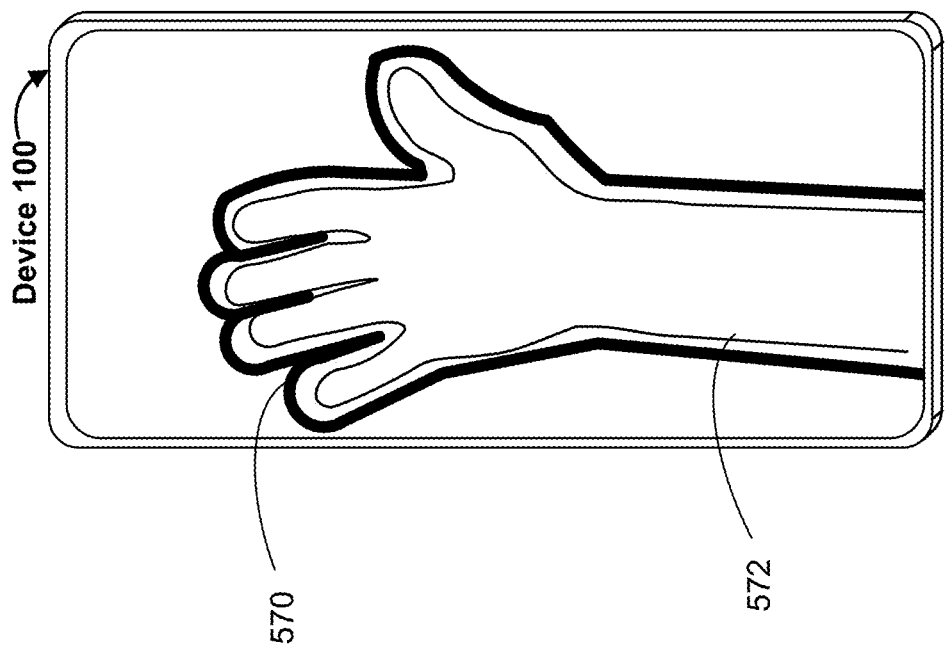
Figure 6A:
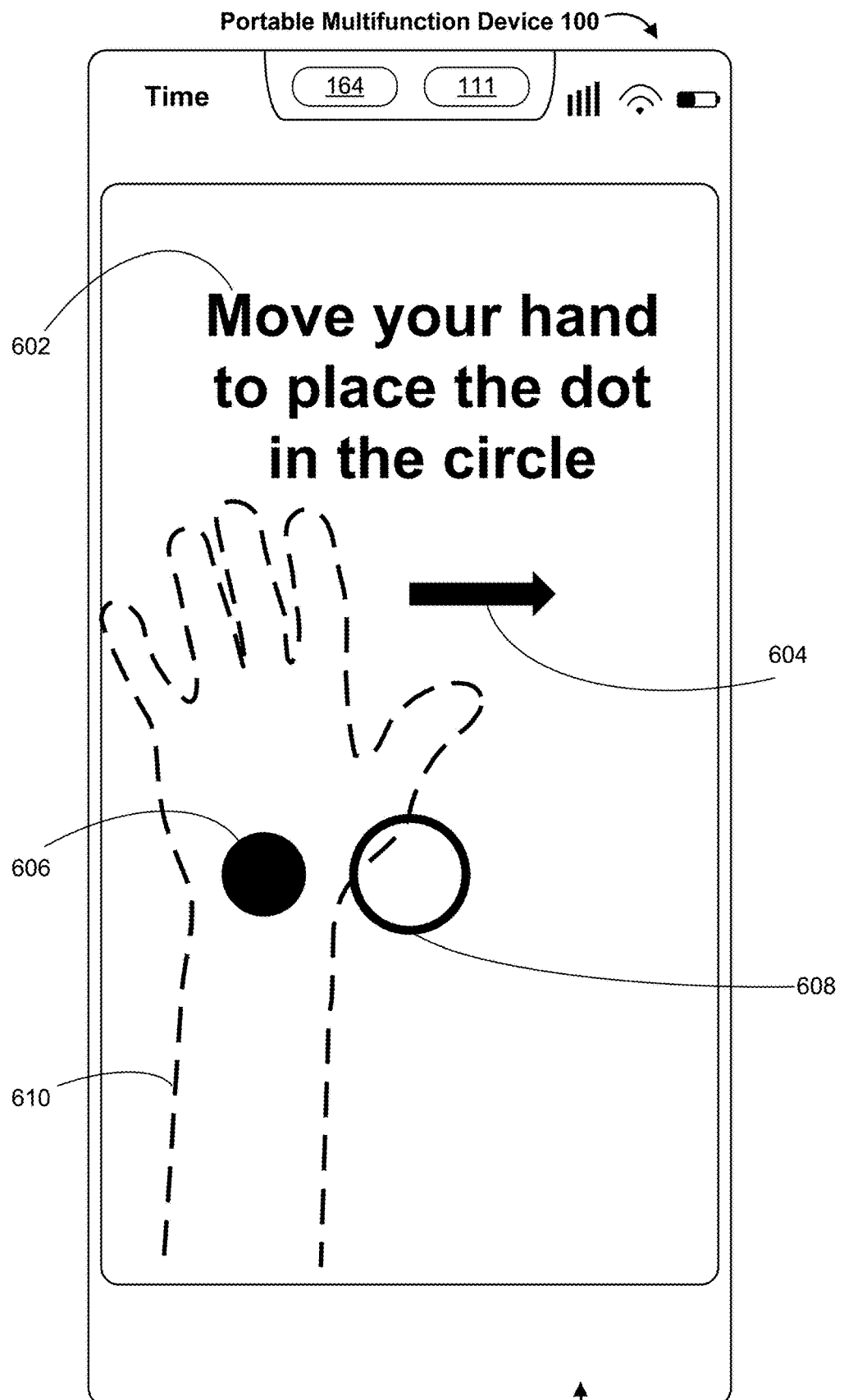
FIGS. 6A-6N illustrate example user interfaces for prompting a user to move a body part to capture one or more images, in accordance with some embodiments.
Figure 6B:
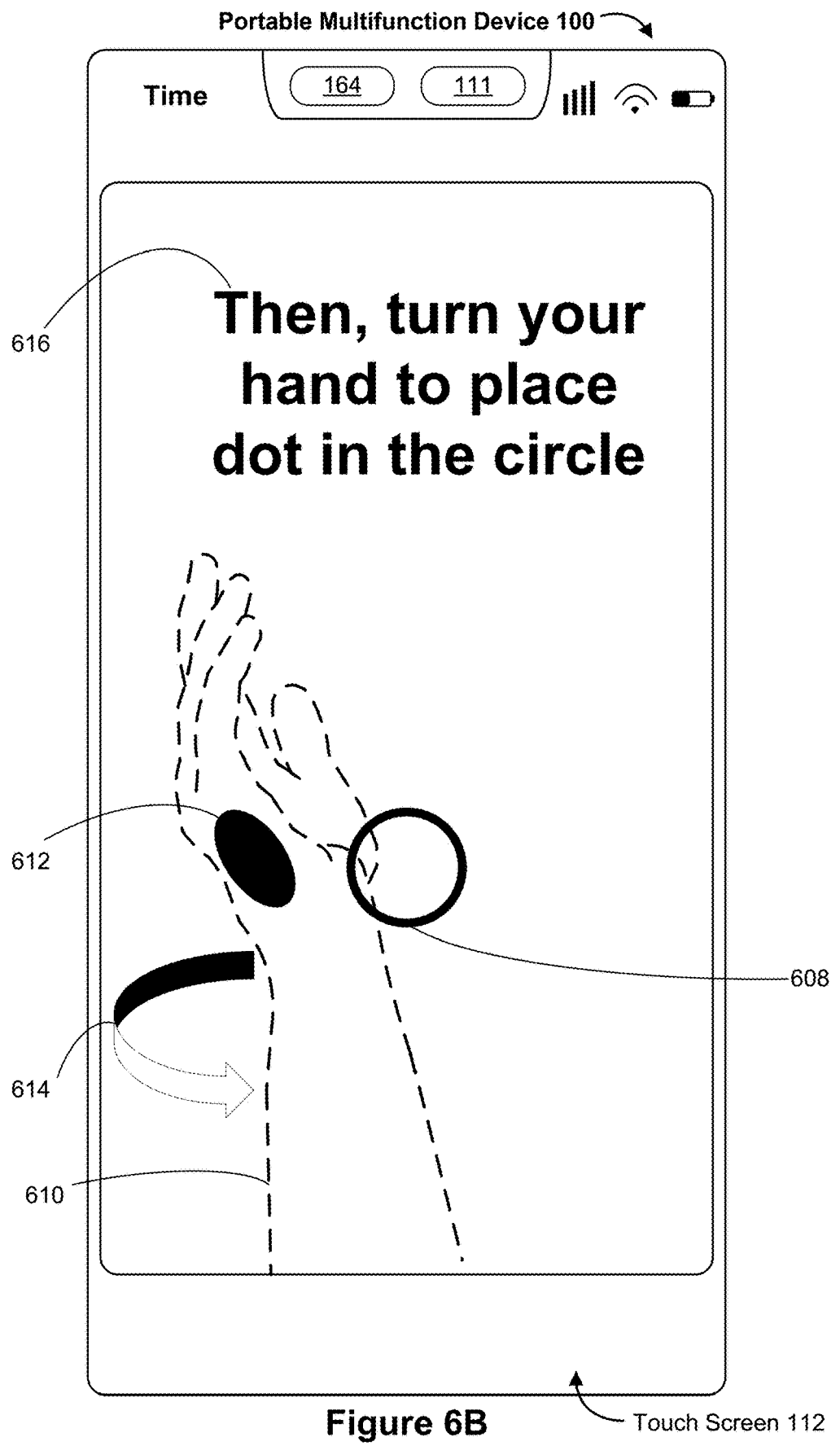

FIGS. 5A-5P illustrate example user interfaces for initiating a process for measuring a body part of a user in accordance with some embodiments. FIGS. 6A-6N illustrate example user interfaces for obtaining a measurement of the body part of the user in accordance with some embodiments.

Figure 7B:
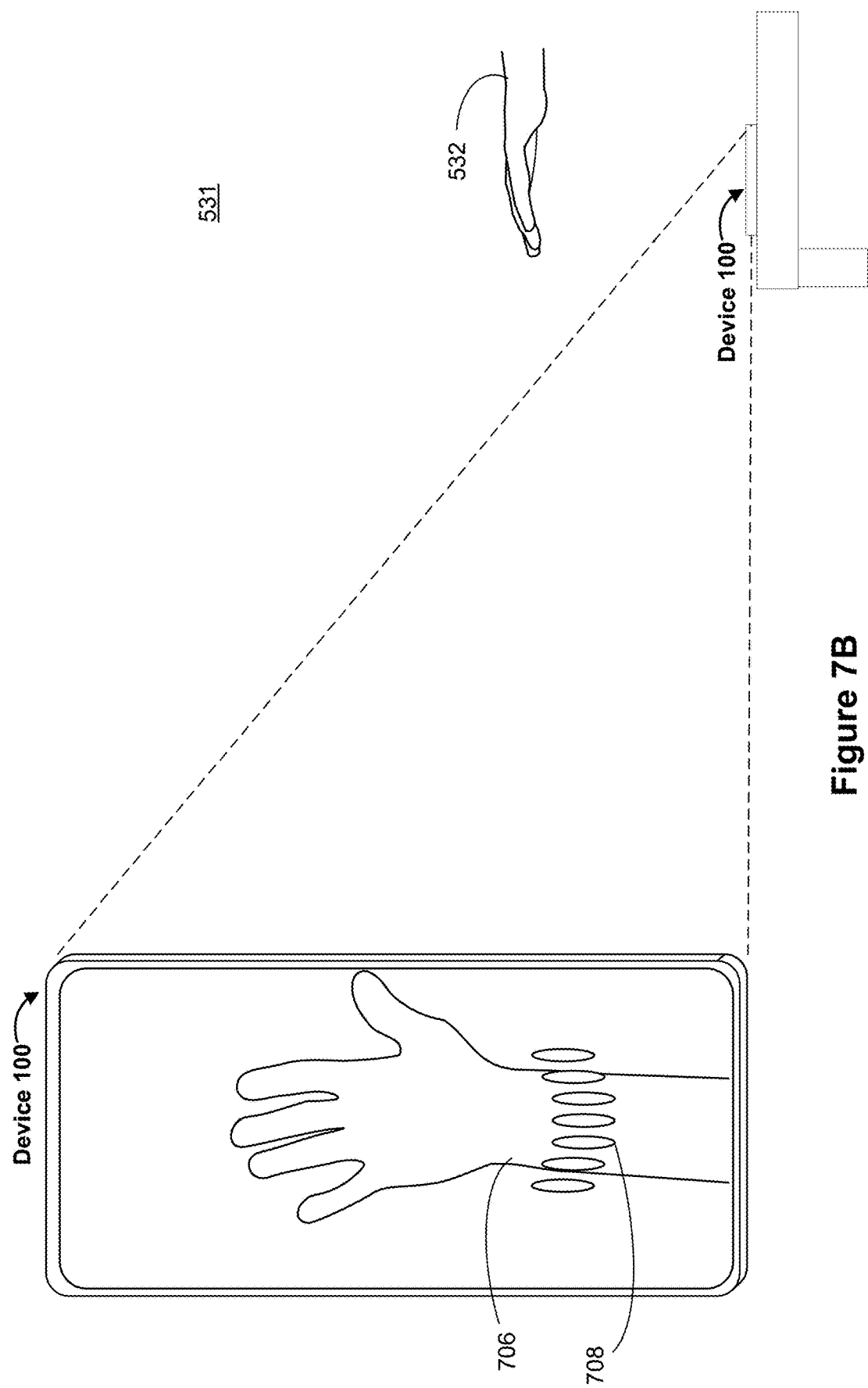
FIGS. 7A-7T illustrate example user interfaces for determining a measurement of a body part of a user in accordance with some embodiments.
Figure 7C:
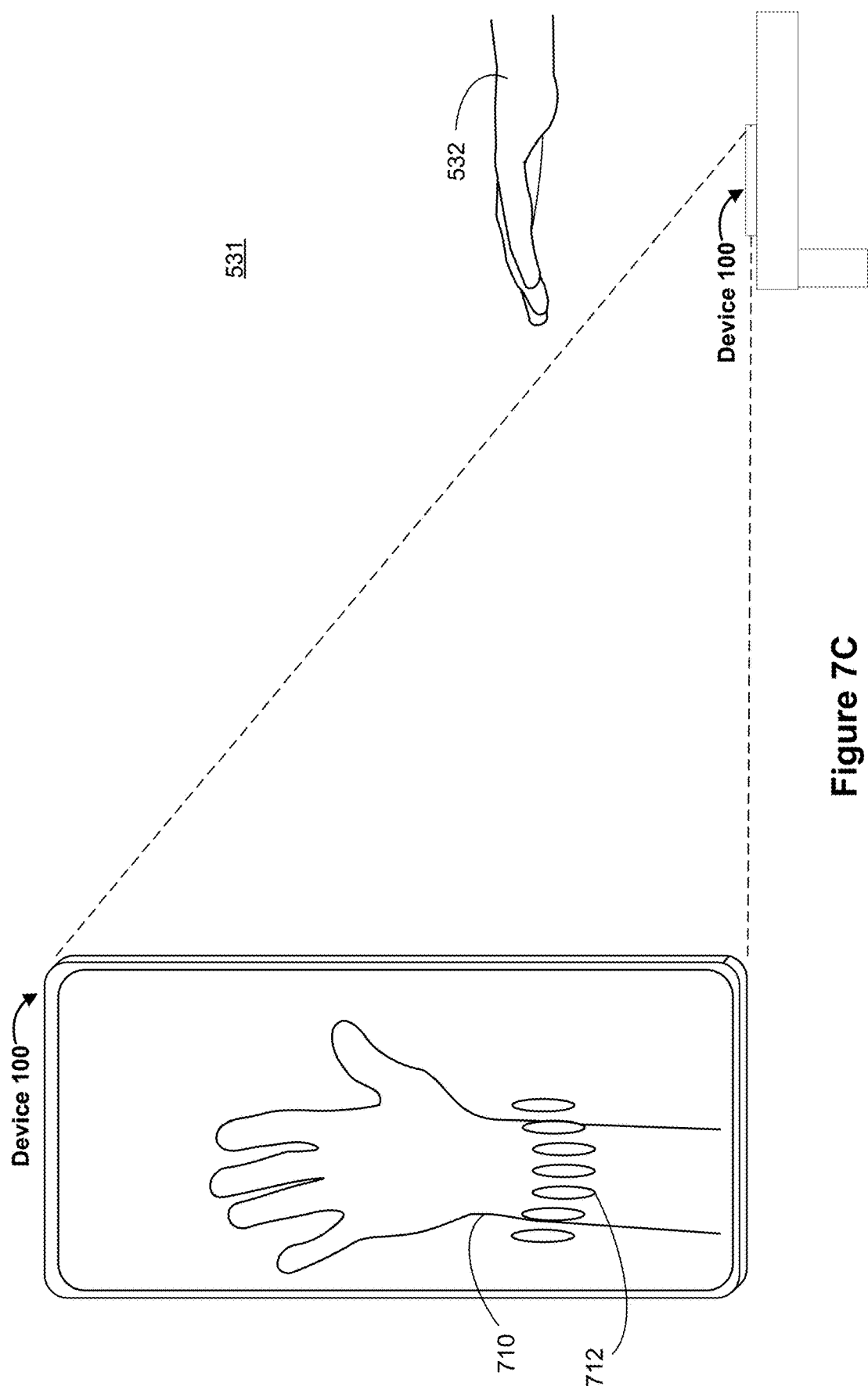
Figure 7D:
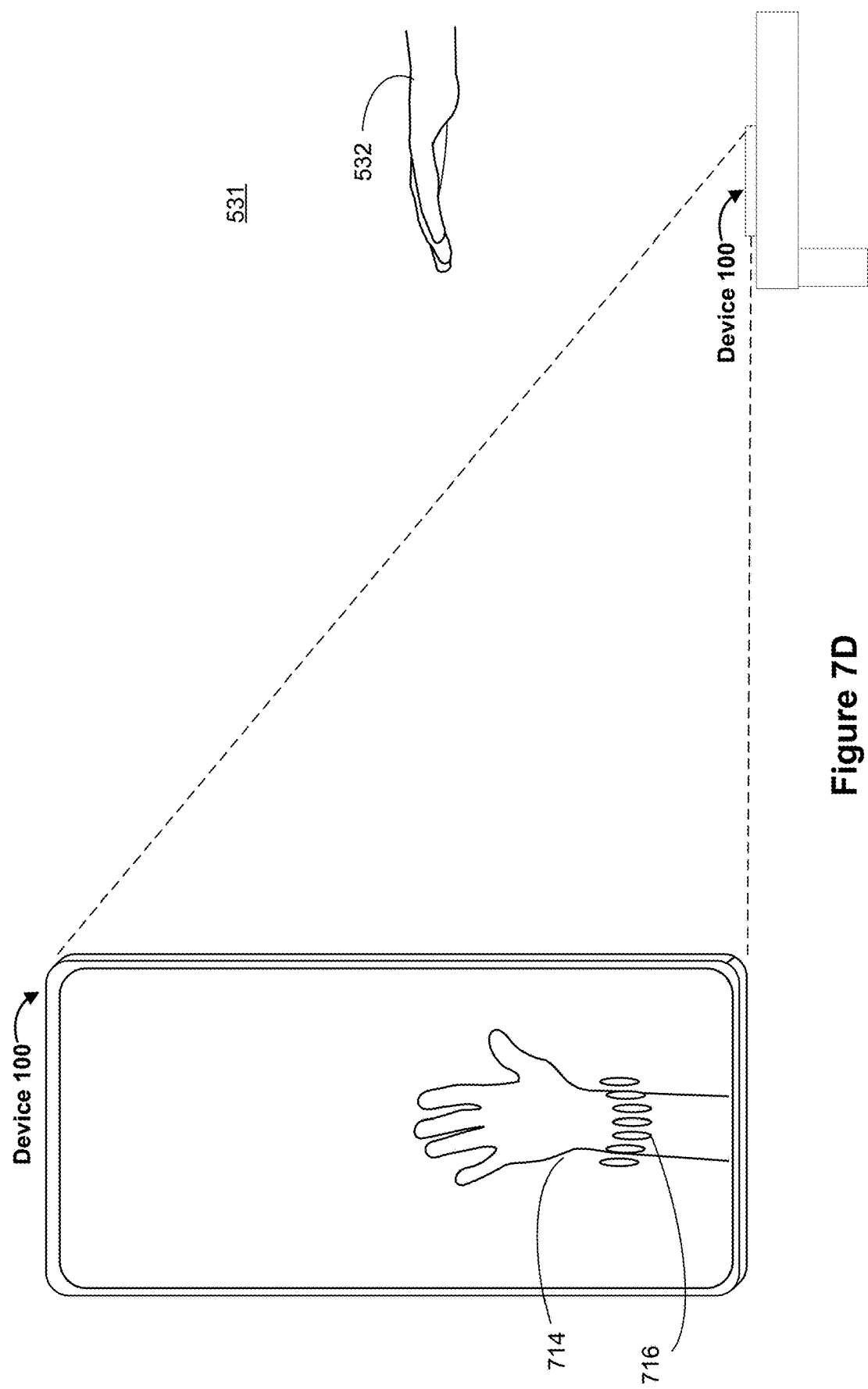
Figure 7G:
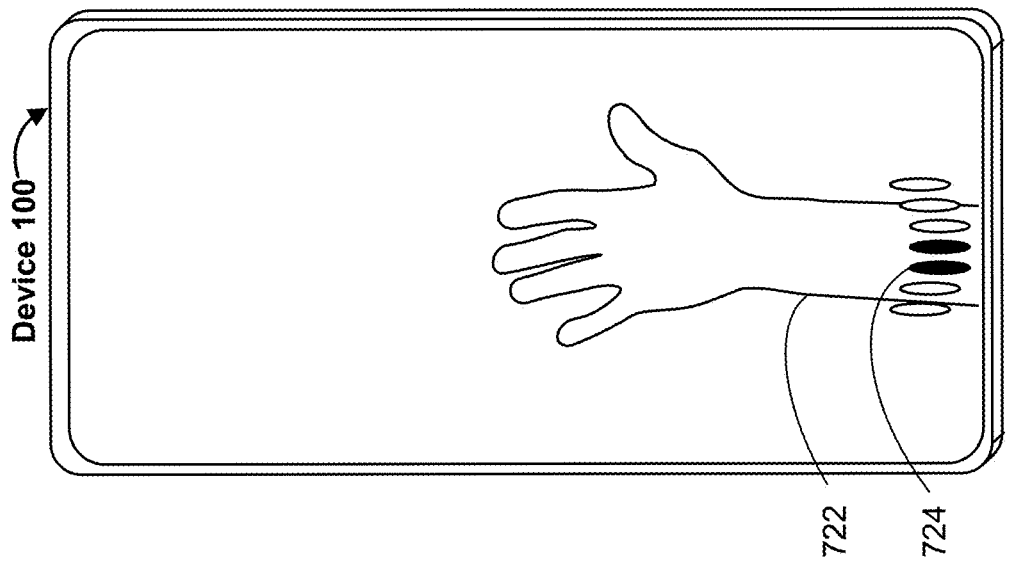
Figure 7F:
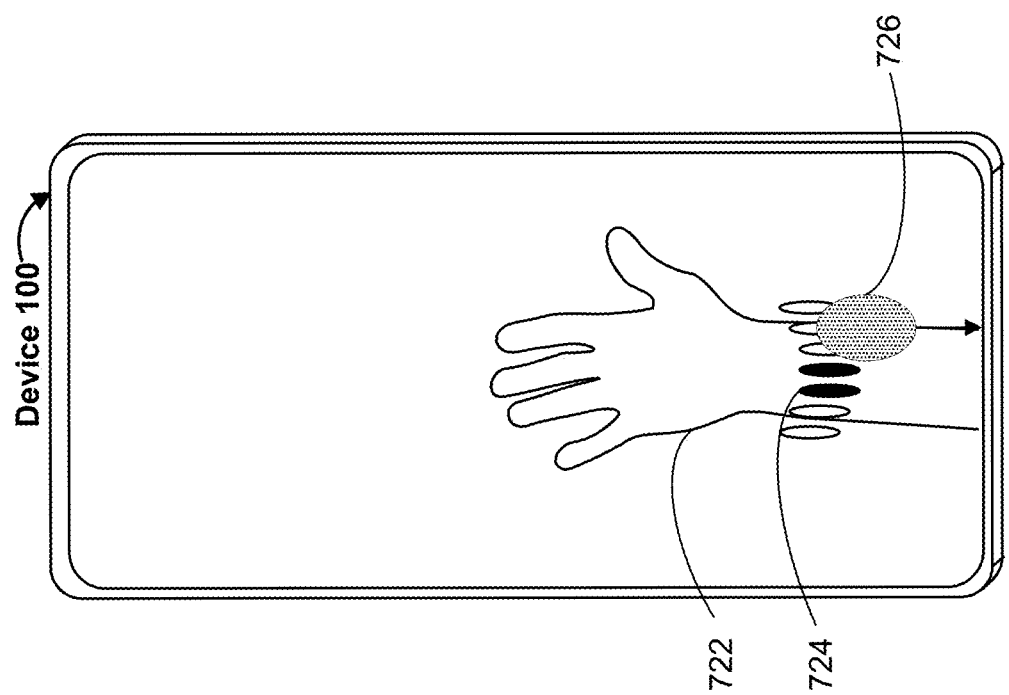
Figure 7I:
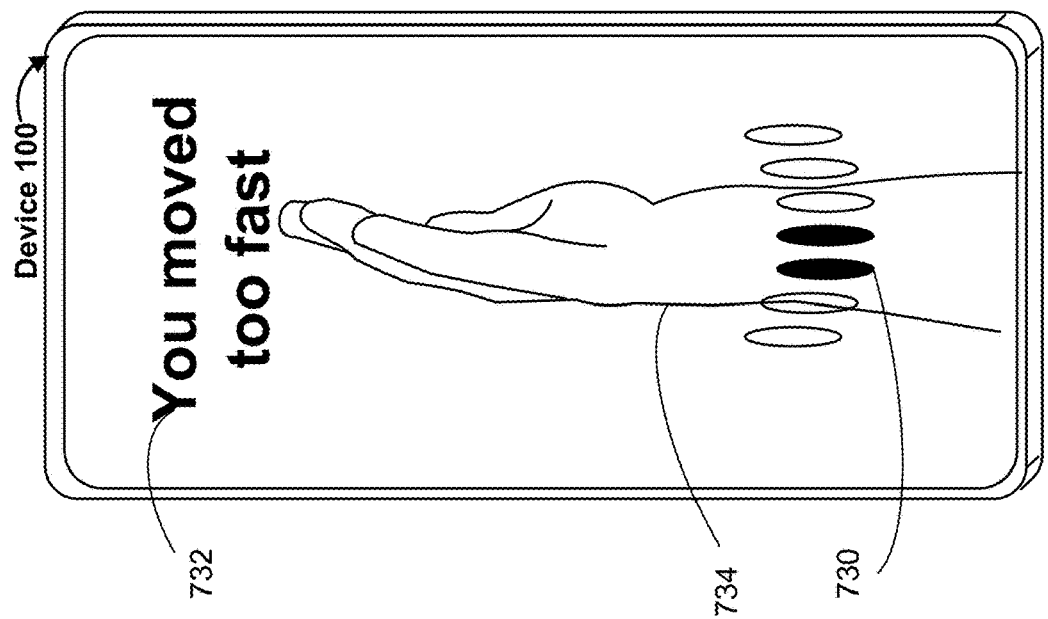
Figure 7H:
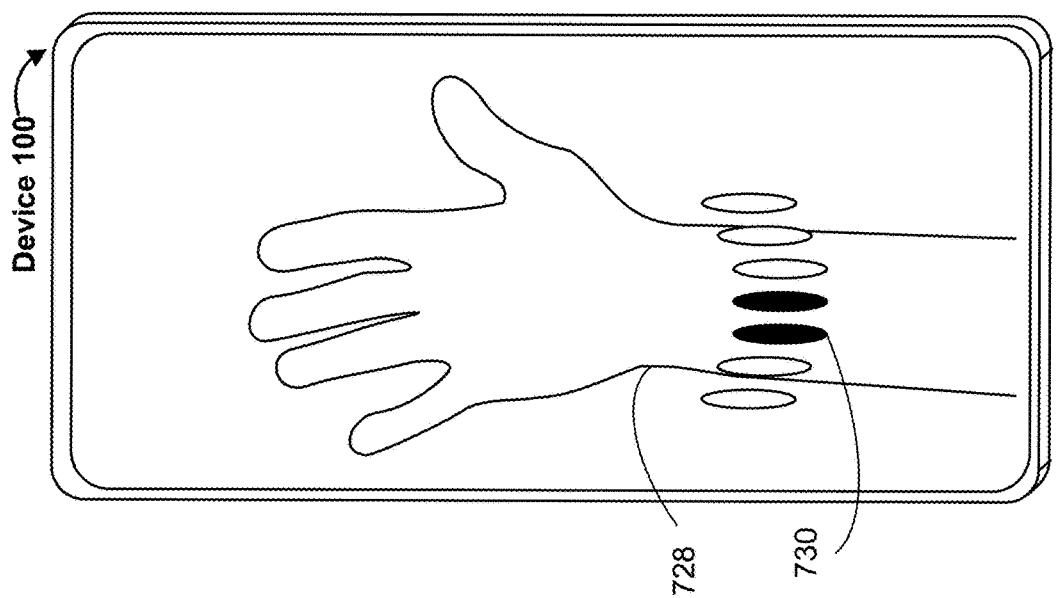
Figure 7K:
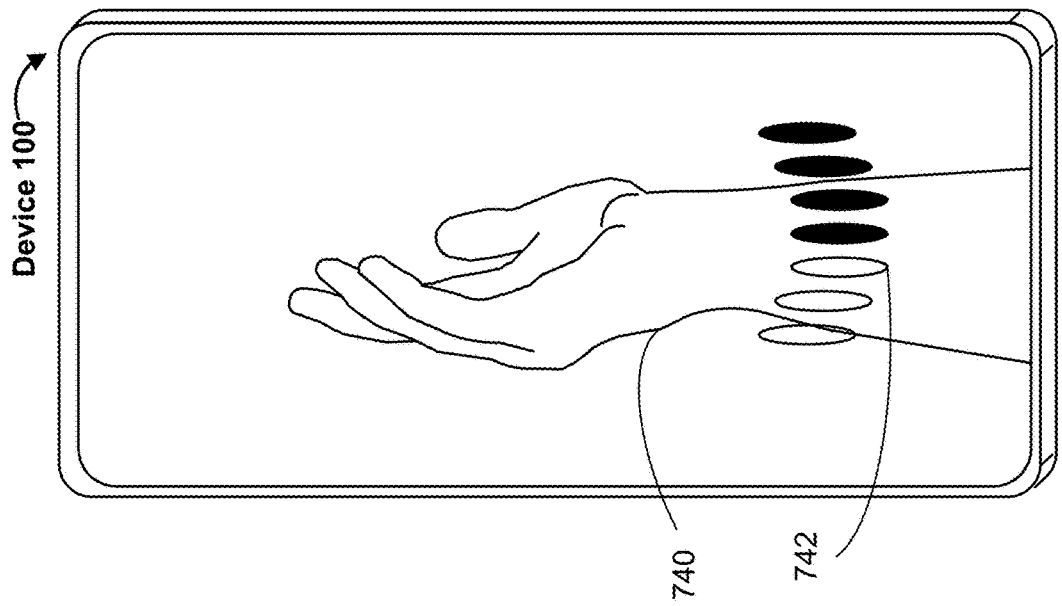
Figure 7J:
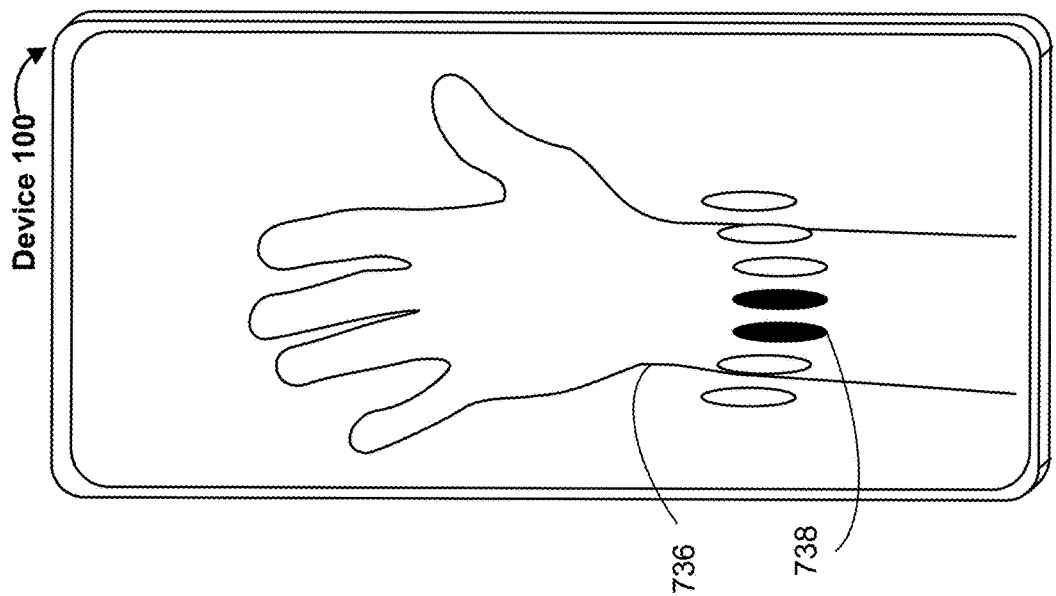
Figure 7M:
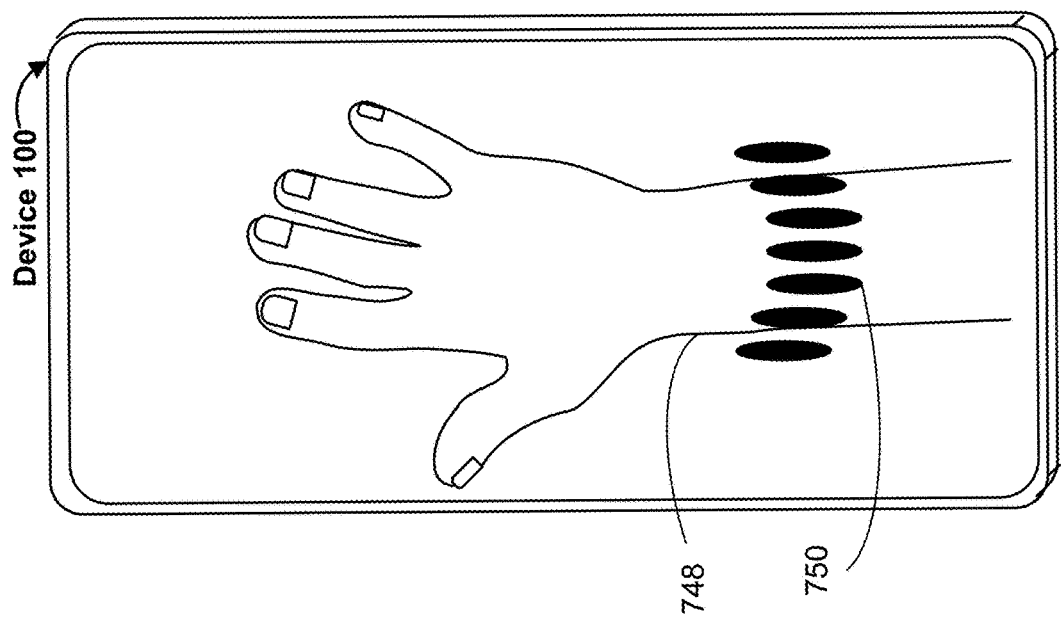
Figure 7L:
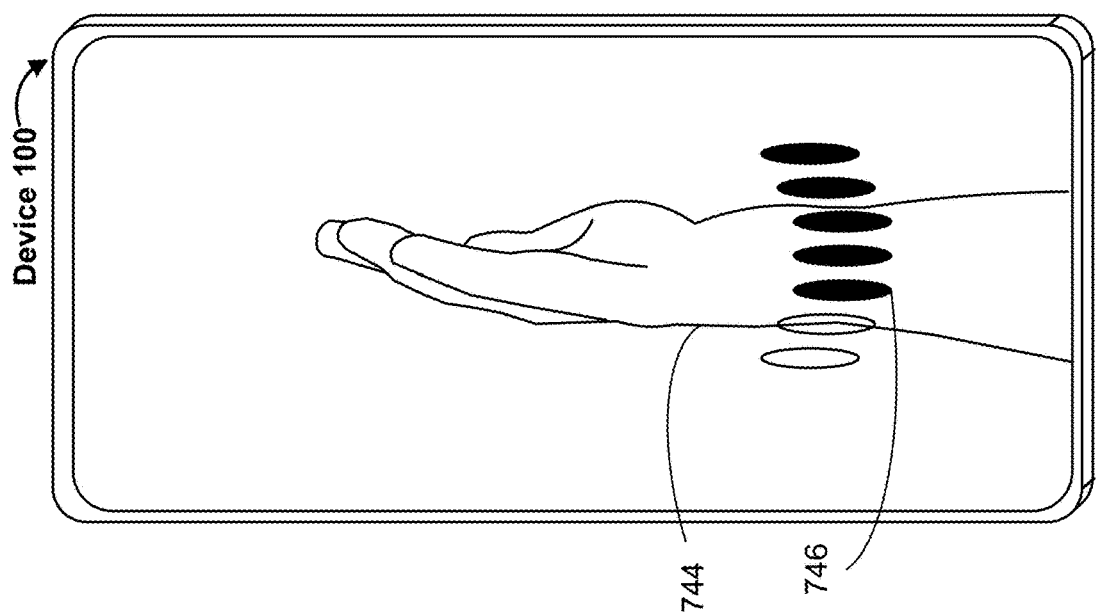
Figure 7N:
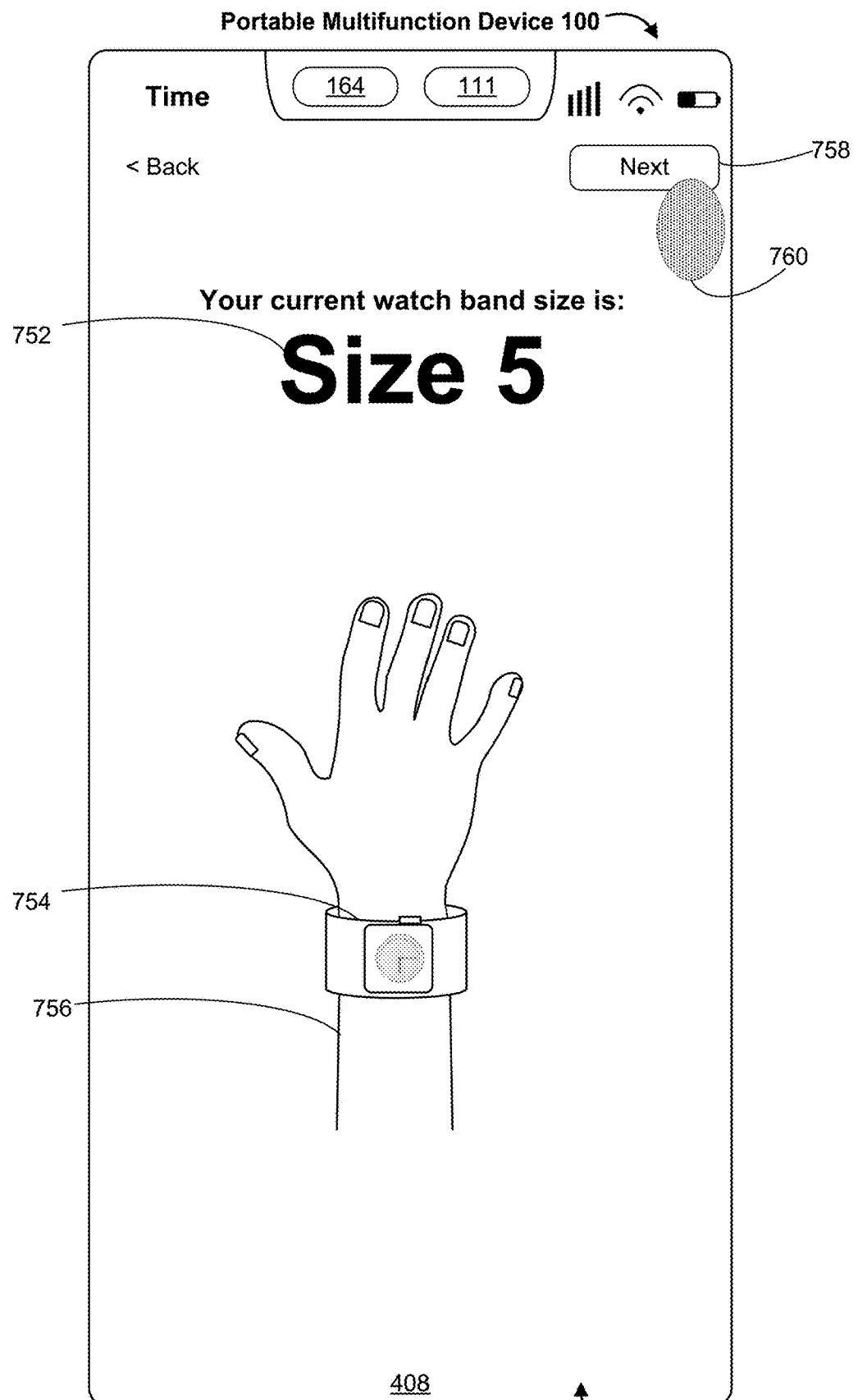
Figure 7O:
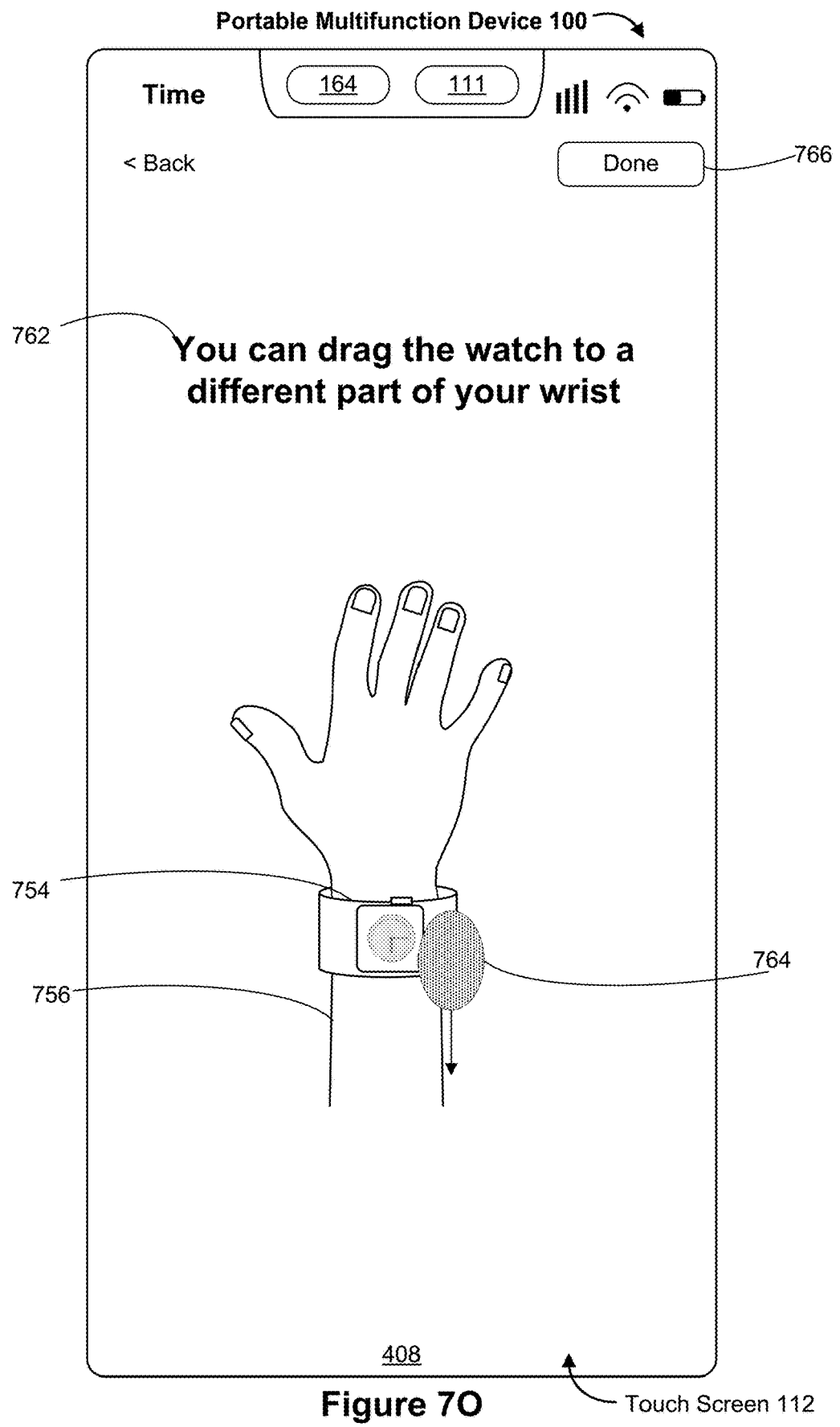
Figure 7P:
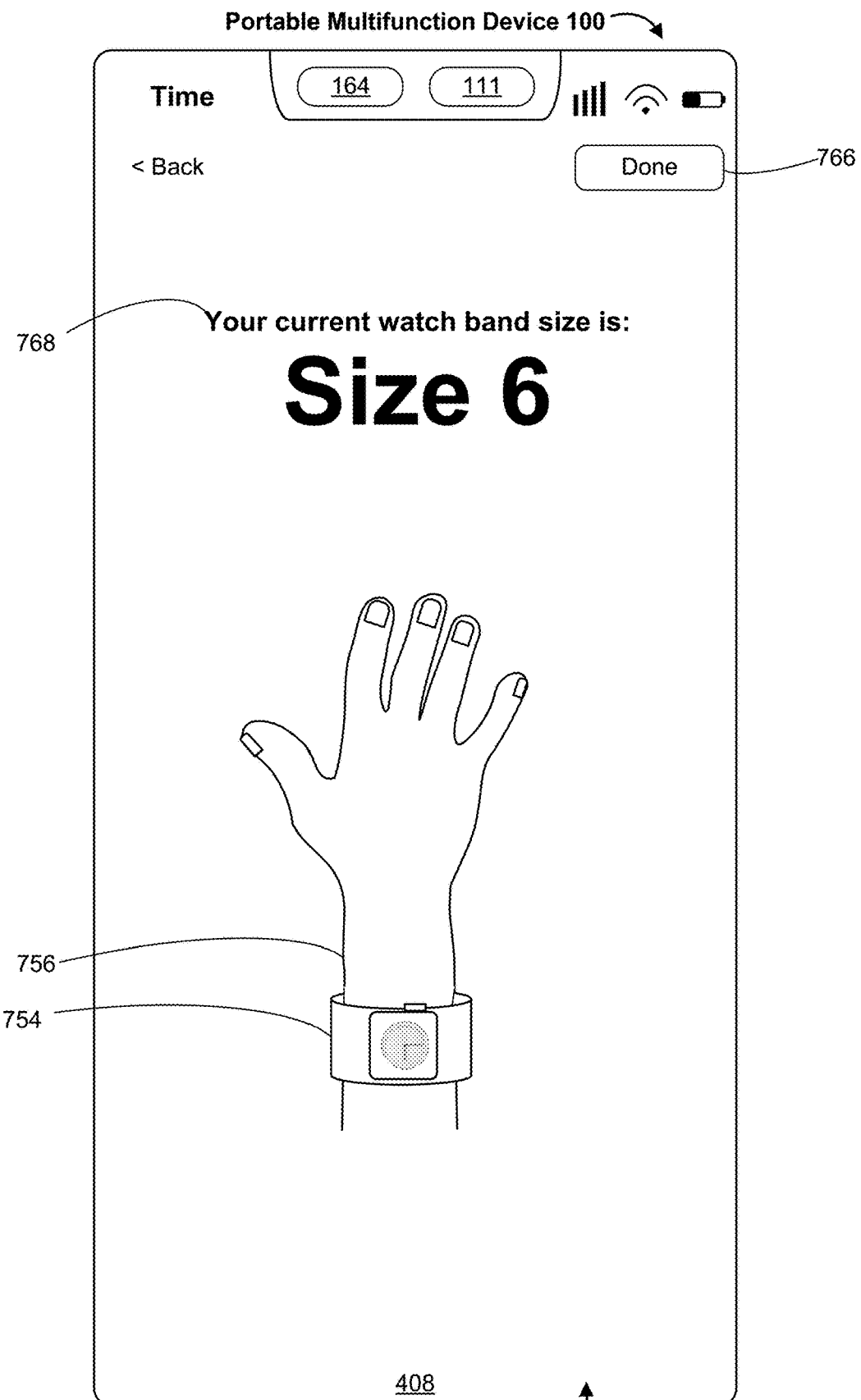
Figure 7Q:
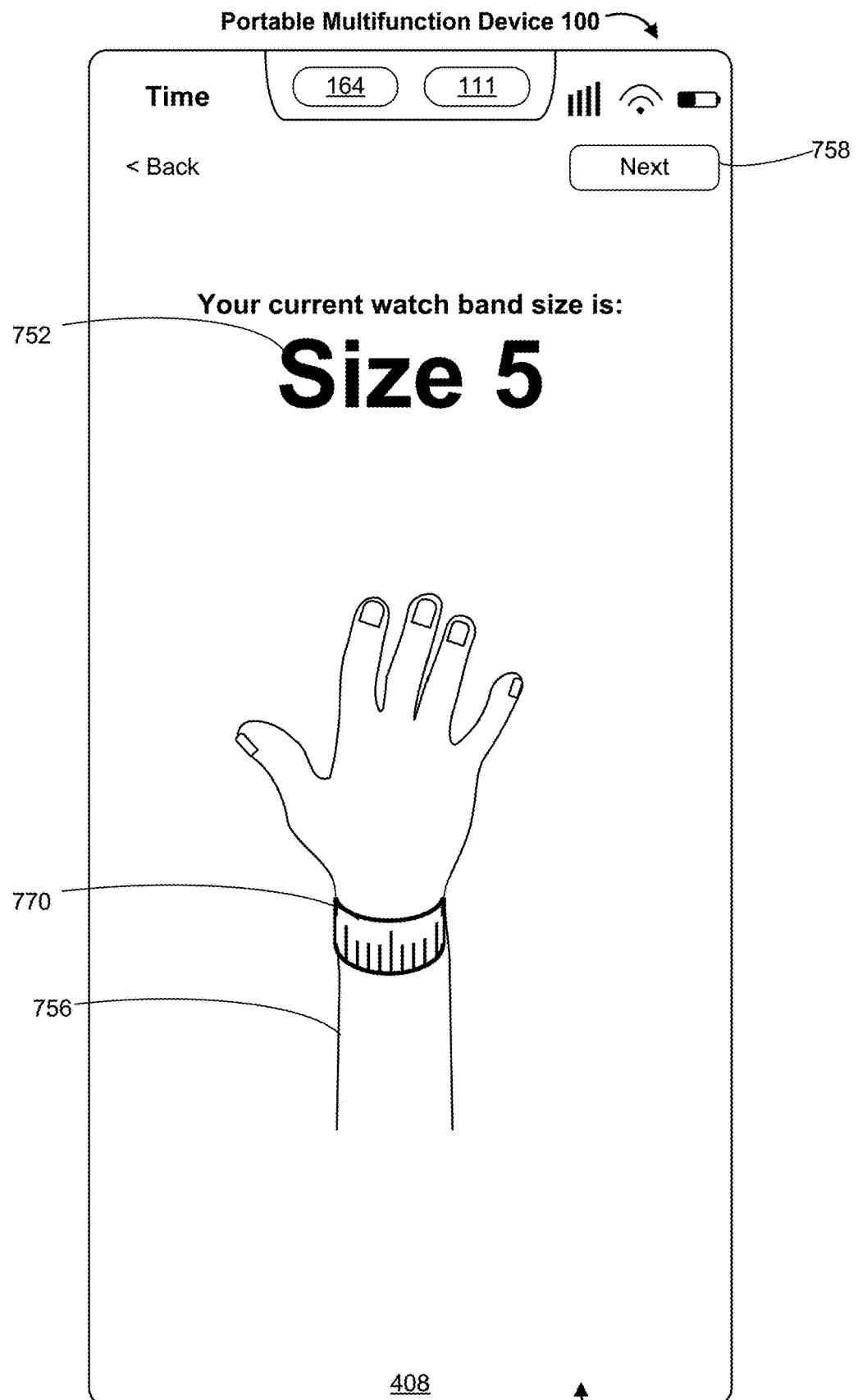
Figure 7R:
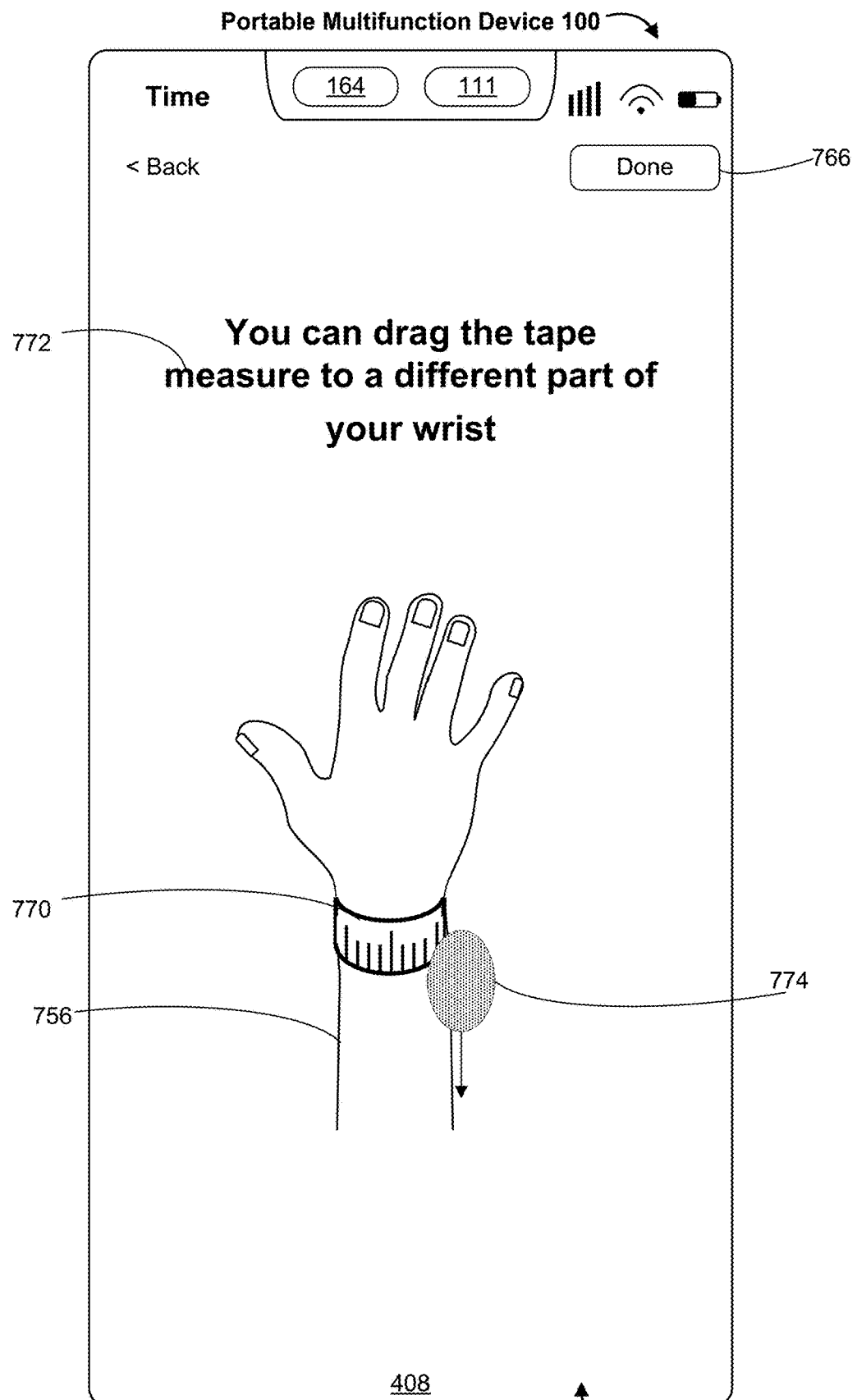
Figure 7S:
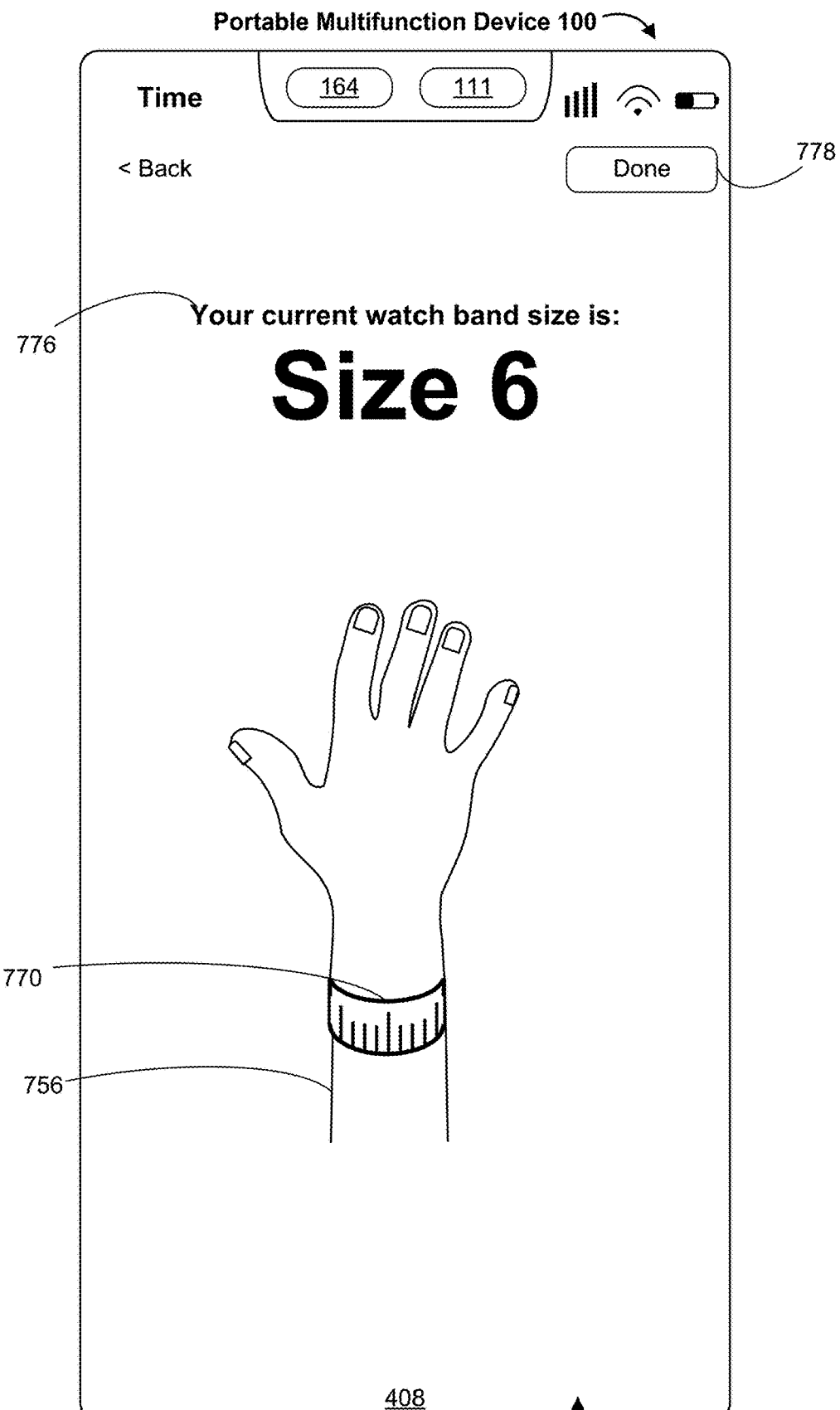
Figure 7T:
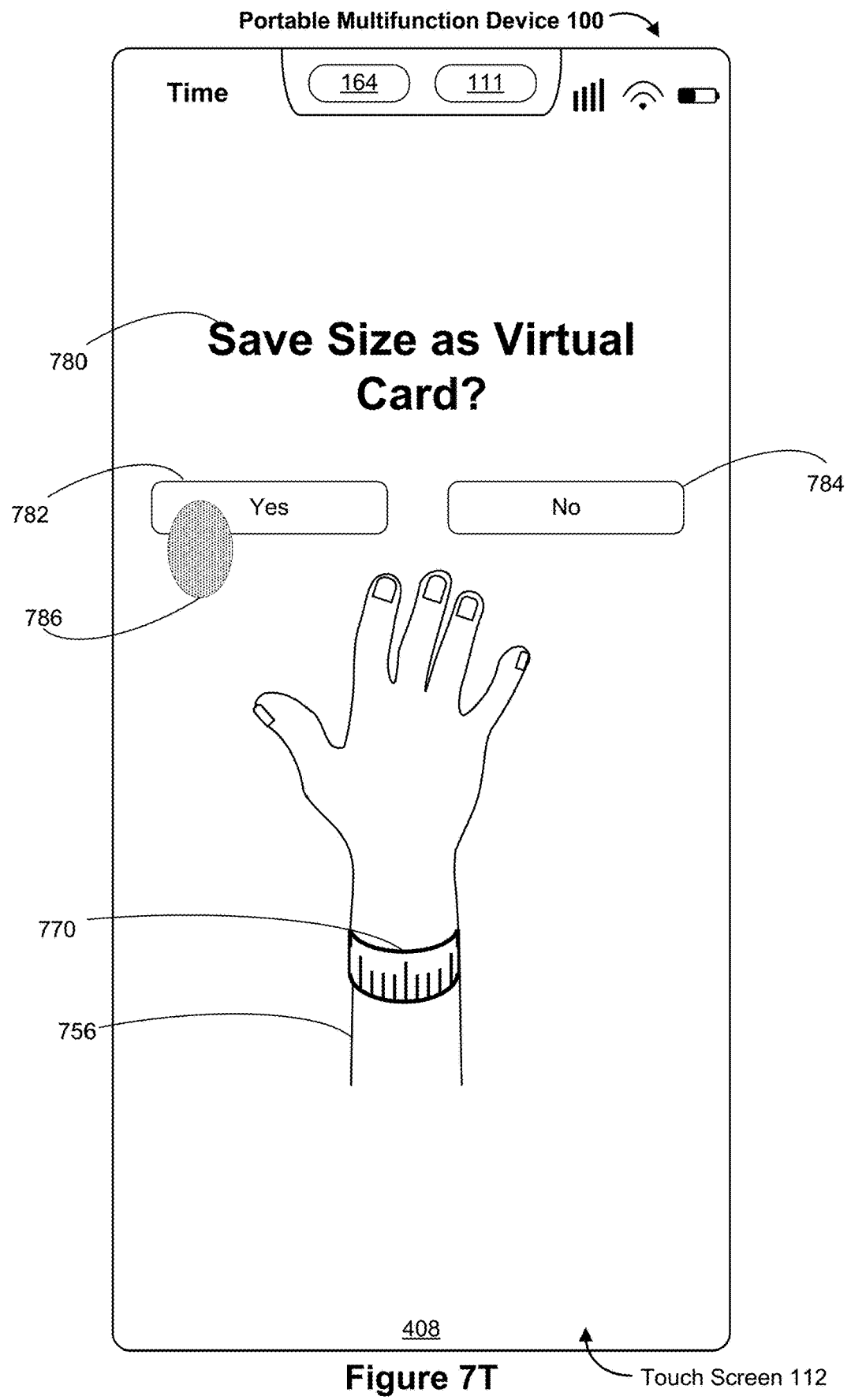

FIGS. 7A-7T illustrate example user interfaces for obtaining a measurement (e.g., by prompting the user to position and move the user's body part, and scanning the user's body part) in accordance with some embodiments. FIGS. 8A-8F illustrate example user interfaces for storing measurement information for the body part of the user in accordance with some embodiments. The user interfaces in these figures are used to illustrate the processes described below, including the processes in FIGS. 9A-9C, 10A-10D, 11A-11C and 12A-12D. For convenience of explanation, some of the embodiments will be discussed with reference to operations performed on a device with a touch-sensitive display system 112. In such embodiments, the focus selector is, optionally: a respective finger or stylus contact, a representative point corresponding to a finger or stylus contact (e.g., a centroid of a respective contact or a point associated with a respective contact), or a centroid of two or more contacts detected on the touch-sensitive display system 112. However, analogous operations are, optionally, performed on a device with a display 450 and a separate touch-sensitive surface 451 in response to detecting the contacts on the touch-sensitive surface 451 while displaying the user interfaces shown in the figures on the display 450, along with a focus selector.

FIGS. 5A-5P illustrate example user interfaces for measuring a body part of a user in accordance with some embodiments.

FIG. 5A illustrates a user interface for a menu of applications on portable multifunction device 100 in accordance with some embodiments. Similar user interfaces are, optionally, implemented on device 300. In some embodiments, the applications provided on the user interface in FIG. 5A include the applications as described with reference to FIG. 4A. A user input 502 is detected by the device on an application icon 448, labeled "Measure." In some embodiments, in response to the user input 502 that is detected on the "Measure" icon, a "Measure" application is launched on the device 100. In some embodiments, within the launched "Measure" application, a user interface is provided within a "Measure" application to initiate measurement of a user's body part. For example, the user interface illustrated in FIG. 5D is optionally presented by the device to the user after launching the "Measure" application.

FIG. 5B illustrates a user input 504 that is detected at a location within the user interface for the menu of applications that corresponds to application icon 449 labeled "Electronics Store." In some embodiments, in response to the device detecting user input 504, an application (e.g., "Electronics Store") is launched by the device.

FIG. 5C illustrates an example user interface that is displayed by the device in the application that is launched in response to user input 504 (e.g., and/or user input 502). For example, FIG. 5C illustrates an example user interface for shopping for an accessory (e.g., a watch and/or a watch band). In some embodiments, the user interface for shopping for an accessory includes an option to measure a size (e.g., of a body part) for the accessory. For example, FIG. 5C illustrates a user interface for shopping for a watch, and provides a button 506 (e.g., a user-selectable affordance or button) to measure a band (e.g., a watch band) size of the user. In some embodiments, the user selects the button 506 via user input 508 (e.g., a tap input).

FIG. 5D illustrates an example user interface 510 that is displayed by the device in response to detecting selection of button 506. It will be understood that, in some embodiments, FIG. 5D is launched from a different application (e.g., and/or after displaying different user interfaces) than the examples shown in FIGS. 5B-5C. For example, in some embodiments, FIG. 5D is launched from the "Measure" application selected in FIG. 5A.

FIG. 5D illustrates a user interface 510 for prompting the user to select a "left" button 514 or a "right" button 516 to indicate which wrist (e.g., left or right) will be measured. In some embodiments, the user interface includes instructions, such as text instructions 512, to "Select your watch-wearing wrist." In some embodiments, the user interface displays a representation of the body part 518 to be measured. For example, for measuring a watch band, the device displays a representation (e.g., an image) of a left and a right forearm, wrist and/or hand. It will be understood that depending on the accessory (e.g., and corresponding body part of the user to be measured), the instructions and/or exemplary displayed representation of the body part change in accordance with the selected accessory.

FIG. 5E illustrates a user input 522 selecting the "Left" button, indicating that the user wears a watch on the user's left wrist (e.g., and/or indicating that the left wrist of the user is the body part to be measured).

In some embodiments, user interface 520 displays a background that is distinct from the background displayed in user interface 510. For example, a color of the background changes (e.g., as illustrated by the change in fill pattern shown in FIGS. 5D-5F) while continuing to display the "left" and "right" buttons and/or the representation of the body part (e.g., the background color changes even as the other elements of the user interface remain the same). In some embodiments, a color of the background changes throughout display of the various user interfaces for providing instructions for initiating measurement of a body part. For example, FIG. 5F illustrates additional (e.g., different) instructions (e.g., "Lay device on flat surface") that are displayed by the device, in addition to the instructions displayed in FIGS. 5D and 5E (e.g., "Select your watch-wearing wrist"); however each of the user interfaces illustrated in FIGS. 5D-5F correspond to instructional user interfaces for initiating measurement of the body part. In some embodiments, the background color changes in accordance with an amount of time (e.g., the color changes every 1 second, 2 seconds, 5 seconds, 1 minute, 5 minutes, etc.). In some embodiments, a predefined number of colors repeat (e.g., cycle) such that the same color is re-displayed after the remaining colors have been displayed.

In some embodiments, in response to the device detecting the user input 522 selecting the "left" or "right" wrist, the user interface 524 illustrated in FIG. 5F is displayed by the device. FIG. 5F illustrates a user interface that provides instructions (e.g., text instructions 526 and/or instructions in the form of an animation 528) to the user on how to measure the user's body part with the device. For example, FIG. 5F includes text instructions 526 the user to "1. Lay device on flat surface" and "2. Place your left hand over the device and rotate your hand". FIG. 5F also optionally illustrates an animation 528 that shows a representation of a forearm/hand being placed over the device 100 (and/or an animation of the forearm/hand rotating).

As described with reference to FIG. 1A, in some embodiments, device 100 includes one or more optical sensors 164 (e.g., as part of one or more cameras). In some embodiments, the one or more optical sensors 164 are used to detect whether the user has placed the user's hand over the device.

FIGS. 5G-5J illustrate a physical environment 531 and example user interfaces displayed by the device as a user moves the user's hand 532 to different positions (e.g., relative to device 100) within the physical environment. In some embodiments, device 100 displays visual cues (e.g., using fading, translucency, colors, etc.) to indicate, to the user, a proper position of the user's hand, relative to the device 100. For example, the proper position of the user's hand is defined by a distance (e.g., or by a predefined range of distances) between the device 100 and the user's hand 532 as well as an orientation of the user's hand relative to device 100. For example, the orientation is determined by a predefined angle (e.g., or range of angles) formed between the user's hand and the device. In an example, a proper orientation of the user's hand corresponds to the user's palm being substantially parallel to the device. In some embodiments, the proper position of the user's hand is further defined by the user's hand being centered (e.g., laterally) within the field of view of the one or more cameras.

FIG. 5G illustrates a physical environment 531 that includes device 100 positioned flat on a table, a user's hand 532 hovering over the device 100, and a ceiling fan 530. In some embodiments, the user's hand 532 and the ceiling fan 530 are in the field of view of one or more cameras of device 100 (e.g., detected by one or more optical sensors 164). In some embodiments, device 100 displays a representation of the field of view of the one or more cameras of the device. For example, the user interface displayed on device 100 is illustrated on the left, in FIG. 5G. The user interface includes a representation of the user's hand 536 and a representation of the ceiling fan 534 that are within the field of view of the one or more cameras of device 100.

FIG. 5H illustrates the user moving the user's hand 532 closer to the device 100, as compared to placement of the hand in FIG. 5G. In some embodiments, the representation of the user's hand 536 displayed on the user interface of device 100 is updated by the device in accordance with the movement of the user's hand 532. For example, as the user moves hand 532 closer to device 100, the representation of the user's hand 536 is updated to a larger representation of the user's hand 540 in FIG. 5H (e.g., as a camera feed of a user's hand would appear larger when the user's hand gets closer to the camera). In some embodiments, as the user's hand 532 moves with respect to the device (e.g., with respect to the one or more cameras), the representation of the user's hand is updated in accordance with the movement of the user's hand (e.g., in the physical environment). In some embodiments, in accordance with the user's hand moving closer to a proper position relative to device 100 (e.g., where the proper position is determined by a distance and/or orientation of the user's hand to be used for measurement), device 100 begins to fade out (e.g., mask out) the background (e.g., objects in the physical environment that are within the field of view of the one or more cameras). For example, FIG. 5H illustrates the representation of ceiling fan 538 fading out (e.g., as indicated by the shaded pattern of the representation) in accordance with the user's hand 532 moving closer to the proper position (e.g., while the user adjusts the user's hand position). For example, once the user's hand is moved into the proper position, the background objects are no longer displayed (e.g., completely faded out), as described with reference to FIG. 5J.

In some embodiments, the representation of the user's hand 544 is displayed as translucent (e.g., and/or faded) as the user moves the user's hand to different positions relative to device 100, as illustrated in FIG. 5I. In some embodiments, the representation of the user's hand transitions from translucent to not translucent in accordance with a determination that the user's hand is in the proper position.

FIG. 5J illustrates an example user interface of the user's hand 532 in a proper position relative to device 100. In some embodiments, in accordance with a determination by the device that the user's hand is in the proper position, a background (e.g., including any physical objects in the physical environment that are in the field of view of the one or more cameras) is removed and replaced with an artificial or virtual background, sometimes herein called a displayed background 546. In some embodiments, the displayed background 546 comprises a color (e.g., selected from the colors displayed on the user interface as described with reference to FIGS. 5D-5F). Accordingly, in accordance with a determination by the device that the user's hand is in the proper position, device 100 displays a user interface that includes the representation of the user's hand 548 without a representation of other objects (e.g., ceiling fan 530) in the field of view of the one or more cameras.

FIGS. 5K-5N illustrate a physical environment 531 and exemplary user interfaces for displaying error conditions to the user. As explained above, before measuring the portion of the user's body part, the body part of the user must be placed in a proper position relative to the device. In some embodiments, while the user's body part (e.g., hand) is within the view of the one or more cameras, a representation of the user's body part is displayed by device 100. In some embodiments, while the user's body part is within the view of the one or more cameras, but is not in the proper position relative to the device, the representation of the user's body part is modified by the device such that a user is able to determine that the body part is not yet in the proper position. For example, in FIGS. 5K-5N, the representation of the user's body part (e.g., representation 552) is displayed as a faded (e.g., at least partially translucent) representation of the user's body part (e.g., as illustrated by the shaded pattern in FIGS. 5K-5N).

FIG. 5K illustrates user's hand 532 positioned farther away from device 100 than the proper position (e.g., the proper position as shown in FIG. 5J). In some embodiments, device 100 displays an indication that the user's hand is not in the proper position. For example, a textual indication 550 is displayed by device 100 ("Hand is too far") indicating that the user's hand is farther away from the device and needs to be moved closer in order to satisfy the proper position.

FIG. 5L illustrates that user's hand 532 is positioned closer to device 100, as compared to the placement of user's hand 532 in FIG. 5K, but in this example, closer to device than a (predefined) proper position. Because user's hand 532 is positioned closer to the device than the proper position, the representation of the user's hand 556 is displayed by the device as faded and a textual indication 554 is displayed by device 100 ("Hand is too close") to indicate that the user's hand is closer to the device than it should be in the proper position. Also note that as the user's hand 532 moves closer to device 100, the representation of the user's hand 556 is displayed by the device larger than the representation of the user's hand 552 when the user's hand 532 is farther away from the device (e.g., as shown in FIG. 5K).

FIG. 5M illustrates an error condition in which the pose of device 100 is not correct. For example, device 100 is tilted on the table. In some embodiments, the orientation of device 100 is determined by one or more accelerometers 167, gyroscopes 168, and/or magnetometers 169 (e.g., as part of an inertial measurement unit (IMU) of device 100) for obtaining information concerning the pose (e.g., position and orientation or attitude) of the device. For example, in some embodiments, the device is considered to have a proper pose when the device is "flat." The device is determined by the device to be "flat" in accordance with a determination that its pose is substantially parallel to the ground (e.g., or other surface, such as a table). In some embodiments, a predefined angle (or range of angles) of the device may be used in determining whether the device is in a proper pose for initiating measurement.

FIG. 5N illustrates an error condition in which the user's hand 566 also includes an accessory 562 (e.g., a bracelet, a watch, etc.) in the physical environment. In some embodiments, in accordance with a determination that the user's hand 566 includes an accessory (e.g., an accessory that is in the field of view of the one or more cameras; or, in another example, an accessory that is determined by the device to be at a location or position that might interfere with determining an accurate measurement of the body part to be measured), the device displays an error, such as textual indication 564 ("Remove jewelry"), instructing the user to remove the accessory before the device will initiate measuring the user's wrist.

Figure 5O:
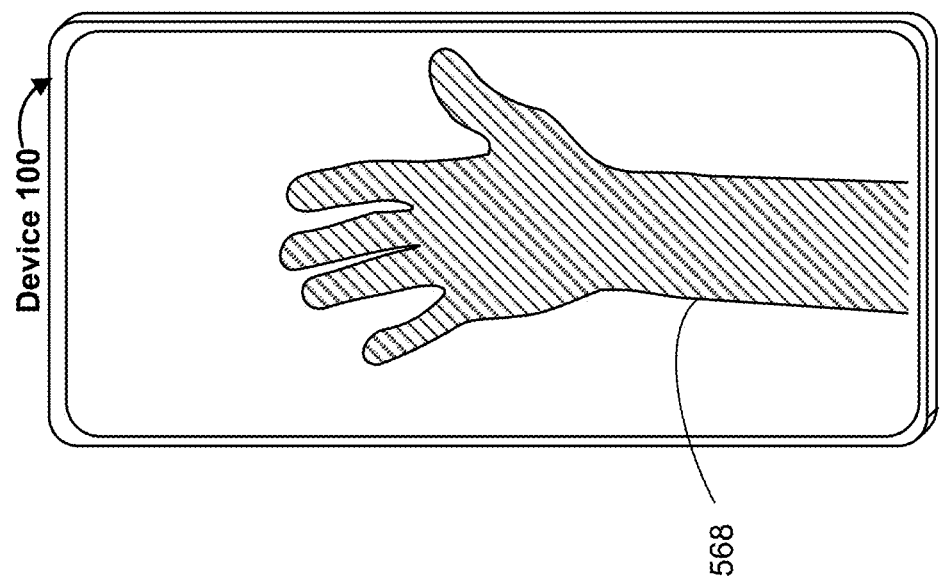

FIG. 5O illustrates a faded representation of the user's hand 568 without displaying a textual indication describing an error. For example, device 100 displays the faded representation of the user's hand to indicate that the user's hand is not in the proper position to initiate measurement (e.g., without an additional indication indicating what the user must do to obtain proper position). Accordingly, the textual indications that appear in accordance with a determination that the user's hand is not in the proper position, as described with reference to FIGS. 5K-5N, are optionally not displayed.

FIG. 5P illustrates an optional indication of the user's hand being in the proper position. For example, in accordance with the determination by the device that the user's hand is in the proper position to initiate measurement (e.g., at a predefined distance and/or at a predefined orientation relative to device 100), an animated outline 570 is optionally displayed by device 100. In some embodiments, animated outline 570 comprises a same shape as the representation of the user's hand 572 (e.g., the animated outline follows the contours of the representation of the user's hand). In addition, in some embodiments, in accordance with a determination that the user's hand is in the proper position, the representation of the user's hand 572 is no longer displayed as translucent (e.g., as indicated by the fill pattern illustrated in FIG. 5O being removed in FIG. 5P).

FIGS. 6A-6N illustrate example user interfaces for measuring a portion of a user's body part, using images of the body part captured by one or more cameras of an electronic device. The one or more captured images optionally include depth information, from one or more depth sensors of the electronic device, to facilitate determination of the measurement by the device. For example, FIGS. 6A-6B illustrate instructional user interfaces that explain, to the user, a first set of actions (e.g., aligning dot 606 with target 608) that the user must take in order to have the user's wrist measured by device 100. FIG. 6A illustrates a user interface that includes instructions, optionally including textual instruction 602 ("Move your hand to place the dot in the circle"), a non-textual instruction 604 (e.g., an arrow indicating in which direction to move the hand/wrist), and/or an animated instruction in which a representation 610 of a hand and wrist are animated to move in the direction of the arrow. In some embodiments, the animation includes displaying dot 606 (e.g., a first visual indicator) move into alignment with target 608.

FIG. 6B illustrates a user interface that includes instructions for the user to perform a second set of actions (e.g., aligning dot 612 with target 608) after the user has completed the first set of actions indicated by the instructions illustrated in FIG. 6A. For example, after the user places the dot 606 into target 608, as instructed by FIG. 6A, the user is then instructed to place the dot 612 into target 608. In some embodiments, target 608 is located in a same position within the user interfaces illustrated in both FIGS. 6A and 6B (e.g., the target 608 is the same target). FIG. 6B also illustrates a user interface that includes a plurality of instructions, optionally including a textual instruction 616 ("Then, turn your hand to place the dot in the circle"), a non-textual instruction 614 (e.g., an arrow indicating in which direction to turn the hand/wrist), and/or an animated instruction in which a representation 610 of a hand and wrist are animated to move in the direction of the arrow such that dot 612 (e.g., a third visual indicator) moves into target 608.

In some embodiments, the instructions of FIGS. 6A-6B are displayed to the user before measurement of the user's body part begins. For example, the instructions illustrated by FIGS. 6A-6B provide a preview to the user of the steps the user will need to complete in order to obtain a measurement.

FIGS. 6C-6N illustrate exemplary user interfaces that are displayed as the user performs the actions indicated by the instructions presented in FIGS. 6A-6B. For example, FIGS. 6C-6N illustrate the user interfaces that update as the user moves the user's hand and/or wrist to align the dot(s) within the target(s).

Figure 6C:
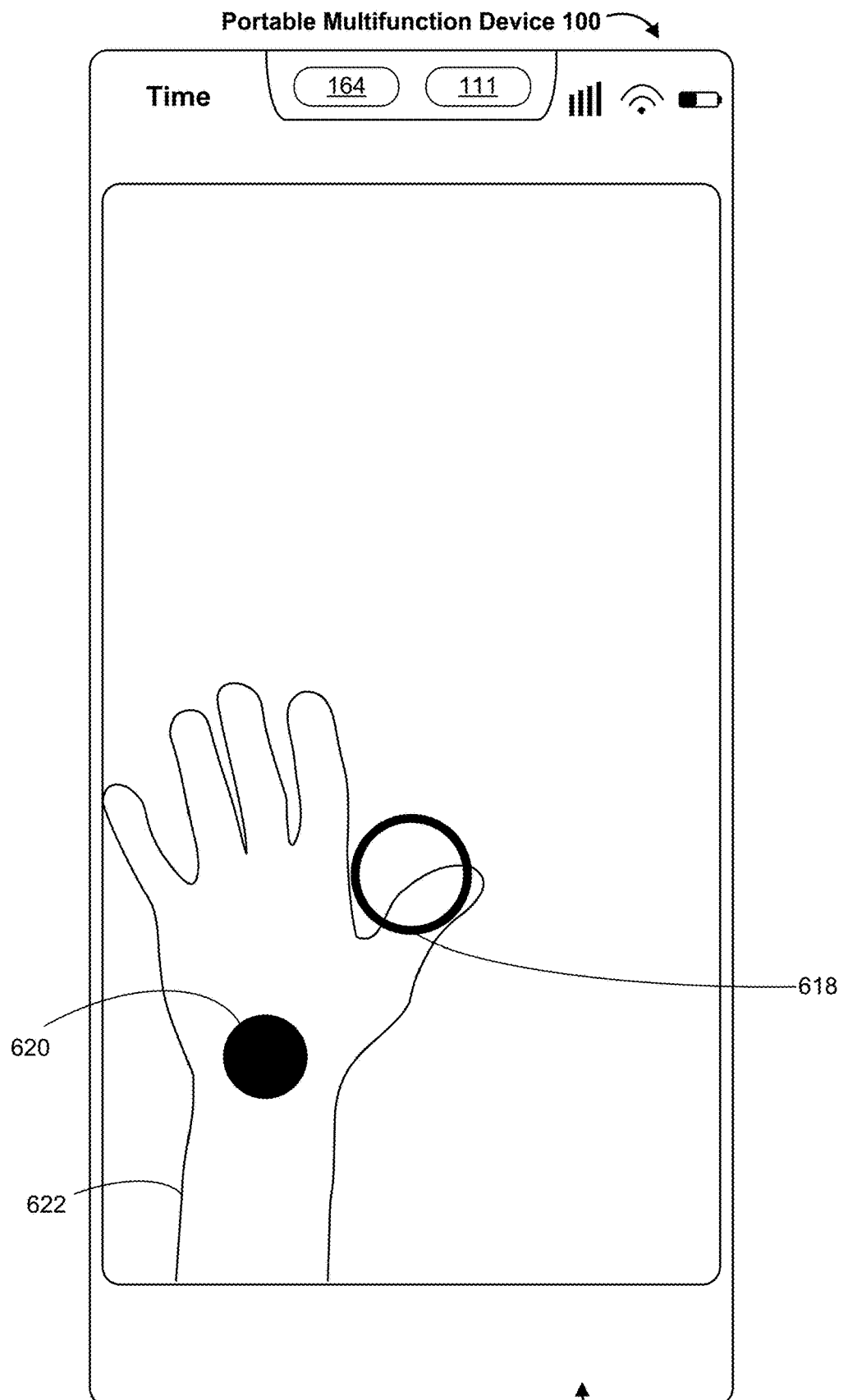

FIG. 6C illustrates a user interface that displays representation 622 of a user's hand and wrist corresponding to the user's hand that is in a field of view of the one or more cameras of device 100. The user interface includes dot 620, which is fixed to the portion of the representation 622 of the user's hand (e.g., dot 620 is fixed to the representation of the user's palm). Thus, as the user's hand moves relative to device 100 (e.g., relative to the field of view of the one or more cameras), displayed representation 622 is updated on the display accordingly and dot 620 is displayed as moving with the user's hand. The user interface also includes target 618, which is displayed at a fixed position within the user interface (e.g., target 618 does not move as the user's hand moves relative to device 100).

Figure 6D:
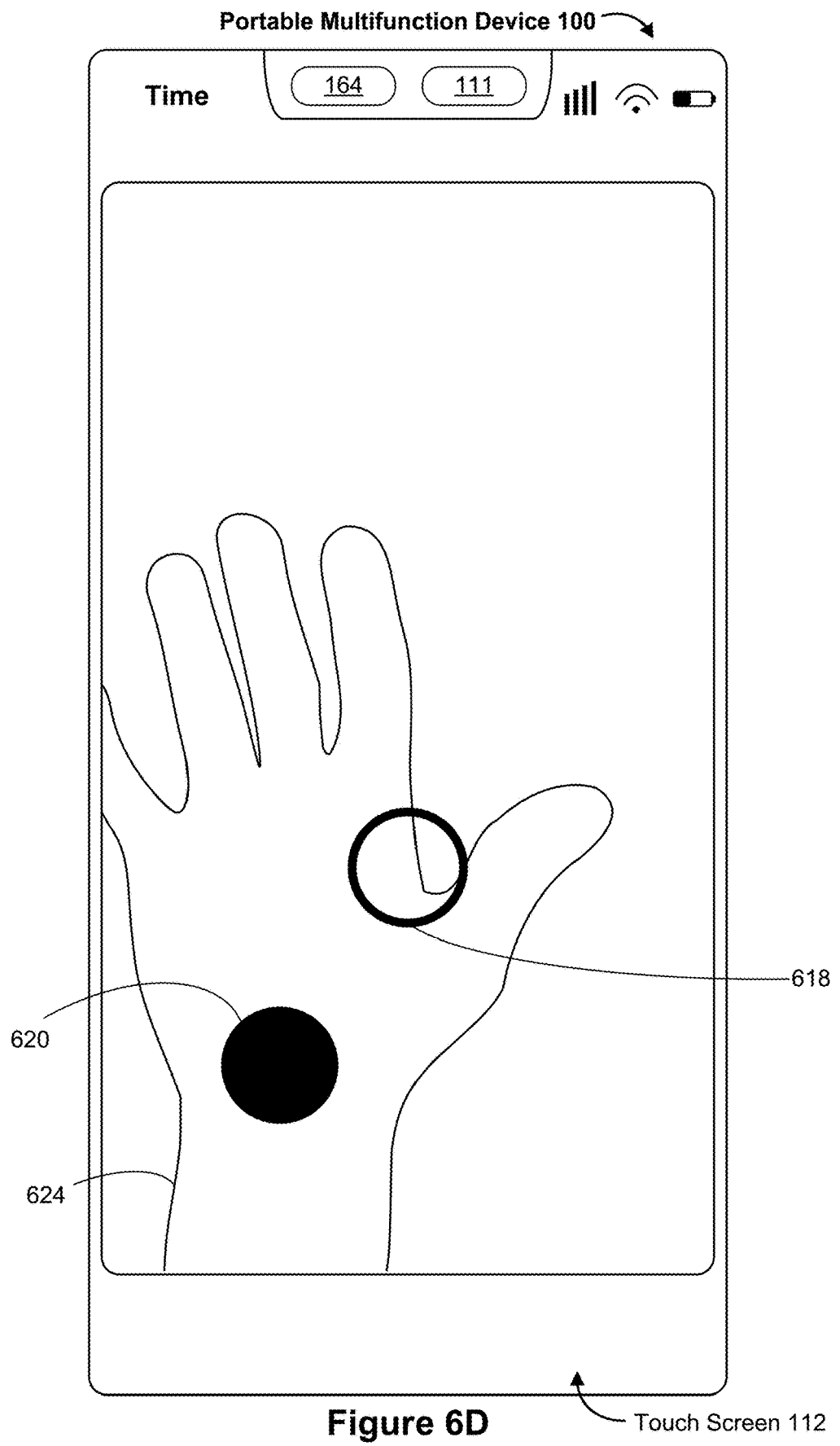

FIG. 6D illustrates a user interface that is displayed in accordance with a user moving the user's hand closer to the device. Thus, representation 624 of the user's hand appears larger than the representation illustrated in FIG. 6C. The size of dot 620 also increases (e.g., proportionally) in accordance with the increase in size of the representation 624. Target 618 remains unchanged in both position and size (e.g., relative to the user interface displayed in FIG. 6C).

Figure 6E:
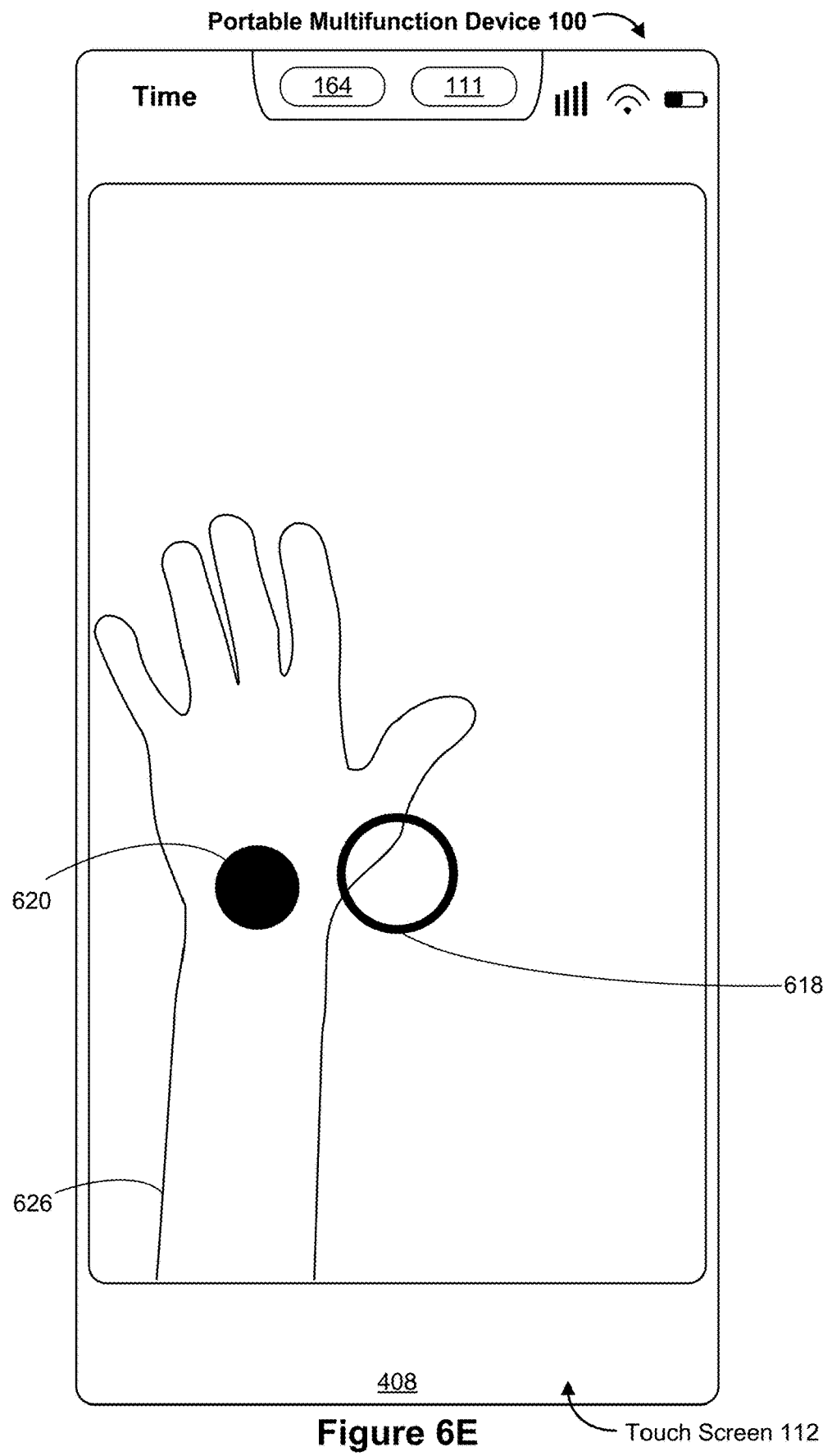

FIG. 6E illustrates a user interface that is displayed in accordance with a user moving the hand farther away from the device (e.g., relative to FIG. 6D). Accordingly, the representation 626 of the user's hand and wrist appears smaller in the user interface, and the size of dot 620 is updated in accordance with the currently displayed size of the representation 626 of the user's hand. Dot 620 also remains in the same relative position to the representation of the user's hand (e.g., dot 620 appears attached, or fixed, to the center of the palm of the representation of the user's hand). Thus, as the user's hand moves away from the device (e.g., changes the distance between the device and the hand; up or down along an axis that is perpendicular to the display of device 100) and/or as the user's hand moves in any direction (e.g., left, right, up, or down along an axis that is parallel to the display of device 100), the size and position of the representation of the user's hand and wrist is updated on the display, and the size and position of dot 620 is also updated on the display.

Because dot 620 is displayed by the device with a location and size that is fixed relative to a portion of the representation of the user's hand, dot 620 can indicate to the user how the user needs to move their hand in order to be in proper position (e.g., such that dot 620 is aligned within target 618). For example, the size of dot 620 indicates to a user whether the user's hand is too close or too far (e.g., whether the dot is too big or too small to fit/align within the target) and location of dot 620 indicates to the user a direction in which the user needs to move their hand relative to the device.

Figure 6F:
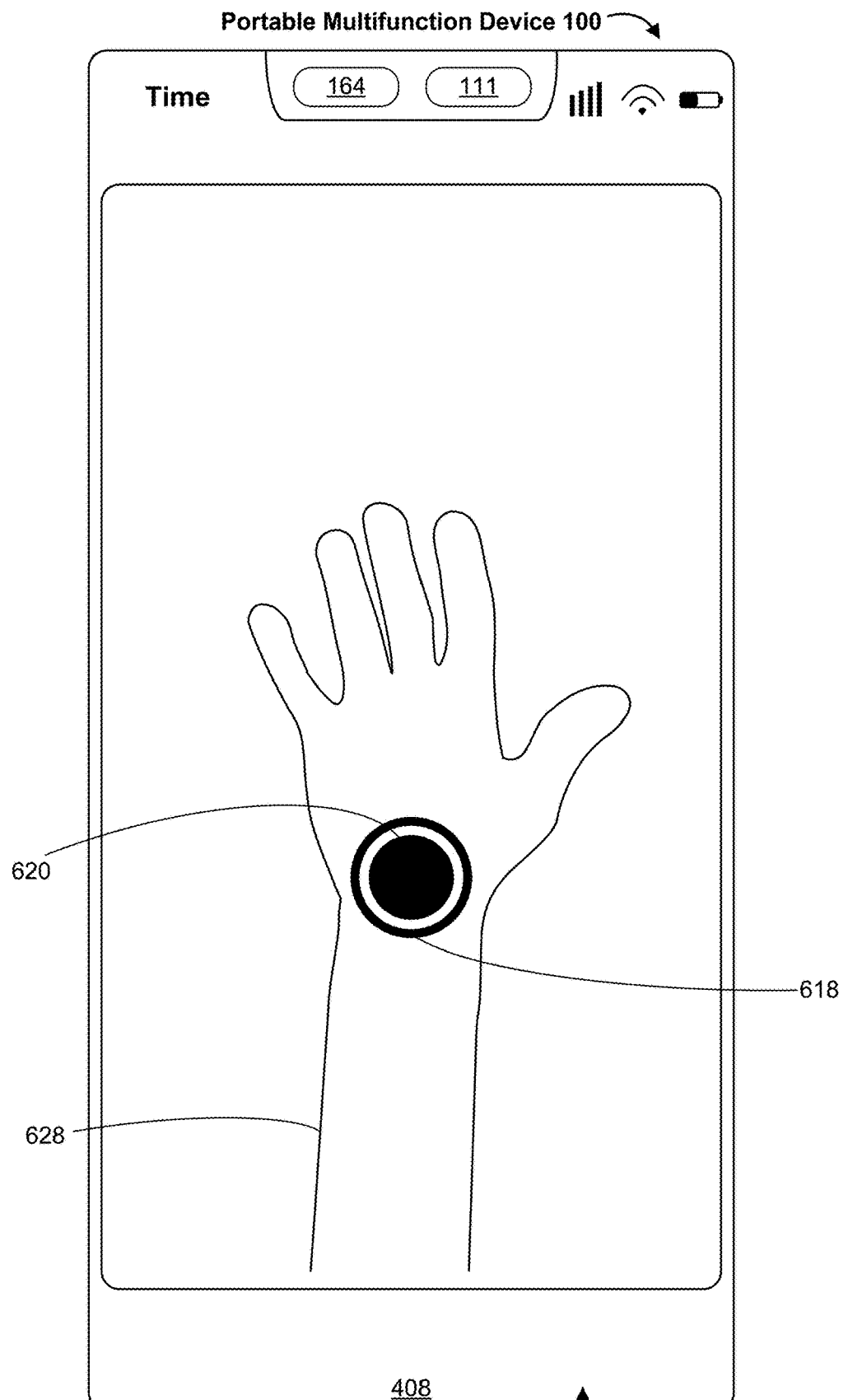

FIG. 6F illustrates the representation 628 of the user's hand in proper position such that dot 620 is aligned (e.g., centered) within target 618.

Figure 6G:
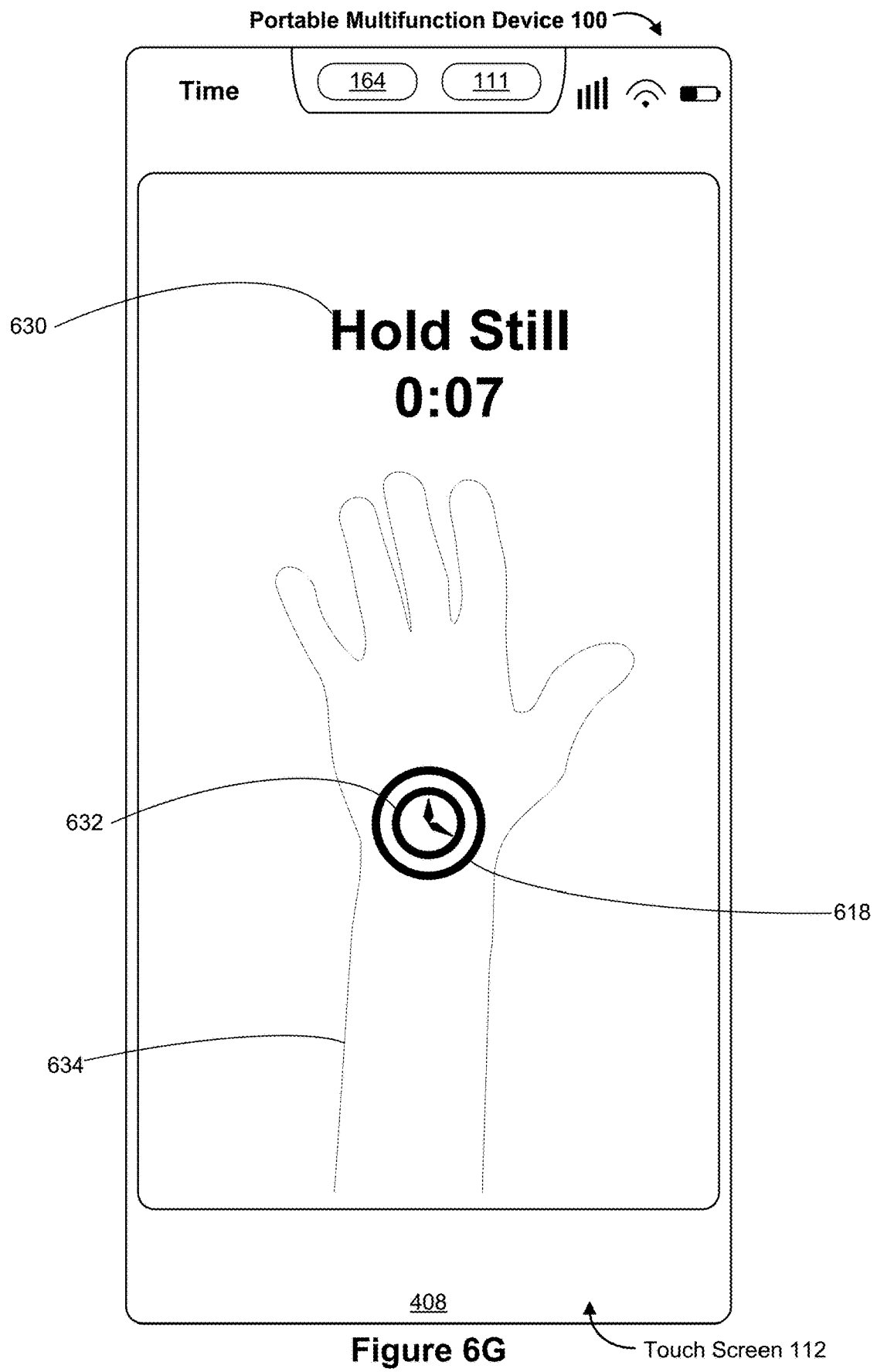

In response to dot 620 properly aligning with target 618, a timer 632 is displayed by the device, as illustrated in FIG. 6G, in accordance with some embodiments. In some embodiments, the display of dot 620 by the device is animated to transition into timer 632. In some embodiments, target 618, optionally, continues to be displayed by the device. In some embodiments, optional textual instructions 630 ("Hold Still 0:07") are displayed to the user in response to the user aligning dot 620 with target 618. In some embodiments, textual instructions 630 include an amount of time (e.g., "0:07") that the user must maintain the position of their hand relative to the device. In some embodiments, the amount of time is updated (e.g., every second) to display a countdown to the user. In some embodiments, device 100 captures one or more images of the user's hand/wrist while the user maintains the position of their hand. In some embodiments, the amount of time displayed is determined by the device in accordance with an amount of time needed for the device to capture the one or more images of the user's hand in the proper position. For example, device 100 uses the one or more images captured to determine a measurement of the user's wrist. As noted elsewhere, the one or more captured images optionally include depth information, from one or more depth sensors, to facilitate determination of the measurement by the device.

Figure 6H:
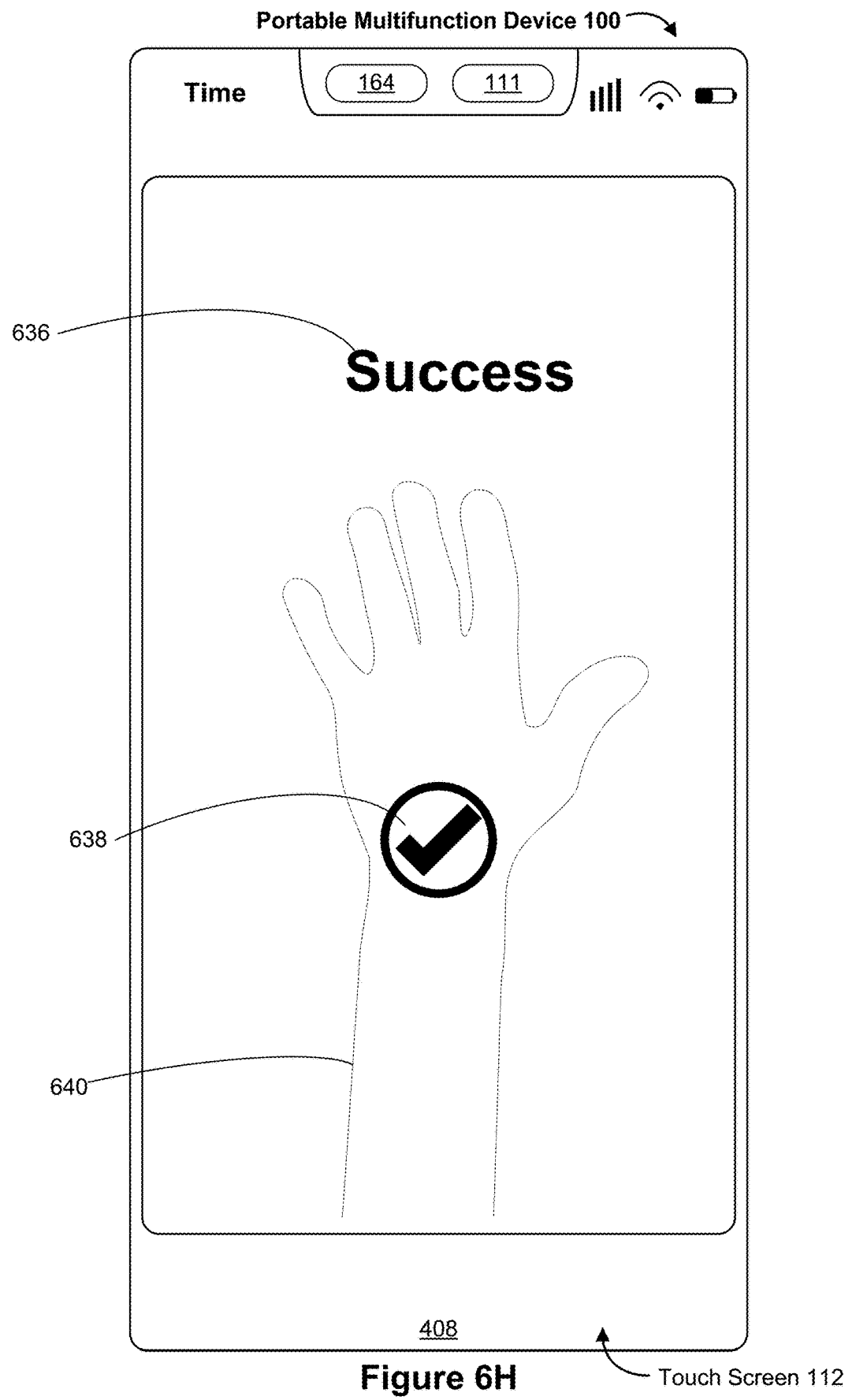

After the amount of time has expired (e.g., the timer goes to "0"), a success message is displayed, as illustrated in FIG. 6H, in accordance with some embodiments. In some embodiments, the success message comprises one or more of: a textual indication 636 ("Success"), a non-textual indication (e.g., check mark 638), and/or a screen flash (e.g., or other animation) to indicate that the amount of time has expired. In some embodiments, the representation 640 of the user's hand and/or wrist continues to be displayed concurrently with the success message(s).

Figure 6I:
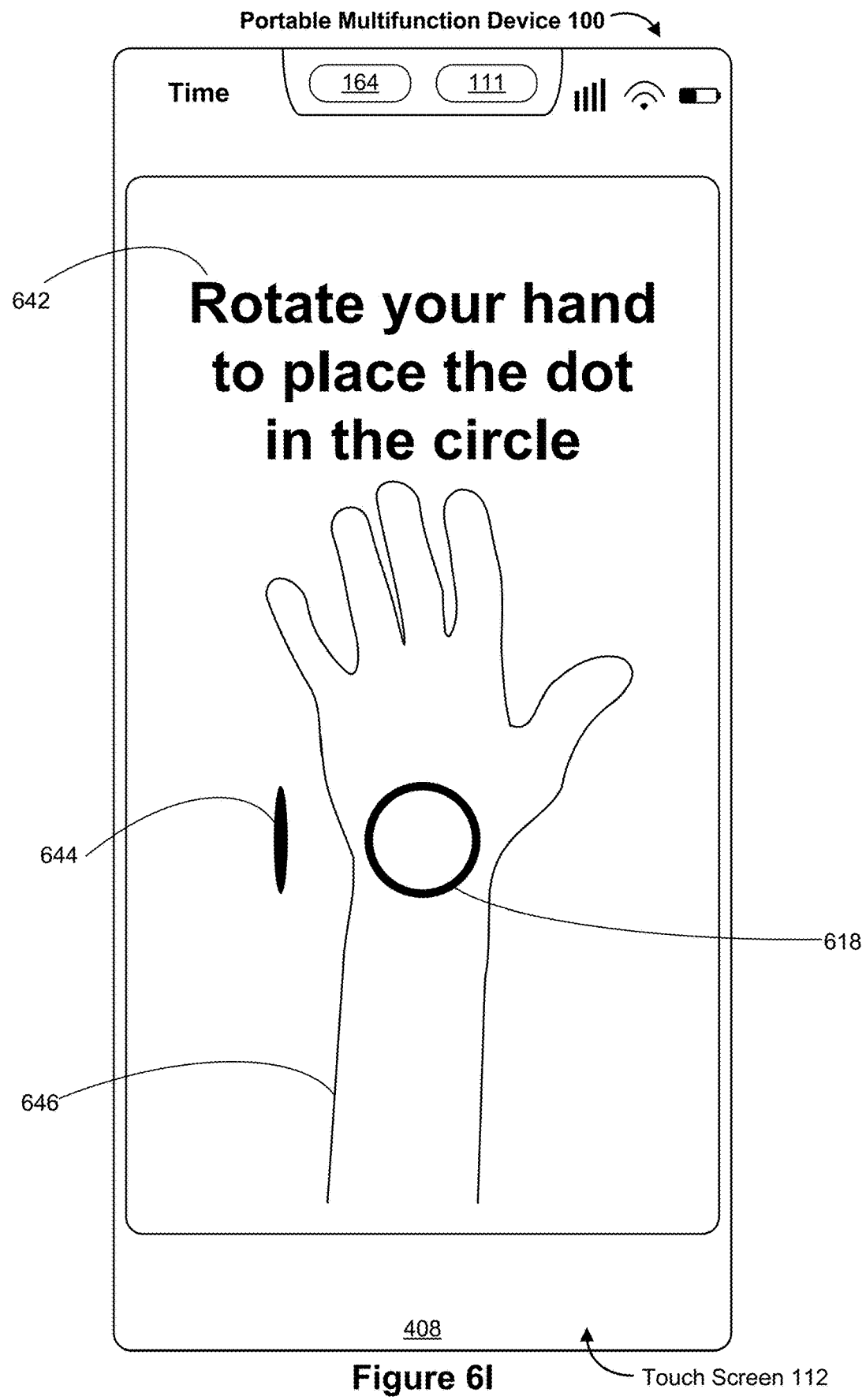

FIG. 6I illustrates an exemplary user interface that is displayed to instruct the user to position the user's hand into a second proper position (e.g., a distinct position from the proper position described with reference to FIGS. 6C-6H). In some embodiments, representation 646 of the user's hand begins in the position illustrated in FIG. 6I as the user's hand was already in that position while obtaining the first "success" message in FIG. 6H. FIG. 6I optionally includes textual instructions 642 ("Rotate your hand to place the dot in the circle") indicating to the user how to move the user's hand to achieve the second proper position.

In some embodiments, dot 644 appears in a fixed position relative to a portion of the representation of the user's hand that is different than the portion of the representation of the user's hand where dot 620 was fixed (e.g., the palm of the representation of the user's hand). For example, FIG. 6I illustrates that dot 644 is fixed to an area next to the side of the user's hand. For example, dot 644 is fixed to a position that is not directly on (e.g., overlapping with) the user's hand, but instead there is space between the fixed position and the user's hand. Furthermore, in this example dot 644's fixed position relative to a portion of the representation of the user's hand is a fixed position in three-dimensional space, and the dot 644 has an orientation such a back surface of dot 644 faces an outer edge of the user's hand and is perpendicular to a front surface of the user's palm. In some embodiments, a side view of dot 644 is displayed in the user interface illustrated in 6I (e.g., dot 644 appears as an oval, indicating that this is a side view of a circular dot), which indicates that the dot needs to be moved (e.g., rotated) with the user's hand in order to view dot 644 from a frontal perspective.

Target 618 is displayed in the user interfaces shown in FIGS. 6I-6L. As the user moves the user's hand (e.g., and the representation of the user's hand is updated in the user interfaces shown in FIGS. 6I-6L), target 618 is maintained in a same position in the user interface. In some embodiments, target 618 as displayed in FIGS. 6I-6L is the same target as the target displayed in FIGS. 6C-6F (e.g., the target is in the same position to guide the user to both the first and second proper positions).

Figure 6J:
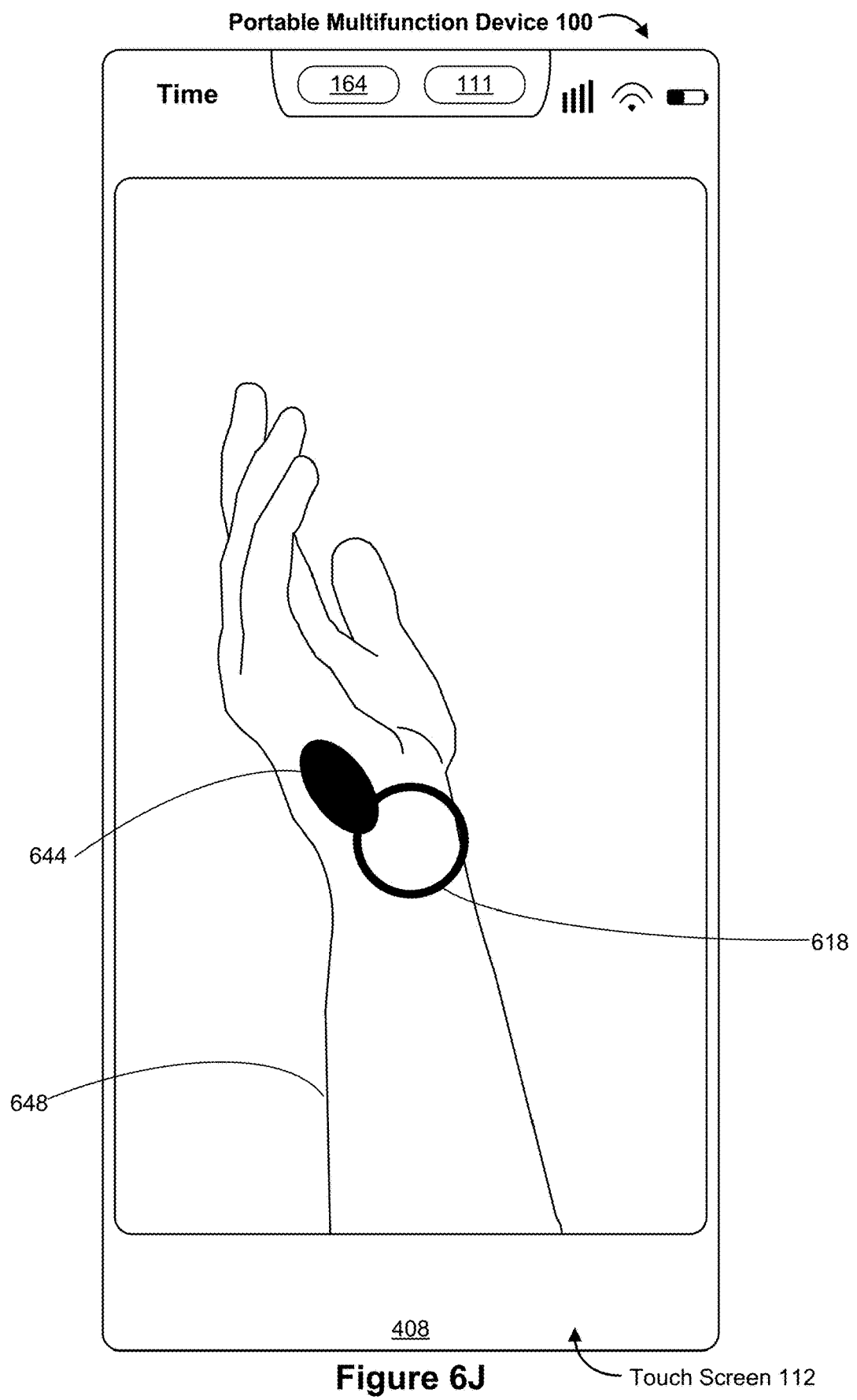

FIG. 6J illustrates an exemplary user interface that is displayed as the user moves (e.g., rotates) the user's hand relative to the device. For example, dot 644 is maintained by the device in a same relative position to the representation of the user's hand. For example, dot 644 appears to float in front of the representation 648 of the user's hand as the user turns the user's hand. In some embodiments, a shape of dot 644 is updated by the device to indicate an angle of where the dot is in a three-dimensional space displayed on the user interface of the device. For example, in FIG. 6J, dot 644 continues to be displayed at a fixed location relative to the representation 648 of the user's hand (e.g., the fixed location as defined by a gap between the dot and the representation and at a particular distance below the pinky finger shown in the representation of the user's hand).

Figure 6K:
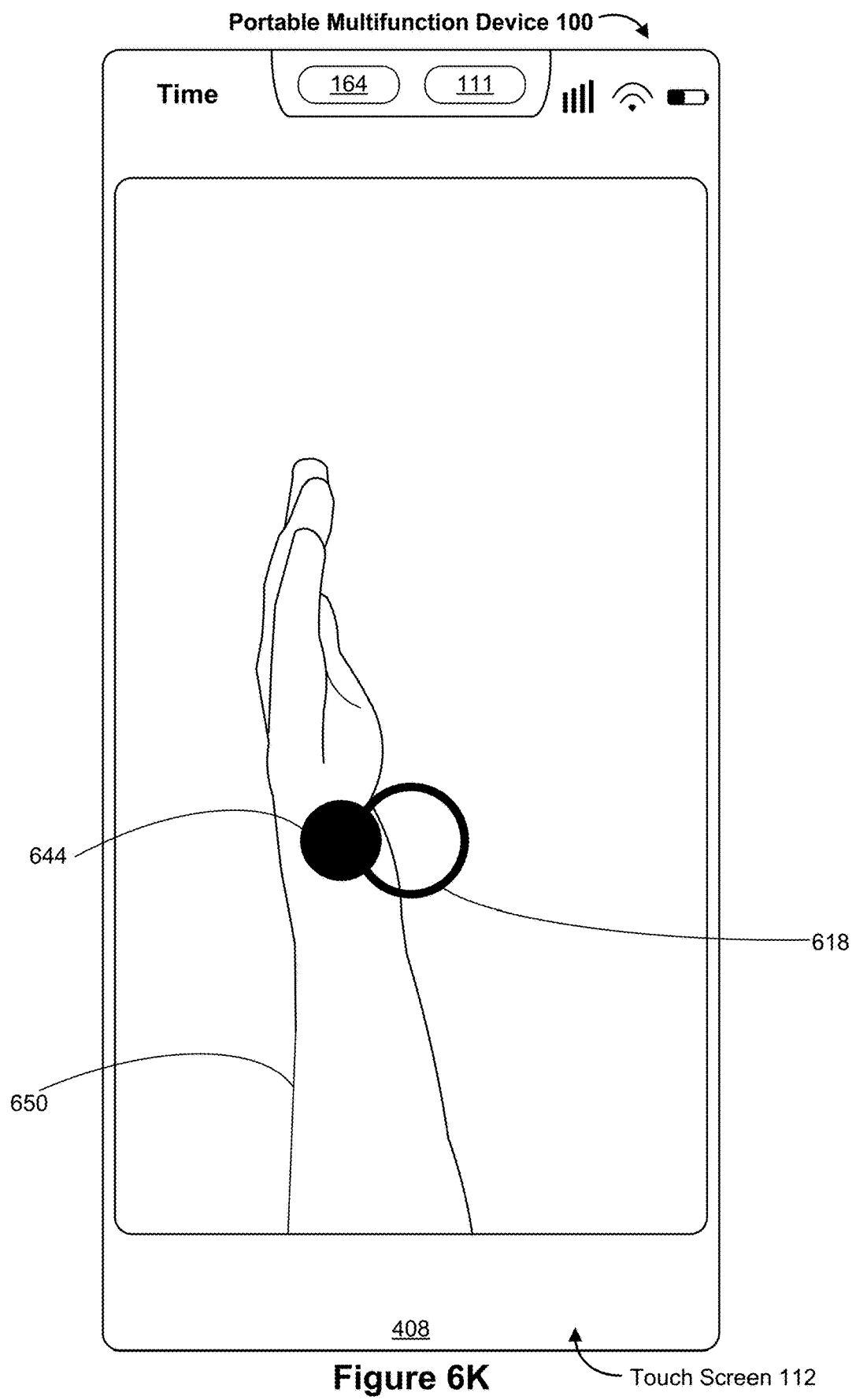

FIG. 6K illustrates a user interface in which the dot 644 now appears as a circle, indicating that the user has rotated the user's hand by the proper amount. Dot 644 is maintained in a same relative position to the representation 650 of the user's hand (e.g., at a particular distance beneath the pinky finger).

Figure 6L:
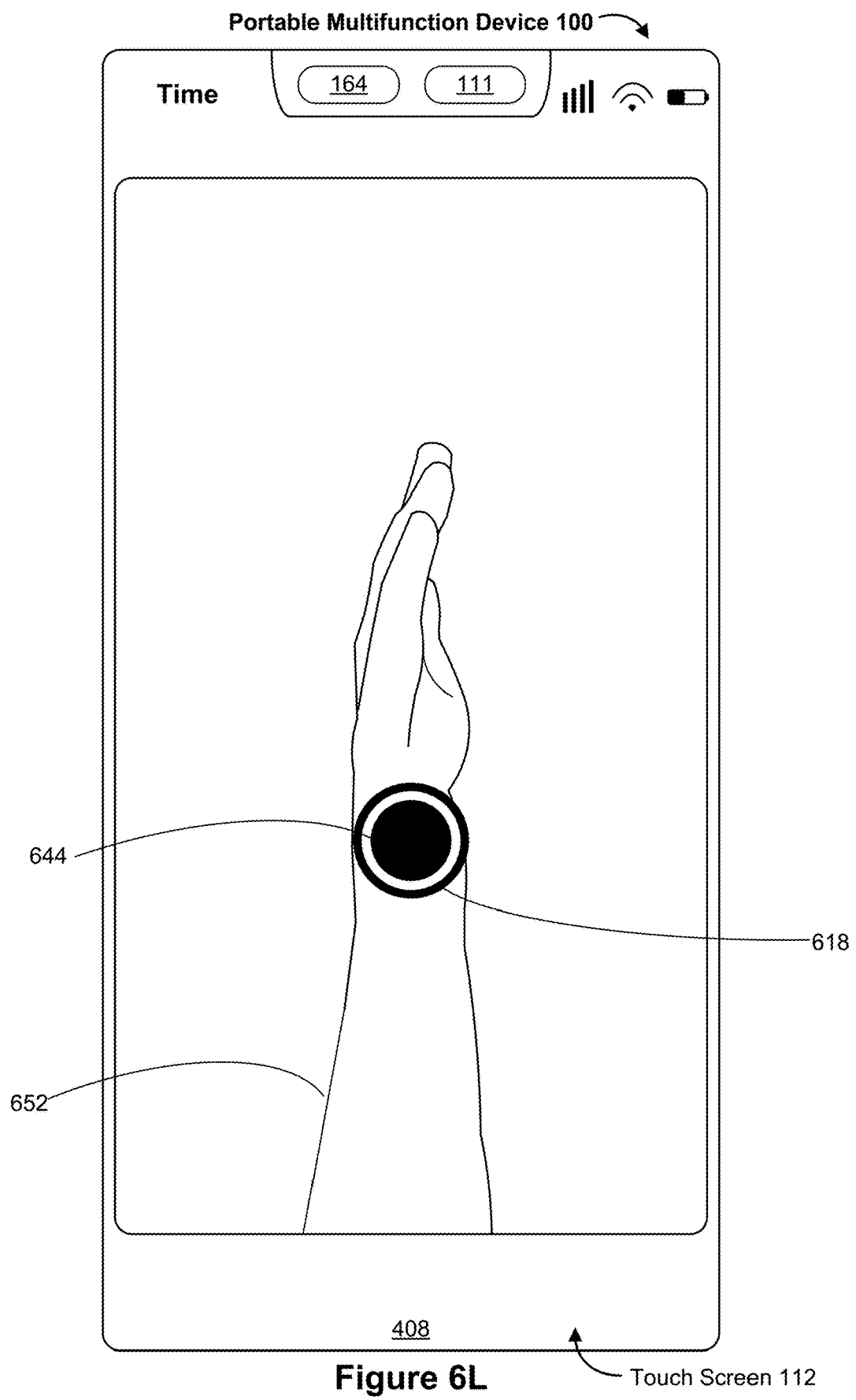

FIG. 6L illustrates a user interface that is displayed in accordance with a determination by the device that the user has moved the user's hand into a second proper position. For example, representation 652 of the user's hand has been turned approximately 90 degrees relative to the position of the representation 640 of the user's hand illustrated in FIG. 6H. Dot 644 is aligned within target 618, indicating that the second proper position has been achieved.

Figure 6M:
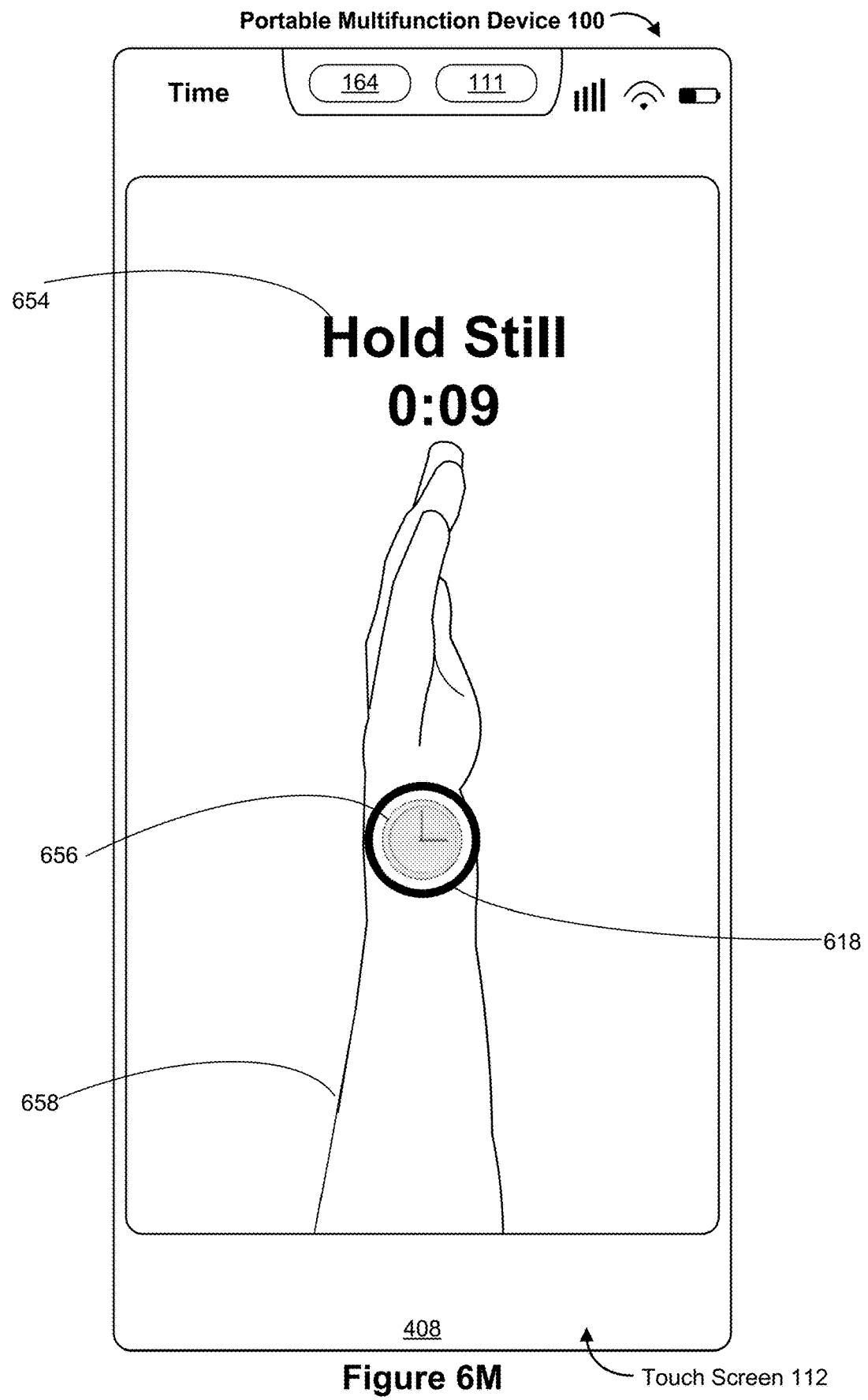
Figure 6N:
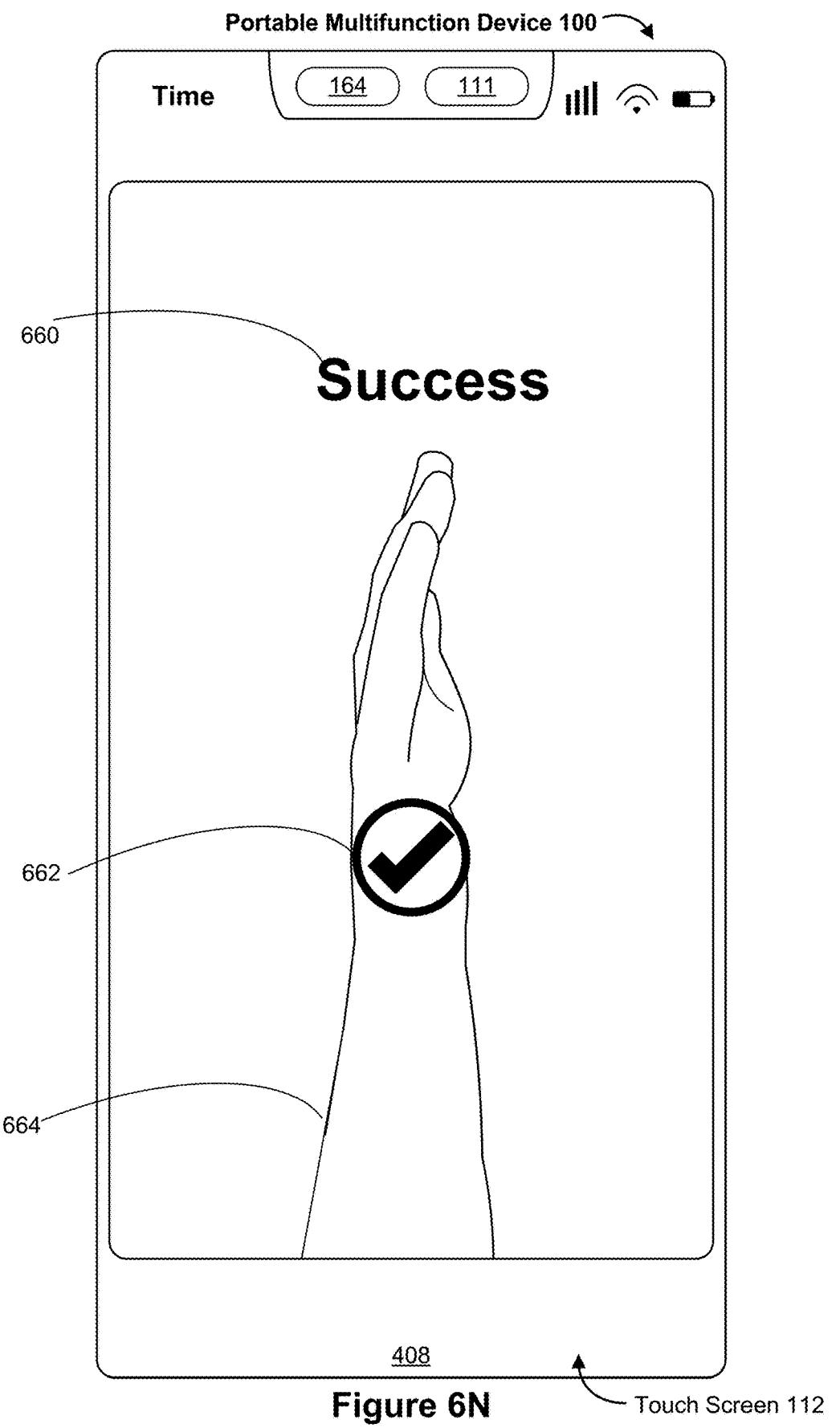

In response to the user achieving the second proper position, the user interface illustrated in FIG. 6M is displayed, in accordance with some embodiments. For example, in some embodiments, in response to dot 644 properly aligning with target 618, a timer 656 is displayed. In some embodiments, timer 656 is a distinct timer from timer 632 illustrated in FIG. 6G. In some embodiments, dot 620 (e.g., and/or target 618) is animated to transition into timer 656. In some embodiments, target 618, optionally, continues to be displayed. In some embodiments, optional textual instructions 654 ("Hold Still 0:09") are displayed to the user in response to the user aligning dot 644 with target 618. In some embodiments, textual instructions 654 include an amount of time (e.g., "0:09") that the user must maintain the position of their hand (e.g., indicated by representation 658 of the user's hand) relative to the device. In some embodiments, the amount of time is updated (e.g., every second) to display a countdown to the user. In some embodiments, device 100 captures a second set of one or more images of the user's hand/wrist while the user maintains the position of their hand illustrated in FIG. 6M. For example, device 100 uses the one or more images captured as described with reference to FIG. 6G and the second set of one or more images captured to determine (e.g., calculate) the measurement of the user's wrist.

After the amount of time has expired (e.g., the timer goes to "0"), a success message is displayed, as illustrated in FIG. 6N, in accordance with some embodiments. In some embodiments, the success message comprises one or more of: a textual indication 660 ("Success"), a non-textual indication (e.g., check mark 662), and/or a screen flash (e.g., or other animation) to indicate that the amount of time has expired. In some embodiments, the representation 664 of the user's hand and/or wrist continues to be displayed concurrently with the success message(s).

FIGS. 7A-7E illustrate exemplary user interfaces for displaying a virtual bracelet 704 concurrently with a representation 702 of a user's hand and/or wrist. In some embodiments, virtual bracelet 704 comprises one or more indicators that change visual appearance as the device scans the user's hand and/or wrist. In some embodiments, FIG. 7A is an instructional user interface that demonstrates, using an animation that updates the appearance of the indicators as an animated hand rotates, to a user how to obtain a scan of the user's hand using the virtual bracelet as a visual guide.

For example, FIG. 7A illustrates the virtual bracelet 704 having a plurality of indicators (e.g., oval-shaped openings) that change color as the representation 702 of the user's hand is rotated. In some embodiments, the change in visual appearance of the indicators comprises changing a color of one or more of the indicators, changing a brightness of one or more of the indicators (e.g., to make the one or more indicators glow), and/or changing a transparency level of one or more indictors. FIG. 7A illustrates an example of how the indicators are, or would be, updated as the user's hand is rotated. For example, in the animated instructional user interface of FIG. 7A, as the representation of a user's hand rotates, the virtual bracelet appears to rotate with the representation of the user's hand, such that the visual indicators are filled from left to right as the representation of the user's hand rotates. It is noted that the animation in the instructional user interface of FIG. 7A may be displayed even if the user's actual hand does not move, or regardless of whether the user's hand is moving or stationary, as this is an instructional user interface. Further, it will be understood that the example of "filling" one or more of the indicators, as described, for example, below with reference to FIGS. 7J-7M, can correspond to any method of changing the visual appearance of the one or more of the indicators (e.g., changing a brightness, changing a color, and/or changing a transparency of the one or more of the indicators).

FIG. 7B illustrates a physical environment 531 that includes device 100 positioned flat on a surface (e.g., a table) and a user's hand 532 positioned over the device 100 in a field of view of one or more cameras of the device 100. A user interface that is displayed by device 100 is illustrated on the left side of FIG. 7B. For example, the user interface includes a display of a representation 706 of the user's hand 532 (e.g., a representation as captured by the field of view of the one or more cameras of device 100) and display of a virtual bracelet 708.

In some embodiments, as illustrated in FIG. 7B, when the user's hand 532 is positioned too far away from device 100, the virtual bracelet 708 does not update any of the indicators of virtual bracelet 708, which indicates that the user's hand has not yet been scanned at this position (e.g., because the user's hand is not in a proper position to be scanned). In some embodiments, determination by the device of a distance of the user's hand or other body part from device 100 is based, at least in part, on depth information obtained from one or more depth sensors of the device 100, or images captured by the device's one or more cameras, or both.

In some embodiments, the user's hand 532 moves to the left (e.g., relative to an axis that is substantially parallel to the one or more cameras of the device), and in response to the user's hand moving to the left, the representation 710 of user's hand, illustrated in FIG. 7C, is displayed as moving to the left (e.g., relative to the position of the representation shown in FIG. 7B). Virtual bracelet 712 appears in a same relative position compared to the representation 710 of the user's hand, such that as the representation of the user's hand moves, the virtual bracelet moves (e.g., proportionally) with the representation.

FIG. 7D illustrates an exemplary user interface that is displayed when the user's hand 532 has moved away from device 100 (e.g., there is an increased distance between the device (e.g., the one or more cameras of the device) and the user's hand). As the user's hand moves farther away from device 100, the representation 714 of the user's hand appears smaller. Displayed virtual bracelet 716 also appears smaller (e.g., relative to the representation and virtual bracelet illustrated in FIG. 7C) in accordance with (e.g., proportionally to) the smaller representation 714 of the user's hand.

FIG. 7E illustrates an exemplary user interface that is displayed when the user's hand 532 has moved closer to device 100 (e.g., there is a decrease in distance between the device (e.g., the one or more cameras of the device) and the user's hand). As the user's hand moves closer to device 100, the representation 718 of the user's hand appears larger in the user interface. Displayed virtual bracelet 720 also appears larger (e.g., relative to the representations and virtual bracelets illustrated in FIGS. 7C and 7D) in accordance with (e.g., proportionally to) the larger representation 718 of the user's hand.

FIGS. 7F-7G illustrate optional user interfaces in which a user input 726 moves a position of virtual bracelet 724 relative to the representation 722 of the user's hand. In some embodiments, the virtual bracelet 724 is located at a position relative to the representation of the user's hand that will be measured by device 100. For example, if the virtual bracelet is moved farther away from the user's hand (e.g., up the user's forearm), the device will measure a size of the forearm that corresponds to the location of the virtual bracelet. In some embodiments, an instruction is provided to the user indicating that the user should move (e.g., using a drag input 726) the virtual bracelet to a position where the user wears (e.g., plans to wear) the accessory for which the measurement is taken. For example, as described above, the user's wrist is measured by the device to determine a size of a watch band. Thus, the user is optionally instructed by the device to move the virtual bracelet to a portion of the user's forearm (e.g., wrist) where the user wears a watch band.

FIGS. 7H-7I illustrate optional user interfaces that are displayed if the user has rotated their hand (e.g., wrist) too quickly. For example, the device determines a rate at which the user may rotate their hand in order for the device to obtain an accurate measurement (e.g., by scanning the user's wrist and/or hand). If the user rotates the user's hand too fast (e.g., faster than the determined rate at which the device allows for scanning the user's hand/wrist), the device forgoes filling additional indicators of virtual bracelet 730 (e.g., only the same two indicators of virtual bracelet 730 appear filled in FIGS. 7H-7I even though the user has moved the user's hand, as indicated by the change in position of the representation 728 of the user's hand to the position of the representation 734 of the user's hand). The device optionally displays an error message, such as textual indication 732 ("You moved too fast").

FIGS. 7J-7M illustrate optional user interfaces that are displayed as the user rotates the user's hand, and the device 100 updates the indicators of the virtual bracelet in accordance with successful movement (e.g., scanning) of the user's hand. For example, FIG. 7J illustrates two of the indicators of virtual bracelet 738 are filled. In some embodiments, the center-most indicators of virtual bracelet 738 are displayed by the device as filled in accordance with a determination by the device that the user has positioned the user's hand and/or wrist at a proper distance from device 100. In some embodiments, if the user's hand is not in a proper position (e.g., orientation and/or distance) relative to device 100, or fails to meet other preconditions for scanning the user's hand, the device 100 provides an indication of an error condition as described with reference to FIGS. 5K-5N. In some embodiments, the indication of the error condition comprises displaying the representation 736 of the user's hand as translucent until the user's hand is in proper position. In some embodiments, the indication of the error condition comprises forgoing filling any of the indicators of virtual bracelet 738 (e.g., as shown in FIGS. 7B-7E).

In some embodiments, as the user rotates (e.g., turns) the user's hand and/or wrist (e.g., within the physical environment), the representation 740 of the user's hand is updated in accordance with a current position of the user's hand. For example, representation 740 of the user's hand shows that the user has rotated the user's hand as compared with the position of representation 736 of the user's hand illustrated in FIG. 7J. In some embodiments, as the representation of the user's hand rotates, the virtual bracelet 738 (FIG. 7J), 742 (FIG. 7K) is rotated with (e.g., fixed to) the representation of the user's hand. In some embodiments, the filled indicators of the virtual bracelet remain filled as the device continues scanning the user's hand/wrist. For example, as the user's hand rotates, additional indicators appear on the display to indicate to the user that the user must continue rotating their hand in that direction (e.g., until all of the indicators of virtual bracelet that are displayed are filled, as illustrated in Figure [5M] 7M). For example, in FIG. 7J, the indicators that are displayed near the center of the representation 736 of the user's hand (e.g., palm) are filled, and as the user's hand rotates to the position in FIG. 7K, the indicators displayed near the center of the representation 740 of the user's hand (e.g., palm) remain filled, additional indicators (e.g., the indicators displayed under the representation of the user's pinky) are filled, while remaining indicators on the far left side are unfilled (e.g., the indicators displayed near the "back" of the representation of the user's hand).

FIG. 7L shows additional indicators of virtual bracelet 746 displayed, including one or more of the previously filled indicators shown in FIG. 7K. The representation 744 of the user's hand is updated as the user's hand rotates in the field of view of the one or more cameras. For example, FIG. 7L illustrates that the user has continued rotating the user's hand, as illustrated by the displayed position of the representation 744 of the user's hand. Additional indicators of virtual bracelet 746 are filled as the user continues rotating the user's hand.

FIG. 7M illustrates that all of the displayed indicators of virtual bracelet 750 are filled, indicating that scanning of the user's hand is complete (e.g., there are no additional indicators of the virtual bracelet to be filled, so the user does not need to further rotate the user's hand in order to fill the displayed indicators). The representation 748 of the user's hand illustrated in FIG. 7M illustrates that the user's hand has been rotated from having the front of the user's hand (e.g., palm) in the field of view of the one or more cameras, as illustrated in FIG. 7J, to the back of the user's hand being in the field of view of the one or more cameras.

In some embodiments, as the user rotates the user's hand, indicators of the virtual bracelet are successively (e.g., and/or gradually) filled such that only an indictor next to an already-filled indicator may be filled. In some embodiments, one or more indicators of the virtual bracelet may not be filled. In some embodiments, the indicators of the bracelet fill in an order and/or a direction to indicate to the user a direction in which to rotate the user's hand.

For example, as illustrated in FIGS. 7J-7M, additional portions of the virtual bracelet are filled in accordance with the rotation of the user's hand. In some embodiments, the indicators of the virtual bracelet fill as the user's hand rotates in accordance with a determination by the device that the user's hand is in a proper position and/or that the user's hand is moving at a rate in which the device can scan the user's hand and/or wrist.

In some embodiments, if the user rotates the user's hand in the opposite direction from a predefined direction (e.g., the direction illustrated in FIGS. 7J-7M), the one or more indicators that were filled are updated to remove the filling. For example, after the user rotates their hand clockwise, and one or more indicators fill, if the user at least partially rotates their hand counterclockwise, one or more of the filled indicators are unfilled.

FIGS. 7N-7P illustrate example user interfaces for displaying a measurement to the user. In some embodiments, a measurement is displayed to the user automatically after the device has successfully scanned the portion of the user's body, for example, after the success message illustrated in FIG. 6N and/or after all of the indicators of virtual bracelet 750 have been filled (as illustrated in FIG. 7M). FIG. 7N illustrates one or more size indicators as determined by the device in accordance with the measured portion of the user's body. For example, the user interface includes textual indication 752 ("Your current watch band size is: Size 5"). In some embodiments, the sizing user interface includes an image 756 of the user's hand. In some embodiments, image 756 of the user's hand is generated from an image captured of the user's hand during and/or after scanning the user's hand (e.g., device 100 captures an image (or screenshot) of the user's hand while it is in the position illustrated in FIG. 7M. Thus, the user need not maintain the user's hand within the field of view of the one or more cameras while the user interface of FIG. 7N is displayed.

In some embodiments, the user interface includes a displayed watch and/or watch band 754 at a position that at least partially overlaps the image 756 of the user's hand. For example, watch band 754 is generated (e.g., as a digital image) and displayed at a position of the user's wrist that was measured as described with reference to FIGS. 6C-6N and/or FIGS. 7J-7M. In some embodiments, the user interface includes a button 758 for the user to navigate to a next user interface (e.g., by selecting button 758 with user input 760).

In response to the selection of button 758, the user interface in FIG. 7O is displayed. In some embodiments, as illustrated in FIG. 7O, a textual instruction 762 is provided ("You can drag the watch to a different part of your wrist")

to indicate, to the user, that the user is enabled to select watch band 754 and move the watch band to a different portion of the image 756 of the user's wrist. For example, a user who wears a watch band farther from the wrist and further up the forearm is enabled to move (e.g., using a drag and/or swipe gesture) the watch band 754 to a different location on the user's wrist. In response to the user input 764, the device updates the size indicator in accordance with the new portion of the user's wrist/forearm that the watch band 754 is displayed over, as illustrated in FIG. 7P. For example, FIG. 7P illustrates that watch band 754 has moved down on image 756 and has updated display of the size indicator from a Size 5 to Size 6 (e.g., displayed as textual indicator 768, "Your current watch band size is: Size 6"). In some embodiments, the user is enabled to continue adjusting the placement of watch band 754 relative to image 756 of the user's hand (e.g., until the user is satisfied with the placement of the watch band). As the user changes the placement of the watch band 754, the size indicator is also updated to provide a measurement for the portion of the wrist at which the watch band 754 is placed. In some embodiments, upon completion of moving the watch band 754, the user is enabled to select "Done" button 766 to display a next user interface, for example the user interface illustrated in FIG. 7P.

FIGS. 7Q-7S illustrate example user interfaces similar to the user interfaces illustrated in FIGS. 7N-7P, with displayed watch band 754 replaced with displayed measuring tape 770. For example, FIG. 7R illustrates a textual indication 772 ("You can drag the tape measure to a different part of your wrist") and the device receives user input 774 (e.g., a drag gesture, a swipe gesture) that moves measuring tape 770 in the downward direction (e.g., relative to the orientation of the device as illustrated in FIG. 7R). FIG. 7S illustrates that the size indicator 776 is updated to show that the size of the user's wrist corresponding to the updated placement of measuring tape 770 is now "Size 6" instead of Size 5. In some embodiments, upon completion of moving the measuring tape 770, the user is enabled to select "Done" button 778 to display a next user interface, for example the user interface illustrated in FIG. 7T.

FIG. 7T illustrates an example user interface for a user to save the user's size. For example, FIG. 7T includes a text prompt 780 ("Save size as virtual card?") and provides the user with buttons 782 "yes" and 784 "no" that the user is enabled to select. For example, user input 786 selects button 782 "yes" which causes the device to initiate a process for saving the user's size. Optionally, FIG. 7T includes an image of the user's hand 756 with measuring tape 770 or watch band 754 (not shown).

Figure 8A:
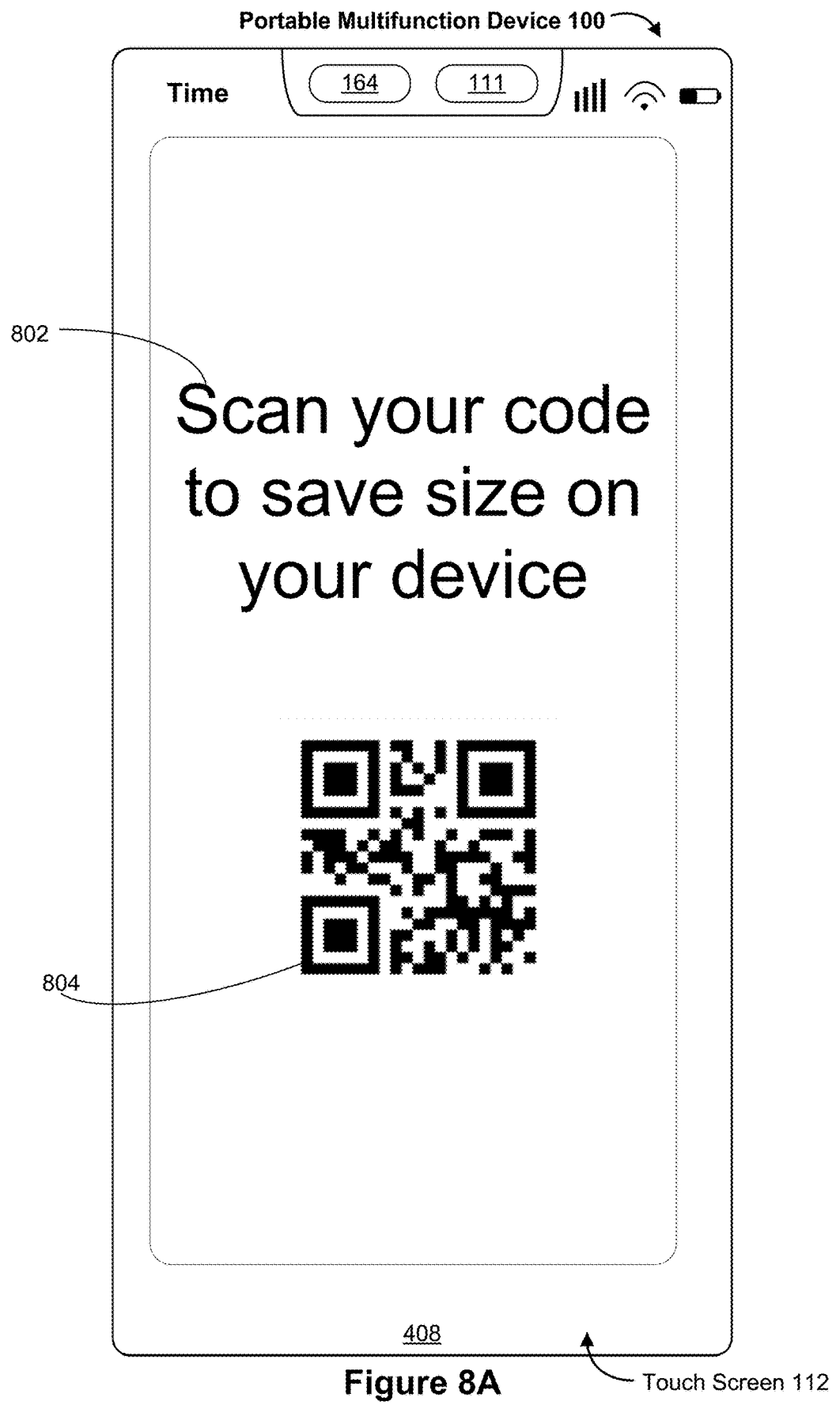
FIGS. 8A-8F illustrate example user interfaces for storing a measurement of a body part of a user in accordance with some embodiments.
Figure 9A:
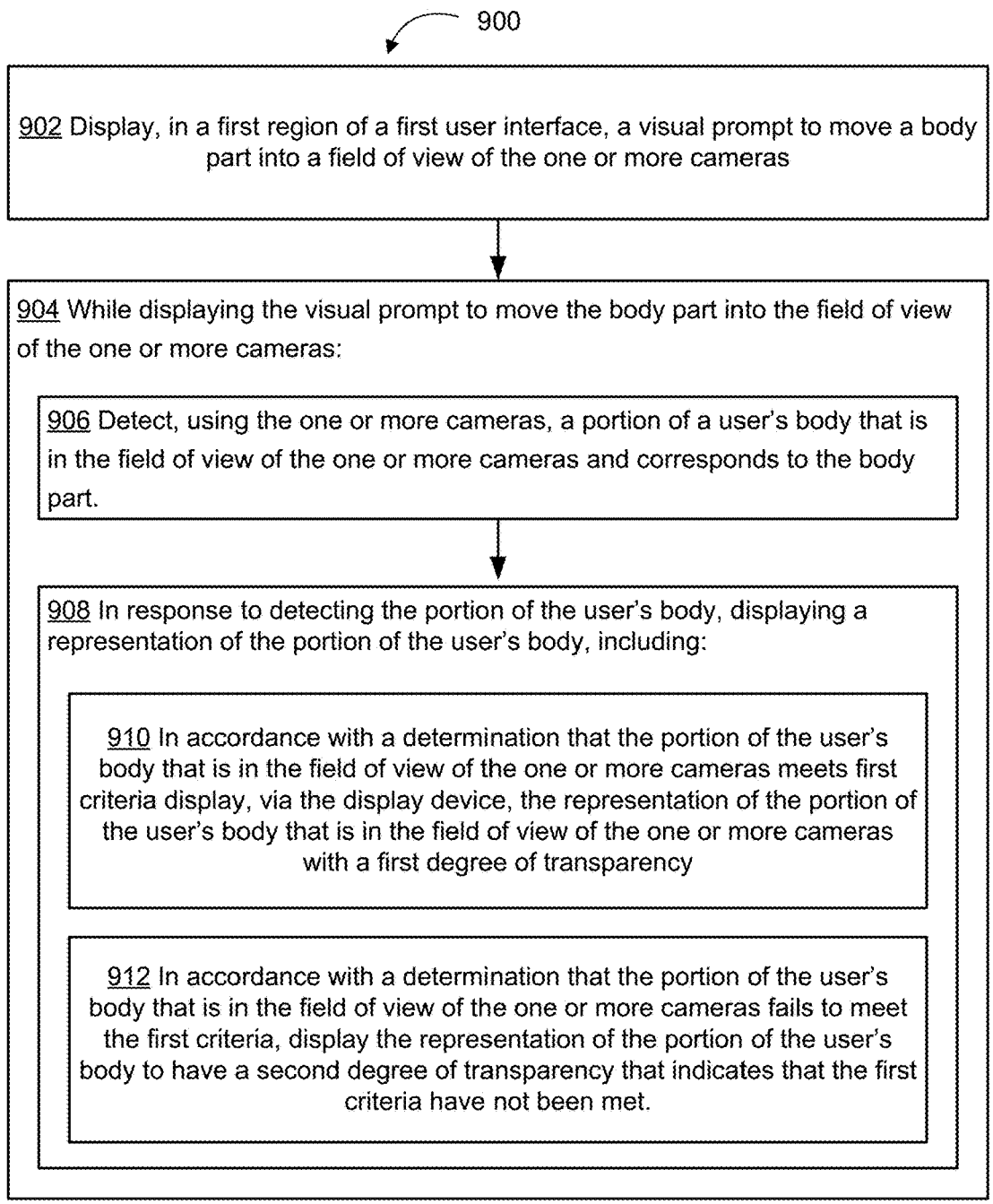

In response to the user selecting button 782 "yes" in FIG. 7T, in some embodiments, a QR code 804 (e.g., or other computer readable or machine-readable code) is displayed, as illustrated in FIG. 8A. Optionally, QR code 804 is generated by device 100 in response to the user selecting button 782; or, alternatively, the QR code 804 is generated or stored in advance of the user selecting button 782, and is retrieved for display in response to the user selecting button 782. In some embodiments, the QR code 804 includes the sizing information to be saved and/or additional information about the accessory (e.g., watch band) to which the sizing information corresponds.

As shown in FIG. 8A, the user interface displayed by device 100 optionally includes textual instructions 802 ("Scan your code to save size on your device") for loading the sizing information onto another device (e.g., distinct from the device that performed the scanning/measuring).

Figure 8B:
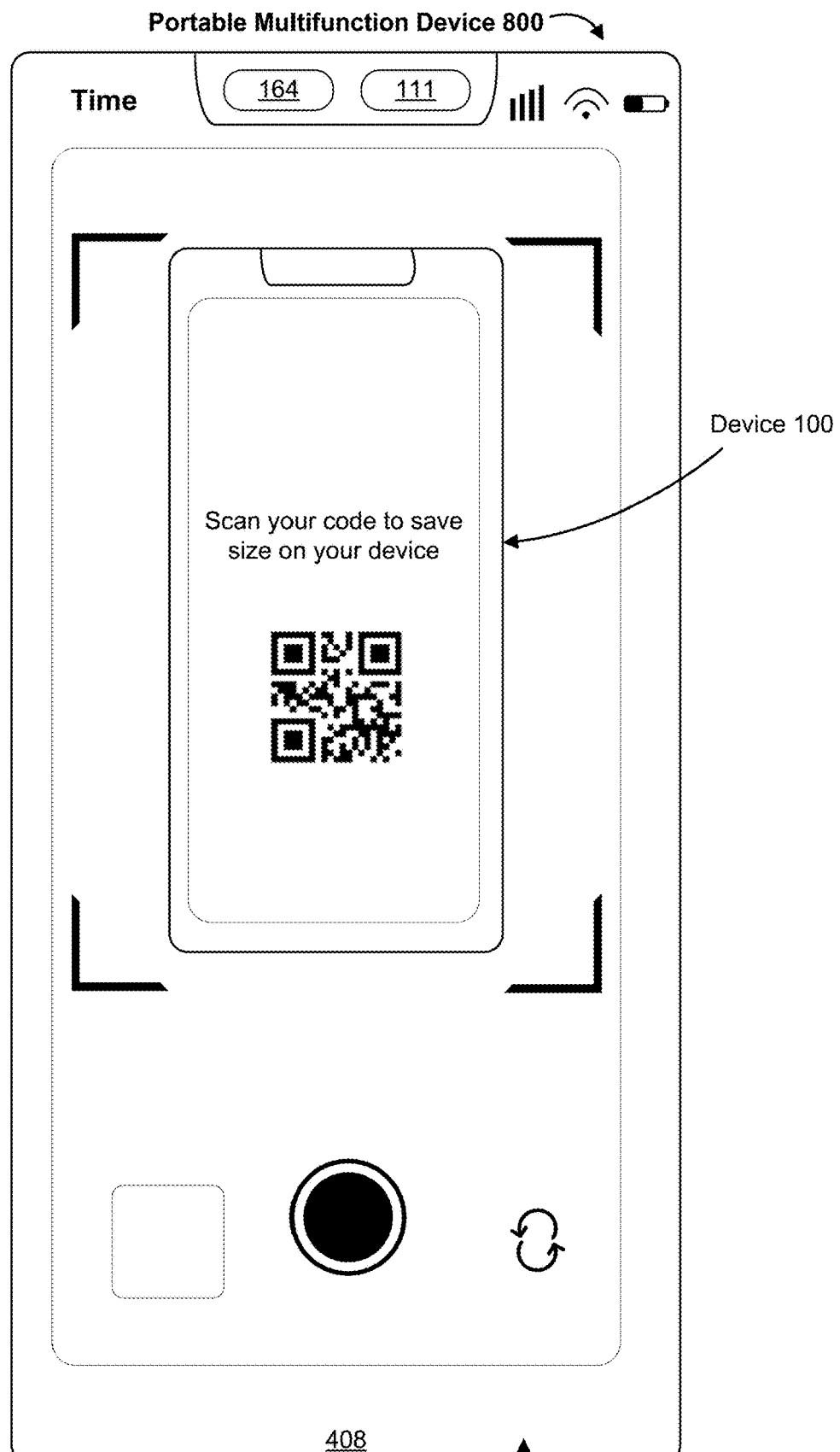

For example, in some situations or embodiments, device 100 is a device that does not belong to the user, but the user can scan, using another device (e.g., the user's device 800, FIG. 8B) QR code 804 in order to transfer (e.g., and save) the user's sizing information to the user's device that performs the scanning. For example, FIG. 8B illustrates user device 800 (e.g., associated with the user who has obtained sizing information) scanning the code displayed on device 100. In some embodiments, user device 800 is configured to scan the QR code using one or more cameras of device 800. For example, device 800 in FIG. 8B illustrates a camera application that displays a field of view of the one or more cameras of device 800. The field of view of the one or more cameras includes a view of device 100 (which is displaying the QR code 804).

Figure 8C:
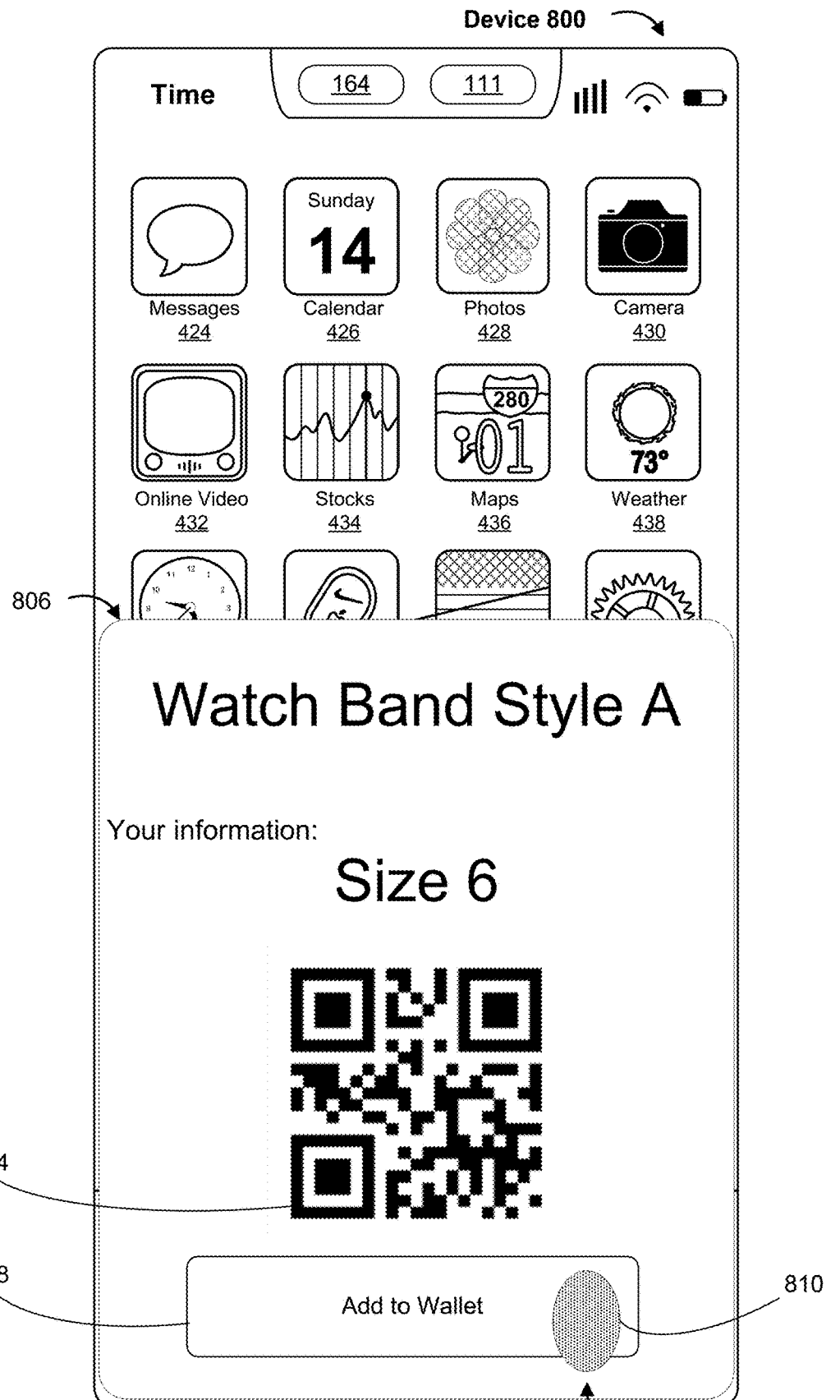

In some embodiments, in response to capturing (e.g., scanning) the QR code displayed on device 100, device 800 generates and displays a miniature application 806 (e.g., an app clip), as illustrated in FIG. 8C (e.g., a user interface of the miniature application 806 is displayed). In some embodiments, the miniature application 806 is not a downloaded application (e.g., from the App Store), but is a temporarily stored (e.g., cached) application that stores QR code 804. In some embodiments, the miniature application 806 displays a virtual card that includes information about the user's size and/or information about the accessory. For example, miniature application 806 optionally displays additional information about the user's size and/or information about the accessory (e.g., displayed text ("Watch Band Style A" and/or "Your information: Size 6")). In some embodiments, miniature application 806 displays QR code 804. In some embodiments, QR code 804 includes information about the user's size and/or the accessory.

In some embodiments, miniature application 806 provides an option for saving the information about the user's size and/or information by selecting button 808 ("Add to Wallet"). In some embodiments, in response to a user selection 810 of button 808, the virtual card (e.g., as displayed in miniature application 806) is stored in a virtual wallet on the user's device 800 (e.g., as displayed in FIG. 8F).

Figure 8D:
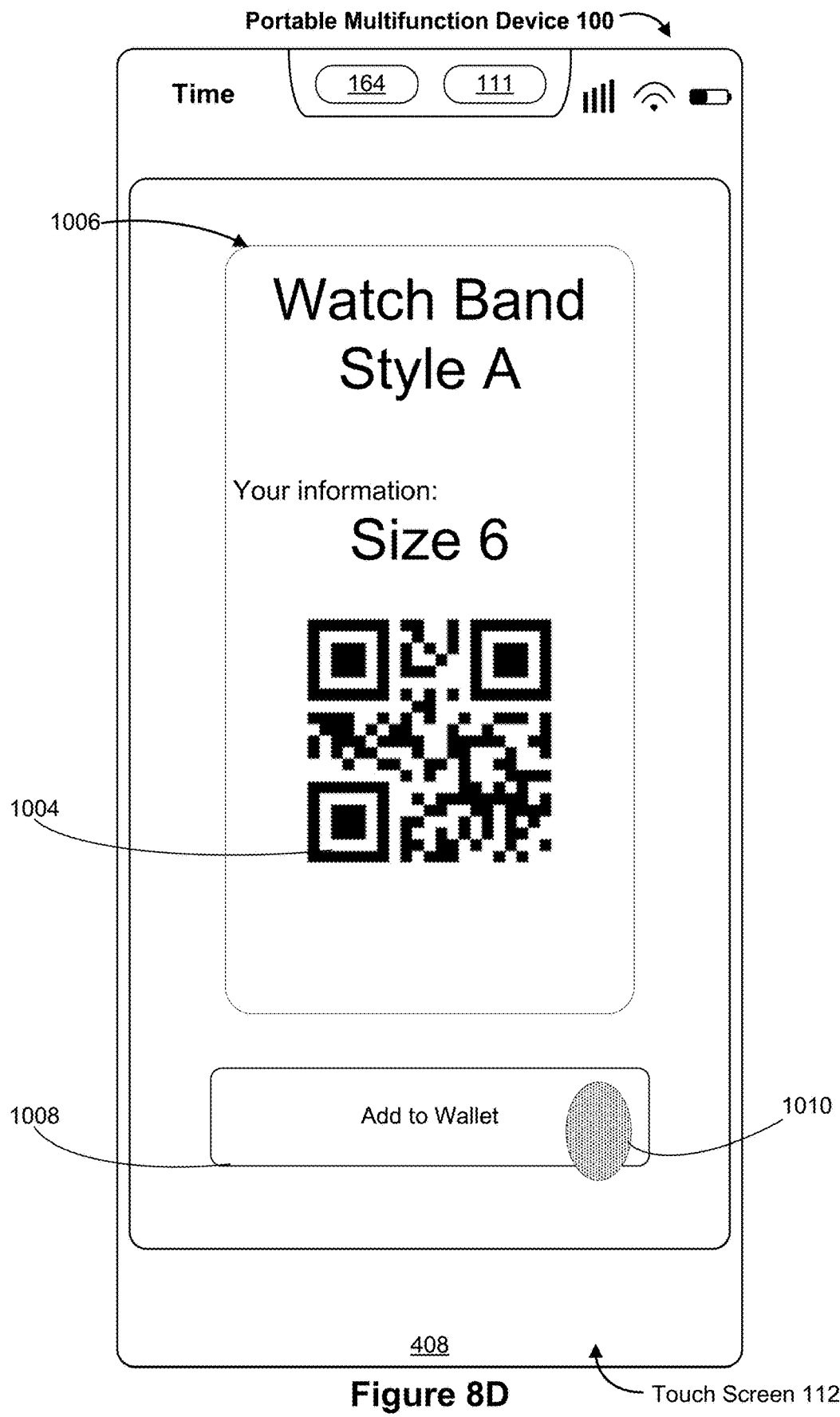

In some embodiments, device 100 is the user's device (e.g., the scanning was performed on the user's device and thus the user does not need to scan a QR code from device 100 to save the user's sizing information), and in response to the user selecting button 782 "yes" in FIG. 7T, device 100 displays the user interface illustrated in FIG. 8D (e.g., instead of prompting the user to scan the QR code onto the user's device, since the user's device was used to perform the scanning). For example, the user interface optionally includes display of a virtual card 1006. The virtual card 1006 optionally includes information about the user's size and/or the accessory (e.g., shown as text "Watch Band Style A" and "Your information: size 6"). In some embodiments, the virtual card 1006 includes QR code 1004, which also stores information about the user's size and/or the accessory. In some embodiments, the virtual card 1006 further includes a user-selectable affordance (e.g., a button 1008 that includes text, such as "Add to Wallet") that provides the user with an option to store the virtual card in a virtual wallet of device 100. For example, in response to user input 1010, the device stores the virtual card 1006 in a virtual wallet stored on the device. In some embodiments, instead of displaying the virtual card 1006 illustrated in FIG. 8D, device 100 displays QR code 1004 in a miniature application (e.g., an app clip), as discussed above with reference to FIG. 8C.

In some embodiments, after the sizing information (e.g., as stored in virtual card 1006, including QR code 804 or QR code 1004) is stored to the virtual wallet of the user's device (e.g., device 800 as described with reference to FIGS. 8A-8C, or device 100 as described with reference to FIG. 8D), a prompt 812 (see FIG. 8E) is provided to the user that allows the user to open (e.g., view) the sizing information for the accessory in the virtual wallet on the device. For example, the prompt 812 ("Open Watch Size Information in Wallet") is generated when a user is within a predefined geographic area (e.g., near a store that sells the accessory). In some embodiments, the prompt 812 is displayed on a current user interface that is displayed on the device when the prompt is generated. For example, in FIG. 8E, the prompt 812 is generated and displayed over a lock screen that is displayed on the user's device.

Figure 8E:
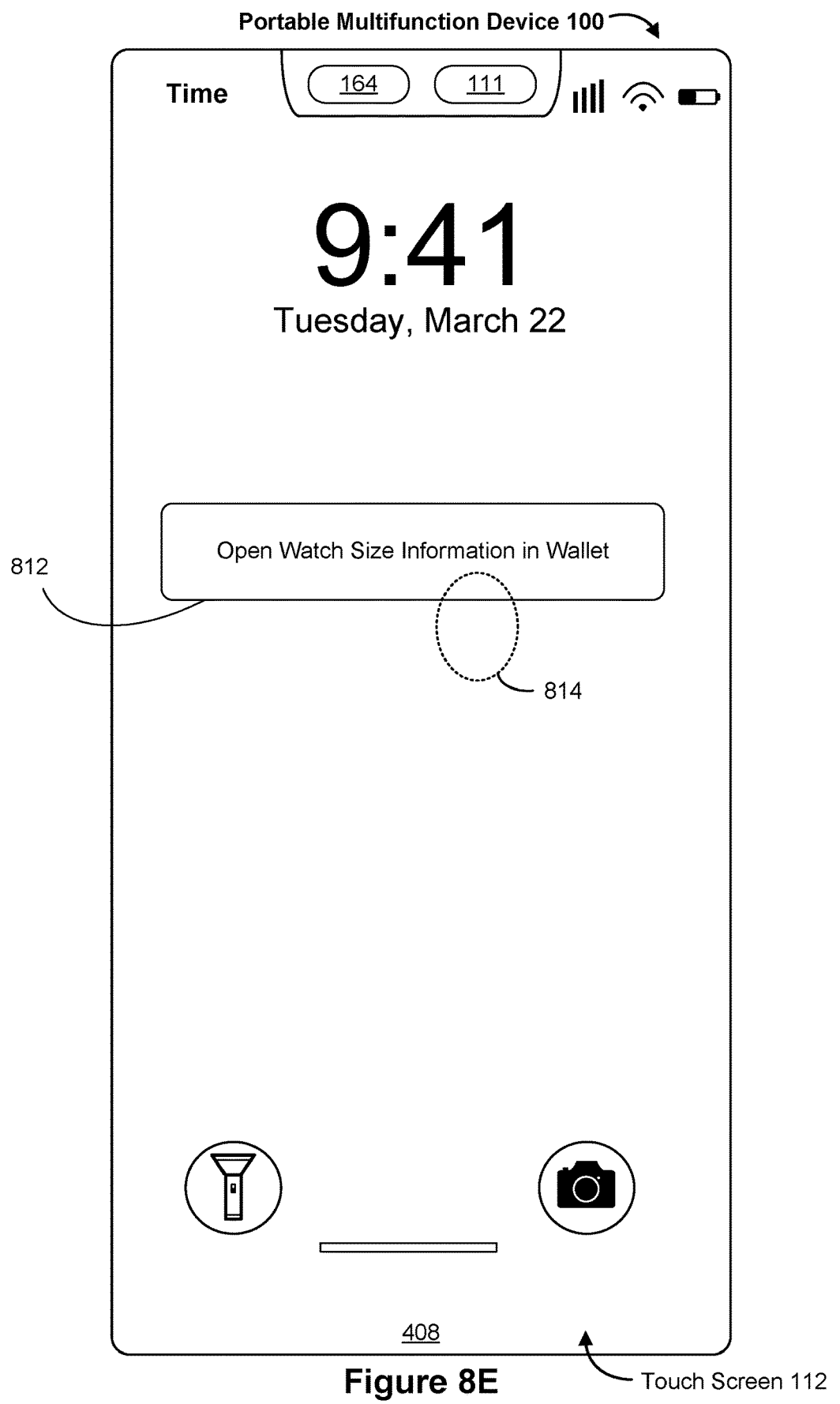
Figure 8F:

In some embodiments, in response to the user selecting the prompt 812 with user input 814, the sizing information (e.g., stored as a virtual card) is displayed within the virtual wallet of the user on the user's device (e.g., device 100 or device 800), as illustrated in FIG. 8F. For example, the sizing information includes information about the accessory ("Watch Band Style A") and/or information about the user's size ("Your information: Size 6"). In some embodiments, the sizing information is stored as a QR code. In some embodiments, the QR code is displayed in the virtual wallet, as illustrated in FIG. 8F.

FIGS. 9A-9C are flow diagrams illustrating method 900 of providing visual feedback to a user to indicate a correct position for measurement in accordance with some embodiments. Method 900 is performed at a computer system (e.g., portable multifunction device 100, device 300, or device 800) that includes (and/or is in communication with) a display generation component (e.g., a display, optionally touch-sensitive, a projector, a head-mounted display, a heads-up display, or the like), one or more cameras (and optionally one or more depth sensors), and one or more input devices, optionally one or more pose sensors, optionally one or more sensors to detect intensities of contacts with the touch-sensitive surface, and optionally one or more tactile output generators. All references to images captured by the one or more cameras of the computer system shall be understood to optionally include depth information from one or more depth sensors (e.g., one or more time-of-flight sensors, structured-light sensors (also known as structured-light scanners), etc.) of the computer system, to facilitate measurement of objects in view of the one or more cameras. Some operations in method 900 are, optionally, combined and/or the order of some operations is, optionally, changed.

As described below, method 900 provides an intuitive way of indicating to a user how to position a portion of the user's body for measurement by automatically detecting a current position of the portion of the user's body and showing guides that indicate the correct position. Changing the visual properties of a visual prompt according to a current position of the user's body provides visual feedback to the user that indicates whether the user's body has achieved the proper position for measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

The computer system displays (902), in a first region of a first user interface, a visual prompt to move a body part into a field of view of the one or more cameras. For example, as described with reference to FIG. 5F, in some embodiments, the computer system displays a visual prompt such as text instructions 526 and/or a representation of the body part (e.g., an animation 528). In some embodiments, the visual prompt comprises an outline of the body part, or a stylized representation (e.g., an animation and/or image) of the body part. For example, FIG. 5F illustrates an animated representation of a hand and wrist.

While displaying the visual prompt (904) to move the body part into the field of view of the one or more cameras, the computer system detects (906), using the one or more cameras, a portion of a user's body that is in the field of view of the one or more cameras and corresponds to the body part. For example, FIGS. 5G-5J illustrate a physical environment 531 in which the user's hand 532 is positioned within the field of view of the one or more cameras of device 100.

In response to detecting the portion of the user's body, the computer system displays (908) a representation of the portion of the user's body. For example, as described with reference to FIGS. 5G-5J, the user's hand 532 is placed within the field of view of the one or more cameras of device 100, and device 100 displays a representation of the user's hand (e.g., representation 548, FIG. 5J).

In accordance with a determination by the computer system that the portion of the user's body that is in the field of view of the one or more cameras meets first criteria, the computer system displays (910), via the display device, the representation of the portion of the user's body that is in the field of view of the one or more cameras with a first degree of transparency (e.g., the representation of the portion of the user's body is displayed without any fading and/or translucence). In some embodiments, the first criteria comprise position criteria for a pose, orientation, speed of rotation, and/or distance of the portion of the user's body relative to the computer system. For example, the first criteria include a requirement that a distance between the portion of the user's body and the one or more cameras is above a first threshold distance. In some embodiments, the first criteria include a requirement that a distance between the portion of the user's body and the one or more cameras is below a second threshold distance. In some embodiments, the first criteria include a requirement that the distance between the portion of the user's body and the one or more cameras is above the first threshold distance and below the second threshold distance (e.g., between the threshold distances). In some embodiments, the first criteria include a requirement that a rate of rotation of the portion of the user's body is less than a threshold rate of rotation (e.g., the first criteria is not met when the user moves the arm too quickly). In some embodiments, the first criteria include a requirement that the portion of the user's body is aligned (e.g., with respect to location, angle, etc.) with the visual prompt. In some embodiments, the representation of the portion of the user's body is displayed without displaying other objects that are within the field of view of the one or more cameras (e.g., as described with reference to FIG. 5J). For example, only the representation of the portions of the user's body is displayed and superimposed over a background of the user interface.

In accordance with a determination by the computer system that the portion of the user's body that is in the field of view of the one or more cameras fails to meet the first criteria (e.g., with respect to the representation of the first body part, or position with respect to the device, distance from the device, or speed of movement), the computer system displays (912) the representation of the portion of the user's body to have a second degree of transparency that indicates that the first criteria have not been met. In some embodiments, the second degree of transparency is greater than the first degree of transparency. For example, as described with reference to FIGS. 5K-5M, in accordance with a determination by the device that the user's hand 532 is not in a proper position relative to device 100, device 100 displays a representation of the user's hand as at least partially translucent (e.g., transparent) in FIGS. 5K-5M (e.g., as indicated by the fill pattern of the representation of the user's hand in FIGS. 5K-5M). In accordance with a determination that the user's hand 532 is in the proper position relative to the device (e.g., as illustrated in FIG. 5J), the representation 548 of the user's hand is not displayed as translucent.

In some embodiments, while displaying the visual prompt to move the body part into the field of view of the one or more cameras, the computer system displays (914) an animated transition in which at least a portion of the visual prompt is moved to a location that is near the representation of the portion of the user's body. In some embodiments, the animated transition is initiated in response to detecting the portion of the user's body. For example, as illustrated in FIG. 5P, in some embodiments, the visual prompt comprises an outline 570 of the portion of the user's body, and in response to the user's hand being in the field of view of the one or more cameras, outline 570 is moved so as to form an outline around the representation 572 of the user's hand.

Displaying a plurality of user interface elements, including a visual prompt and a representation of the portion of the user's body, provides the user with an intuitive way of determining that the portion of the user's body is in a correct position to be measured by the device without requiring additional input from the user to check whether the portion of the user's body will be measured by the device. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, at least a portion of the visual prompt comprises (916) an outline that snaps to (e.g., surrounds) the representation of the portion of the user's body. For example, as illustrated in FIG. 5P, outline 570 snaps to the representation 572 of the user's hand.

Snapping the visual prompt to the representation of the portion of the user's body provides visual feedback to the user indicating that the portion of the user's body has been automatically detected within the field of view of the one or more cameras without requiring the user to provide additional input to begin the measurement process. Providing improved visual feedback to the user and reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the at least a portion of the visual prompt is displayed (918) in a shape that matches a shape of the representation of the portion of the user's body in the field of view of the one or more cameras. In some embodiments, the visual prompt (e.g., outline) traces the contours of the portion of the user's body (e.g., as illustrated in FIG. 5P).

Matching the shape of the visual prompt to the shape of the portion of the user's body makes it easier for the user visualize that the portion of the user's body has been detected by the one or more cameras and/or that the portion of the user's body is in the proper position to begin measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the visual prompt comprises (920) a representation of a hand or a representation of another body part that is to be measured. For example, as illustrated in FIG. 5F (e.g., animation 528 of a hand) and FIG. 5P (e.g., outline 570 of a hand), the visual prompt includes a representation of a hand. In some embodiments, the visual prompt comprises an outline of a hand, wrist and/or forearm. In some embodiments, the representation of the body part in the visual prompt is a representation of a right hand or left hand, in accordance with a selection received from the user (e.g., as described with reference to FIG. 5E).

Providing a visual prompt in the shape of a hand indicates to the user that the user's hand is the portion of the user's body that will be measured. Displaying the visual prompt as a hand improves the visual feedback to the user by making it easier for the user to determine that the user should place the user's hand into the field of view of the one or more cameras. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the portion of the user's body comprises (922) a hand. For example, as described with reference to FIGS. 5G-5N, the user's hand 532 is illustrated in the physical environment 531 such that the user's hand 532 is within a field of view of one or more cameras of device 100.

Automatically detecting a user's hand that is positioned over the camera(s) of the device such that the device determines a size of an accessory that is worn on or near the user's hand makes it easier for a user to obtain sizing information without requiring the user to manually input measurements of the user's body. Reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in accordance with the determination by the computer system that the portion of the user's body that is in the field of view of the one or more cameras fails to meet the first criteria, the computer system displays (924) text that indicates that the first criteria have not been met (and optionally includes an indication of what changes can be made in order to meet the first criteria). For example, FIGS. 5K-5N illustrate text prompts that indicate that the first criteria have not been met (e.g., wherein satisfying the first criteria indicates that a proper position of the user's hand has been satisfied). In some embodiments, the first criteria include a criterion that the computer device is stationary. In some embodiments, the first criteria comprises that the computer device is positioned at a first orientation (e.g., laid flat, or at an angle substantially perpendicular to the ground) and the displayed text (displayed in accordance with a determination that the first criteria have not been met) comprises an instruction to lay the device flat (e.g., at the first orientation), for example as illustrated in FIG. 5M. In some embodiments, the first criteria includes a requirement that a distance (as determined by the computer system) between the portion of the user's body and the one or more cameras is above a first threshold distance (e.g., the hand needs to be at least the first threshold distance away from the one or more cameras) and the displayed text, displayed in accordance with a determination by the computer system that the first criteria have not been met, comprises an indication that the portion of the user's body is too close, for example as illustrated in FIG. 5L. In some embodiments, the first criteria includes a requirement that a distance between the portion of the user's body and the one or more cameras is below a second threshold distance (e.g., the hand needs to be within a second distance to the one or more cameras) and the displayed text, displayed in accordance with a determination by the computer system that the first criteria have not been met, comprises an indication that the portion of the user's body is too far away, for example, as illustrated in FIG. 5K. In some embodiments, the first criteria includes a requirement that the portion of the user's body is unobstructed with accessories (e.g., rings, watches, bracelets) and the displayed text, displayed in accordance with a determination that the first criteria have not been met, comprises an indication to take one or more objects off the portion of the user's body (e.g., remove rings, remove watch, remove bracelet, etc.), for example as illustrated in FIG. 5M. In some embodiments, such as the examples provided above, the displayed text, displayed in accordance with a determination by the computer system that the first criteria have not been met, indicates an error condition with respect to position of the user's hand or other body part, or with respect to the computer device.

Providing error notifications indicating that the user has not placed the portion of the user's body into a proper position for measurement by the computer system makes it easier for the user to know how to adjust the portion of the user's body to be in the proper position without requiring the user to provide user inputs asking the device if the measurement has been successful. Providing improved visual feedback to the user and reducing the number and/or extent of inputs needed to perform an operation, by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the computer system device by enabling the user to use the computer system more quickly and efficiently.

In some embodiments, displaying the representation of the portion of the user's body to have a second degree of transparency that indicates that the first criteria have not been met comprises (926) visually deemphasizing (e.g., fading) the representation of the portion of the user's body. For example, as illustrated in FIG. 5L, in accordance with a determination by the computer system that the distance between the portion of the user's body and the one or more cameras is not above the first threshold distance, device 100 visually deemphasizes (e.g., fades) the representation 556 of the portion of the user's body. As illustrated in FIG. 5K, in some embodiments, in accordance with a determination by the computer system that a distance between the portion of the user's body and the one or more cameras is not below the second threshold distance, device 100 visually deemphasizes (e.g., fades) the representation 552 of the portion of the user's body. In some embodiments, increase in the distance of the user's hand from the respective threshold distance causes the computer system to increase an amount of visual deemphasis (e.g., as the user's hand is moved farther from the second threshold, a degree of transparency of the representation of the user's hand increases, and as the user moves the user's hand closer to the device, the degree of transparency of the representation of the user's hand gradually decreases (e.g., proportionally to the change in distance of the user's hand)).

Visually deemphasizing (e.g., fading) the representation of the portion of the user's body provides visual feedback informing the user that the portion of the user's body is not in a proper position within the field of view of the one or more cameras and prompting the user to move the portion of the user's body if the user wishes the computer system to measure the portion of the user's body. Providing improved visual feedback to the user enhances the operability of the computer system and makes the user-device interface more efficient (e.g., by helping the user to achieve an intended result and reducing user mistakes when operating/interacting with the system), which, additionally, reduces power usage and improves battery life of the device by enabling the user to use the computer system more quickly and efficiently.

In some embodiments, the portion of the user's body is in a physical environment, for example, physical environment 531 illustrated in FIGS. 5G-5N. In some embodiments, prior to detecting the portion of the user's body, the computer system displays (928) a background. For example, the background is a computer-generated background (e.g., wallpaper) that does not include display of physical object(s) (e.g., a light, a ceiling fan, a ceiling, etc.) that are in the physical environment behind the user's hand. In some embodiments, in response to detecting the portion of the user's body is in the field of view of the one or more cameras, the computer system displays the representation of the portion of the user's body that is in the field of view of the one or more cameras over the background (without displaying a physical environment in the field of view of the one or more cameras). For example, before user's hand 532 is within the field of view of the one or more cameras of device 100, ceiling fan 530 is within the field of view of the one or more cameras, and a representation 534 of the ceiling fan is displayed by device 100 without displaying representation of the user's hand. In accordance with the user's hand 532 being positioned within the field of view of the one or more cameras, a representation 548 of the user's hand is displayed over a computer-generated background 546, as shown in FIG. 5J.

Removing a view of the physical environment and only displaying a representation of the portion of the user's body provides information about the portion of the user's body without distraction, making it easier for the user to adjust a position of the portion of the user's body. Providing improved visual feedback to the user enhances the operability of the computer system and makes the user-device interface more efficient (e.g., by helping the user to achieve an intended result and reducing user mistakes when operating/interacting with the system), which, additionally, reduces power usage and improves battery life of the computer system by enabling the user to use the computer system more quickly and efficiently.

In some embodiments, the portion of the user's body is in a physical environment, and the computer system displays (930) a representation of the field of view of the one or more cameras that includes a representation of the physical environment (e.g., displaying a representation of a portion of the physical environment that is behind the user's hand). In some embodiments, in response to the computer system detecting the portion of the user's body is in the field of view of the one or more cameras, the computer system visually deemphasizes (e.g., masks out) the representation of the physical environment. For example, as illustrated in FIG. 5H, the representation 538 of the ceiling fan is visually deemphasized by the computer system (e.g., faded) as compared to the representation 534 of the ceiling fan shown in FIG. 5G. In some embodiments, replacing display of the representation of the physical environment includes displaying a background and the representation of the portion of the user's body. For example, as illustrated in FIGS. 5I-5J, in some embodiments, the background displayed in FIG. 5I (e.g., including representation 542 of the ceiling fan) is replaced, as shown in FIG. 5J, with a background 546 while maintaining display of the representation 548 of the user's hand.

Changing the appearance of the user interface to visually deemphasize portions of the physical environment provides visual feedback to the user indicating that the device has detected the portion of the user's body. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the computer system by enabling the user to use the computer system more quickly and efficiently.

In some embodiments, in response to detecting the portion of the user's body, in accordance with the determination that the portion of the user's body meets the first criteria, the computer system displays (932) an indicator that at least partially overlays the representation of the portion of the user's body. For example, as illustrated in FIG. 7B, in some embodiments, an indicator (e.g., virtual bracelet 708) is displayed in accordance with a determination by the computer system that the representation 706 of the user's hand meets the first criteria (e.g., is in the proper position). In some embodiments, as described in more detail with reference to the method 1000, the indicator is updated by the computer system to indicate an extent of scanning (e.g., to determine depth information) of the portion of the user's body that has been completed by the computer system. In some embodiments, the indicator represents a progress of the movement of the portion of the user's body (for the one or more cameras to capture a plurality of views).

Displaying visual indicators relative to the representation of the portion of the user's body provides visual feedback to the user identifying the proper position of the portion of the user's body and a proper movement (e.g., direction of rotation) to follow in order to obtain one or more measurements by the computer system of the portion of the user's body. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the computer system by enabling the user to use the computer system more quickly and efficiently.

In some embodiments, the computer system displays (934) a second user interface. In some embodiments, the second user interface includes an option to select (e.g., purchase) a product having a plurality of size options, selectable in accordance with a measurement by the computer system of the portion of the user's body that is in a field of view of the one or more cameras and an affordance that, when selected, initiates display of the first user interface by the computer system. For example, as illustrated in FIG. 5C, a user interface for shopping for an accessory (e.g., watch) includes button 506 ("Measure your band size") that, when selected, initiates display by the computer system of the instructional measurement interface illustrated in FIG. 5D for measuring the user's wrist.

Providing additional options for selecting different accessories that come in different sizes on a user interface before measuring a respective portion of the user's body avoids cluttering the user interface by automatically identifying which portion of the user's body needs to be measured in accordance with the selected type of accessory. Providing options for measuring different portions of the user's body based on a selected accessory without cluttering the user interface with additional displayed measuring options (e.g., to change the portion of the user's body that is to be measured) enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displays (936), in a third user interface (e.g., prior to displaying the first user interface) an instruction to identify (e.g., select) the first body part as a right-side body part or a left-side body part. For example, as illustrated in FIGS. 5D-5E, in some embodiments, user interface 510 includes selectable buttons 514 and 516 to allow a user to select the left wrist or the right wrist.

Providing additional options for selecting which side of a portion of the user's body should be measured avoids cluttering the user interface for aligning the portion of the user's body for measurement by only displaying guidance for the selected side of the user's body to be measured. Providing options for measuring different sides (e.g., right or left) of the portion of the user's body without cluttering the user interface with additional guidance related to portions of the user's body that are not to be measured enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displays (938), in the first user interface, a first color in a second region of the first user interface (e.g., the second region surrounds the representation of the first body part displayed by the computer system on the first user interface). In some embodiments, the color(s) are displayed by the computer system in the first user interface without regard to whether the portion of the user's body is in the field of view of the one or more cameras. In some embodiments, the computer system replaces display of the first color with display of a second color, distinct from the first color (e.g., in accordance with a determination by the computer system that a time criterion has been met). In some embodiments, the computer system changes the color periodically (e.g., every 3 seconds, every 5 seconds, etc.). In some embodiments, the colors represent one or more colors of the product that are available to be selected/purchased by the user (e.g., watch band colors). In some embodiments, replacing display of the first color with display of the second color includes cross-fading between the first color and the second color (e.g., a gradual fading). For example, as explained above with reference to FIGS. 5D-5E, in some embodiments a background color changes (e.g., as indicated by the change in pattern of the background of user interface 510 to user interface 520).

Automatically changing colors of a background to display a plurality of colors that correspond to colors of a selected accessory provides visual feedback to the user illustrating options of the possible colors the user may select for the accessory in which the user is being measured without requiring additional user inputs for the user to view different color options. Providing improved visual feedback to the user and reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the computer system by enabling the user to use the computer system more quickly and efficiently.

It should be understood that the particular order in which the operations in FIGS. 9A-9C have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein (e.g., methods 1000, 1100 and 1200) are also applicable in an analogous manner to method 900 described above with respect to FIGS. 9A-9C. For example, the user interface objects described above with reference to method 900 optionally have one or more of the characteristics of the user interface objects described herein with reference to other methods described herein (e.g., methods 1000, 1100 and 1200). For brevity, these details are not repeated here.

FIGS. 10A-10D are flow diagrams illustrating method 1000 of providing virtualized progress indicators for measuring a portion of a user's body in accordance with some embodiments. Method 1000 is performed at a computer system (e.g., portable multifunction device 100, device 300, or device 800) that includes (and/or is in communication with) a display generation component (e.g., a display, optionally touch-sensitive, a projector, a head-mounted display, a heads-up display, or the like), one or more cameras (and optionally one or more depth sensors), and one or more input devices, optionally one or more pose sensors, optionally one or more sensors to detect intensities of contacts with the touch-sensitive surface, and optionally one or more tactile output generators. Some operations in method 900 are, optionally, combined and/or the order of some operations is, optionally, changed.

As described below, method 1000 provides an intuitive way to intelligently provide visual feedback to a user to indicate progress of the device automatically measuring a portion of the user's body as the portion of the user's body moves, without requiring the user to provide inputs while the user moves the portion of the user's body to obtain measurements. Providing improved visual feedback to the user and performing an operation (e.g., automatically) when a set of conditions has been met without requiring further user input enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

The computer system displays (1002), in a user interface (for measuring a portion of the user's body), a first representation of a body part that is in a field of view of the one or more cameras. For example, as illustrated in FIG. 7B, the user's hand 532 is in the field of view of the one or more cameras of device 100, which displays a representation 706 of the user's hand.

The computer system detects (1004), using the one or more cameras, movement of the body part, wherein the displayed first representation of the body part is updated in accordance with the movement of the body part. For example, as described with reference to FIGS. 7B-7E, as the user's hand 532 moves with respect to device 100, the representation 718 of the user's hand is updated in accordance with the movement of the user's hand 532 in the physical environment 531. In some embodiments, the computer system and/or the one or more cameras of the computer system are stationary (e.g., the device 100 remains unmoved). In some embodiments, the movement comprises a rotation of the body part. For example, as illustrated in FIGS. 7J-7M, as the user's hand rotates, the representation of the user's hand is rotated on the display of device 100.

While displaying the first representation of the body part, the computer system displays (1006) an indicator (e.g., a progress indicator, such as the virtual bracelet described with reference to FIGS. 7A-7M) at a fixed location relative to the first representation of the body part. For example, as described with reference to FIGS. 7B-7E and FIGS. 7J-7M, a virtual bracelet is displayed at a fixed location relative to the representation of the user's hand.

The indicator is displayed (1008) by the computer system at a first position in the user interface that overlays at least a portion of the representation of the body part. In some embodiments, the indicator is at least partially translucent or semitransparent (e.g., as illustrated in FIGS. 7E-7L, the representation of the user's hand is visible through the virtual bracelet). The indicator is updated in accordance with the movement of the body part (e.g., the virtual bracelet is displayed in a same relative position as the user's hand moves up, down, left, right, etc., as described with reference to FIGS. 7B-7E). The indicator includes an indication of a suggested direction of movement of the body part. For example, the indicator is updated to light up (e.g., fill) additional portions of the indicator to show progress of the movement (e.g., the indicators of virtual bracelet fill as the user rotates the user's hand, as described with reference to FIGS. 7J-7M).

In some embodiments, the indication of the suggested direction of movement comprises (1010) an animation of the indicator indicating the direction of movement. In some embodiments, the indicator is animated in accordance with the movement of the body part. In some embodiments, the indicator is animated without detecting movement of the body part (e.g., the indicator is animated to light up or otherwise indicate a suggested direction of movement before detecting movement of the body part). For example, FIG. 7A illustrates an instructional user interface in which the indicators of the virtual bracelet are animated to fill as animated representation 702 of a hand rotates (e.g., wherein the user's hand is not moving; or, in some embodiments, the animated representation 702 is displayed regardless of whether the user's hand is stationary or moving).

Displaying an animation showing a direction in which a user should rotate a body part to obtain one or more measurements of the body part provides visual feedback to the user indicating whether the user has turned the body part in the correct, or incorrect, direction. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the body part is (1012) a wrist and/or a hand. For example, in FIGS. 5G-5N, the user's hand 532 is illustrated in the physical environment 531 such that the user's hand 532 is within a field of view of one or more cameras of device 100.

Automatically detecting a user's hand that is positioned over the cameras of the device and measuring the user's hand to determine a size of an accessory that is worn on or near the user's hand makes it easier for a user to obtain sizing information without requiring the user to manually input measurements of the user's body, and without requiring the user to manually make measurements of the user's body (e.g., using a physical tape measure). Reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the body part is in a physical environment, and the computer system displays (1014), in the first user interface, a background. For example, the background is a computer-generated background. In some embodiments, the background is an augmented reality environment that displays virtual objects concurrently with physical objects that are in the physical environment. In some embodiments, the background is not a representation of the physical environment that is within the field of view of the one or more cameras. For example, as described with reference to FIG. 5J, device 100 does not display objects, other than the user's body or body part, that are within the field of view of the one or more cameras (e.g., ceiling fan 530) and instead displays background 546 as a colored background or other computer-generated background. In some embodiments, the computer system detects, using the one or more cameras, a portion of the physical environment and the body part that are within the field of view of the one or more cameras. In some embodiments, the computer system displays the representation of the body part over the background without displaying a representation of the portion of the physical environment that is within the field of view of the one or more cameras. For example, FIG. 5J illustrates the representation 548 of the user's hand without displaying a representation of the ceiling fan 530 that is in the physical environment 531 within the field of view of the one or more cameras of device 100.

Removing a view of the physical environment and only displaying a representation of the portion of the user's body provides information about the portion of the user's body without distraction, making it easier for the user to adjust a position of the portion of the user's body. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displays (1016) a background having a first color and replaces display of the background having the first color with display of a background having a second color. In some embodiments, the background is displayed in a second user interface prior to displaying the first user interface (e.g., the color cycles through before the body part is detected using the one or more cameras). In some embodiments, the background color is changed by the computer system in accordance with a determination that a time criterion has been met. For example, the computer system changes the color periodically (e.g., every 3 seconds, every 5 seconds, etc.). For example, as described with reference to FIGS. 5D-5F, a color of the background of user interface 510 (FIG. 5D) is changed by the computer system to another color in user interface 520 (FIG. 5E), which includes the same user interface elements as user interface 510, and the background of user interface 520 is updated upon transitioning to displaying another user interface 524 (FIG. 5F).

Automatically changing colors of a background to display a plurality of colors provides visual feedback to the user, and optionally may illustrate colors the user may select for an accessory. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the first color and the second color correspond to (1018) color options for a physical object to be worn on the body part. In some embodiments, the physical object comprises a wrist band or a watch band. In some embodiments, the body part is measured to determine a size for the physical object. In some embodiments, the first color and the second color are colors of watch bands that are available for purchase.

Automatically changing colors of a background to display a plurality of colors that correspond to colors of a selected accessory provides visual feedback to the user illustrating options of the possible colors the user may select for the accessory in which the user is being measured without requiring additional user inputs for the user to view different color options. Providing improved visual feedback to the user and reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system detects (1020) movement of the body part in a first direction and in response to detecting the movement of the body part in the first direction, the computer system displays the representation of the body part at a second position in the user interface in accordance with the movement of the body part and displays the indicator at the fixed location relative to the first representation of the body part displayed at the second position. In some embodiments, detecting movement of the body part in the first direction comprises detecting movement of the body part laterally (e.g., left, right, up, down) along an axis that is parallel to a position (e.g., an external surface) of the one or more cameras (e.g., not moving closer or farther away from the camera; maintaining a distance from the one or more cameras as the body part moves left, right, up, or down within a plane parallel to the view of the one or more cameras). In some embodiments, the indicator is continually displayed (e.g., appears to move) over the body part as the body part moves in the first direction. For example, as described with reference to FIGS. 7B-7C, as the user's hand 532 moves to the left along an axis that is parallel to a position of the one or more cameras, the representation 710 of the user's hand displayed by device 100 is updated to move to the left, and virtual bracelet 712 moves with the representation 710 of the user's hand (e.g., as compared to FIG. 7B).

Automatically moving the indicators that show progress of the measurement, relative to the representation of the portion of the user's body, provides continual visual feedback to the user so that the user is aware of the progress of the measurement even when the user has moved the portion of the user's body relative to the computer system. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the first representation of the body part and the indicator are displayed (1022) by the computer system at respective first sizes in the user interface. In some embodiments, the computer system detects movement of the body part that changes a distance between the one or more cameras and the body part. In some embodiments, in response to detecting the change in distance between the one or more cameras and the body part, the computer system displays the first representation of the body part at a respective second size (e.g., distinct from the first size of the representation of the body part) in accordance with the changed distance and displays the indicator at a respective second size (e.g., distinct from the first size of the indicator) in accordance with the changed distance. In some embodiments, the indicator maintains its position relative to the representation of the body part, wherein the size of the representation of the body part is updated in accordance with the changed distance. For example, the indicator is scaled by the computer system proportionately such that when the body part is closer to the one or more cameras (zoomed), the representation of the body part increases in size, and accordingly, the indicator increases proportionally in size (e.g., with a same size ratio) such that the indicator continues to overlay the same portion of the representation of the body part as before the detected movement of the body part. In another example, as the body part moves farther away from the one or more cameras, the indicator is scaled by the computer system to maintain its position and size relative to the body part (e.g., the indicator becomes smaller as the body part moves farther away). For example, as illustrated in FIGS. 7D and 7E, as the user's hand 532 moves away from and closer to the device 100, the representation of the user's hand and the virtual bracelet are updated on the display of device 100 such that the virtual bracelet is displayed at a size proportional to the size of the representation of the user's hand.

Automatically changing a size of the indicators that show progress of the measurement, relative to the representation of the portion of the user's body, provides continual visual feedback to the user so that the user is aware of the progress of the measurement even when the user has moved the portion of the user's body closer or farther to the computer system. The size of the indicator further provides visual feedback to the user to indicate whether the portion of the user's body is too close or too far away from the computer system. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system detecting movement of the body part comprises (1024) detecting rotation of the body part. In some embodiments, the computer system, while detecting rotation of the body part, scans, using the one or more cameras, one or more images to determine a measurement of the body part and updates the indicator to indicate a progress of scanning the one or more images. For example, FIGS. 7J-7M illustrate the representation of the user's hand rotating as the user rotates the user's hand in the physical environment.

Automatically animating the indicators that show progress of the measurement, as the user rotates the body part, provides continual visual feedback to the user so that the user is aware of the progress of the measurement as the user continues moving and rotating the user's body part relative to the computer system. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the indication displayed by the computer system of the suggested direction of movement of the body part comprises (1026) an indication to rotate the body part. For example, the indication indicates rotation around an axis defined by the indication. In some embodiments, the indication indicates a speed of rotation, and/or indicates a direction (e.g., clockwise or counterclockwise with respect to the axis) of rotation. In some embodiments, the indication comprises a text prompt to rotate the body part. In some embodiments, the indication comprises an animation (e.g., of an arrow) to prompt rotation of the body part.

Animating the indicators to show a correct direction of rotation of the body part to obtain one or more measurements of the body part provides visual feedback to the user indicating whether the user should rotate their body part in a different direction (e.g., clockwise or counterclockwise) relative to the computer system. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, while displaying the first representation of the body part, the computer system captures (1028), using the one or more cameras, one or more images of the body part. For example, as the user rotates the user's hand as described in FIGS. 7J-7M, the device captures one or more images (e.g., scans) the user's hand (e.g., at different positions as the user's hand rotates). In some embodiments, the one or more images are used to determine a measurement of the body part. In some embodiments, the computer system displays, in a second user interface, a size corresponding to the measurement of the body part. In some embodiments, the size is a size of the body part. In some embodiments, the size is a size of an accessory (e.g., watch band) for the body part. For example, as illustrated in FIG. 7N, the device displays a size of a watch band (e.g., Size 5) as determined from the measurement of the user's wrist.

Automatically capturing an image of the user's body part and using the image to determine a measurement of the user's body part, and a corresponding size, makes it easier for the user to obtain sizing information without the user manually taking a photograph of the user's body and/or manually inputting measurements into the computer system. Reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the fixed location relative to the first representation of the body part is (1030) a first fixed location relative to the first representation of the body part. In some embodiments, the computer system receives a first user input in a first direction, and, in response to the first user input, updates the first fixed location of the indicator (e.g., virtual bracelet 724, FIG. 7F) relative to the body part to a second fixed location, distinct from the first fixed location, relative to the body part. In some embodiments, the first user input is a drag user input to move the indicator to the second fixed location corresponds to a liftoff position of the drag user input. For example, FIGS. 7F-7G illustrate the user changing a location of an indicator, virtual bracelet 724, relative to the representation 722 of the user's hand (e.g., before scanning).

Changing a location of the indicator relative to the representation of the user's body part to indicate a different portion of the user's body part will be measured improves visual feedback for the user by displaying, using the location of the indicator, which portion of the user's body part is going to be measured. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system replaces (1032) display of the indicator at the first position in the user interface with a user interface element at the first position in the user interface. In some embodiments, the user interface element is displayed at the fixed location relative to the first representation of the body part, and the user interface element indicates a first size of a portion of the body part corresponding to the portion of the representation of the body part at the fixed location. In some embodiments, the user interface element comprises an AR object (that appears to be worn on the representation of the body part). For example, the virtual bracelet illustrated in FIGS. 7B-7M is an AR object that appears to be worn on the user's wrist. In some embodiments, the user interface element comprises a virtual measuring tape (e.g., as illustrated in FIGS. 7Q-7S). In some embodiments, the user interface element comprises a virtual accessory, such as a virtual watch (e.g., as illustrated in FIGS. 7N-7P). In some embodiments, the user interface element comprises a representation of a product that is offered for sale (e.g., a product that is selected in FIG. 5C). In some embodiments, the user interface element comprises a representation of a watch having options as configured (selected) by the user (e.g., the user selects color, shape, style, etc. of the watch). In some embodiments, the user interface element is a different size than the indicator. For example, the virtual bracelet is a different size than the watch 754 in FIG. 7P and a different size than the measuring tape shown in FIG. 7Q. In some embodiments, the indicator is replaced in response to completing the measurement. For example, an animated transition is used to replace the virtual bracelet shown in FIG. 7M with the watch 754 in FIG. 7N, or to replace the measuring tape shown in FIG. 7Q with the watch 754 in FIG. 7N.

Automatically transitioning the indicator to a user interface object that is also displayed relative to the representation of the portion of the user's body improves visual feedback for the user by indicating that the measurement of the portion of the user's body has been successful, and thus the progress indicator is no longer displayed. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the fixed location relative to the first representation of the body part is a first fixed location and the computer system receives (1034) a second user input to move the user interface element (e.g., a drag input). In some embodiments, in response to receiving the second input, the computer system moves the user interface element (e.g., a drag input) from the first position in the user interface that overlays at least a portion of the representation of the body part to a third fixed location (e.g., distinct from the first fixed location) relative to the first representation of the body part. For example, the fixed location is at a predefined location on the user's wrist (e.g., moved from a first distance from wrist bone to a second distance from the wrist bone). In some embodiments, the user interface element is maintained at the location relative to the user's wrist as the user's wrist moves in the field of view of the one or more cameras. In some embodiments, the user updates the fixed location of the user interface element after the scanning (e.g., measuring) of the body part is complete. For examples, as illustrated in FIGS. 7O-7P, the user drags the watch band 754 to another position on the representation of the user's wrist.

Providing a user with the ability to change a location of the user interface element relative to the representation of the user's body part improves visual feedback for the user by allowing a user to move the user interface element over the representation of the user's body part such that the user can visualize which portion of the user's body part is measured for a size determination. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in accordance with a determination that the user interface element is at the third fixed location relative to the first representation of the body part, the computer system updates (1036) the user interface element to indicate a second size of a portion of the body part corresponding to the third fixed location. For example, the size of the user's wrist in FIG. 7N is "Size 5" when the watch 754 is at a first fixed location and, after the user interface element is moved to a different location on the representation of the user's hand, as illustrated in FIG. 7P, the size of the user's wrist corresponds to "Size 6."

Changing a location of the user interface element relative to the representation of the user's body part, and automatically updating a size associated with the respective location, improves visual feedback for the user by displaying, using the user interface element, which portion of the user's body part corresponds to the displayed size. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system captures (1038) an image (e.g., screenshot, optionally including depth information from one or more depth sensors) that includes the first representation of the body part and the user interface element at the first fixed location relative to the first representation of the body part. In some embodiments, the user interface element indicates a size of the portion of the body part corresponding to the first fixed location of user interface element. For example, in some embodiments, the representation of the user's hand illustrated in FIG. 7N is not a representation of a current field of view of the one or more cameras (e.g., the user has moved the user's hand out of the field of view of the one or more cameras), and the representation displayed in FIG. 7N is an image captured of the user's hand (e.g., prior to the user removing the user's hand from the field of view of the one or more cameras).

Automatically capturing an image of the user's body part, optionally including depth information, and using the image to determine a measurement of the user's body part, and a corresponding size, makes it easier for the user to obtain sizing information without requiring the user to maintain the user's body part in a proper position relative to the computer system, manually take a photograph of the user's body and/or manually input measurements into the computer system. Reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, while displaying the image, the computer system receives (1040) a third user input (e.g., on the image displayed on the display device) to move the user interface element to a different fixed location relative to the first representation of the body part in the image (e.g., as described with reference to FIGS. 7N-7S).

Providing a user with the ability to change a location of the user interface element relative to the representation of the user's body part improves visual feedback for the user by allowing a user to move the user interface element over the representation of the user's body part such that the user can visualize which portion of the user's body part is measured for a size determination. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the user interface is a first user interface and the computer system displays (1042) a second user interface, the second user interface including an option to select (e.g., purchase) a product having a plurality of size options, selectable in accordance with a measurement of the body part that is in the field of view of the one or more cameras and an affordance that, when selected, initiates display of the first user interface. For example, FIG. 5C illustrates a user interface for selecting a watch (e.g., and/or a watch band with a plurality of size options). In some embodiments, to select a size option, the user selects button 506 "Measure your band size."

Providing additional options for selecting different accessories that come in different sizes on a user interface before measuring a respective portion of the user's body avoids cluttering the user interface by automatically identifying which portion of the user's body needs to be measured in accordance with the selected type of accessory. Providing options for measuring different portions of the user's body based on a selected accessory without cluttering the user interface with additional displayed measuring options (e.g., to change the portion of the user's body that is to be measured) enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the user interface is (1044) a user interface within a respective application executed by the computer system. In some embodiments, the respective application is a measure application for measuring one or more objects, such a user's body part, as described with reference to FIG. 5A. In some embodiments, the respective application is an online store (e.g., "Electronics Store") application, as described with reference to FIG. 5B. In some embodiments, the respective application is a watch application, which is configured to communicate (e.g., includes instructions for communicating) between a first electronic device and a watch (e.g., or other wearable device).

Providing measurement functionality within additional applications that are already present on the computer system avoids cluttering the user interface by allowing the measurement feature to be launched from within an existing application. Providing options for measuring the user's body part using existing applications without cluttering the user interface with an additional application for measuring the user's body enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the indicator is gradually changed (1046) in appearance by the computer system as the body part moves, to indicate an amount of progress toward completing a scan or measurement of the body part as the body part is rotated, or an amount of progress toward completing a rotation of the body part. For example, as illustrated in FIGS. 7J-7M, the virtual bracelet is updated to gradually change (e.g., fill the indicators of the virtual bracelet) as the user's hand rotates. In some embodiments, the indicator comprises openings (e.g., ovals) that are progressively filled in accordance with the movement of the body part.

Progressively animating portions of the indicator to show the progress of rotation of the user's body part provides visual feedback to the user to indicate which portions of the user's body part have successfully been scanned and/or measured. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in response to the computer system detecting movement of the body part, in accordance with a determination by the computer system that the movement of the body part moves at a speed that is below a threshold speed, the computer system gradually changes (1048) an appearance of indicator in appearance as the body part moves to indicate a progress of movement of the body part toward a target pose.

In some embodiments, in accordance with a determination by the computer system that the movement of the body part moves at a speed that is above the threshold speed, the computer system forgoes at least a portion of a change in appearance of indicator in appearance as the body part moves to indicate that movement of the body part toward the target pose was too fast. For example, as described with reference to FIGS. 7H-7I, the indicators of the virtual bracelet 730 are not filled by the computer system in accordance with a determination by the computer system that the user is rotating the user's wrist too quickly (e.g., above the threshold speed). In some embodiments, the criteria include a requirement that a rate of rotation of the portion of the user's body is less than a threshold rate of rotation (e.g., the first criteria is not met when the user moves the arm too quickly).

Visually animating portions of the indicator that correspond to a progress of rotation of the user's body part provides visual feedback to the user by using the unanimated portions of the indicator to represent portions of the user's body part that were not scanned and/or measured because the body part of the user was rotated too fast. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

It should be understood that the particular order in which the operations in FIGS. 10A-10D have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein (e.g., methods 900, 1100 and 1200) are also applicable in an analogous manner to method 1000 described above with respect to FIGS. 10A-10D. For example, the user interface objects described above with reference to method 1000 optionally have one or more of the characteristics of the user interface objects described herein with reference to other methods described herein (e.g., methods 900, 1100 and 1200). For brevity, these details are not repeated here.

FIGS. 11A-11C are flow diagrams illustrating method 1100 of generating a machine-readable code that stores information about a measurement in accordance with some embodiments. Method 1000 is performed at a computer system (e.g., portable multifunction device 100, device 300, or device 800) that includes (and/or is in communication with) a display generation component (e.g., a display, optionally touch-sensitive, a projector, a head-mounted display, a heads-up display, or the like), one or more cameras (and optionally one or more depth sensors), and one or more input devices, optionally one or more pose sensors, optionally one or more sensors to detect intensities of contacts with the touch-sensitive surface, and optionally one or more tactile output generators. Some operations in method 1100 are, optionally, combined and/or the order of some operations is, optionally, changed.

As described below, method 1100 provides an intuitive way to automatically detect a portion of a user's body, determine a measurement for the portion of the user's body, and embed information about the measurement in a machine-readable code. Embedding information in a scannable (e.g., computer readable) code allows the computer system to store and share sizing and/or accessory information for a user, thus eliminating the need for a user to remember their own sizing information and/or requiring the user to select a method for sharing the sizing information. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

The computer system detects (1102), using the one or more cameras, a portion of a user's body that is in the field of view of the one or more cameras.

The computer system scans (1104) the portion of the user's body that is in the field of view of the one or more cameras to determine a measurement of the portion of the user's body that is in the field of view of the one or more cameras. For example, the computer system uses methods as described with reference to FIGS. 6C-6N and/or FIGS. 7J-7M to scan and measure a body part of the user (e.g., the user's wrist).

The computer system, after scanning the portion of the user's body, generates (1106) a machine-readable code that includes information that identifies one or more sizing parameters of a wearable object based on the measurement of the portion of the user's body or that describes the measurement of the portion of the user's body. In some embodiments, the machine-readable code is configured to be scanned for purchasing the wearable object (e.g., an accessory).

In some embodiments, after scanning the portion of the user's body, the computer system displays (1108) a first user interface, the first user interface including a user-interface object that, when selected, generates the machine-readable code. In some embodiments, the computer system detects a user input selecting the user-interface object and, in response to detecting the user input, generates the machine-readable code. For example, as shown in FIG. 7T, the computer system receives an input 786 selecting button 782 "Yes" to save the user's size as a virtual card. In response to the input, the computer system generates a QR code (e.g., QR code 804, FIG. 8A, or QR code 1004, FIG. 8D).

Displaying a plurality of user interface elements, including an option to directly save sizing information obtained by the device, provides the user with quick and easy access to available functionality of a measurement user interface without requiring the user to navigate through complex menu hierarchies. Providing additional control options and reducing the number of inputs needed to perform an operation enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the machine-readable code comprises (1110) a QR code. For example, the QR codes illustrated in FIGS. 8A and 8D. In some embodiments, the QR code is configured to be scanned at a store for purchasing a wearable object (e.g., and/or an accessory for a wearable object). For example, the user purchases a wearable object having the one or more size parameters identified by the machine-readable code.

Embedding information as a QR code allows the computer system to easily share sizing and/or accessory information stored in the QR code, thus eliminating the need for a user to manually input the embedded information to share the information with another device. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, a second computer system (e.g., a second electronic device), scans (1112) the machine-readable code and, in response to scanning the machine-readable code, initiates a process for displaying information about the wearable object on the second computer system (e.g., second electronic device) or a third computer system (e.g., third electronic device) communicatively coupled to the second computer system. In some embodiments, the second computer system and the third computer system are the same computer system (e.g., an electronic device that includes one or more cameras for scanning the machine-readable code and a display device to display the information about the wearable object or accessory). For example, as illustrated in FIG. 8B, in some embodiments, a second electronic device 800 scans the machine-readable code that is displayed on device 100. In some embodiments, the second electronic device is a scanner and the third electronic device is an electronic device with a display device that is communicatively coupled to the scanner.

Obtaining information from another electronic device by scanning a machine-readable code displayed on the other device eliminates the need for a user to manually input information that is stored in the machine-readable code. Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the second computer system or the third computer system, in accordance with a determination that the machine-readable code has been scanned, displays (1114) a first application on a first portion, less than all, of user interface displayed using a display generation component of the second computer system or third computer system. In some embodiments, the first application includes the information that identifies the one or more sizing parameters of the wearable object or that describes the measurement of the portion of the user's body within a first application. For example, as illustrated in FIG. 8C, device 800 displays a machine-readable code (e.g., QR code 804) within a first application 806 on a portion of the display.

Providing an application (e.g., a miniature application) that includes the information that was stored in the machine-readable code avoids cluttering the user interface by only displaying the stored information without requiring the user to download an application to view the information. Providing the information stored in the machine-readable code on a portion of the display enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the second computer system or the third computer system, in response to scanning the machine-readable code, displays (1116), using a display generation component of the second computer system or third computer system, a card that includes information about the wearable object, including the information stored in the machine-readable code that identifies one or more sizing parameters of the wearable object. For example, in some embodiments, a card, such as virtual card 1006 illustrated in FIG. 8D, is displayed in response to the second electronic device scanning the machine-readable code. In some embodiments, the displayed card includes additional information, obtained from the machine-readable code, about the wearable object, which is in addition to the one or more sizing parameters. Such additional information may include, for example, as a color, style, material or other feature of the wearable object.

For example, in FIG. 8D, the displayed card includes additional information (e.g., style information; model or product identifying information) about the wearable object (e.g., "Watch Band Style A").

Providing a displayed card, sometimes herein called a virtual card, that includes the information that was stored in the machine-readable code improves visual feedback to the user by displaying the stored information and/or the machine-readable code such that the user can see the information displayed on the user's device. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displays (1118) an option for adding a virtual card that includes the information about the wearable object to a virtual wallet, and, in response to detecting a user input selecting the option, stores the virtual card in the virtual wallet. For example, as described with reference to FIGS. 7T and 8D, in some embodiments (e.g., when the user saves the virtual card to a same device that was used to scan and measure the user's wrist), device 100 stores the virtual card. In some embodiments, the virtual wallet is stored on the (first) computer system or for a user of the first computer system. In some embodiments, a user can access the virtual card by opening the virtual wallet. In some embodiments, a display of the virtual card includes the machine-readable code (e.g., as illustrated in FIGS. 8E-8F). In some embodiments, the virtual card displays information stored in the machine-readable code (e.g., in addition to, or instead of, displaying the machine-readable code). For example, the virtual card includes text indicating a size of the user's body part, or a sizing parameter of a wearable object or accessory, and/or text indicating information about the wearable object or accessory (e.g., "Watch Band Style A").

Displaying a user interface element for saving a virtual card to the user's virtual wallet, while displaying the virtual card that includes the sizing information, provides the user with quick and easy access to available functionality of a virtual wallet without requiring the user to navigate through complex menu hierarchies. Providing additional control options and reducing the number of inputs needed to perform an operation enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, at a respective computer system on which the virtual card is stored or accessed, in accordance with a determination that the respective computer system is within a predefined proximity to a predefined location, the respective computer system displays (1120), using a display generation component of the respective computer system, a visual prompt for displaying the virtual card that is stored in the virtual wallet. For example, in accordance with a determination that the respective computer system (and/or the user of the respective computer system) is within a threshold distance (e.g., 10 feet, 20 feet, etc.) of a predefined location, such as a store (e.g., that sells the wearable object and/or an accessory for the wearable object, such as a watch band), a visual prompt is automatically (without user input) generated and displayed on the respective computer system. For example, as described with reference to FIG. 8E, in some embodiments, a prompt (e.g., notification) 812 is generated and displayed on the device that stores the virtual card. In some embodiments, displaying the visual prompt is performed in conjunction with providing a notification (e.g., a sound, a vibration, or other alert).

Automatically providing a notification to a user according to a user's location, including providing a user interface element for opening a virtual card that is stored in the user's virtual wallet, reduces the number of inputs required from the user and provides the user with quick and easy access to available functionality of the virtual wallet without requiring the user to navigate through complex menu hierarchies. Providing additional control options and reducing the number of inputs needed to perform an operation enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the respective computer system detects (1122) a user input selecting the visual prompt for displaying the virtual card and, in response to detecting the user input selecting the visual prompt, displays, using the display generation component of the respective computer system, the virtual card. For example, in response to the user selecting the visual prompt, the virtual card is displayed (e.g., within a user interface for the virtual wallet), as described with reference to FIGS. 8E-8F.

Automatically providing a user interface element, that when selected by the user, opens the virtual card that is stored in the user's virtual wallet reduces the number of inputs required from the user and provides the user with quick and easy access to available functionality of the virtual wallet without requiring the user to navigate through complex menu hierarchies. Providing additional control options and reducing the number of inputs needed to perform an operation enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, displaying the virtual card includes (1124) the displaying the machine-readable code. For example, the virtual card 1006 in FIG. 8D includes displaying QR code 1004.

Displaying a machine-readable code, such as a QR code, in the virtual card reduces the number of inputs required to share the information stored in the machine-readable code with another device, such that the other device only need to scan the machine-readable code (e.g., instead of requiring additional user inputs for the user to select an alternative method for sharing and/or recipients for sharing the information). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently In some embodiments, displaying the virtual card includes (1126) displaying a description of the wearable object. For example, the virtual card 1006 in FIG. 8D includes displaying a description about the watch band (e.g., "Style A"). In some embodiments, the description of the wearable object includes a description of the one or more sizing parameters (e.g., "Size 6" is displayed in FIG. 8D). In some embodiments, the description of the wearable object includes a description of a set or class of wearable objects (e.g., a watch band that fits the 44 mm model of a watch, or a watch band of a particular style with a particular size (e.g., small, medium, large, 1, 2, 3, 4, 5, 6, 7, 8, 9, etc.)). In some embodiments, the description of the wearable object includes a color (e.g., including characteristics of the wearable object that are selected by the user in the application (e.g., electronics store, or measure app) before measuring their wrist (e.g., the wearable object displayed in FIG. 5C).

Displaying information about the wearable object within the virtual card improves visual feedback to the user by displaying the stored information such that the user can see the information displayed on the user's device. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

It should be understood that the particular order in which the operations in FIGS. 11A-11C have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein (e.g., methods 900, 1000 and 1200) are also applicable in an analogous manner to method 1100 described above with respect to FIGS. 11A-11C. For example, the user interface objects described above with reference to method 1100 optionally have one or more of the characteristics of the user interface objects described herein with reference to other methods described herein (e.g., methods 900, 1000 and 1200). For brevity, these details are not repeated here.

FIGS. 12A-12D are flow diagrams illustrating method 1200 of prompting a user to adjust a position of the user's body part into a correct position for measurement in accordance with some embodiments. Method 1200 is performed at a computer system (e.g., portable multifunction device 100, device 300, or device 800) that includes (and/or is in communication with) a display generation component (e.g., a display, optionally touch-sensitive, a projector, a head-mounted display, a heads-up display, or the like), one or more cameras (and optionally one or more depth sensors), and one or more input devices, optionally one or more pose sensors, optionally one or more sensors to detect intensities of contacts with the touch-sensitive surface, and optionally one or more tactile output generators. Some operations in method 900 are, optionally, combined and/or the order of some operations is, optionally, changed.

As described below, method 1200 provides an intuitive way to provide visual feedback to a user to indicate a proper positioning of a portion of the user's body for the device to automatically measure the portion of the user's body, without requiring the user to provide inputs while the user moves the portion of the user's body to obtain the measurements.

Providing improved visual feedback to the user and performing an operation (e.g., automatically) when a set of conditions has been met without requiring further user input enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

The computer system displays (1202), at a first fixed location within a first user interface, a first visual prompt (e.g., target) indicating a position for moving a body part into a field of view of the one or more cameras. In some embodiments, the first visual prompt comprises an outline of a circle fixed to the center of the display. For example, as illustrated in FIGS. 6C-6M, target 618 is displayed at a same location within each user interface shown in FIGS. 6C-6M.

While displaying (1204) the first visual prompt indicating the position for moving the body part into the field of view of the one or more cameras, the computer system detects (1206), using the one or more cameras, a portion of a user's body that is in the field of view of the one or more cameras and corresponds to the body part. For example, as described with reference to FIGS. 5G-5N, within a physical environment 531, a user's hand 532 is moved into the field of view of the one or more cameras of device 100. In some embodiments, the detecting includes scanning (e.g., for measurement) the portion of the user's body.

In response to detecting (1208) the portion of the user's body in the field of view of the one or more camera, the computer system displays (1210) a representation of the portion of the user's body and displays (1212) a second visual prompt that is fixed at a predefined position relative to the representation of the portion of the user's body, wherein a position (e.g., a current position) of the second visual prompt relative to a position of the first visual prompt indicates a movement of the body part that is required to satisfy a body part positioning precondition. In some embodiments, the computer system determining the position of the second visual prompt relative to the position of the first visual prompt comprises the computer system determining a separation between (e.g., distance and direction from) the first visual prompt and the second visual prompt. In some embodiments, the second visual prompt comprises a circle (e.g., smaller than the first visual prompt) that is fixed to a position on (or next to) the portion of the representation of the user's body. For example, the first visual prompt is in the center of the display and the second visual prompt is fixed to a center of the user's palm/hand. In some embodiments, the second visual prompt, when aligned with the first visual prompt, fills the first visual prompt. For example, in FIGS. 6C-6F, dot 620 (e.g., a second visual prompt) is displayed by the computer system at a position relative to the representation 622 of the user's hand. As the user moves the user's hand into a proper position, the dot 620 is moved by the computer system (e.g., proportionally) with the representation of the user's hand until dot 620 aligns with target 618 to be in the proper position (e.g., to satisfy the body part positioning precondition).

In some embodiments, while displaying the first visual prompt and the second visual prompt, the computer system detects (1214) movement of the body part. In some embodiments, in response to detecting movement of the body part, the computer system moves the second visual prompt on the display without moving the first visual prompt on the display. For example, as the representation of the user's hand moves on display 100 in FIGS. 6C-6F, dot 620 moves with the representation of the user's hand (e.g., to maintain its relative position to the representation of the user's hand), and target 618 remains in a same fixed location as the representation of the user's hand moves.

Automatically moving the representation of the portion of the user's body in the user interface in accordance with how the user is moving the user's body (e.g., as determined by the one or more cameras) provides continual visual feedback to the user so that the user is aware of where and how to move the portion of the user's body such that the representation of the portion of the user's body is in a proper position for scanning. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in accordance with a determination by the computer system that the body part moves a first amount, the computer system moves (1216) the second visual prompt on the display by a second amount that corresponds to the first amount of movement of the body part. In some embodiments, in accordance with a determination by the computer system that the body part moves a third amount different from the first amount, the computer system moves the second visual prompt on the display by a fourth amount that corresponds to the third amount of movement of the visual prompt and is different from the second amount of movement of the body part. In some embodiments, the first amount is proportional to the second amount (e.g., a predefined scaling factor) and the third amount is proportional to the fourth amount. For example, as illustrated in FIGS. 6E-6F, as the user moves the user's hand in the physical environment (e.g., to the right), the representation of the user's hand displayed on device 100 is updated in accordance with a current view of the one or more cameras of device 100 (e.g., to the right), and dot 620 is moved by the computer system with the representation of the user's hand (e.g., to maintain its position relative to the representation of the user's hand). For example, as the user moves the user's hand by a different amount (e.g., to the right), the dot 620 is moved by the computer system a proportional amount (e.g., in the same direction).

Automatically moving the second visual prompt that is fixed relative to the representation of the portion of the user's body, as the user moves the user's body part, provides continual visual feedback to the user so that the user is aware of how to adjust the portion of the user's body in order to align the second visual prompt with the target. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in accordance with a determination that the body part moves in a first direction, the computer system moves (1218) the second visual prompt on the display in a second direction that corresponds to the first direction of movement of the body part. In some embodiments, in accordance with a determination that the body part moves in a third direction different from the first direction, the computer system moves the second visual prompt on the display in a fourth direction that corresponds to the third direction of movement of the body part and is different from the second direction. In some embodiments, the first respective direction is the same as the first direction and the second respective direction is the same as the second direction. For example, as illustrated in FIGS. 6E-6F, as the user moves the user's hand in the physical environment (e.g., to the right), the representation of the user's hand displayed on device 100 is updated by the device in accordance with a current view of the one or more cameras of device 100 (e.g., to the right), and dot 620 moves with the representation of the user's hand (e.g., to maintain its position relative to the representation of the user's hand).

Automatically moving the second visual prompt that is fixed relative to the representation of the portion of the user's body, as the user moves the user's body part, provides continual visual feedback to the user so that the user is aware of how to adjust the portion of the user's body in order to align the second visual prompt with the target. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the first visual prompt is displayed (1220) by the computer system at a fixed size and at a fixed position in the first user interface as the body part of the user moves. In some embodiments, the first visual prompt is fixed by the computer system in the user interface such that the first visual prompt does not move as the user's hand moves. In some embodiments, the second visual prompt is moved by the computer system as the user's hand moves (e.g., the first visual prompt is fixed at a particular position in the user interface while the second visual prompt moves as the user's hand moves). For example, as illustrated in FIGS. 6C-6F, the dot 620 is fixed relative to the representation of the user's palm.

Maintaining the first visual prompt (e.g., the target) at a fixed location within the user interface provides continual visual feedback to the user so that the user is aware of where and how to move the portion of the user's body in order to align the second visual prompt, that is fixed to the representation of the portion of the user's body, with the target that is fixed within the user interface. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, a displayed size of the second visual prompt is updated (1222) by the computer system in accordance with a change in position of the body part relative to the one or more cameras. For example, in accordance with a determination by the computer system that the body part moves closer to the one or more cameras (e.g., and the representation of the portion of the user's body increases in size), the computer system increases the size of the second visual prompt by a corresponding amount (e.g., proportionally) to the change in size of the body part. For example, as illustrated in FIGS. 6C-6E, the representation of the user's hand increases in size (shown in FIG. 6D) and the dot 620 also increases (e.g., proportionally) in size such that the dot 620 is proportional to a current size of the representation of the user's hand.

Automatically updating a size of the second visual prompt that such that it is proportional to the size of the representation of the portion of the user's body provides continual visual feedback to the user so that the user knows if the user should move the portion of the user's body closer or farther to the device in order for the second visual prompt to fit within the target. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in accordance with a determination that the portion of the user's body changes position relative to the one or more cameras, the computer system updates (1224) a position of the second visual prompt within the first user interface while maintaining the position of the second visual prompt at the fixed predefined position relative to the representation of the portion of the user's body. For example, as described with reference to FIG. 6C-6E, as the user's hand moves in the physical environment, the displayed representation of the user's hand is updated by the computer system, and dot 620 (e.g., the second visual prompt) is updated in position by the computer system so as to remain in a same fixed position relative to the representation of the user's hand.

Automatically moving the second visual prompt that is fixed relative to the representation of the portion of the user's body, without moving the target (e.g., the first visual prompt), provides continual visual feedback to the user so that the user is aware of where and how to move the portion of the user's body in order to align the second visual prompt with the target. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the second visual prompt is displayed (1226) by the computer system at a first angle. In some embodiments, in accordance with a determination that the body part changes position relative to the one or more cameras, the computer system updates the second visual prompt to be displayed at a second angle. In some embodiments, the second angle is determined based on the changed position of the body part. In some embodiments, the second visual prompt is a virtual object that is rotated relative to a plane of the display, so that it starts at a significant angle (e.g., substantially perpendicular) relative to the plane of the display and then rotates so that it is substantially parallel to the display. For example, in some embodiments, dot 644 in FIGS. 6I-6K is displayed by the computer system so as to being at an angle such that the dot 644 appears as an oval (e.g., as if viewing the side of dot 644), and as the representation of the user's hand is rotated, the angle at which dot 644 is displayed is also updated by the computer system in accordance with how much the user's hand has rotated.

Automatically changing an angle of display of the second visual prompt that is fixed relative to the representation of the portion of the user's body provides continual visual feedback to the user so that the user is aware of an angle of rotation that the user must move the user's body in order to align the second visual prompt with the target. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displays (1228) text that includes instructions to move the body part (and, optionally, instructions indicating a manner of moving the body part) in order to satisfy the body part positioning precondition. In some embodiments, the second visual prompt is displayed concurrently with the text that includes the instructions. In some embodiments, the text is displayed before displaying the second visual prompt. For example, the text includes an instruction to move the portion of the user's body to align the second visual prompt with the first visual prompt in the first user interface. For example, as illustrated in FIG. 6A, the device provides text instructions 602 and displays an example dot 606 and target 608 to instruct the user to place the dot 606 into the circle.

Displaying text instructions to the user to explain how the user achieves a proper position of the user's body for measurement improves the visual feedback to the user so that the user knows how to move the user's body in order to obtain the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in response to the body part satisfying the body part positioning precondition, the computer system displays (1230) a first timer indicating an amount of time that the user must maintain the body part in a position satisfying the body part positioning precondition. For example, FIG. 6G illustrates a text prompt 630 that includes a time (e.g., a countdown time) and a timer 632 (e.g., a countdown timer). In some embodiments, the body part positioning precondition comprises a requirement that the user position the second visual prompt inside of (e.g., on top of) the first visual prompt (e.g., align the dot within the circle) and in response to the second visual prompt aligning with the first visual prompt, by the computer system displays a time and/or timer indicating that the user must maintain the second visual prompt aligned with the first visual prompt for a predetermined amount of time (e.g., 1 second, 3 seconds, 5 seconds, 15 seconds, 30 seconds, 1 minute. 3 minutes, 5 minutes). In some embodiments, the second visual prompt is transformed into or presented by the computer system to include the first timer (e.g., by adding a moving user interface element such as a line or dot that moves in a predetermined pattern such as sweeping around a circle in the predefined amount of time).

Displaying a timer to the user to indicate an amount of time the user must maintain the position of the user's body improves the visual feedback to the user so that the user knows how long to stay still in order to obtain the first measurement scan. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in response to the body part satisfying the body part positioning precondition, the computer system displays (1232) an indication (e.g., a success message or indication) that a first scan of the body part is complete. In some embodiments, the first scan of the body part comprises capturing an image of the body part. For example, the first scan comprises a captured image of the user's palm, and the displayed indication indicates that the first scan has been successfully completed, as illustrated in FIG. 6H. In some embodiments, the indication is, or includes, a change in the appearance of the timer. For example, the computer system updates the display of the timer (e.g., timer 618, FIG. 6G) so as to make an animated transition to a visual prompt (e.g., similar to the second with a change in color or intensity as compared to the previously displayed second visual prompt) at the time of the precondition is satisfied.

Displaying a success message to the user to indicate that the first scan has been completed improves the visual feedback to the user so that the user is aware that the first measurement scan is successful and the user knows, without further inquiry, that the user does not need to restart the process to obtain a measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displaying the indication that the first scan of the body part is complete comprises (1234) the computer system increasing brightness of the displayed first user interface from a first level to a second level for a predetermined time period, and, after increasing the brightness to the second level, decreasing the brightness of the displayed first user interface (e.g., to the first level or to a level below or close to the first level). For example, before displaying FIG. 6H, the device generates a flash (e.g., or other animated transition) on the display. In some embodiments, the second level is brighter than the first level (e.g., the display flashes white). In some embodiments, the second level is darker than the first level.

Displaying a flashing animation to the user to indicate that the first scan has been completed improves the visual feedback to the user so that the user knows that the first measurement scan has been obtained and that the user does not need to continue maintaining the user's body in the same proper position for the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the computer system displaying the indication that the first scan of the body part is complete comprises (1236) the computer system displaying a check mark. In some embodiments, the check mark is displayed at the position of the first visual prompt. For example, the check mark is displayed by the computer system in the open circle of the first visual prompt (e.g., as illustrated in FIG. 6H, check mark 638 is displayed at a location within the user interface where the target was displayed).

Displaying a check mark to indicate that the first scan has been completed improves the visual feedback to the user so that the user knows that the first measurement scan has been obtained and that the user does not need to continue maintaining the user's body in the same proper position for the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently In some embodiments, in accordance with a determination by the computer system that the body part satisfies the body part positioning precondition, the computer system displays (1238) text that includes instructions to move the body part in order to satisfy a second body part positioning precondition, maintains display of the first visual prompt at the first fixed location within the first user interface, and replaces the second visual prompt with a third visual prompt that is fixed at a second predefined position (e.g., in a simulated three dimensional space) relative to the representation of the portion of the user's body. In some embodiments, a position of the third visual prompt relative to a position of the first visual prompt indicates a movement of the body part that is required to satisfy the second body part positioning precondition. For example, after the first scan is complete (e.g., the first image is captured) in response to satisfying the first body part positioning precondition, the computing device displays an instruction for completing a second scan (e.g., capturing a second image) in accordance with a determination that the body part satisfies a second body part positioning precondition (e.g., that is different than the first body part positioning precondition). For example, the first body part precondition comprises a condition for aligning the second visual prompt (e.g., fixed to a portion of the user's palm) with the first visual prompt and the second body part precondition comprises a condition for aligning the third visual prompt (e.g., fixed to a location near the side of the user's hand) with the first visual prompt. For example, FIG. 6I illustrates text instructions 642 instructing the user to align dot 644 (e.g., the third visual prompt) with target 618 in order to satisfy the second body part positioning precondition.

Displaying text instructions to the user to explain how the user achieves a proper position of the user's body for measurement improves the visual feedback to the user so that the user knows how to obtain the second measurement scan. Displaying a success message to the user to indicate that the second scan has been completed improves the visual feedback to the user so that the user is aware that the second measurement scan is successful and the user does not need to restart the process to obtain a measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in response to the body part satisfying the second body part positioning precondition, the computer system displays (1240) a second timer indicating an amount of time that the user must maintain the body part in a position satisfying the second body part positioning precondition. In some embodiments, the second timer is distinct from the first timer (e.g., a different amount of time on the timer and/or a different timer is displayed). In some embodiments, the second timer is displayed by the computer system so as to indicate that the user must maintain the third visual prompt aligned with the first visual prompt for a predetermined amount of time (e.g., 1 second, 3 seconds, 5 seconds, 15 seconds, 30 seconds, 1 minute. 3 minutes, 5 minutes). In some embodiments, the third visual prompt is transformed into or presented by the computer system to include the second timer, e.g., by adding a moving user interface element such as a line or dot that moves in a predetermined pattern, such as a sweep hand or dot that sweeps around a circle until it completes a 360 degree cycle in the predefined amount of time. For example, FIGS. 6L-6M illustrate that once dot 644 has been aligned with target 618 (in FIG. 6L), timer 656 is displayed (in FIG. 6M).

Displaying a timer to the user to indicate an amount of time the user must maintain the position of the user's body improves the visual feedback to the user so that the user knows how long to stay still in order to obtain the second measurement scan. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, in accordance with a determination by the computer system that the body part satisfies the second body part positioning precondition, the computer system displays (1242) an indication that a second scan of the body part is complete. For example, the computer system captures a second image of the body part (e.g., at a different angle and/or a different portion of the body part). In some embodiments, the indication comprises a screen flash, a check mark, or instructions to move to a next user interface (e.g., "Continue"). For example, FIG. 6N illustrates a text prompt 660 with a success message and a check mark 662.

Displaying a success message to the user to indicate that the second scan has been completed improves the visual feedback to the user so that the user is aware that the second measurement scan is successful and the user does not need to restart the process to obtain the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, before scanning, using the one or more cameras, the portion of the user's body, the computer system displays (1244) one or more instructions on the display device. For example, FIGS. 6A-6B illustrate instructional user interfaces before scanning (e.g., detecting) the user's hand/wrist.

Displaying instructions, in the form of an animation and/or a text prompt, to the user to explain how the user achieves a proper position of the user's body for measurement improves the visual feedback to the user so that the user knows how to obtain the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the one or more instructions include (1246) instructions for placing the computing device into a proper position for scanning. In some embodiments, the instructions include an instruction to lay device flat on a table. In some embodiments, the instructions for placing the computing device are displayed in response to determining that the device is not flat. For example, the device displays an error message that the device is not flat, as illustrated in FIG. 5M.

Providing instructions indicating that the user has not placed the device at a proper pose (e.g., flat) for measuring makes it easier for the user to know how to adjust the device to be in a proper position without requiring the user to provide additional user inputs asking the device if the measurement has been successful. Providing improved visual feedback to the user and reducing the number and/or extent of inputs needed to perform an operation by performing the operation (e.g., automatically) when a set of conditions has been met enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the one or more instructions include (1248) instructions for selecting which body part will be scanned using the one or more cameras. For example, the computing device prompts the user to select whether to scan a left body part (e.g., wrist/hand) or a right body part (e.g., a right wrist/hand, as illustrated in FIGS. 5D-5E.

Providing additional options for selecting which side of a portion of the user's body should be measured avoids cluttering the user interface for aligning the portion of the user's body for measurement by only displaying guidance for the selected side of the user's body to be measured. Providing options for measuring different sides (e.g., right or left) of the portion of the user's body without cluttering the user interface with additional guidance related to portions of the user's body that are not measured enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the one or more instructions include (1250) instructions for moving the body part such that the body part is in the field of view of the one or more cameras. For example, the instructions include instructions for how to move hand (e.g., in a particular direction) such that the entire body part is in the field of view of the one or more cameras (e.g., instructions to move closer, farther, to roll up sleeve and/or remove jewelry, etc.). For example, FIG. 5F illustrates instructions to "Place your left hand over the device and rotate your hand." FIGS. 5K-5N illustrate error conditions that include instructions for the user to move their hand into a proper position within the field of view of the one or more cameras.

Displaying instructions, in the form of an animation and/or a text prompt, to the user to explain how the user achieves a proper position of the user's body for measurement improves the visual feedback to the user so that the user knows how to obtain the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, the one or more instructions include (1252) displaying a representation of a body part in a position that satisfies the body part positioning precondition. For example, FIGS. 6A-6B include an animation of a representation 610 of a user's hand that rotates to move the dot (e.g., dot 606 and/or dot 612) into target 608. In some embodiments, the one or more instructions also include displaying a representation of the body part in a position that satisfies the second body part positioning precondition. For example, the representation 610 of the user's hand in FIGS. 6A-6B are animated to rotate as an example of the device successfully scanning a user's palm and a side of a user's hand.

Displaying an animation that demonstrates to the user to how to move the representation of the body part into the proper position for measurement improves the visual feedback to the user so that the user knows how to obtain the measurement. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

In some embodiments, before displaying the second visual prompt, the computer system updates (1254) display of the representation of the portion of the user's body. For example, the representation of the portion of the user's body updates the representation to be translucent or faded. In some embodiments, the representation of the portion of the user's body is updated as the body part of the user moves (e.g., changes positions) such that the representation of the portion of the user's body is updated in accordance with the movement of the body part that is in the field of view of the one or more cameras. For example, as described with reference to FIGS. 5K-5M, the representation of the user's hand is faded (e.g., displayed with a degree of transparency) when the user's hand is not in a proper position. In some embodiments, after the user's hand is in a proper position for scanning the user's hand, the representation of the user's hand no longer appears translucent (or partially transparent), and the second visual prompt (e.g., dot 620) appears at its predefined fixed location relative to the representation of the user's hand.

Visually deemphasizing (e.g., fading) the representation of the portion of the user's body provides visual feedback informing the user that the portion of the user's body is not in a proper position within the field of view and prompting the user to move the portion of the user's body if the user wishes to measure the portion of the user's body. Providing improved visual feedback to the user enhances the operability of the system and makes the user-device interface more efficient (e.g., by helping the user to achieve an intended result and reducing user mistakes when operating/interacting with the system), which, additionally, reduces power usage and improves battery life of the device by enabling the user to use the device more quickly and efficiently.

It should be understood that the particular order in which the operations in FIGS. 12A-12D have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein (e.g., methods 900, 1000 and 1100) are also applicable in an analogous manner to method 1200 described above with respect to FIGS. 12A-12D. For example, the user interface objects described above with reference to method 1200 optionally have one or more of the characteristics of the user interface objects described herein with reference to other methods described herein (e.g., methods 900, 1000 and 1100). For brevity, these details are not repeated here.

The operations described above with reference to FIGS. 9A-9C, 10A-10D, 11A-11C, and 12A-12D are, optionally, implemented by components depicted in FIGS. 1A-1B. For example, are, optionally, implemented by event sorter 170, event recognizer 180, and event handler 190. Event monitor 171 in event sorter 170 detects a contact on touch-sensitive display 112, and event dispatcher module 174 delivers the event information to application 136-1. A respective event recognizer 180 of application 136-1 compares the event information to respective event definitions 186, and determines whether a first contact at a first location on the touch-sensitive surface (or whether rotation of the device) corresponds to a predefined event or sub-event, such as selection of an object on a user interface, or rotation of the device from one orientation to another. When a respective predefined event or sub-event is detected, event recognizer 180 activates an event handler 190 associated with the detection of the event or sub-event. Event handler 190 optionally uses or calls data updater 176 or object updater 177 to update the application internal state 192. In some embodiments, event handler 190 accesses a respective GUI updater 178 to update what is displayed by the application. Similarly, it would be clear to a person having ordinary skill in the art how other processes can be implemented based on the components depicted in FIGS. 1A-1B.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best use the invention and various described embodiments with various modifications as are suited to the particular use contemplated.

What is claimed is:

1. A method, comprising:
  at a computer system in communication with a display device and one or more cameras:
    displaying, via the display device, in a user interface, a first representation of a body part that is in a field of view of the one or more cameras, wherein the body part is a body part of a person and the first representation of the body part is displayed with a first size;
    detecting, using the one or more cameras, movement of the body part by the person, wherein the person is positioned to view the display device as the person moves the body part and the displayed first representation of the body part is updated in accordance with the movement of the body part;
while displaying the first representation of the body part with the first size as the movement of the body part continues, displaying, via the display device, in the user interface, a respective user interface element that includes a plurality of indicators at fixed locations relative to the first representation of the body part, wherein:
   the respective user interface element is displayed with a respective first size in the user interface;
   a first indicator of the plurality of indicators is displayed at a first position in the user interface that overlays at least a portion of the first representation of the body part;
   a second indicator of the plurality of indicators, which is concurrently displayed with the first indicator and the first representation of the body part, is displayed at a second position in the user interface that does not overlay the first representation of the body part;
   the plurality of indicators is updated in accordance with the movement of the body part by the person to indicate progress toward performing an operation; and
   the respective user interface element includes an indication of a suggested direction of movement of the body part by the person;
detecting movement of the body part that changes a distance between the one or more cameras and the body part; and
in response to detecting the movement of the body part that changes a distance between the one or more cameras and the body part:
   displaying the first representation of the body part with a second size in accordance with the changed distance; and
   displaying the respective user interface element that includes the plurality of indicators, including the first indicator and the second indicator, with a respective second size in accordance with the changed distance.

2. The method of claim 1, wherein the indication of the suggested direction of movement comprises an animation of the respective user interface element indicating the suggested direction of movement.

3. The method of claim 1, wherein the body part is a wrist and/or a hand.

4. The method of claim 1, wherein the body part is in a physical environment; and
the method further includes:
   displaying, in a first user interface, a background;
   detecting, using the one or more cameras, a portion of the physical environment and the body part that are within the field of view of the one or more cameras; and
   displaying the first representation of the body part over the background without displaying a representation of the portion of the physical environment that is within the field of view of the one or more cameras.

5. The method of claim 1, further comprising:
displaying a background having a first color; and
replacing display of the background having the first color with display of a background having a second color.

6. The method of claim 5, wherein the first color and the second color correspond to color options for a physical object to be worn on the body part.

7. The method of claim 1,
wherein detecting the movement of the body part comprises detecting movement of the body part in a first direction;
the method further comprising:
   in response to detecting the movement of the body part in the first direction:
      displaying the first representation of the body part at a third position in the user interface in accordance with the movement of the body part; and
      displaying the respective user interface element that includes the plurality of indicators at the fixed locations relative to the first representation of the body part displayed at the third position.

8. The method of claim 1, wherein:
while the first representation of the body part is displayed with the first size and the respective user interface element is displayed with the respective first size in the user interface, the plurality of indicators is updated to fill at least one indicator displayed with a first indicator size in accordance with the movement of the body part by the person;
the movement of the body part that changes a distance between the one or more cameras and the body part is detected after the plurality of indicators is updated to fill the at least one indicator displayed with the first indicator size; and
displaying the respective user interface element that includes the plurality of indicators with the respective second size in accordance with the changed distance in response to detecting the change in the distance between the one or more cameras and the body part includes displaying the at least one filled indicator with a second indicator size in accordance with the changed distance.

9. The method of claim 1, wherein:
detecting the movement of the body part comprises detecting rotation of the body part; and
the method further comprises:
   while detecting the rotation of the body part, scanning, using the one or more cameras, one or more images to determine a measurement of the body part; and
   updating the respective user interface element to indicate a progress of scanning or measuring the body part.

10. The method of claim 1, wherein the indication of the suggested direction of movement of the body part comprises an indication to rotate the body part.

11. The method of claim 1, further comprising, while displaying the first representation of the body part, capturing, using the one or more cameras, one or more images of the body part, wherein the one or more images are used to determine a measurement of the body part; and
displaying, in a second user interface, a size corresponding to the measurement of the body part.

12. The method of claim 1, wherein:
the fixed locations relative to the first representation of the body part are first fixed locations relative to the first representation of the body part; and
the method further comprises:
   receiving a first user input in a first direction; and
   in response to the first user input, updating the first fixed locations of the plurality of indicators relative to the body part to second fixed locations, distinct from the first fixed locations, relative to the body part.

13. The method of claim 1, further comprising:
replacing display of the respective user interface element in the user interface with a second user interface element in the user interface, wherein the second user interface element is displayed at a fixed location relative to the first representation of the body part, and the second user interface element indicates a first size of a portion of the body part corresponding to the portion of the first representation of the body part at the fixed location.

14. The method of claim 13, wherein the fixed location relative to the first representation of the body part is a first fixed location; and
the method further comprises:
receiving a second user input to move the second user interface element; and
in response to receiving the second user input, moving the second user interface element from the first fixed location in the user interface to a third fixed location relative to the first representation of the body part.

15. The method of claim 14, further comprising, in accordance with a determination that the second user interface element is at the third fixed location relative to the first representation of the body part, updating the second user interface element to indicate a second size of a portion of the body part corresponding to the third fixed location.

16. The method of claim 13, further comprising, capturing an image that includes the first representation of the body part and the second user interface element at the fixed location relative to the first representation of the body part, wherein the second user interface element indicates the first size of the portion of the body part corresponding to the fixed location of the second user interface element.

17. The method of claim 16, further comprising, while displaying the image, receiving a third user input to move the second user interface element to a different fixed location relative to the first representation of the body part in the image.

18. The method of claim 1, wherein the user interface is a first user interface; and
the method further comprises:
displaying a second user interface, the second user interface including:
an option to select a product having a plurality of size options, selectable in accordance with a measurement of the body part that is in the field of view of the one or more cameras; and
an affordance that, when selected, initiates display of the first user interface.

19. The method of claim 1, wherein the user interface is a user interface within a respective application executed by the computer system.

20. The method of claim 1, wherein the plurality of indicators that is updated in accordance with the movement of the body part is updated by gradually changing in appearance as the body part moves to indicate a progress of rotation of the body part.

21. The method of claim 1, including in response to detecting the movement of the body part:
in accordance with a determination that the movement of the body part moves at a speed that is below a threshold speed, gradually changing an appearance of the respective user interface element as the body part moves to indicate a progress of movement of the body part toward a target pose; and
in accordance with a determination that the movement of the body part moves at a speed that is above the threshold speed, forgoing at least a portion of a change in appearance of the respective user interface element as the body part moves to indicate that the movement of the body part toward the target pose was too fast.

22. The method of claim 1, wherein the plurality of indicators that is updated in accordance with the movement of the body part is updated gradually in accordance with the movement of the body part to indicate a progress of scanning and measuring the body part.

23. The method of claim 1, wherein:
detecting the movement of the body part by the person includes detecting movement of the body part in a first direction;
the plurality of indicators is updated in accordance with the movement of the body part in the first direction, including filling one or more of the plurality of indicators; and
the method further includes:
after detecting the movement of the body part in the first direction, detecting movement of the body part in a second direction opposite the first direction; and
updating the plurality of indicators in accordance with the movement of the body part in the second direction, including removing the filling of at least one of the plurality of indicators.

24. A computer system, comprising:
a display generation component;
one or more cameras;
one or more input devices;
one or more processors; and
memory storing one or more programs, wherein the one or more programs are configured to be executed by the one or more processors, the one or more programs including instructions for:
displaying, via the display generation component, in a user interface, a first representation of a body part that is in a field of view of the one or more cameras, wherein the body part is a body part of a person and the first representation of the body part is displayed with a first size;
detecting, using the one or more cameras, movement of the body part by the person, wherein the person is positioned to view the display generation component as the person moves the body part and the displayed first representation of the body part is updated in accordance with the movement of the body part;
while displaying the first representation of the body part with the first size as the movement of the body part continues, displaying, via the display generation component, in the user interface, a respective user interface element that includes a plurality of indicators at fixed locations relative to the first representation of the body part, wherein:
the respective user interface element is displayed with a respective first size in the user interface;
a first indicator of the plurality of indicators is displayed at a first position in the user interface that overlays at least a portion of the first representation of the body part;
a second indicator of the plurality of indicators, which is concurrently displayed with the first indicator and the first representation of the body part, is displayed at a second position in the user interface that does not overlay the first representation of the body part;

the plurality of indicators is updated in accordance with the movement of the body part by the person to indicate progress toward performing an operation; and the respective user interface element includes an indication of a suggested direction of movement of the body part by the person;

detecting movement of the body part that changes a distance between the one or more cameras and the body part; and in response to detecting the movement of the body part that changes a distance between the one or more cameras and the body part:

displaying the first representation of the body part with a second size in accordance with the changed distance; and displaying the respective user interface element that includes the plurality of indicators, including the first indicator and the second indicator, with a respective second size in accordance with the changed distance.

25. The computer system of claim 24, wherein the body part is a wrist and/or a hand.

26. The computer system of claim 24, wherein the body part is in a physical environment; and
the one or more programs further include instructions for:
displaying, in a first user interface, a background;
detecting, using the one or more cameras, a portion of the physical environment and the body part that are within the field of view of the one or more cameras; and
displaying the first representation of the body part over the background without displaying a representation of the portion of the physical environment that is within the field of view of the one or more cameras.

27. The computer system of claim 24,
wherein detecting the movement of the body part comprises detecting movement of the body part in a first direction;
the one or more programs further including instructions for:
in response to detecting the movement of the body part in the first direction:
displaying the first representation of the body part at a third position in the user interface in accordance with the movement of the body part; and
displaying the respective user interface element that includes the plurality of indicators at the fixed locations relative to the first representation of the body part displayed at the third position.

28. The computer system of claim 24, wherein:
while the first representation of the body part is displayed with the first size and the respective user interface element is displayed with the respective first size in the user interface, the plurality of indicators is updated to fill at least one indicator displayed with a first indicator size in accordance with the movement of the body part by the person;
the movement of the body part that changes a distance between the one or more cameras and the body part is detected after the plurality of indicators is updated to fill the at least one indicator displayed with the first indicator size; and
displaying the respective user interface element that includes the plurality of indicators with the respective second size in accordance with the changed distance in response to detecting the change in the distance between the one or more cameras and the body part includes displaying the at least one filled indicator with a second indicator size in accordance with the changed distance.

29. The computer system of claim 24, wherein:
detecting the movement of the body part comprises detecting rotation of the body part; and
the one or more programs further include instructions for:
while detecting the rotation of the body part, scanning, using the one or more cameras, one or more images to determine a measurement of the body part; and
updating the respective user interface element to indicate a progress of scanning or measuring the body part.

30. The computer system of claim 24, wherein the one or more programs further include instructions for:
while displaying the first representation of the body part, capturing, using the one or more cameras, one or more images of the body part, wherein the one or more images are used to determine a measurement of the body part; and
displaying, in a second user interface, a size corresponding to the measurement of the body part.

31. The computer system of claim 24, wherein:
the fixed locations relative to the first representation of the body part are first fixed locations relative to the first representation of the body part; and
the one or more programs further include instructions for:
receiving a first user input in a first direction; and
in response to the first user input, updating the first fixed locations of the plurality of indicators relative to the body part to second fixed locations, distinct from the first fixed locations, relative to the body part.

32. The computer system of claim 24, wherein the one or more programs further include instructions for:
replacing display of the respective user interface element in the user interface with a second user interface element in the user interface, wherein the second user interface element is displayed at a fixed location relative to the first representation of the body part, and the second user interface element indicates a first size of a portion of the body part corresponding to the portion of the first representation of the body part at the fixed location.

33. The computer system of claim 24, wherein the user interface is a first user interface; and
the one or more programs further include instructions for:
displaying a second user interface, the second user interface including:
an option to select a product having a plurality of size options, selectable in accordance with a measurement of the body part that is in the field of view of the one or more cameras; and
an affordance that, when selected, initiates display of the first user interface.

34. The computer system of claim 24, wherein the plurality of indicators that is updated in accordance with the movement of the body part is updated by gradually changing in appearance as the body part moves to indicate a progress of rotation of the body part.

35. The computer system of claim 24, the one or more programs further including instructions for, in response to detecting the movement of the body part:
in accordance with a determination that the movement of the body part moves at a speed that is below a threshold speed, gradually changing an appearance of the respective user interface element as the body part moves to indicate a progress of movement of the body part toward a target pose; and in accordance with a determination that the movement of the body part moves at a speed that is above the threshold speed, forgoing at least a portion of a change in appearance of the respective user interface element as the body part moves to indicate that the movement of the body part toward the target pose was too fast.

36. The computer system of claim 24, wherein the plurality of indicators that is updated in accordance with the movement of the body part is updated gradually in accordance with the movement of the body part to indicate a progress of scanning and measuring the body part.

37. The computer system of claim 24, wherein:
   detecting the movement of the body part by the person includes detecting movement of the body part in a first direction;
   the plurality of indicators is updated in accordance with the movement of the body part in the first direction, including filling one or more of the plurality of indicators; and
   the one or more programs further include instructions for:
      after detecting the movement of the body part in the first direction, detecting movement of the body part in a second direction opposite the first direction; and
      updating the plurality of indicators in accordance with the movement of the body part in the second direction, including removing the filling of at least one of the plurality of indicators.

38. A non-transitory computer readable storage medium storing one or more programs, the one or more programs comprising instructions that, when executed by a computer system that includes and/or is in communication with a display generation component, one or more cameras, and one or more input devices, cause the computer system to:
   display, in a user interface, a first representation of a body part that is in a field of view of the one or more cameras, wherein the body part is a body part of a person and the first representation of the body part is displayed with a first size;
   detect, using the one or more cameras, movement of the body part by the person, wherein the person is positioned to view the display generation component as the person moves the body part and the displayed first representation of the body part is updated in accordance with the movement of the body part;
   while displaying the first representation of the body part with the first size as the movement of the body part continues, display, via the display generation component, in the user interface, a respective user interface element that includes a plurality of indicators at fixed locations relative to the first representation of the body part, wherein:
      the respective user interface element is displayed with a respective first size in the user interface;
      a first indicator of the plurality of indicators is displayed at a first position in the user interface that overlays at least a portion of the first representation of the body part;
      a second indicator of the plurality of indicators, which is concurrently displayed with the first indicator and the first representation of the body part, is displayed at a second position in the user interface that does not overlay the first representation of the body part;
      the plurality of indicators is updated in accordance with the movement of the body part by the person to indicate progress toward performing an operation; and
      the respective user interface element includes an indication of a suggested direction of movement of the body part by the person;
   detect movement of the body part that changes a distance between the one or more cameras and the body part; and
   in response to detecting the movement of the body part that changes a distance between the one or more cameras and the body part:
      display the first representation of the body part with a second size in accordance with the changed distance; and
      display the respective user interface element that includes the plurality of indicators, including the first indicator and the second indicator, with a respective second size in accordance with the changed distance.

39. The non-transitory computer readable storage medium of claim 38, wherein the body part is a wrist and/or a hand.

40. The non-transitory computer readable storage medium of claim 38, wherein the body part is in a physical environment; and
   the one or more programs further include instructions that cause the computer system to:
      display, in a first user interface, a background;
      detect, using the one or more cameras, a portion of the physical environment and the body part that are within the field of view of the one or more cameras; and
      display the first representation of the body part over the background without displaying a representation of the portion of the physical environment that is within the field of view of the one or more cameras.

41. The non-transitory computer readable storage medium of claim 38,
   wherein detecting the movement of the body part comprises detecting movement of the body part in a first direction;
   the one or more programs further include instructions that cause the computer system to:
      in response to detecting the movement of the body part in the first direction:
         display the first representation of the body part at a third position in the user interface in accordance with the movement of the body part; and
         display the respective user interface element that includes the plurality of indicators at the fixed locations relative to the first representation of the body part displayed at the third position.

42. The non-transitory computer readable storage medium of claim 38, wherein:
   while the first representation of the body part is displayed with the first size and the respective user interface element is displayed with the respective first size in the user interface, the plurality of indicators is updated to fill at least one indicator displayed with a first indicator size in accordance with the movement of the body part by the person;
   the movement of the body part that changes a distance between the one or more cameras and the body part is detected after the plurality of indicators is updated to fill the at least one indicator displayed with the first indicator size; and displaying the respective user interface element that includes the plurality of indicators with the respective second size in accordance with the changed distance in response to detecting the change in the distance between the one or more cameras and the body part includes displaying the at least one filled indicator with a second indicator size in accordance with the changed distance.

43. The non-transitory computer readable storage medium of claim 38, wherein:
detecting the movement of the body part comprises detecting rotation of the body part; and
the one or more programs further include instructions that cause the computer system to:
while detecting the rotation of the body part, scan, using the one or more cameras, one or more images to determine a measurement of the body part; and
update the respective user interface element to indicate a progress of scanning or measuring the body part.

44. The non-transitory computer readable storage medium of claim 38, wherein the one or more programs further include instructions that cause the computer system to:
while displaying the first representation of the body part, capture, using the one or more cameras, one or more images of the body part, wherein the one or more images are used to determine a measurement of the body part; and
display, in a second user interface, a size corresponding to the measurement of the body part.

45. The non-transitory computer readable storage medium of claim 38, wherein:
the fixed locations relative to the first representation of the body part are first fixed locations relative to the first representation of the body part; and
the one or more programs further include instructions that cause the computer system to:
receive a first user input in a first direction; and
in response to the first user input, update the first fixed locations of the plurality of indicators relative to the body part to second fixed locations, distinct from the first fixed locations, relative to the body part.

46. The non-transitory computer readable storage medium of claim 38, wherein the one or more programs further include instructions that cause the computer system to:
replace display of the respective user interface element in the user interface with a second user interface element in the user interface, wherein the second user interface element is displayed at a fixed location relative to the first representation of the body part, and the second user interface element indicates a first size of a portion of the body part corresponding to the portion of the first representation of the body part at the fixed location.

47. The non-transitory computer readable storage medium of claim 38, wherein the user interface is a first user interface; and
the one or more programs further include instructions that cause the computer system to:
display a second user interface, the second user interface including:
an option to select a product having a plurality of size options, selectable in accordance with a measurement of the body part that is in the field of view of the one or more cameras; and
an affordance that, when selected, initiates display of the first user interface.

48. The non-transitory computer readable storage medium of claim 38, wherein the plurality of indicators that is updated in accordance with the movement of the body part is updated by gradually changing in appearance as the body part moves to indicate a progress of rotation of the body part.

49. The non-transitory computer readable storage medium of claim 38, the one or more programs further include instructions that cause the computer system to, in response to detecting the movement of the body part:
in accordance with a determination that the movement of the body part moves at a speed that is below a threshold speed, gradually change an appearance of the respective user interface element as the body part moves to indicate a progress of movement of the body part toward a target pose; and
in accordance with a determination that the movement of the body part moves at a speed that is above the threshold speed, forgo at least a portion of a change in appearance of the respective user interface element as the body part moves to indicate that the movement of the body part toward the target pose was too fast.

50. The non-transitory computer readable storage medium of claim 38, wherein the plurality of indicators that is updated in accordance with the movement of the body part is updated gradually in accordance with the movement of the body part to indicate a progress of scanning and measuring the body part.

51. The non-transitory computer readable storage medium of claim 38, wherein:
detecting the movement of the body part by the person includes detecting movement of the body part in a first direction;
the plurality of indicators is updated in accordance with the movement of the body part in the first direction, including filling one or more of the plurality of indicators; and
the one or more programs further include instructions that cause the computer system to:
after detecting the movement of the body part in the first direction, detect movement of the body part in a second direction opposite the first direction; and
update the plurality of indicators in accordance with the movement of the body part in the second direction, including removing the filling of at least one of the plurality of indicators.

* * * * *